(12) United States Patent
Chen

(10) Patent No.: US 11,531,924 B2
(45) Date of Patent: Dec. 20, 2022

(54) SCALE-UP TOROIDAL ARRAY QUANTUM PROCESSING MEMORY DEVICE WITH CONTROLLABLE AND ADJUSTABLE STATE-SWITCH VALVES OF MAKING AND APPLICATIONS THERETO

(71) Applicant: Ellen Tuanying Chen, Rockville, MD (US)

(72) Inventor: Ellen Tuanying Chen, Rockville, MD (US)

(*) Notice: Subject to any disclaimer, the term of this patent is extended or adjusted under 35 U.S.C. 154(b) by 315 days.

(21) Appl. No.: 16/435,435

(22) Filed: Jun. 7, 2019

(65) Prior Publication Data

US 2022/0101171 A1    Mar. 31, 2022

Related U.S. Application Data

(63) Continuation-in-part of application No. 15/361,068, filed on Nov. 24, 2016, now Pat. No. 10,441,169.

(51) Int. Cl.

| | |
|---|---|
| *G06N 10/40* | (2022.01) |
| *H01L 39/16* | (2006.01) |
| *C12Q 1/00* | (2006.01) |
| *A61N 1/04* | (2006.01) |
| *H01L 39/02* | (2006.01) |
| *H01L 39/22* | (2006.01) |
| *H01L 39/24* | (2006.01) |

(52) U.S. Cl.
CPC .......... *G06N 10/40* (2022.01); *H01L 39/025* (2013.01); *H01L 39/16* (2013.01); *H01L 39/223* (2013.01); *H01L 39/2493* (2013.01); *A61N 1/0456* (2013.01); *C12Q 1/006* (2013.01)

(58) Field of Classification Search
CPC ....... G06N 10/40; H01L 39/025; H01L 39/16; H01L 39/223; H01L 39/2493
See application file for complete search history.

(56) References Cited

U.S. PATENT DOCUMENTS

2017/0191955 A1* 7/2017 Zou ...................... C08G 18/755

FOREIGN PATENT DOCUMENTS

CN           108796655 A    * 11/2018

\* cited by examiner

*Primary Examiner* — Michael C Zarroli

(57) ABSTRACT

The present invention provides a sensor and measuring method. The sensor comprises multiple-layer organo-metallic cross-linked polymers forming various superlattice nanostructured biomimetic membranes for sensing Cooper-pair wave transmissions causing intrinsic magnetic flux quantum observed based on a Josephson junction toroidal array and a controllable state-switch valve having a double-pole electron-relay that promoted Cooper pairs coherently transmitting waves in the membranes within and cross the Josephson toroidal junction barriers at zero-bias. The One-Device-Assembly system enables a femto-joule energy consumption for quantum qubits; or acting as an energy storage device that stores energy 1.53 MJ/cm$^2$ for an application in automobile vehicles.

20 Claims, 87 Drawing Sheets

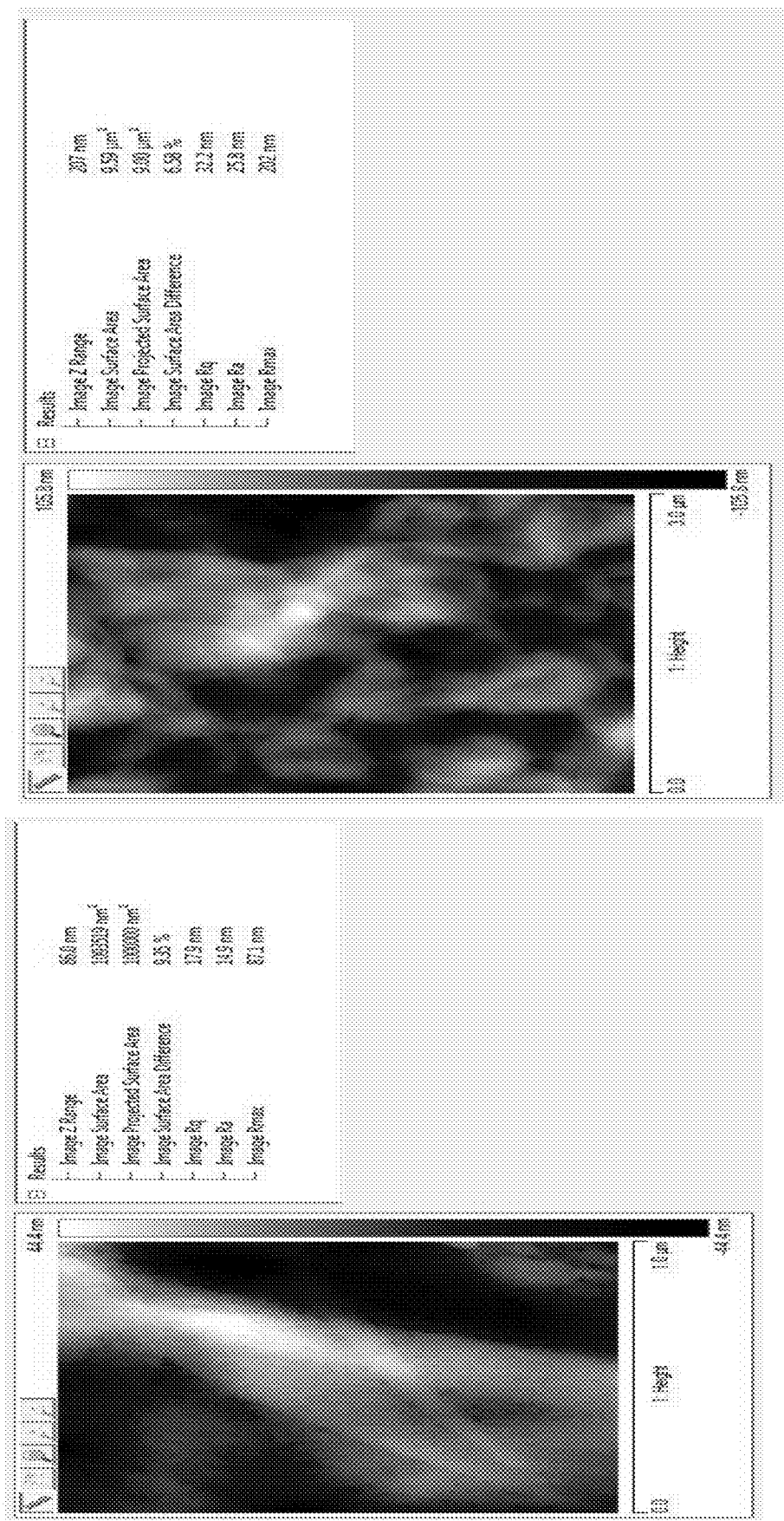

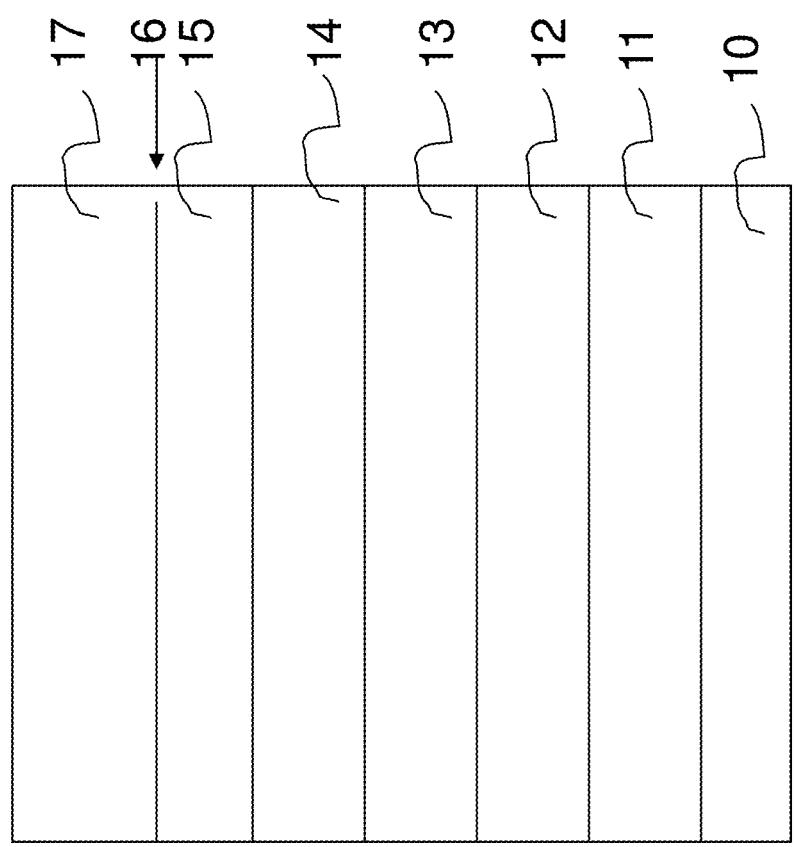

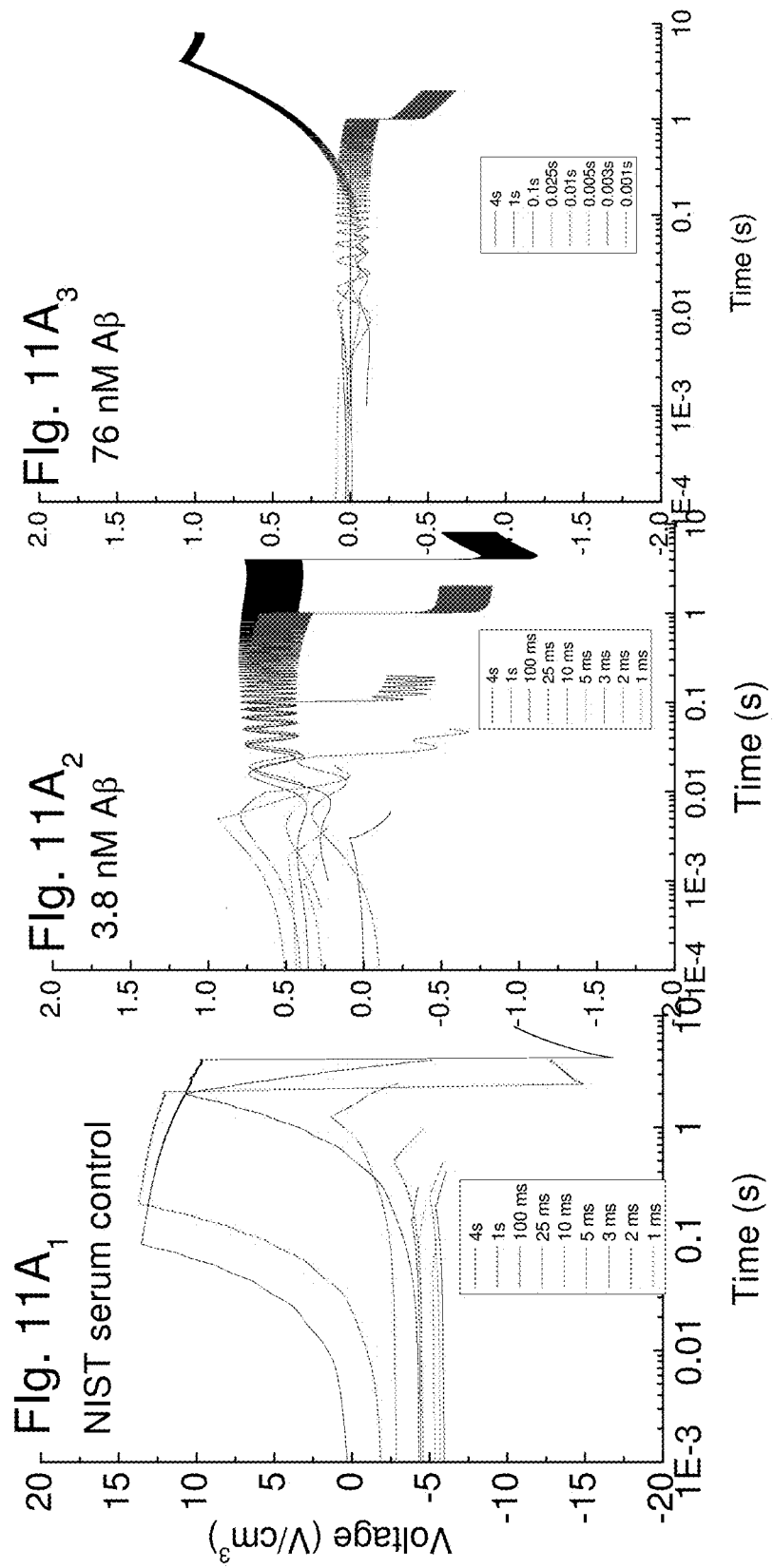

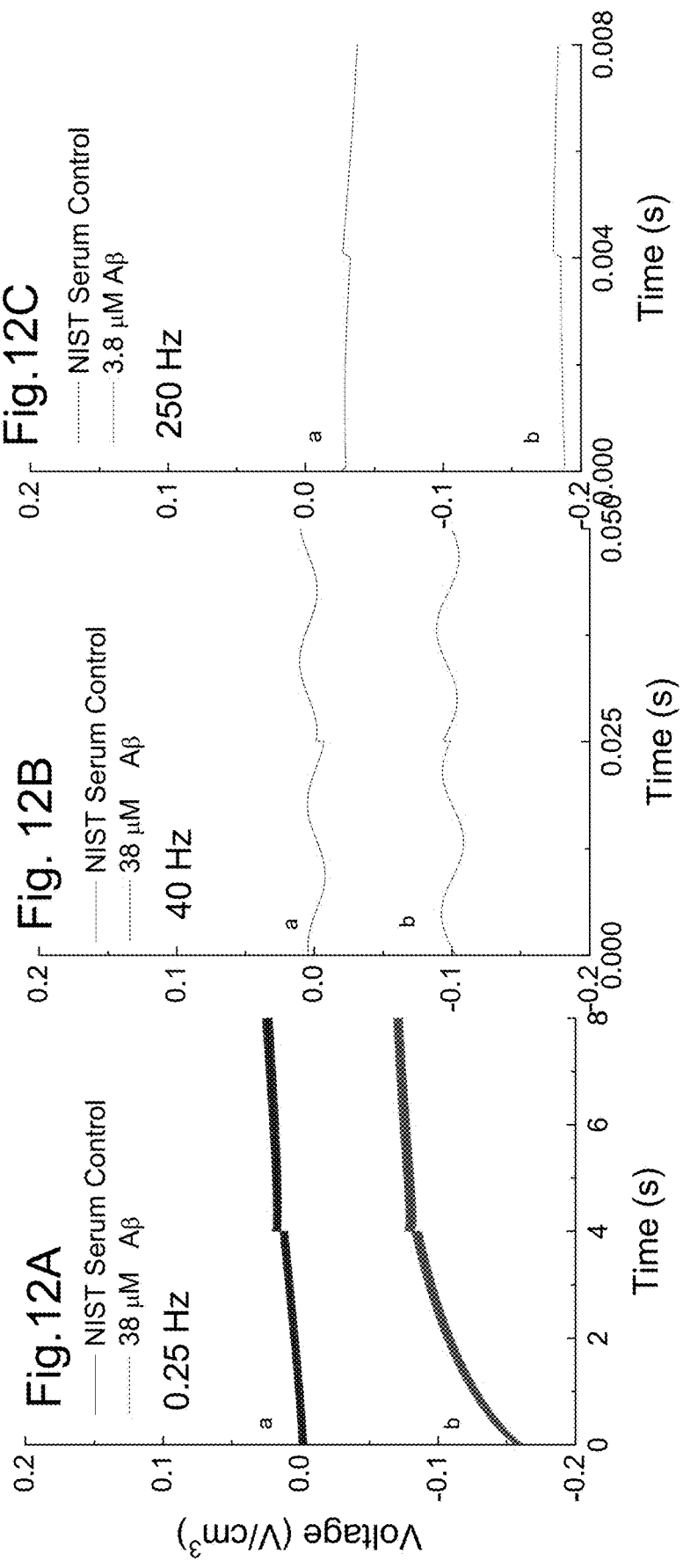

Fig. 20
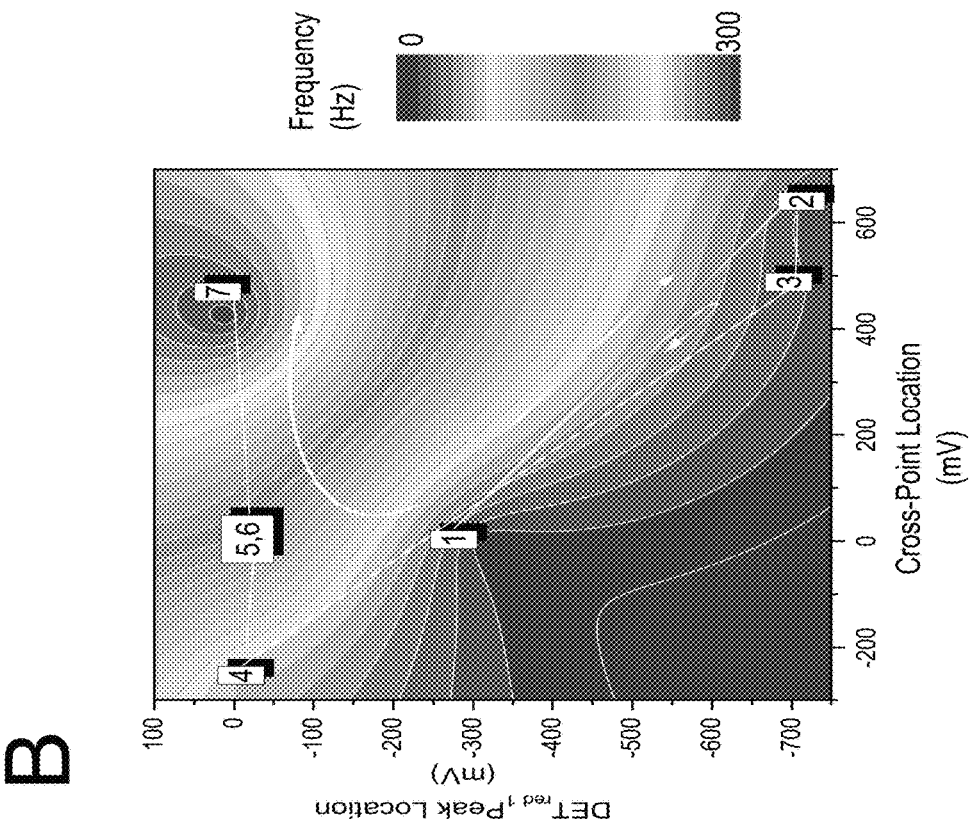
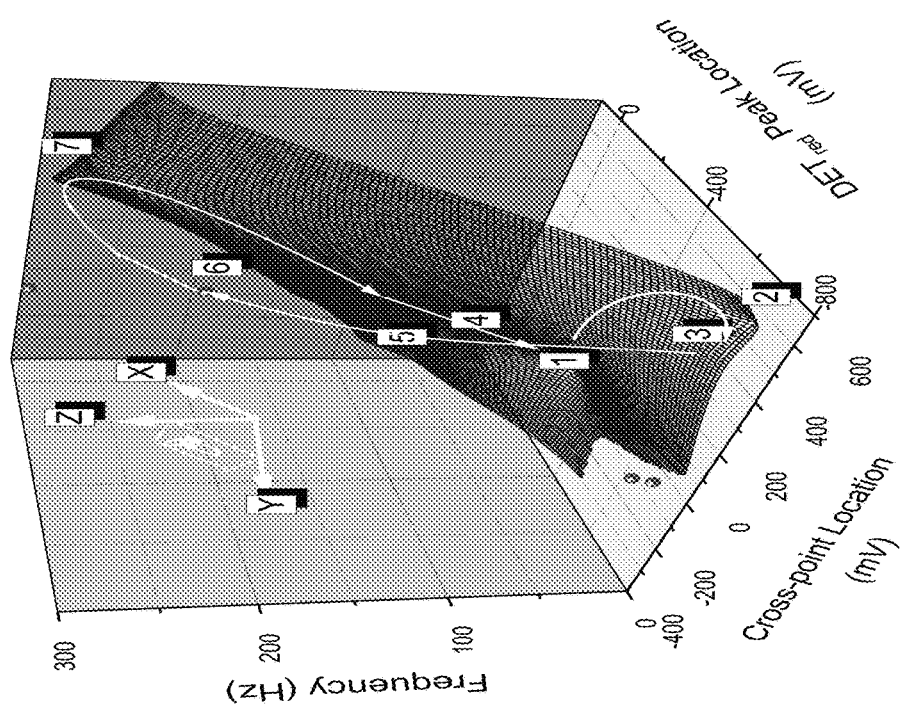

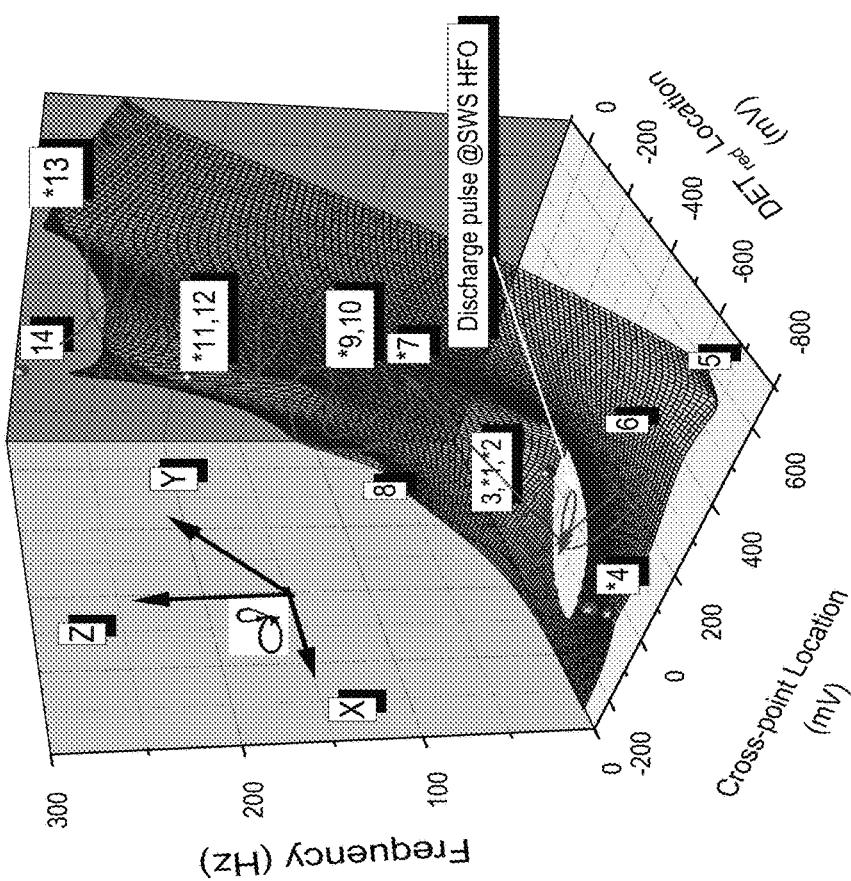
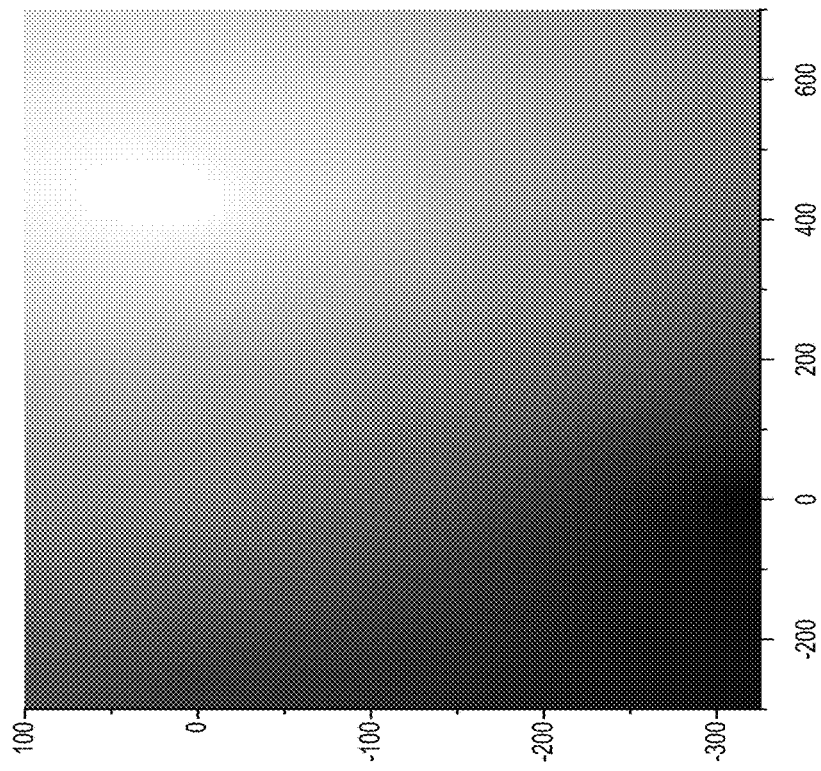
Fig. 21
Fig. 20

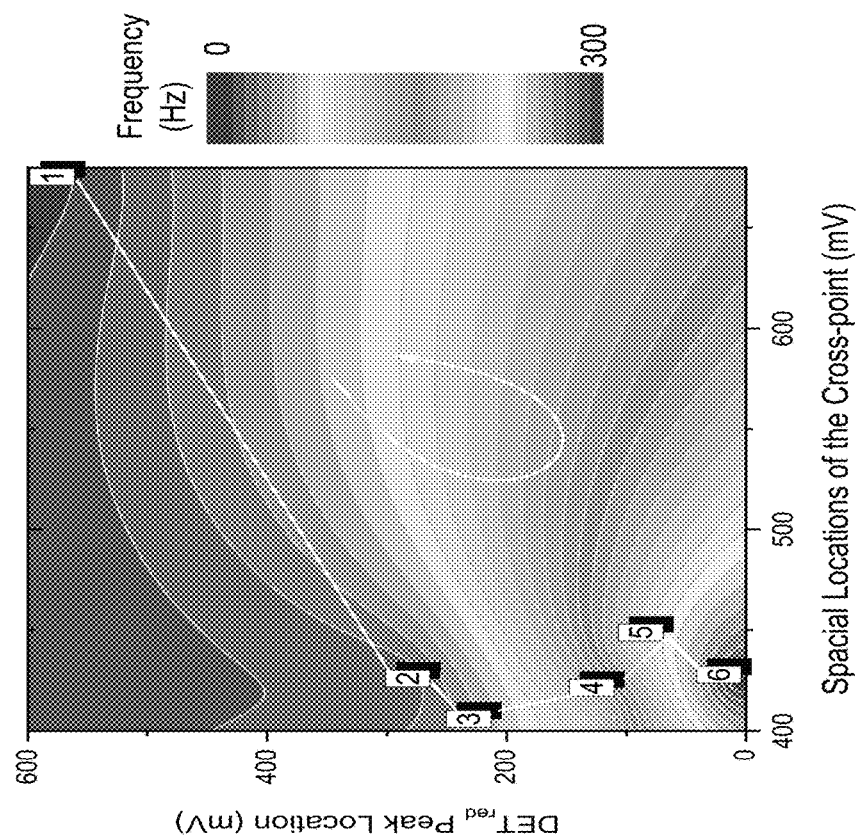
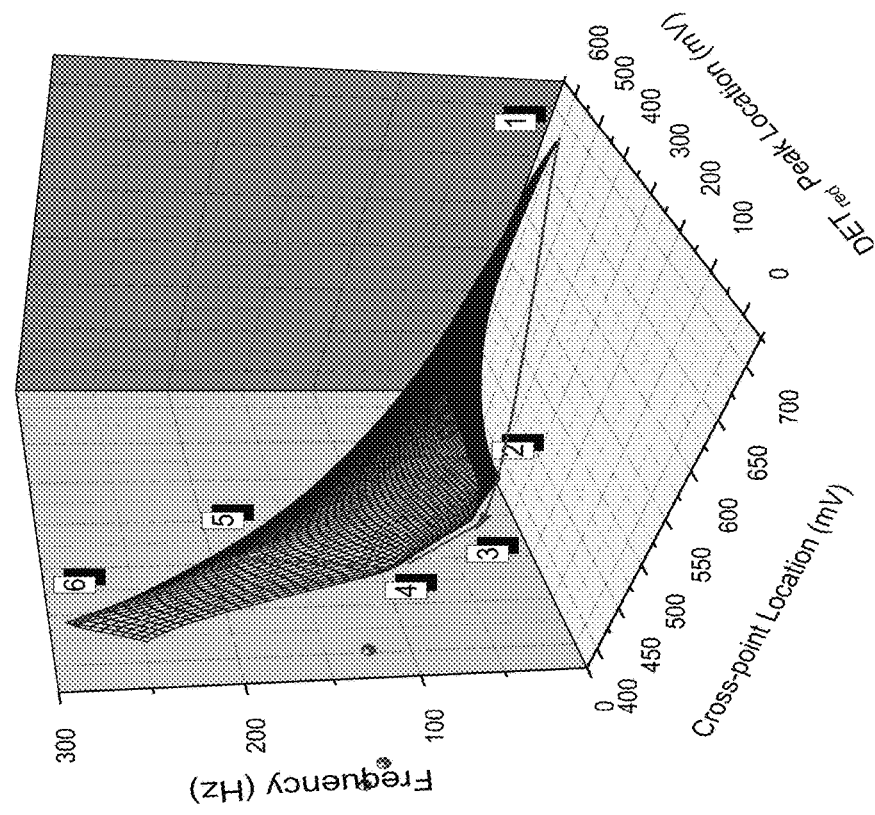
Fig. 24

Fig. 25
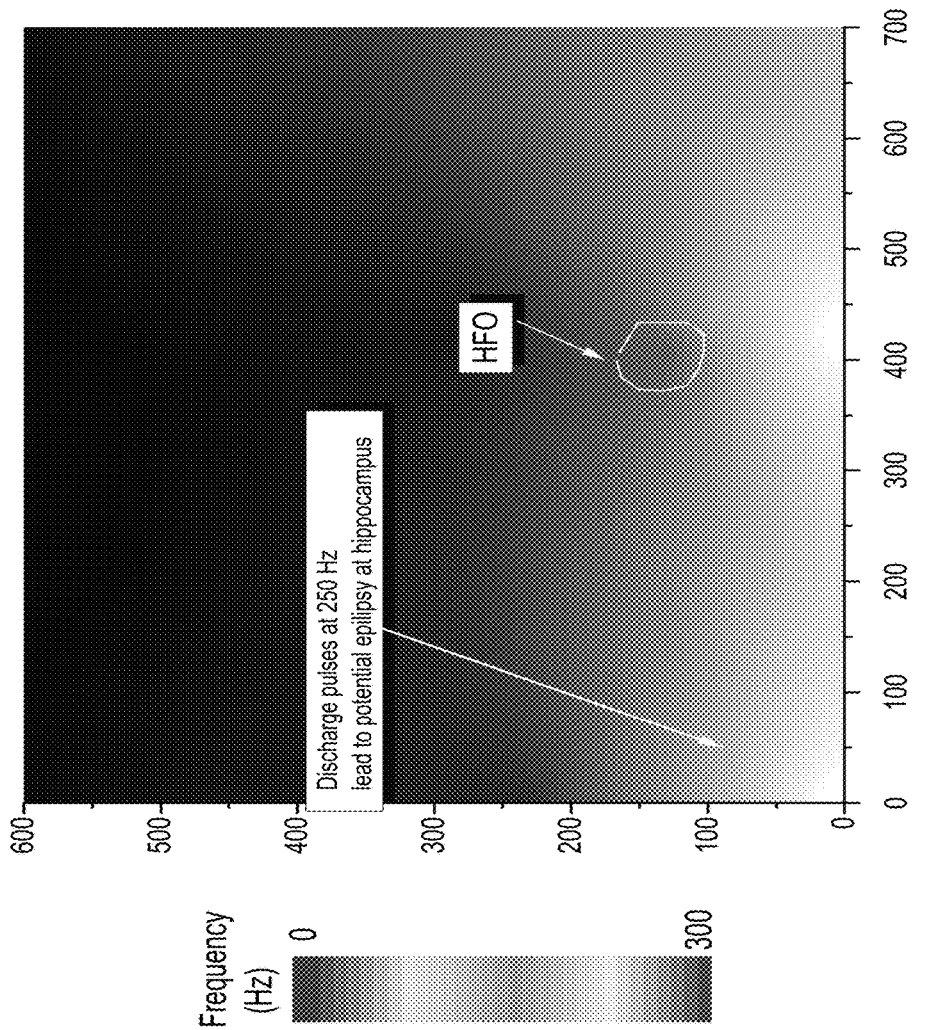
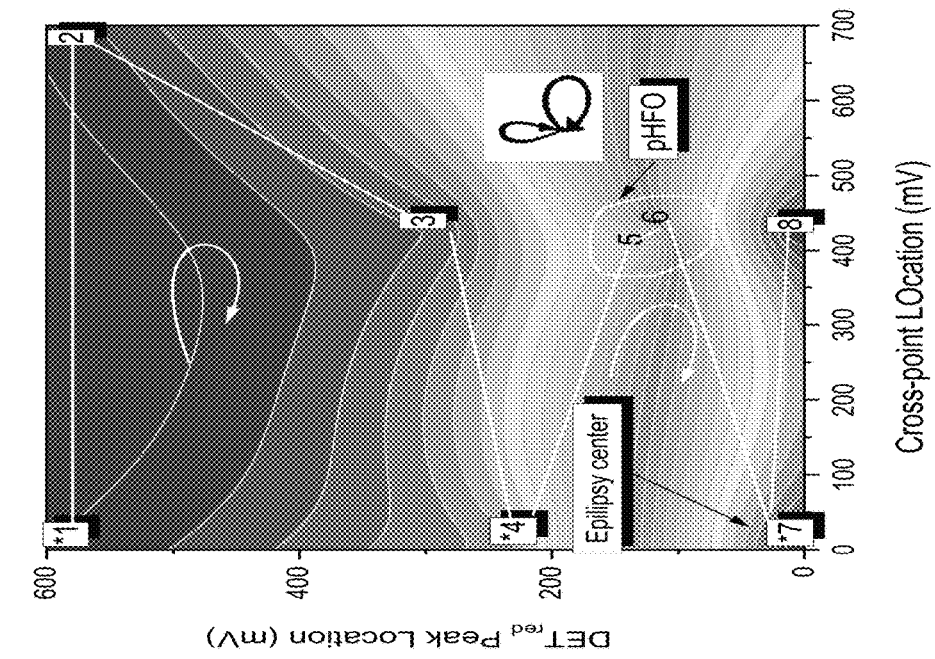

Fig. 26
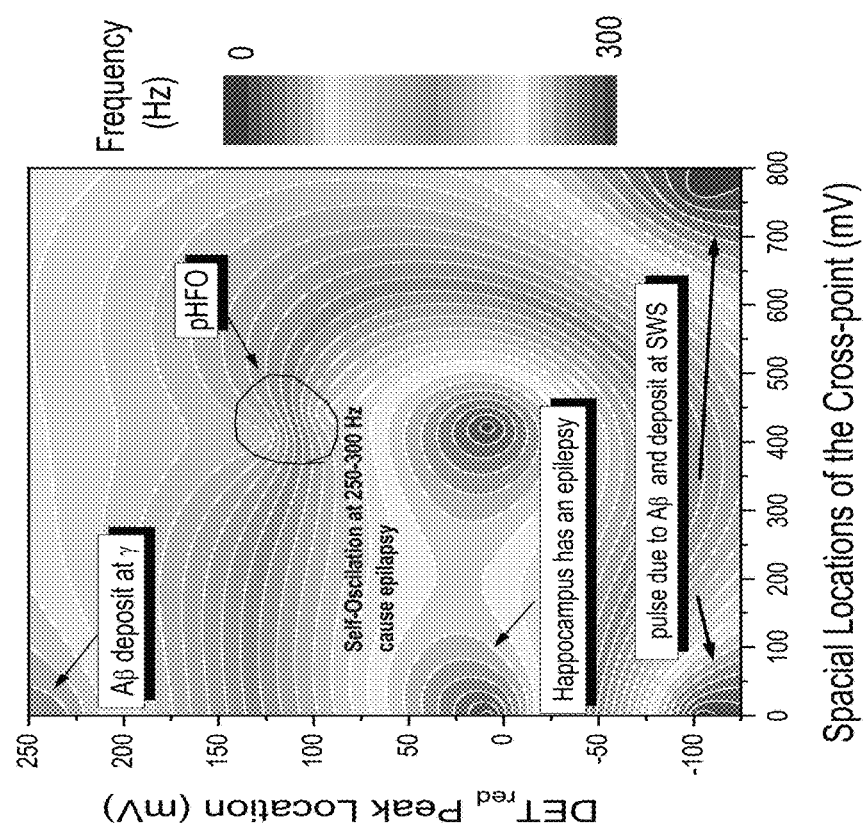
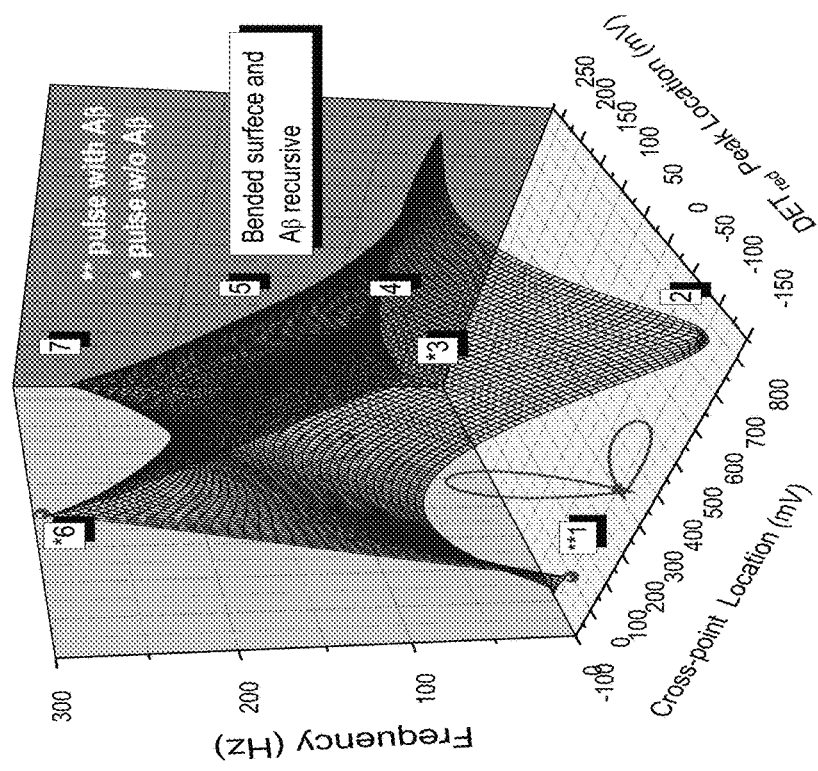

Fig. 27
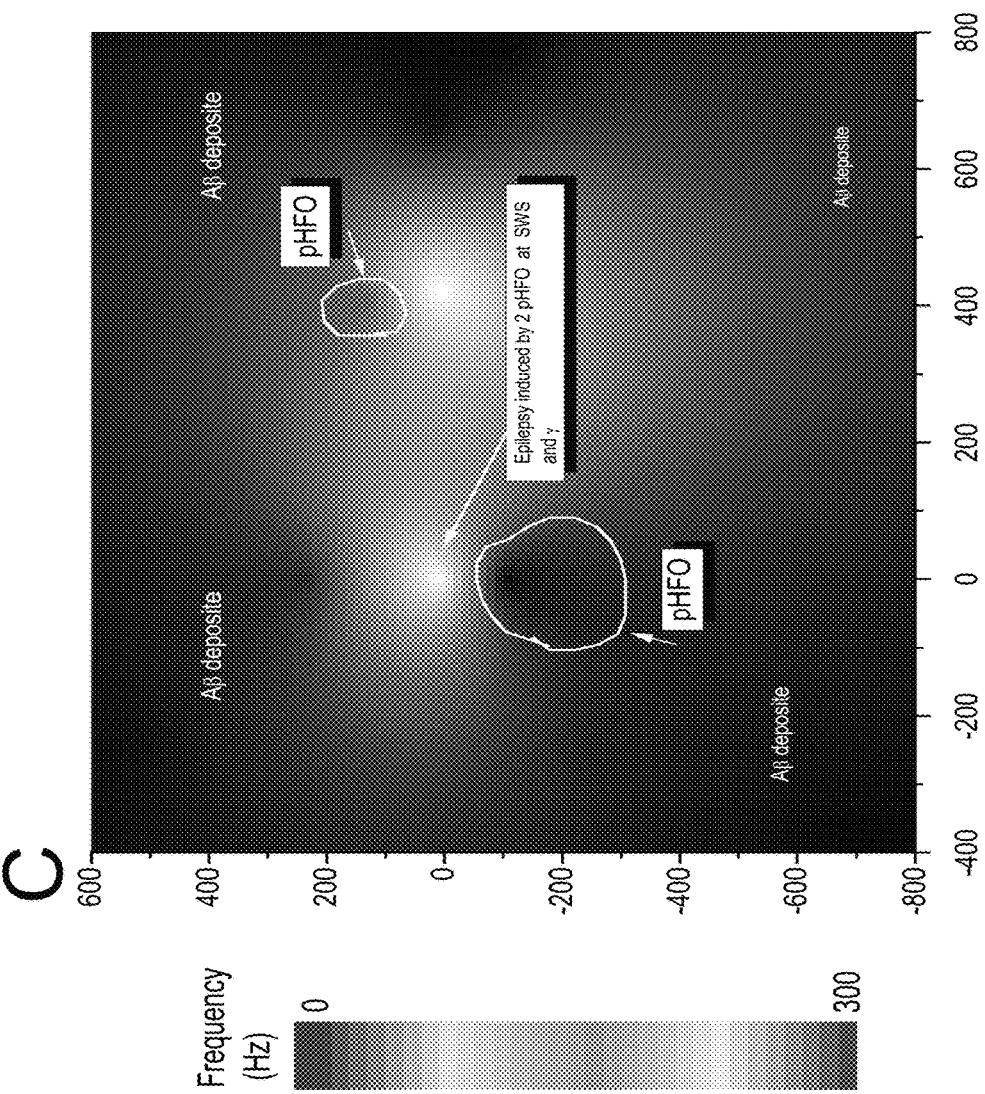
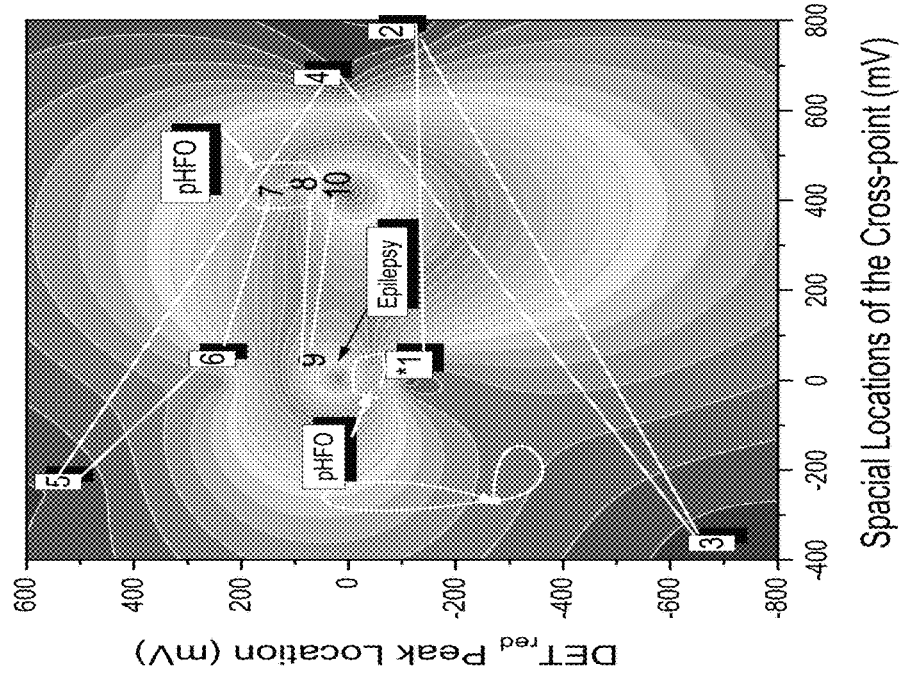

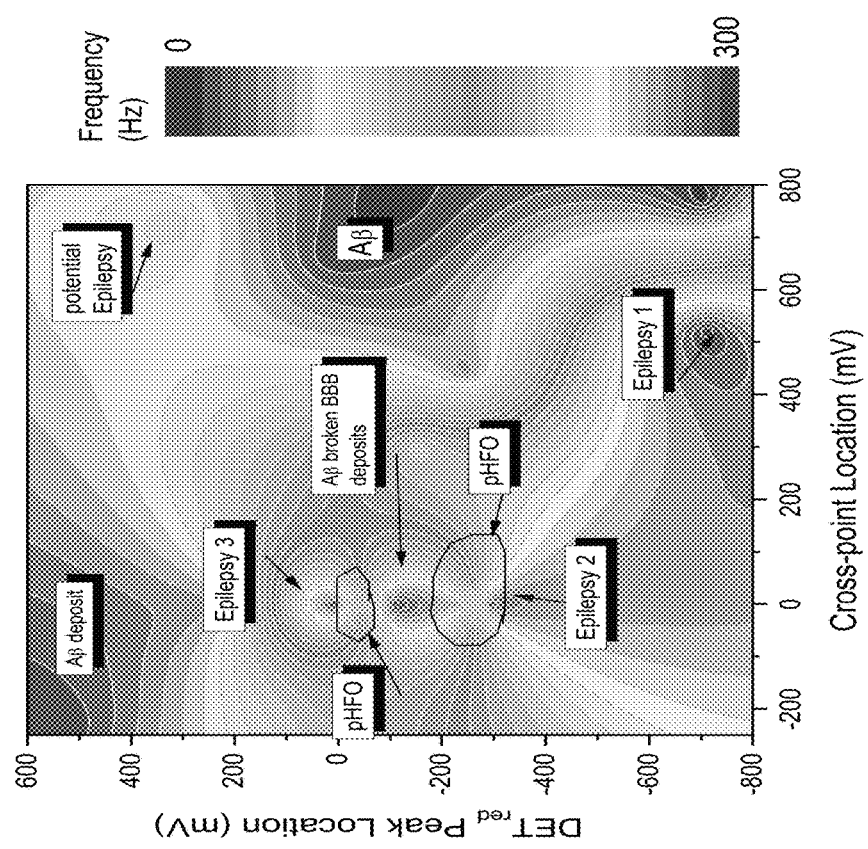
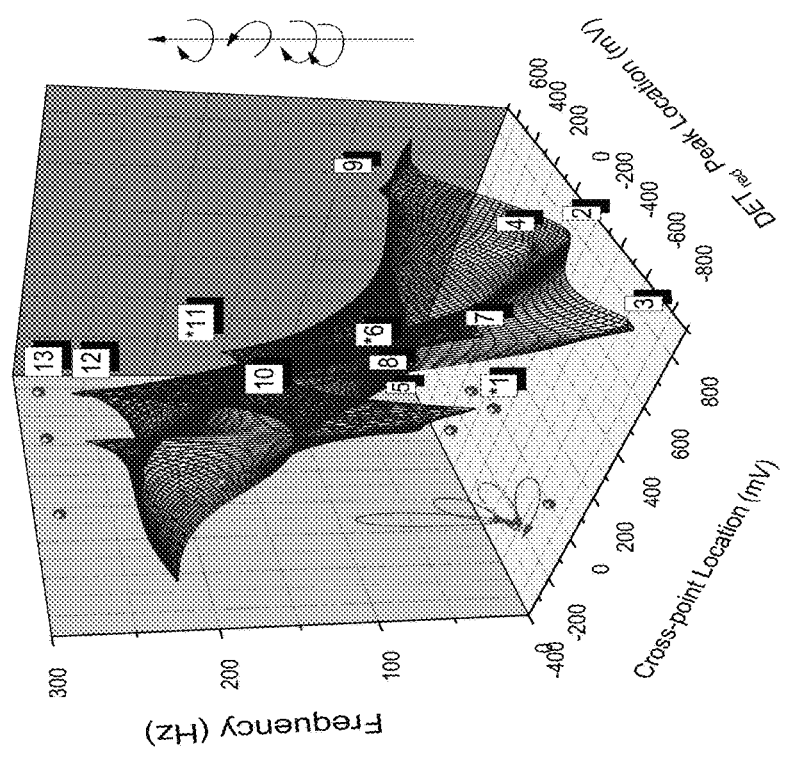
Fig. 28

Fig. 29
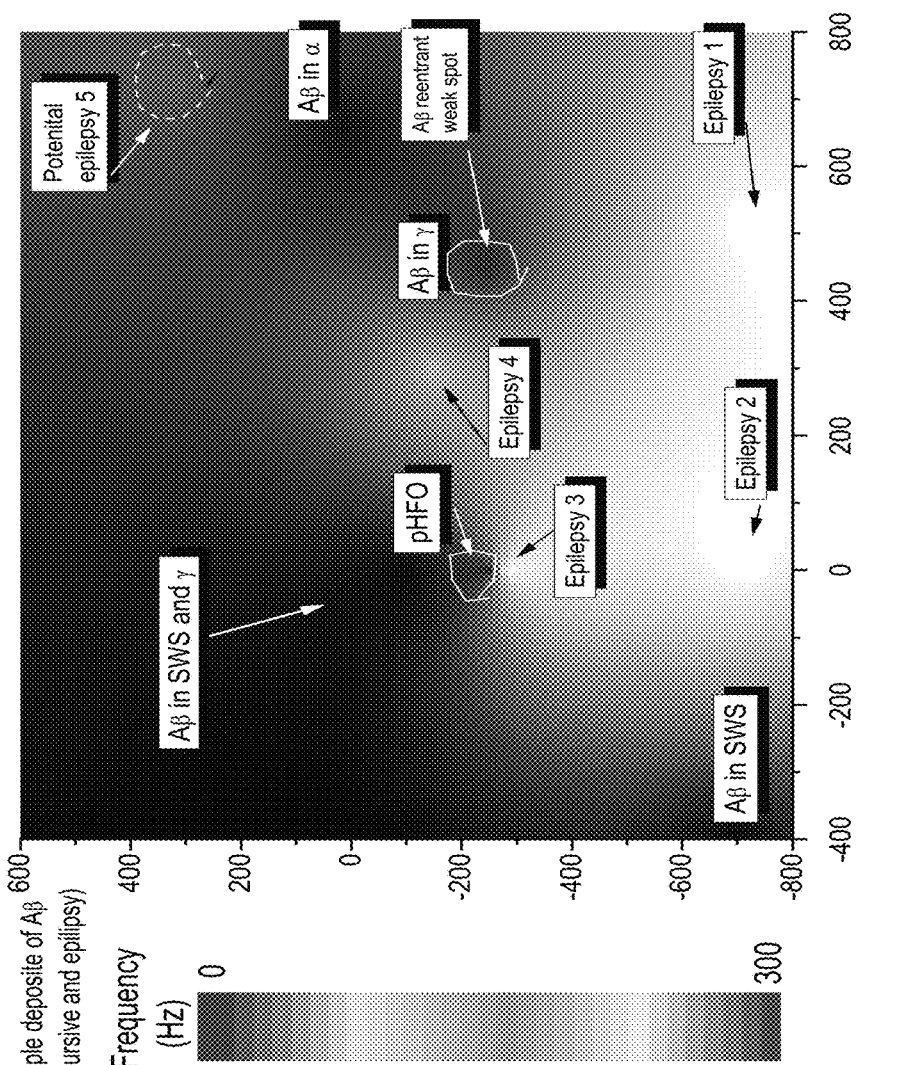
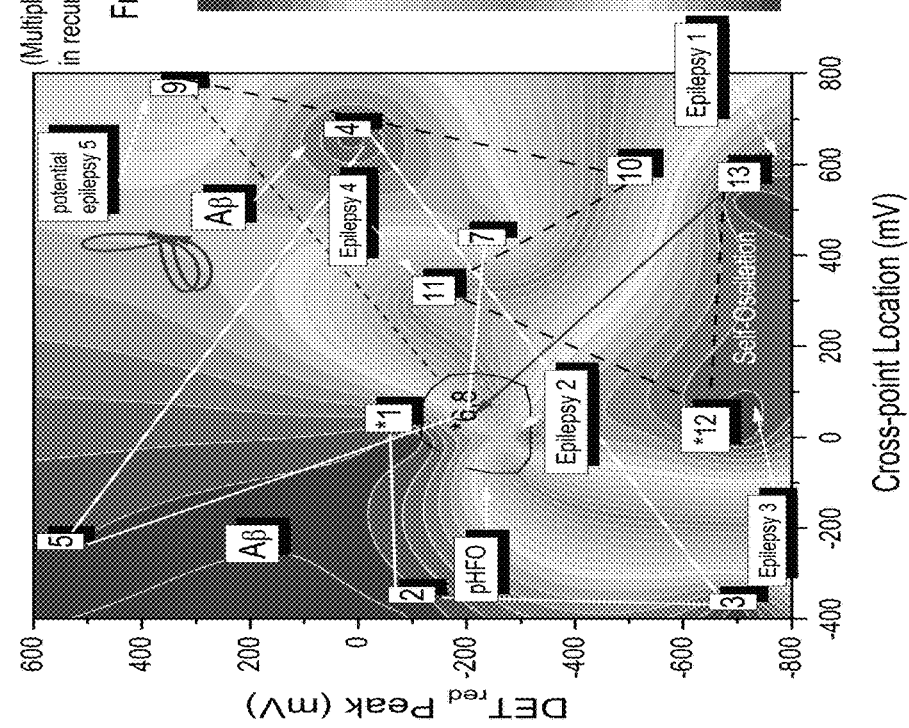

Fig. 31
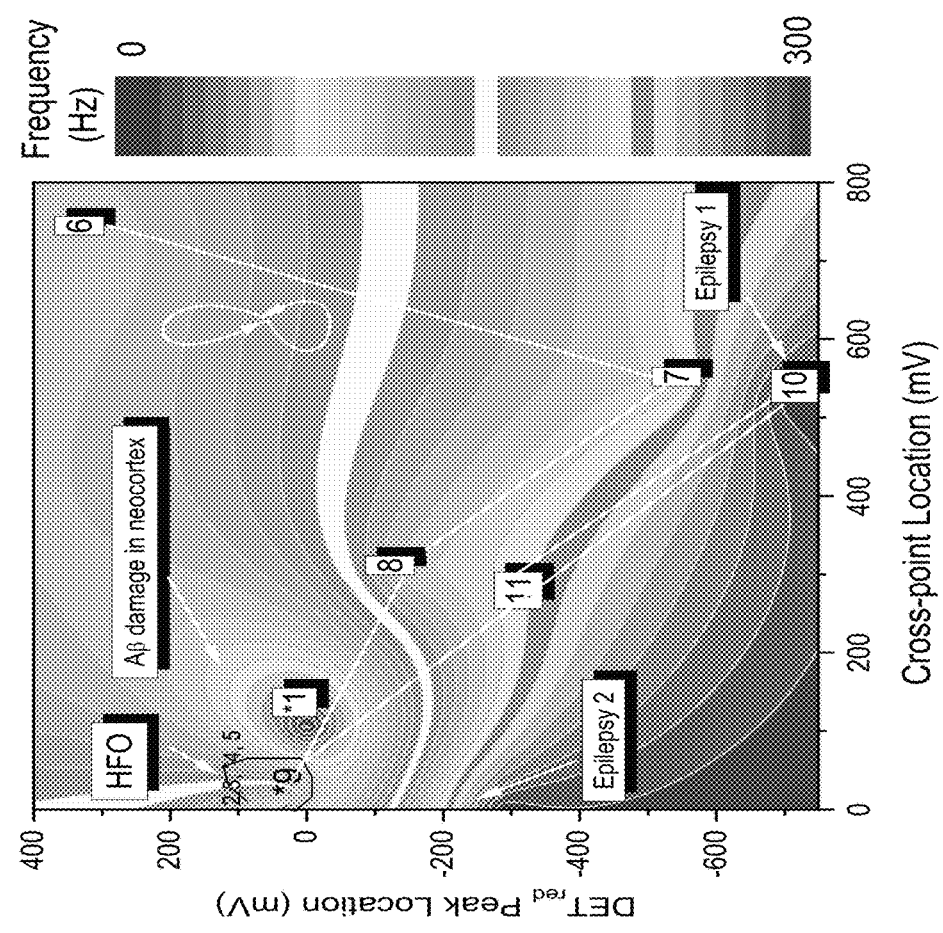
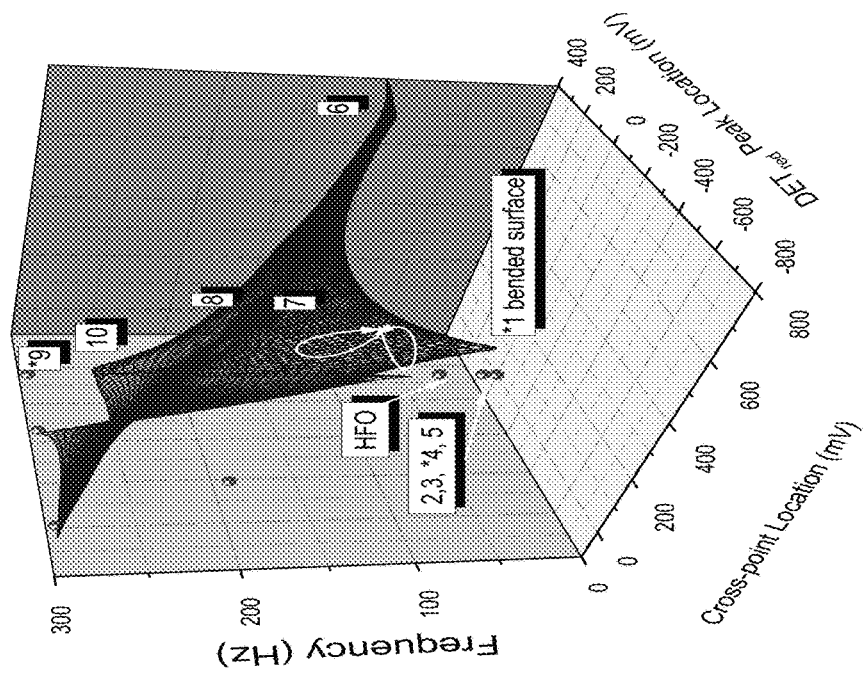

Fig. 32
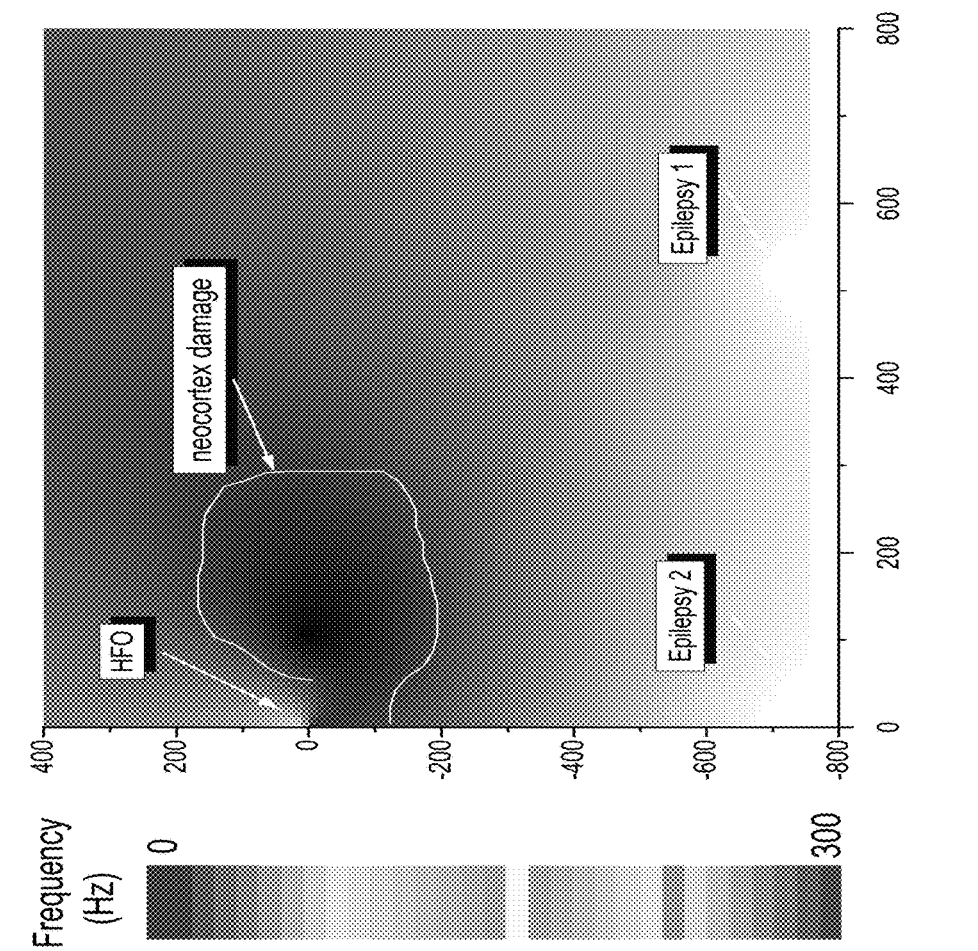
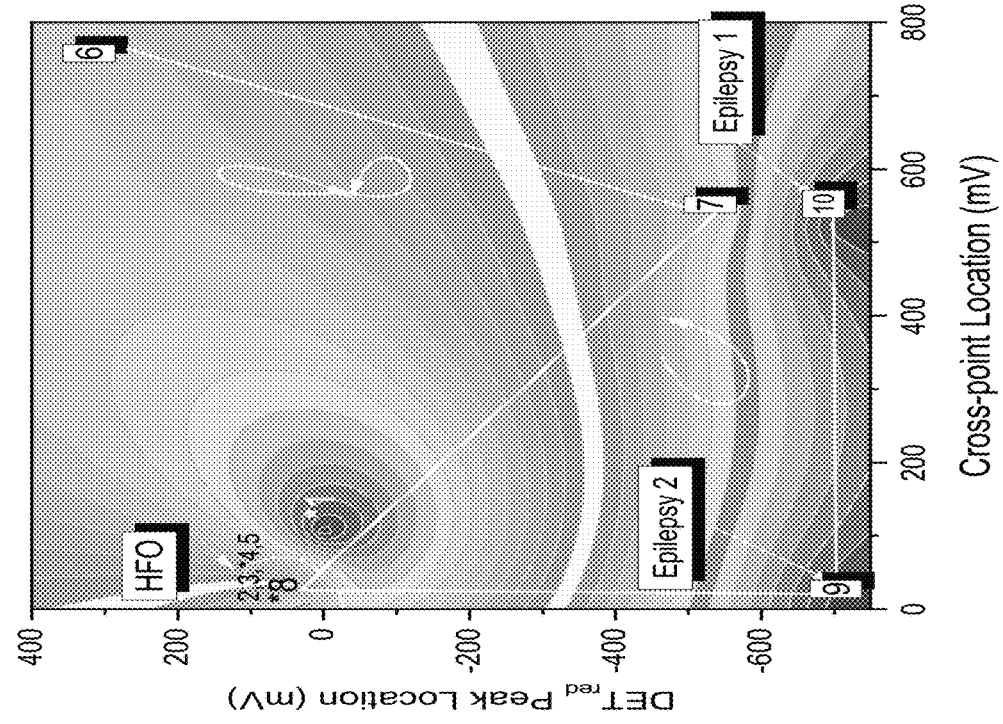

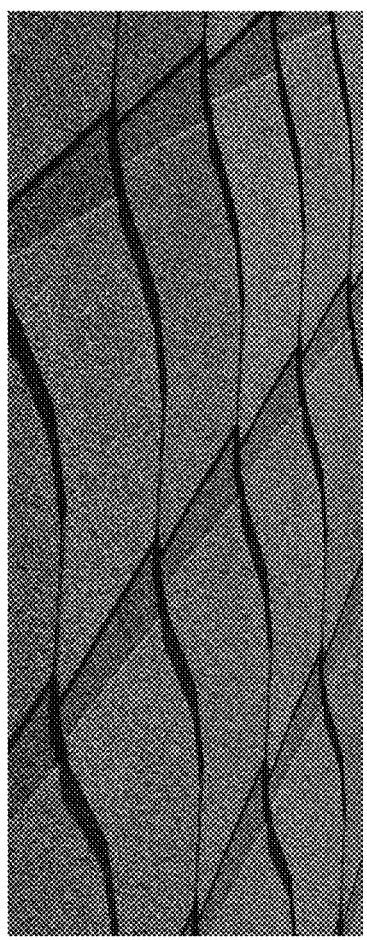
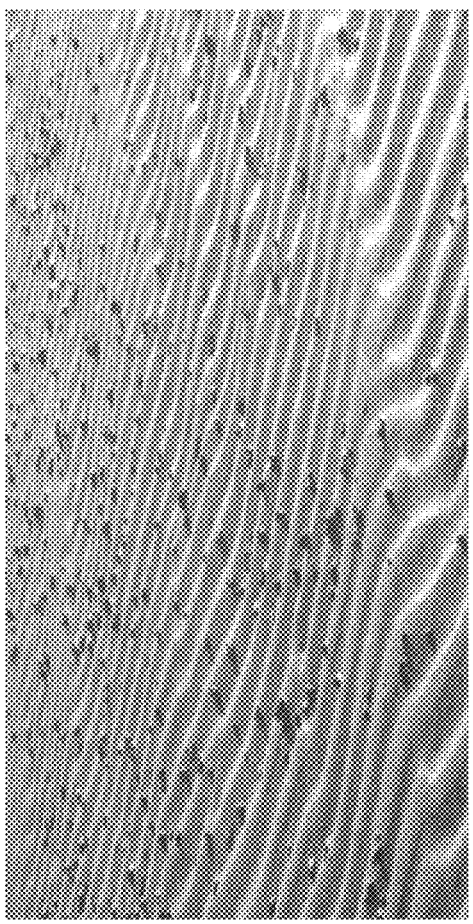
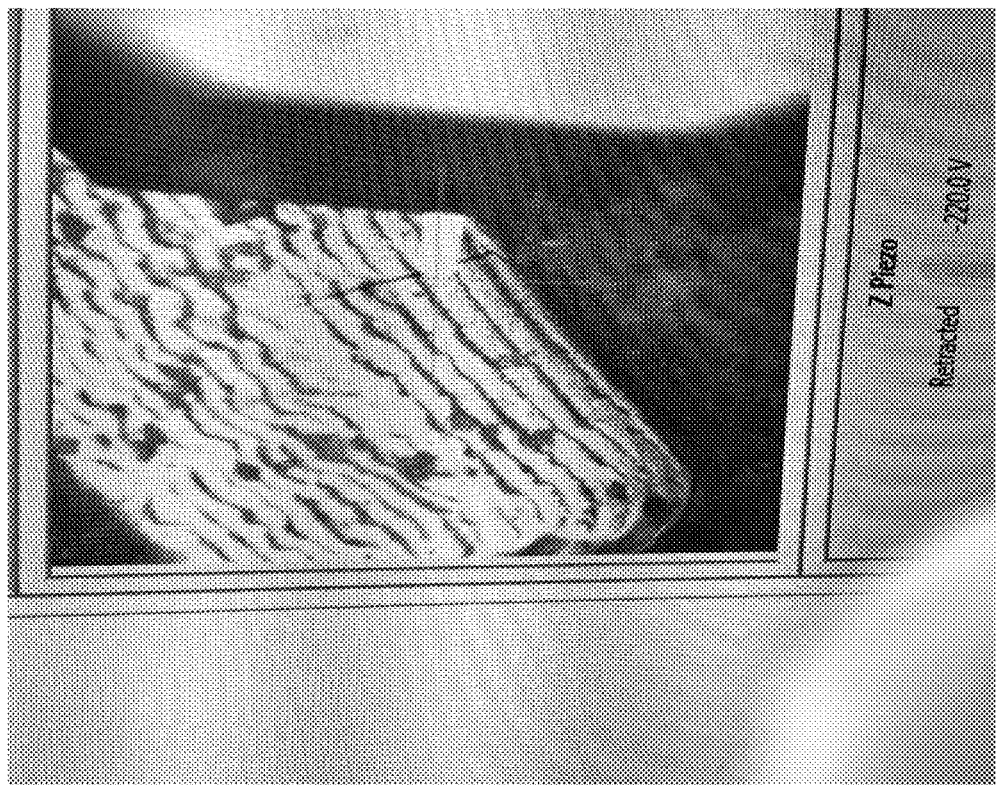

Image Z Range 435 nm
Image Projected Surface Area 24.2 µm²
Image Rq 77.5 nm
Image Ra 61.3 nm
Image Rmax 426 nm Image Z Range 122 nm
Image Surface Area 81000 nm²
Image Projected Surface Area 59393 nm²
Image Rq  24.1 nm
Image Ra  18.3 nm
Image Rmax  123 nm

- Imidazolyl group in the bM-⊞-DMCD toroidal ring
- TCD's COO⁻ group;  ● O-NPA's COO⁻ group
- Cooper pair  ● Water molecule
- Spontaneously harvesting energy and superconducting at room temperature

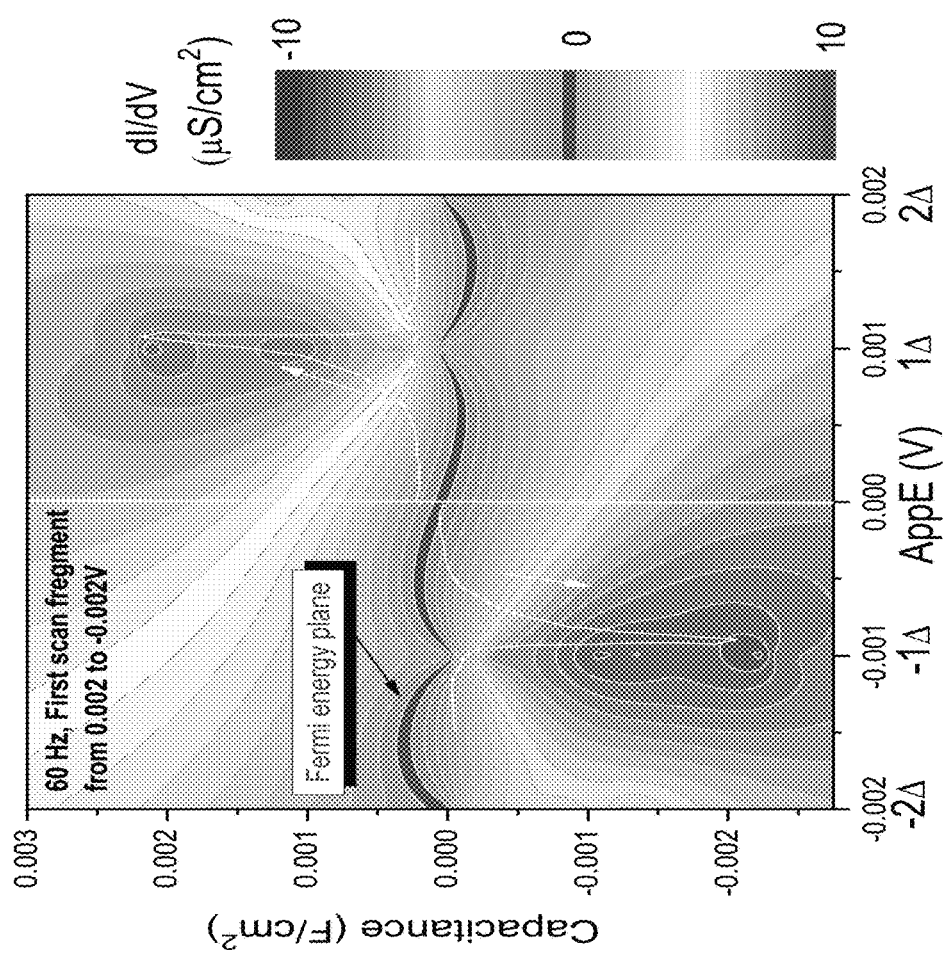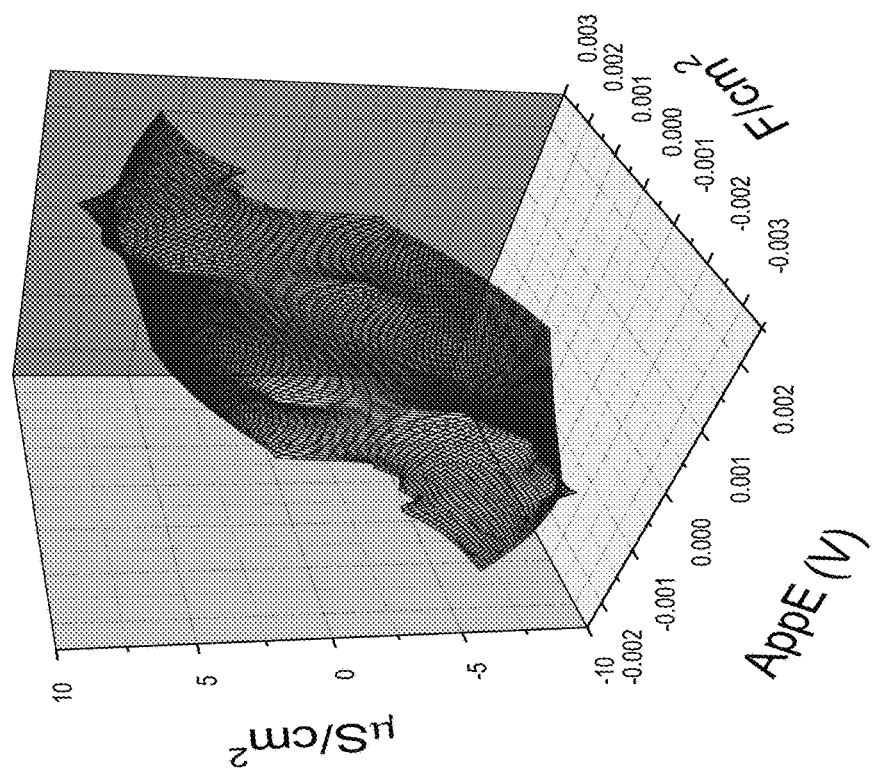

Study of Helix- Copper-pair wave transmission in the Josephson-junction

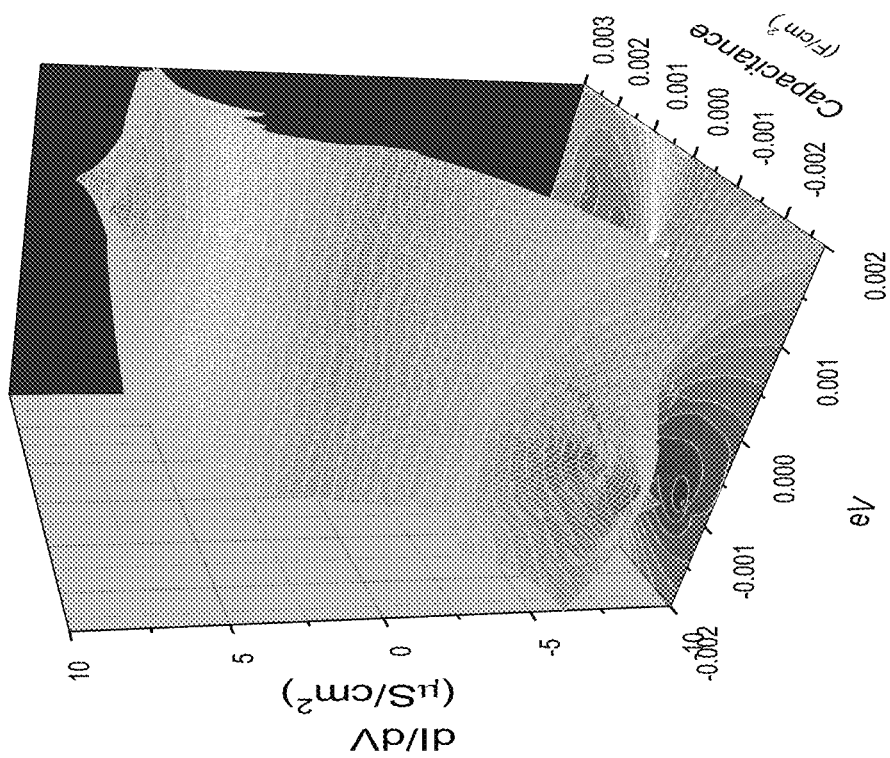
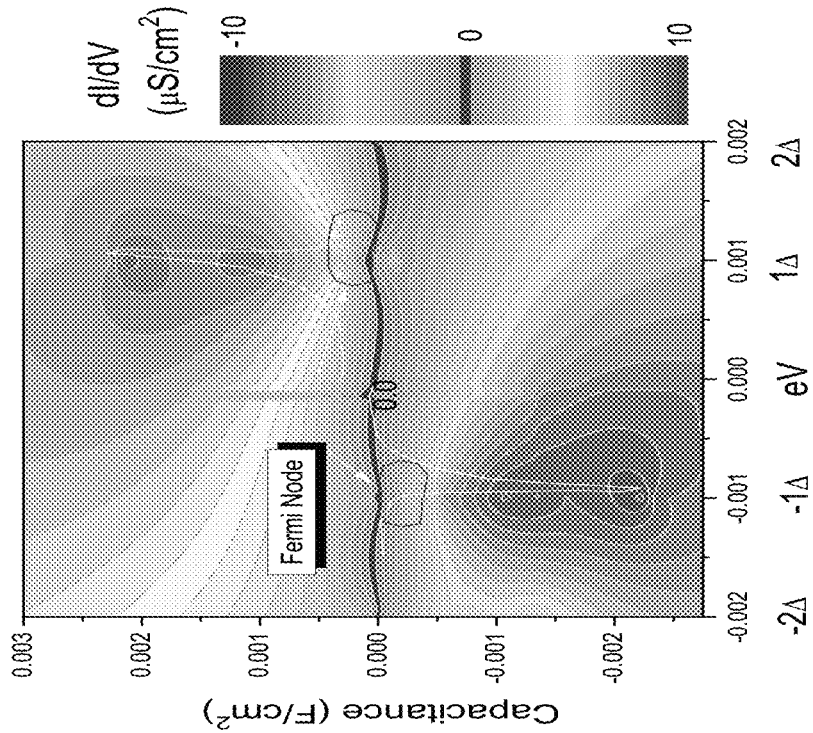
Fig. 50A
Fig. 50B

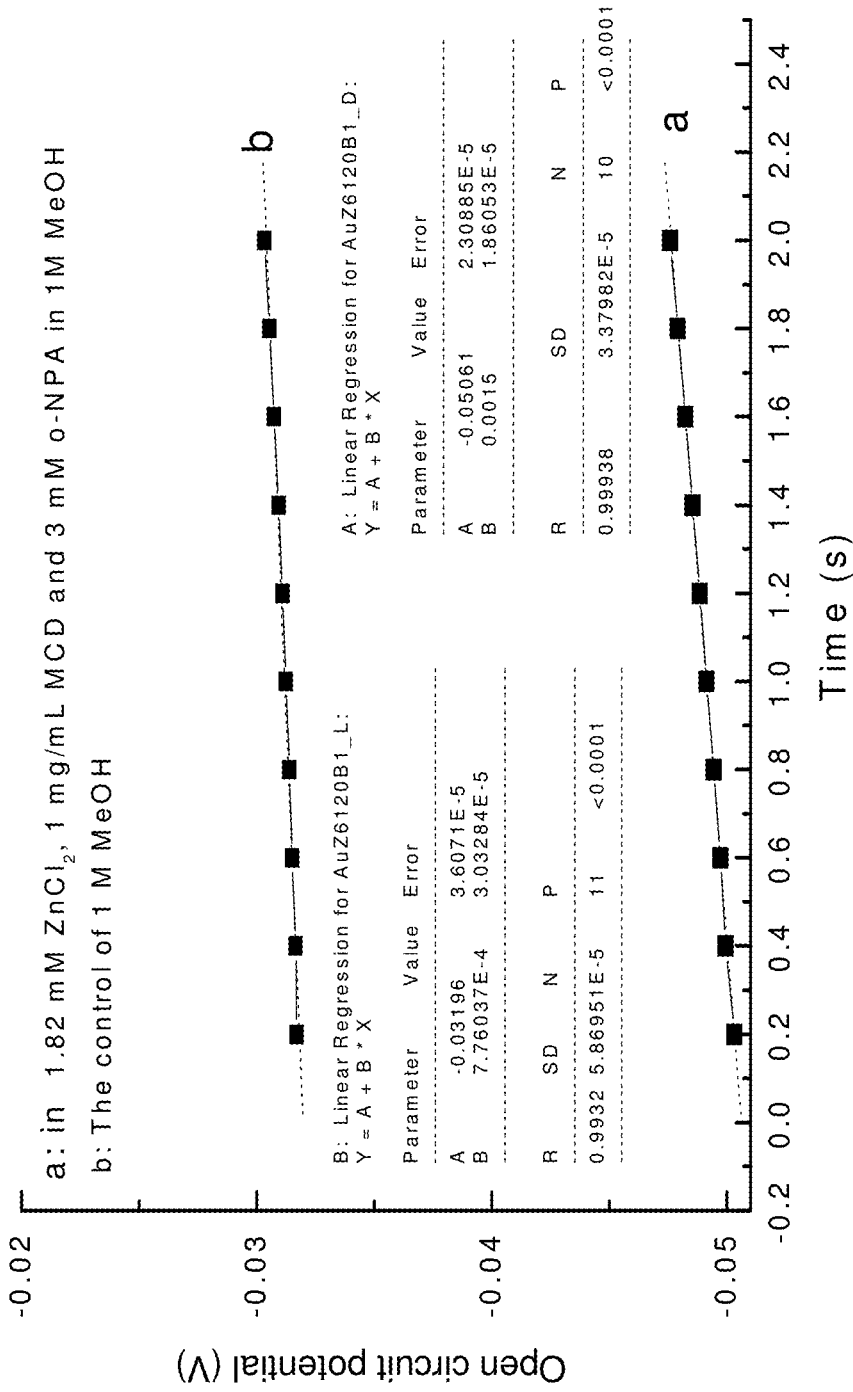
Fig. 56 Study of JJ effect on initial rate of open circuit potential of Au/superconductive mitochondria SAM using the OPO method

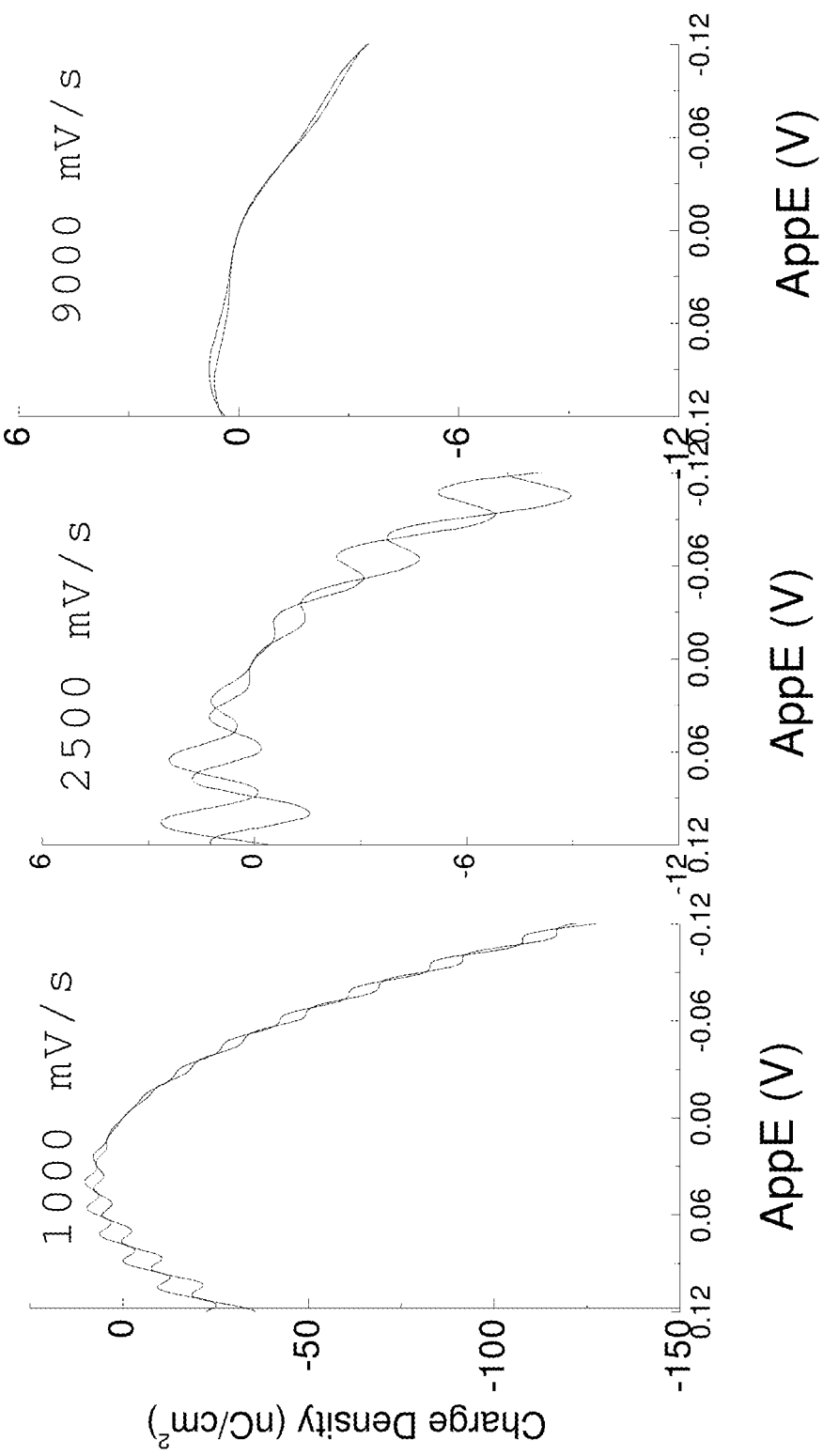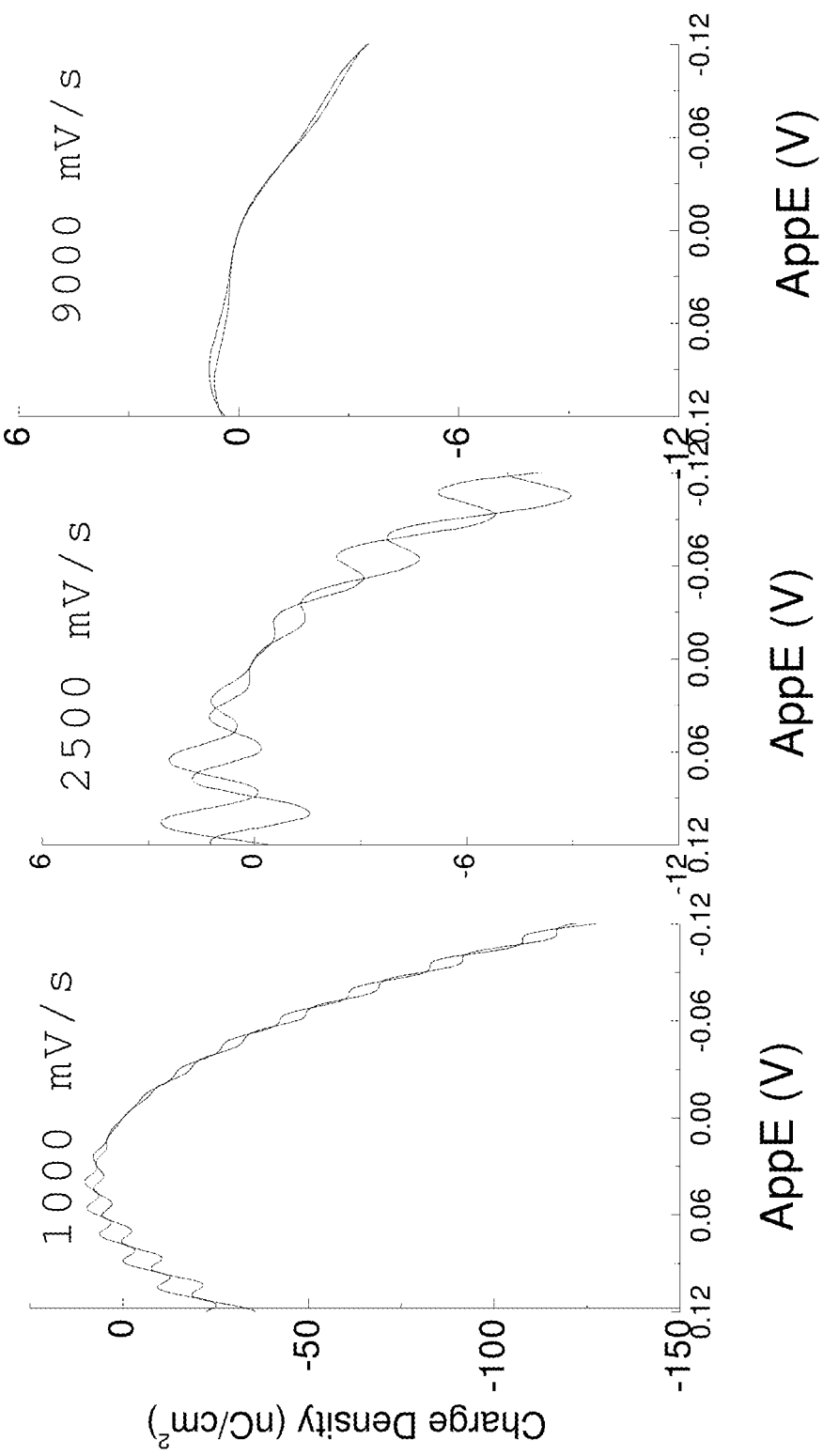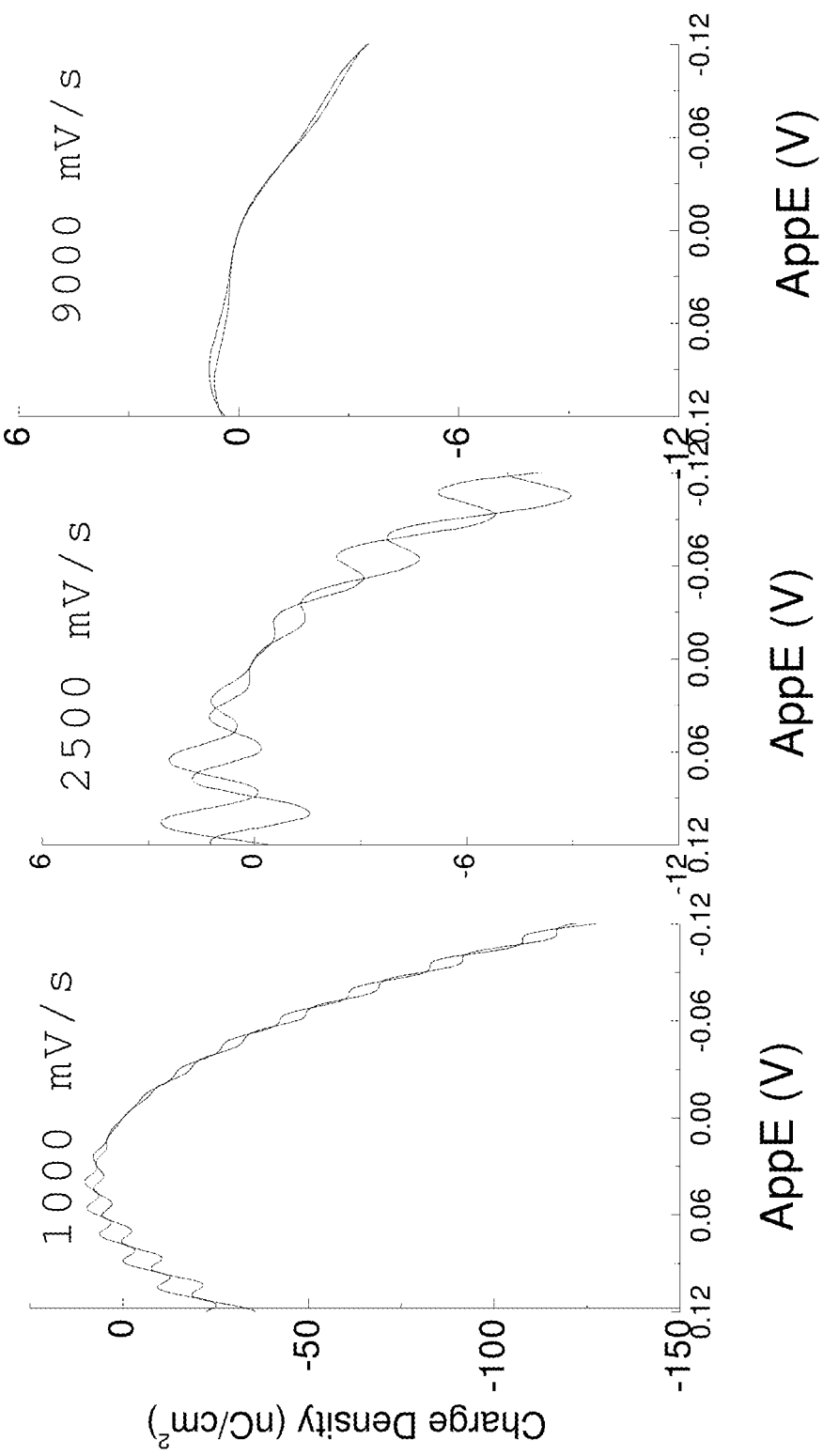

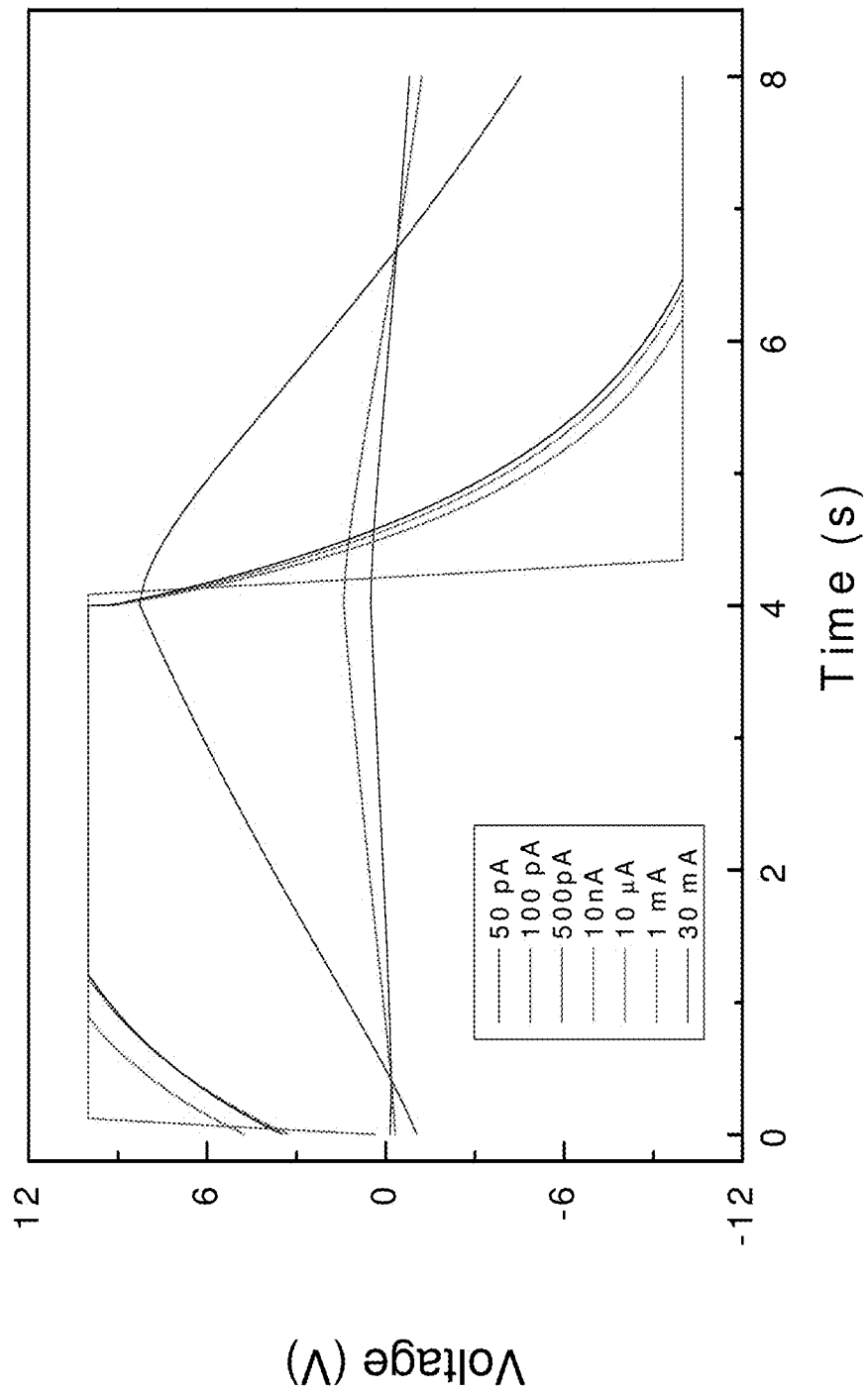

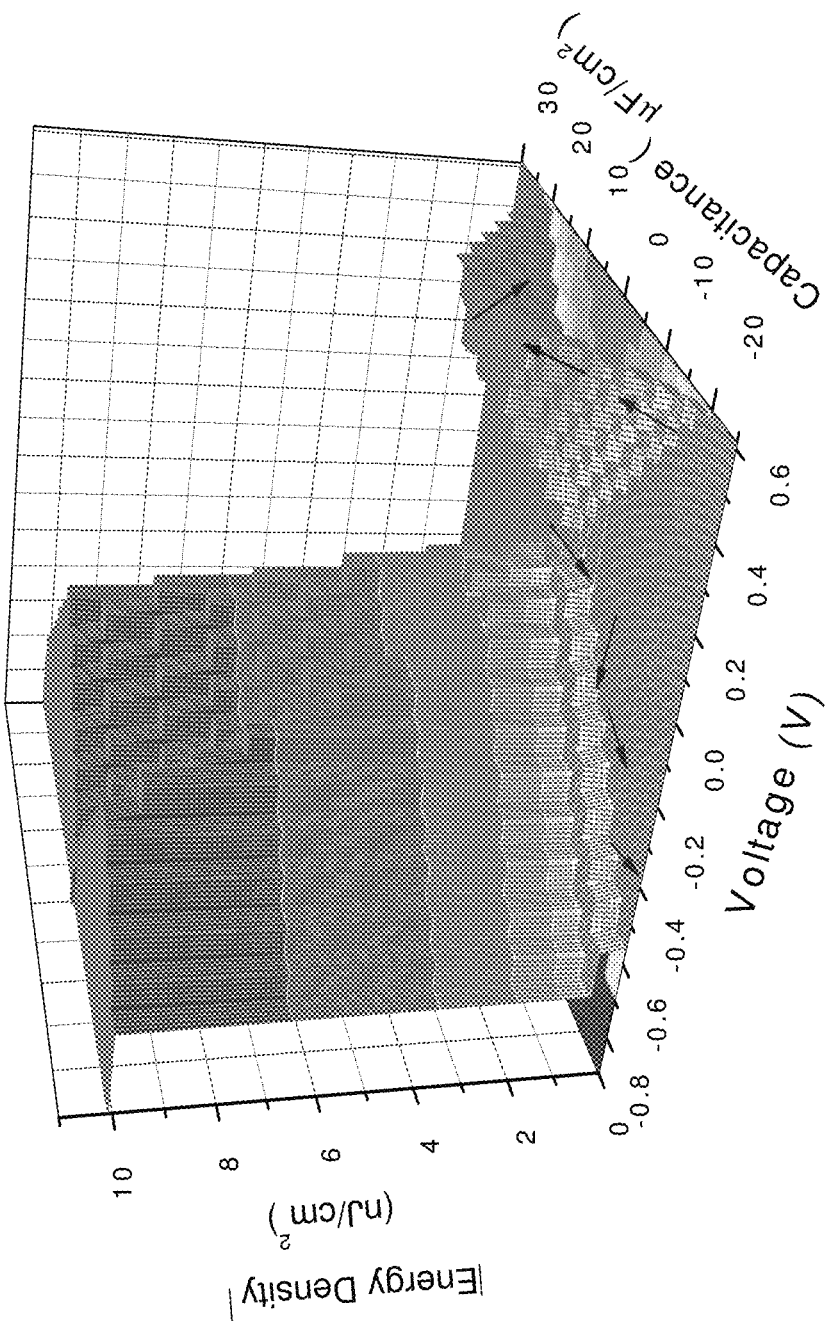
Fig. 66C Cooper Pair's Helix-oscillation in the JJ tunneling reflection affects on energy density, capacitance, and voltage in the S-I-S device in 1.81 mM $ZnCl_2$, 1mg/mL MCD and 3 mM o-NPA in ±50 pA current at 0.25Hz Flexible toroidal Josephson Junction

SCALE-UP TOROIDAL ARRAY QUANTUM PROCESSING MEMORY DEVICE WITH CONTROLLABLE AND ADJUSTABLE STATE-SWITCH VALVES OF MAKING AND APPLICATIONS THERETO

CROSS-REFERENCE TO RELATED APPLICATIONS

This patent application entitled of "Self-Powered Scale-Up Toroidal Array Quantum Processing Memory Device with Controllable and Adjustable State-Switch Valves of Making and Applications Thereto is a Continuation in Part of US patent application that claims the benefit of the U.S. Non Provisional patent application Ser. No. 15/361,068 in titled of "Nano-Biomimetic Mems-Transformer Devices of Making And An Application in Energy-Sensory Images Thereto" filed on Nov. 24, 2016. The entire disclosure of the prior patent application Ser. No. 15/361,068 is hereby incorporated by reference, as is set forth herein in its entirety.

FIELD OF THE INVENTION

The present non provisional patent application titled of "Nanobiomimetic Mems-transformer Devices of Making And An Application in Energy-Sensory Images Thereto" relates to the field of electromagnetic systems and induction. In particular, to a device having the characteristics of mems-capacitive, mems-ristive and mems-inductive comprising of a first and a second nanostructured toroidal membrane along with its applications invented in Energy-Sensory images thereto.

The present CIP invention relates to the field of room temperature superconductors, in particular, to a system having both characteristics in superconducting, mems-ristor/mems-capacitor/mems-inductor and quantum computing acting as a multiple-functioning electronic chip for self-powering and operating with a controllable and adjustable state-switch valve thereto.

BACKGROUND OF THE INVENTION

The shortcomings of artificial neuronal networks (ANN)s systems developed through electric circuitry architectures have no or loose connections to neuroscience were mentioned in the literature [1]. As a consequence, the shortcomings include, not limited to ignore features of biological neural processing systems, such as their extremely low-power consumption features, sensory and flexibility. Memristors and memcapacitors have made significant progresses in the recent decades [2-4]; especially with nanotechnology has been incorporated [5-7]. Many diseases are rooted in circadian rhythm (CR) dysfunction. Severe CR dysfunction leads to memory loss and worsens the quality of life. There are 40 million American reported to have chronic long-term sleep deprivation [8]. Researchers reported that Amyloid-β (Aβ) overturns the acetylcholine (ACH) and melatonin release from a normal CR function to a dysfunctional CR [9-10]. Our group developed a sensor that mimics acetylcholinesterase (ACHE) active sites in the ACHE gorge and is able to detect ACH in fM level compared with a "mutated ACHE neuronal gorge" sensor, whose 14 hydrophobic residue groups were knocked out [7]. Aβ's accumulation and neurofibrillary tangle are identified as major pathological biomarkers linked to Alzheimer's disease (AD) [11-14]. Obviously, it is desirable that the ACH sensor is able to detect sub pM Aβ [15].

Slow-wave sleep (SWS) is closely associated with declarative memory consolidation, and the signal is stronger in SWS than in wakeful time [16-18]. One of the neuronal safe guards to this cognitive function is the bidirectional invariant reentry neuronal network circuitry [19-21]. Many models propose to simulate the closed-loop circuitry's reentry functions, however, very few, if any, to really develop a neuronal device which can correlate the reentrant characteristics of "memory" and the influence of neuronal toxins and visualize its function in an image. We thought a memristor/memcapacitor with biomimetic ACHE neuronal gorge functions might be able to face this challenge [22-23]. A review by Cabaret for organic memristors' capability as artificial neural networks was published [24, 6].

Researchers discovered Alzheimer's disease (AD) patients have lost the sense of smell due to Aβ inhibition of olfactory bulb activity [25-28]. Here, we further propose a hypothesis that memories of an artificial, intelligent neural network are not only associated with the "Sensory Biomarkers", but also correlated with the primary neural network's energy density in a frequency domain that must governed by the memristor/mamcapacitor's rules under the inspiration of our previous work [16].

A normal neural network circuitry constantly fires high frequency oscillation (HFO) (150-200 Hz) producing synchronization within the connection between hippocampus and neocortex for long term memory storage during Slow-Wave Sleeping (SWS), and where pathological high frequency oscillation (pHFO) (200-600 Hz) fires randomly leading to seizures and epilepsy [29-31]. The biggest problem in epilepsy research, as the Editor Noebels explained in the book, is that researchers are "not clear how abnormal synchrony is generated during pHFO. Clearly there is a need for additional studies that will differentiate normal from pathologic HFO in vitro and in vivo."[29]. In this invention, we attempted to find a method to differentiate and predict the presence of pHFO and HFO based on a mems-transformer that embodiments with memcapacitive/memresistive/meminductive characteristics to mimicking neural network circuitries and herein find its applications in the energy-sensory optical images.

Following are the Background of the Invention of the CIP

The quest for room temperature superconductivity has gripped researchers all over the world for decades since they saw the possibility electronic devices can operate more efficiently without energy dissipation [1-4]. The room temperature superconductor may revolutionize the electronic industries [1-4]. As we know current superconductors on the markets or under investigation most operate cryogenically in the range of 4K to 10K. Even so, some superconductors called "high-temperature superconductors" are still operating under cryogenic temperature regimes that the cryogenic cooling system hampered the goal for energy efficiency. The internet super large data centers have large industry scale computer facilities with extraordinary demands for energy, because the low energy efficiency of current computer circuit technologies consuming too much power of computing, storing and moving data between processors and memories, for example, the US data centers estimated to grow from 73 terawatt-hours (TWh) to 200 TWh by 2020 [5-6]. Current computer systems use many semiconductor transistors to switch electronic signals one state at a time at few gigahertz frequencies and facing paramount of task to removing produced heat; Current DC or RF Superconducting Quantum Interference Devices (SQUID) use Josephson Junction technology to not only many times faster of switch time, but also has negligible energy dissipation on the JJ, furthermore, the JJ switch allows different states superpositional transfer, i.e., "0" and "1" can be transferred at the same time. However, the rf SQUID needs to apply hundreds of MHz electromagnetic field externally onto a tank circuit magnetically coupled to the rf SQUID and the dc SQUID needs a dc current applied onto the dc SQUID, in both cases, operating is under cryogenic condition, which is a significant drawback [7-9].

The Josephson Junction (JJ) is a key element in the broader area of superconductivity devices including the SQUIDs [7-10]. The Josephson coupled-superconductor effect is inherent in any superconductor-insulator-superconductor (S-I-S) tunnel junction if the two sides of barriers are sufficiently thin to allow the coupling energy from the cooper pair tunneling at the coherent wave state between the two superconductors to exceed thermal fluctuations [7-13]. Superconductor qubits are vulnerable to low-frequency noise with sources that come from 1/f noise, wave dephasing noise, flux noise, critical current noise, quasiparticle tunneling noise and capacitance noise [11, 14]. The nature of the qubits operating multiple states at the same time is sensitive to decoherence caused by the control and readout circuitry and the environmental noise as well as the qubits itself intrinsic low-frequency noise, than conventional computing [11, 14]. For example, SIS based qubits perform well at high microwave frequency, but not in the range between 10-4-104 Hz, because the wave functions' phase coherence time at the JJ barriers is too short, hence led to decoherence. Many signs of progress had made to reduce the noise and raise coherence times, and a current best record is in the hundreds μs range, one step forward to achieve quantum supremacy [14-20]. Nevertheless, so far superconductor qubits made by dc SQUID or rf SQUID has not demonstrated its function in memory, i.e., remember the past events, likes the human brain cells do.

Circuit elements, like the memristor, memcapacitor and meminductors have the characteristics that depends on the past states through which the system has evolved, have drawn increased interests in applications in sensing, quantum computing, memory and energy storage at the same physical location as the new Storage-class Memory (SCM), i.e., a non-volatile memory technology in between memory and energy storage, which may enable new data access modes and protocols [21-32]. According to a report on disruptive technologies for years, 2020-2030 [21] evaluated the memristive device as a non-volatile memory device that will be the disruptive technologies that impact or completely replace DRAM of the existing high-performance computing technology Salmilehto's group theoretically proposed a rf SQUID design based on the memristive behavior of the device with the superconducting circuit [26]. Sergey's group theoretically studied the property of a qubit can be classified as an ideal memcapacitor for a superconductive charge or an ideal meminductor for quantum flux and searched their applications [25]. Gaurcello's group also theoretically envisioned a memcomputing system with computing directly in/by the meminductive electronic memory circuit which set up intrinsic topological protection against external perturbations [32].

Circular current induced by junctions of aromatic molecules of the delocalized molecules has drawn interest from theoretical scientists [33-34]. Scientists have envisioned its future applications. E. Chen's group identified and evaluated the circular current presented in an organic memristor/memcapacitor device when applied a dc potential on the half memcapacitor cells for multiple 10 cycles using the cyclic voltammetry (CV) method at a fixed scan rate 20 mV/s in 1 M methanol solution without any other reagent. The exponential increase of the current indicates its Schottky diode behavior, i.e., a small potential drop at 0.1V from the origin and then increased nonlinearly that provides higher switching speed and system efficiency [35]. Delocalized electron relay through the multiple residue groups, hydrogen bonding and hydrophobic π-π staking could be the driving force [36]. The heterogeneous surface-controlled electron transfer process in terms of DET constant Ks was calculated according to E. Laviron's method at 107/s, and the diode peak is 192.5/s, and it may reach 220.2/s from the vector contributions from our calculation [37-41]. The vortex force of the circular current laid a foundation to induce a nonferromagnetic field from low frequency to high frequency through turning different angles of the memristive/memcapacitive energy storage device, and it reduced operational energy by 33% [42]. Further, our group discovered the toroidal array nanostructured memristive/memcapacitive device also can act as a neuronal memory device having both memory and energy storage functions with extended memory time at a reentrant neuronal circuitry with higher reentrant energy sensitivity of 0.12 pj/bit/s/$\mu m^3$ without Aβ compared with Aβ, 13 aj/bit/s/$\mu m^3$/nM over Aβ 3.8-471 nM range over 0.003-4 s. [43-46]. Toroidal quantum bits (qubits) were theoretically proposed by Zagoskin's group in 2014, and they theoretically calculated the toroidal superconducting qubit is naturally protected from low-frequency noise because the qubit only interacts with the electromagnetic field through its toroidal moment [14]. In 2015, our group experimentally developed nanostructured two types of toroidal array organic polymer made memcapacitor neuronal prosthesis [45]. From the viewpoint of interference on toroidal Bose-Einstein condensate reported in recent literature [47], which revealed the self-interference of the circular condensate is possible only in the absence of the persistent current with rings in various diameters expansion freely vs. time for the emergence of toroidal matter-wave interference. Our created type one memcapacitor shows no such self-interference and evidenced by no epilepsy centers were observed based upon our invented energy-sensory reentrant dynamic maps and optical images, that indicated the toroidal wall is not leaking (BBB is not broken); but the type 2 memcapacitor has a perturbed circular current and absence of a persistent current, i.e., the BBB is broken and leaking, herein we observed the self-interference [47]. Inspired by our prior work, herein inventing a new type of 3D nanostructured toroidal array superconducting qubits acting as energy storage and a nonvolatile memory device for self-powering computing with low-frequency noise-free and energy dissipation-free is necessary.

SUMMARY OF THE INVENTION

It is an object of the present invention to provide a new generation of the mems-transformer that embodiments with memresistive/memcapacitive/meminductive characteristics that closely linked to neuroscience in particular, they are memory devices which can conduct memory retrieve and storage in biological fluid.

It is an object of the present invention to provide a new generation of mems-transformer that was not made by metal oxide, but of biomimetic organic polymer membrane that mimics a normal cylindrical confined acetylecholenesterase (ACHE) eternal gorge as a "normal brain" prosthesis model with a "biomimetic linen" attached in the gorge thereto.

It is an object of the present invention to provide a new generation of mems-transformer with new method of making multiple-layers membrane with cross-bridge and bars.

It is an object of the present invention to provide a new generation of mem-transformers that are comprising of an biomimetic organic polymer membrane that mimics a mutated acetylecholenesterase (ACHE) eternal gorge with 14 hydrophobic residues groups knocked out, serves as a "damaged brain" prosthesis model.

It is an object of the present invention to provide a new generation mems-transformer that mimics a normal brain circuitry integrity from the "normal brain" device and the "mutated ACHE" device mimics damaged brain circuitry, in particular, the neocortex-hyppocampus circuitries with and without the presence of Aβ.

It is a still further object of the present invention to provide the mems-transformer having an application in an Energy-Sensory brain circuitry image that dynamically displays the circuitry synapse change and the circuitry surface conformation change over frequencies from SWS to 300 Hz in 3D; and in contour color map and in optical image in the presence of an intruder or analyte, such as Aβ, cancer cells, ACH and viral with $10^{-3}$ to $10^{-5}$ s temporal resolution and sub $\mu m^3$ special resolution. The primary group synapse circuitry has a circular current flow special resolution.

It is a still further object of the present invention to provide a method to establish Sensory Biomarker from any brain circuitry that use i-V curves of memristor for cross-point electric field location and the direct electron transfer peak location in a given electrochemical field; and establish a matrix of the Sensory Biomarker at a fixed frequency.

It is a still further object of the present invention to provide a method to establish brain discharge pulse energy infusing into a Sensory Biomarker random gridding correlation matrix in order to enable the communication between brain prosthesis with sensory matrix, pulse energy and the analyte.

It is a still further object of the present invention to provide a method for quantitatively assess the brain reentrant memory sensitivity in less than 1 fj/bit/$\mu m^3$ in biological fluid and senses the energy change in atto WHr.

It is a still further object of the present invention to provide a new generation of energy device to recognize the presence of pHFO from HFO and establish a link to early CR dysfunction and a link to early AD.

It is a still further object of the present invention to provide an Energy-Sensory brain circuitry images that are capable to identify and predict the four stages of epilepsy from asymptomatic to "life threatening".

It is a still further object of the present invention to provide an in vitro diagnosis and monitoring neuronal dysfunction method that monitor before and after the therapeutic administration of medicine through monitor the communication between patient blood specimen and the device prosthesis painlessly, then the results are demonstrated and compared in the Energy-Sensory image suite as a tool for doctors and pharmaceutical drug developers to seek a new road.

It is a still further object of the present invention to provide an Energy-Sensory brain circuitry images that are capable to identify and predict early CR dysfunction.

It is a still further object of the present invention to provide an in vivo healing tool pain-freely to repair neuronal dysfunction patients by put on the flexible device patches over their head at different locations to release stimulate pulses during SWS.

It is a still further object of the present invention to provide orders of magnitudes amplified output voltage or amplified output current without a special electric circuitry added, it is solely depending upon the design and the architecture of the membranes in winding and inserting in the form of a toroid.

Following are the Summaries of the Instant Invention for the CIP Application

It is an object of the present invention to provide a new generation of Josephson junction-based toroidal vortex array quantum bits (qubits) superconductive/mem-element devices comprising of multiple-layer superlattices made by self-assembly cross-linked organometallic polymers that promote cooper pair electrons hopping through the superlattices causing the Friedel-oscillation that paves a road for room temperature quantum superconducting with a mem-element memory capability.

It is an object of the present invention to provide a new generation of Josephson toroidal vortex array qubit devices having arrays of curvature single-wall organic nanotube coordinating with transition metal in $d_\pi$ chelating.

It is an object of the present invention to provide a new generation of Josephson toroidal vortex (JTV) array qubit device facilitating Direct Electron Transfer (DET) forming long-range electron-relay between biomimetic choline acetyltransferase (CHAT) . . . biomimetic mitochondria structure (also having MMP-2 function) . . . inclusion complexions with o-nitrophenyl acetate (o-NPA) into the cavities of the imidazole modified cyclodextrin . . . biomimetic glucose oxidase with nanopore structure, so that the electron-relay (ER) promotes Copper pair waves pass through the boundary of the JTV array. The changing phases of the Cooper pair waves may transmit and store eternal magnetic flux energy without applying an external magnetic field. The goals also are set forth to create an "Controllable and Adjustable Valve", which is capable to switch from a memristive state to a superconducting state based on the above described "included o-NPA in the MCD in 1M methanol as a "Valve" to turn "On" the superconductor state, or without the o-NPA in the MCD cavity, to turn Off the superconduction state by utilizing MCD's ability of "loose the knot", so that it chaperones the state change; by changing the zinc ions' concentration in the methanol solution in the presence of MCD and o-NPA, the "On" either in the memristive state or in the superconducting state can be archived.

It is an object of the present invention to provide a new generation of Josephson toroidal vortex array qubit memory device that possesses extremely high quantum conductance density per superlattice at zero-bias that produces super current having reversible electric potential facilitating information reentrant behavior with a longer qubit coherence time.

It is an object of the present invention to provide a new generation of Josephson toroidal vortex array qubit superconductive/mem-element device having triplicate functions as a sensing device for magnetic flux, as an energy harvesting device and as a memory cell for quantum and mem-computing on the same location on a chip, yet the device is protected from the 1/f noise.

It is an object of the present invention to provide a new generation of Josephson toroidal vortex array quantum superconductive/mem-element device based solely on the driving force of Josephson vortex supercurrent loops created an eternal magnetic flux in which the superconducting phase discontinuities, herein it does not need an external applied magnetic field to be functional.

It is an object of the present invention to provide a new generation of Josephson toroidal vortex array quantum superconductive/mem-element bit device with zero energy dissipation and having self-sufficient lowest energy operation comparing with state-of-art technology. The self-sufficient lowest energy is supplied upon the DET supercurrent through the electron-relay loops.

It is an object of the present invention to provide a new generation of Josephson toroidal vortex array quantum superconductive/mem-element device having the superconductive wave penetrating through μm insulator Josephson junction and further functioning as an energy effective storages device that is an energy source for ordinary industry usage for automobile engines, cell phones, and computers.

It is an object of the present invention to further provide a new generation of Josephson toroidal vortex array quantum superconductive/mem-element device as a sensor for zinc ions.

BRIEF DESCRIPTION OF THE DRAWINGS

FIG. 1E is a bird-view of the enlarged AFM image of the horizontal bridge surface with the cross-section analysis and FIG. 1F is the AFM specifications results of the horizontal bridge membrane surface based on the bird-view. FIG. 1G is a bird-view of the vertical bridge and the underneath arrayed lattices in 9 μM² large area. The results of the specifications of the large area view of the membrane roughness are presented.

FIG. 4D depicts the schematic components of the device 2 having different layers and each one serves their own functions. "10" is the plastic plate; "11" is the Au, or Pt, or metal electrode; "12" is the imidazolyl derived monosubstitute β-dimethylcyclodextrin (m-β-DMCD, in short, MCD) cross-linked with PEG, PVP and TCD forming self-assembled conductive organic membrane with clockwise electron-relay circular currents flow; "13" is the nano air gap between two chucked CD "donuts-like" cavity; "14" is the cross-bar consists of polymers residue groups having counter clockwise electron-relay circular current of TCD . . . MCD . . . PEG . . . PVP wrapping around with ribbon of TCD . . . PEG//TCD . . . PVP; "15" is the nano air gap between 14 and 15 cross-bars; "16" is the slot for injection of biological sample; "17" is the 50 nm thickness pure gold electrode on the plastic substrate.

FIG. 11A$_1$ illustrates device 1's volumetric energy density vs. time using the DSCPO voltage method at ±10 nA over 0.25 to 1000 Hz in NIST serum without spiking Aβ; FIG. 11A$_2$ is the voltage vs. time profiles in the presence of 3.8 nM Aβ; and FIG. 11A$_3$ is the profiles in the presence of 76 nM Aβ.

FIG. 12A, FIG. 12B and FIG. 12C depict the voltage profiles vs. time using the DSCPO method in NIST serum with 38 μM Aβ or without Aβ at ±10 nA on device 2. The blue line refers to serum only without Aβ and without spiking ACH as "a"; the red curve refers to in the presence of 38 μM Aβ as "b" in 0.25 Hz, at 40 Hz and at 250 Hz, respectively.

FIG. 15 panel B depicts the toroidal transformer's longitudinal tunneling effect on device 1 in fresh human capillary whole blood specimens with triplicates using the CA method under the same experimental condition as in FIG. 15 panel A, but step time is 25 ms (a): without spiking Aβ; (b): in the presence of 2.3 nM Aβ.

FIG. 16 panel B depicts Au/"Mutated ACHE Gorge" MEA-insulator-AU/" Normal ACHE Gorge" flat bridge/nanopore MEA configuration in 1 M methanol at room temperature using the DSCPO method at ±1 mA (a); Against the initial activation of the same device in pure water under an applied potential −100 mV using the DC potential amperometry method (b); The insert curve depicts a control curve with a pure gold sensor made of same size, but without a membrane attached, in pure water under an applied potential −100 mV using the DC potential amperometry method.

FIG. 16 panel C depicts 0.5 cm$^2$ GC/TCD/PEG/PVP/CD MEA-insulator-/Pt in an all solid dry state under purge N$_2$ (a); In 1 M methanol with 0.02M o-NPA under purge N$_2$ (b); the insert in an all solid dry state with open air (c); FIG. 16 panel D depicts 0.5 cm$^2$ GC/MCD/PEG/PVP MEA . . . GC/TCD/PEG/PVP/CD/O-NPA with an insulator in 1 M methanol, Pt as current collectors as (a); pure Au in dry state as a control, no purge N$_2$ (b).

FIG. 20, the panel A depicts the synapse circuitry dynamic 3D Energy-Sensory map of Device 1 interacted with NIST serum before discharges a synapse pulse, and without Aβ. The x-axis is the cross-point location (mV), the y-axis is the DET peak location (mV) and the frequency (Hz) as Z-axis. The labels of the alphabetic numbers refer to the peak at each of different frequencies, started at lowest frequency as "1" in "neocortex", final ending is at the highest frequencies in "hippocampus". The panel B depicts the contour map at the same definitions of axis. The panel C depicts the optical image of the Energy-Sensory map. The light intensity emitted comes from the communication between the bipolar circular electro-relay "neuron network" prosthesis and the media of human serum taken as the original background light intensity at the 3D orientations in the electric field.

Followings are the Brief Descriptions of the Drawings for CIP Application

FIG. 34A depicts the photo image of the whole SAM superconductive multiple layers membrane structure on the screen during setting the probe before starting taken an AFM image. FIG. 34B depicts a photo image of a curvature cross-bar structure of a roof shingle matrix that looks like the surface structure of the membrane of the device. FIG. 34C depicts a photo image of a matrix sand waves that are looking like the membrane structure of the device in a macroscopic view.

Figure 35:
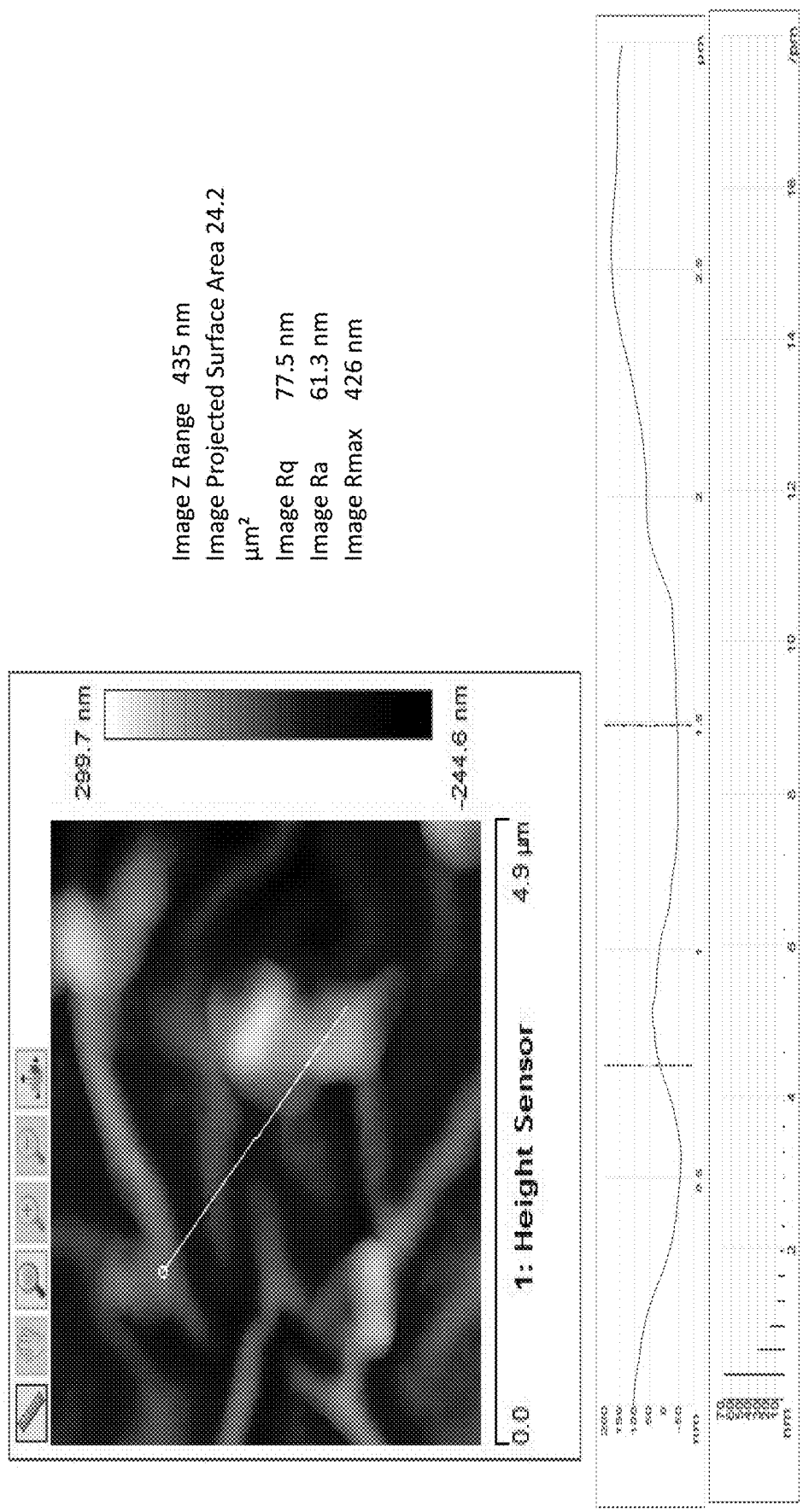

FIG. 35 depicts a bird view of the AFM image in the cross-section analysis of the superconductor SAM membrane in 24.2 μm².

Figure 36:
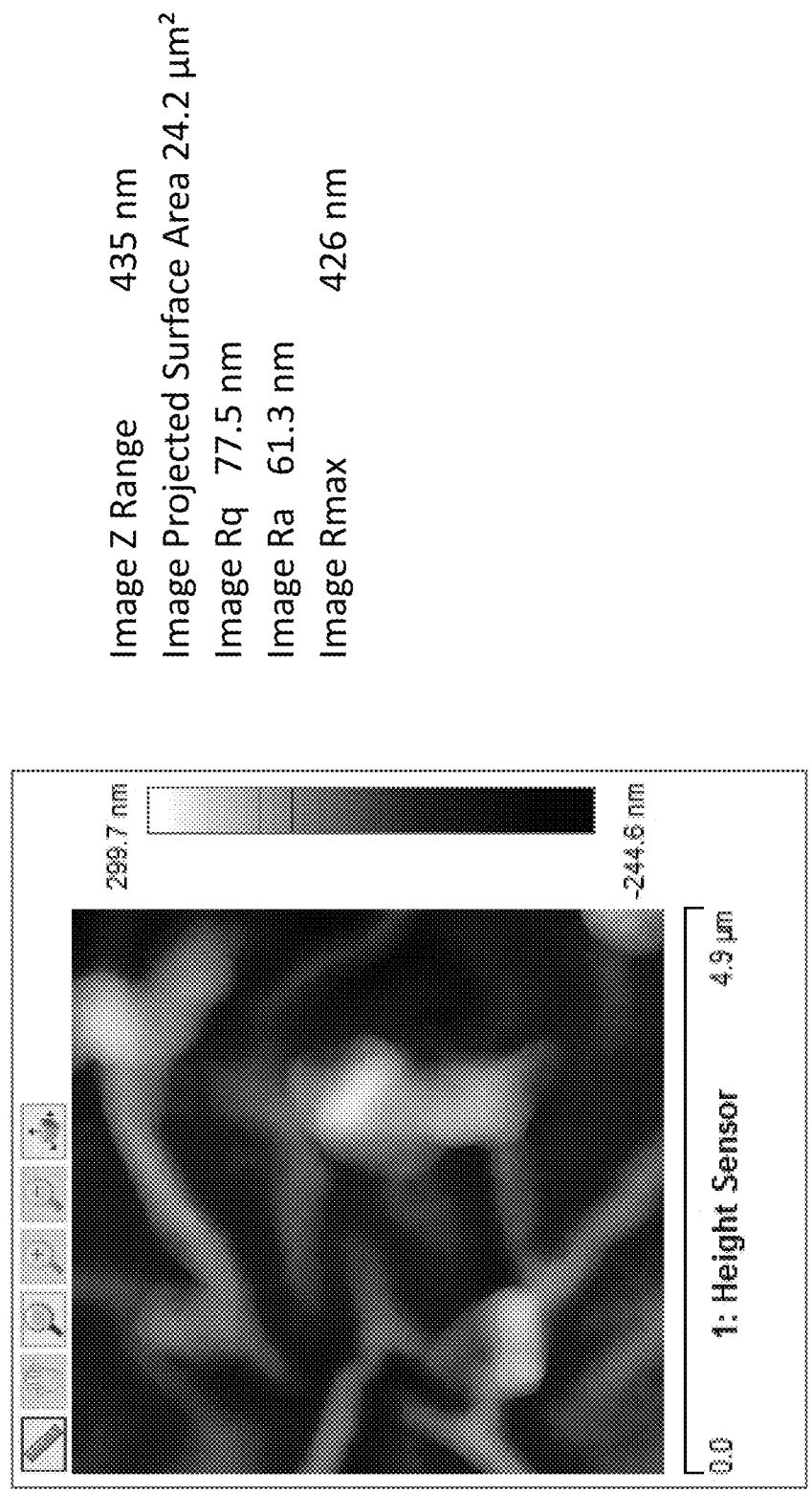

FIG. 36 depicts the close bird-view of the 2D AFM image of the detail conformation orientation of the zinc atoms chelating with groups of cross-linked organic polymers in layers curvature nanotubules jointed with zinc atoms forming super-lattice.

Figure 37:
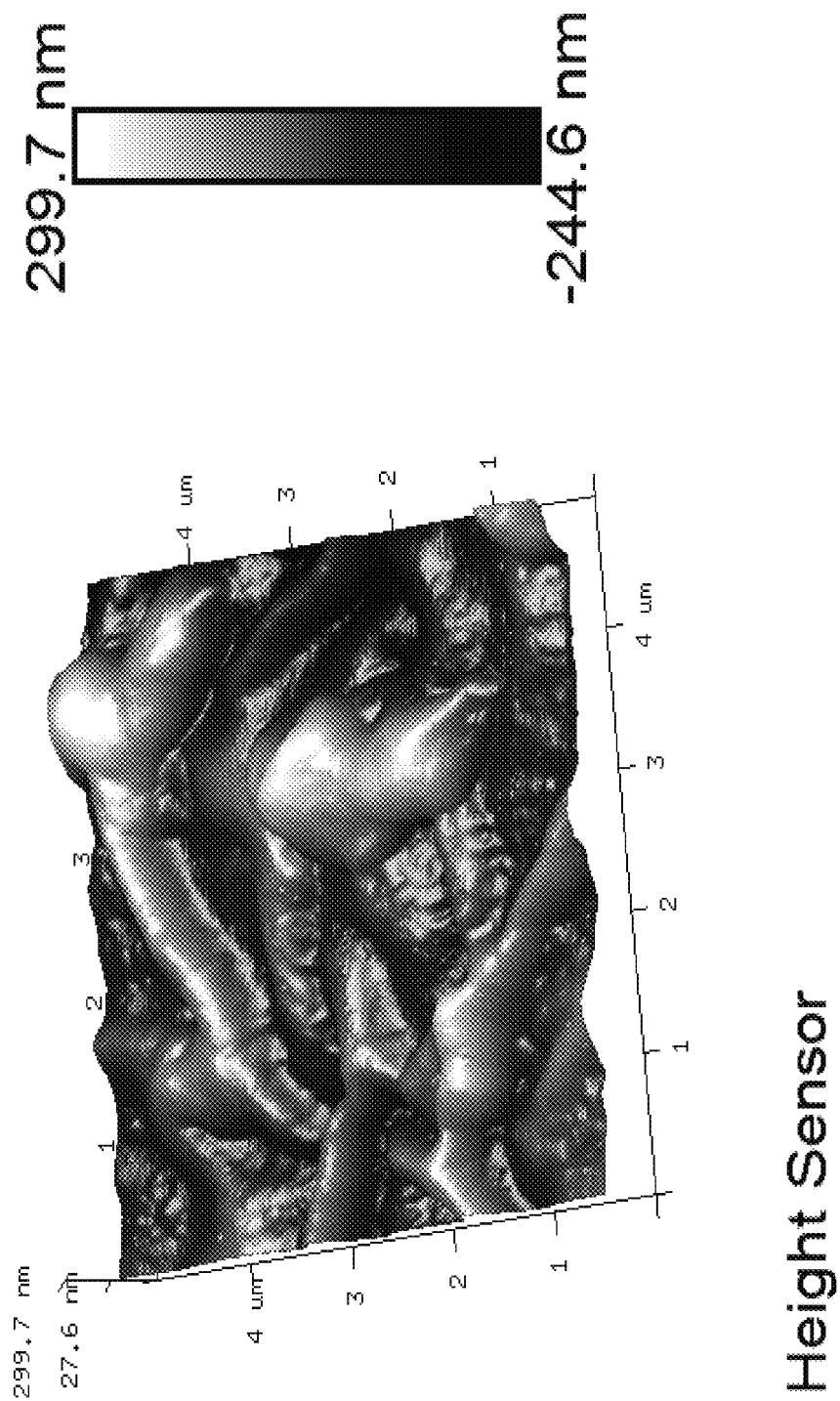

FIG. 37 depicts the 3D bird-view of the membrane AFM image.

Figure 38B:
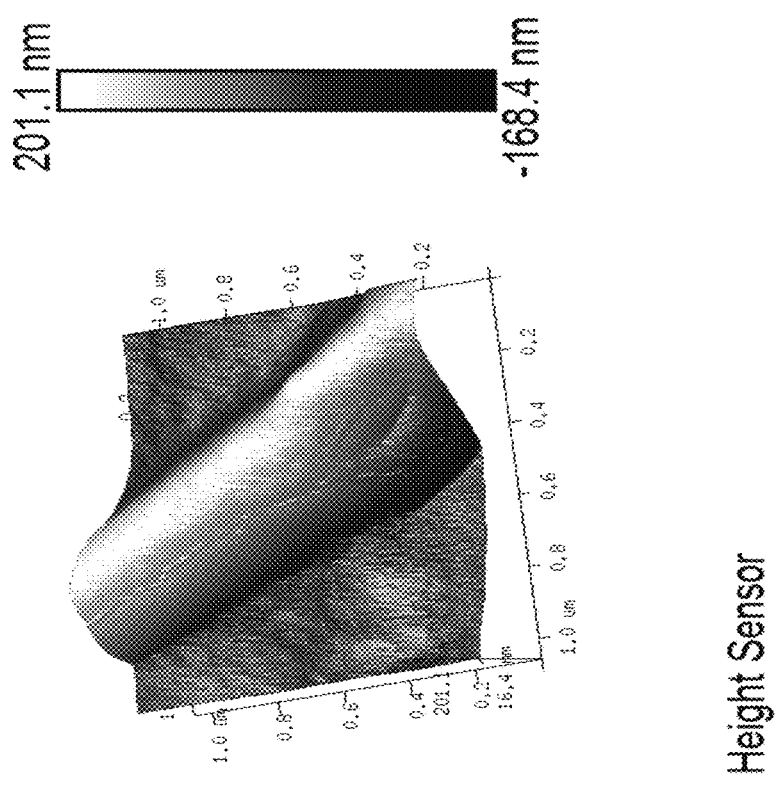
Figure 38A:
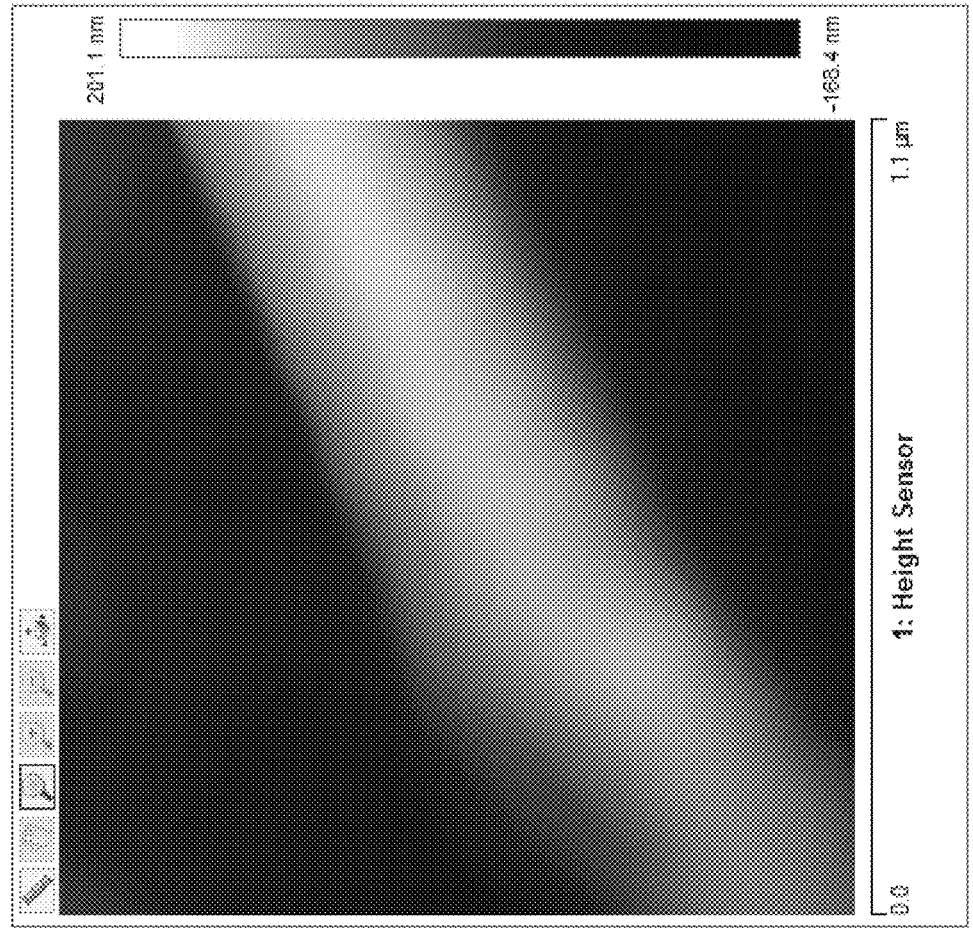

FIG. 38A depicts the bird-view of the 2D AFM image of the single wall nanotubule in 1.21 μm².

FIG. 38B depicts the 3D AFM image in side-view of the single wall nanotubule in 1.0 μm².

Figure 39:
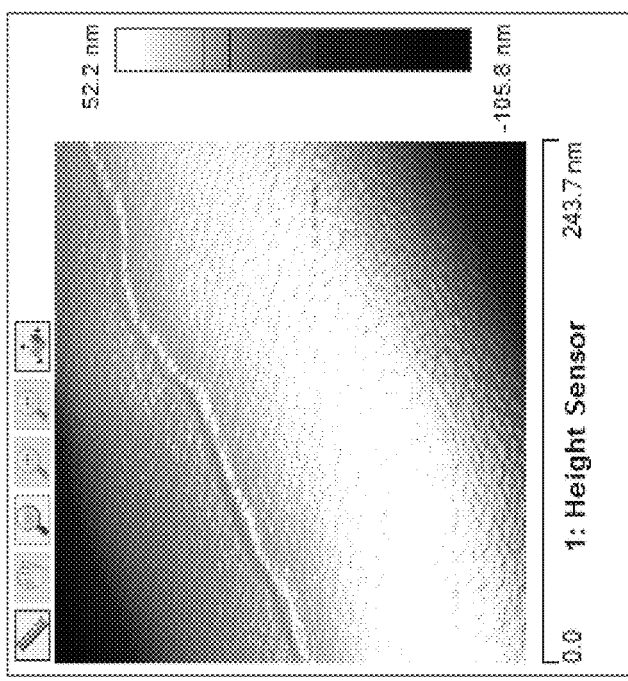

FIG. 39 depicts the bird-view of the 2D AFM image of the detail structure of the single wall nanotubule in 250×250 nm².

Figure 40:
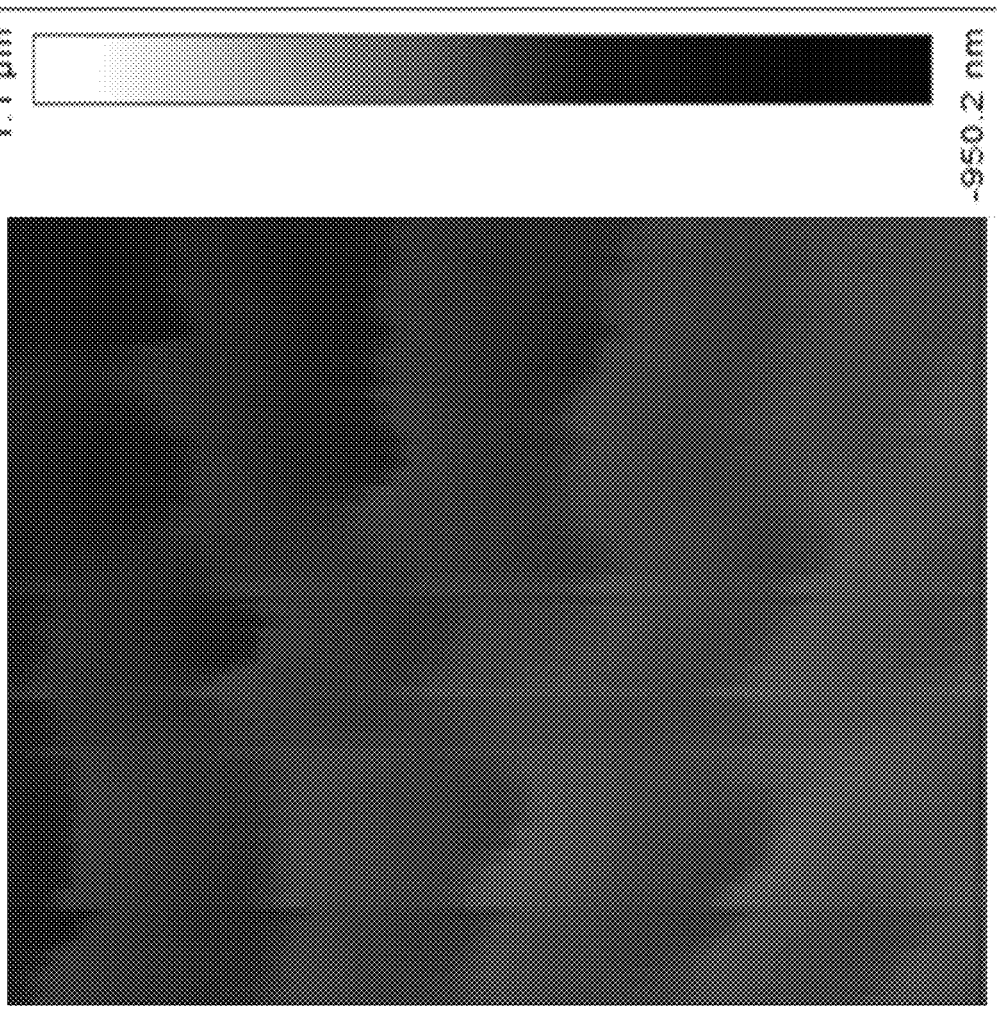
Figure 41:
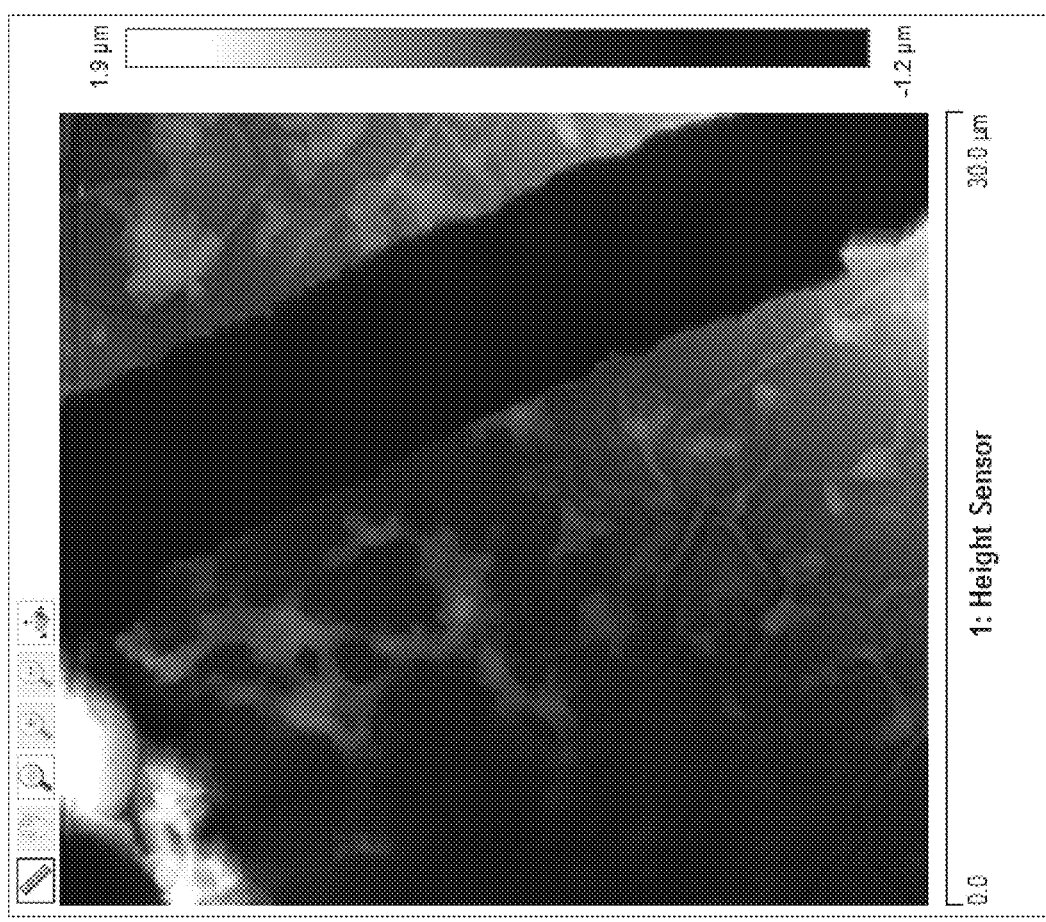

FIG. 40 depicts the bird-view of the 2D AFM image of the wave structure of the membrane under the canal as seen in FIG. 41 under the dark long strip.

FIG. 41 depicts the bird-view of the 2D AFM image of the superconductive SAM membrane of the zinc-organic polymer near the strip canal in 30×30 μm² comprising of 30-50 qubits uniformly laid and connected on the surface shown as the JJ circuitry connected by flexible zinc atom clusters. The canal was about the size of 24.8 μm×7.6 μm×1.2 μm (LWH). The canal was about the size of 24.8 μm×7.6 μm×1.2 μm (LWH). The canal comprised of sine wave membranes as shown in FIG. 40 that covering the canal walls and the canal cavity was filled with air, therefore the canal became another type of flexible Josephson junction separating the superconductive qubits arrays located on banks of the canal.

Figure 42:
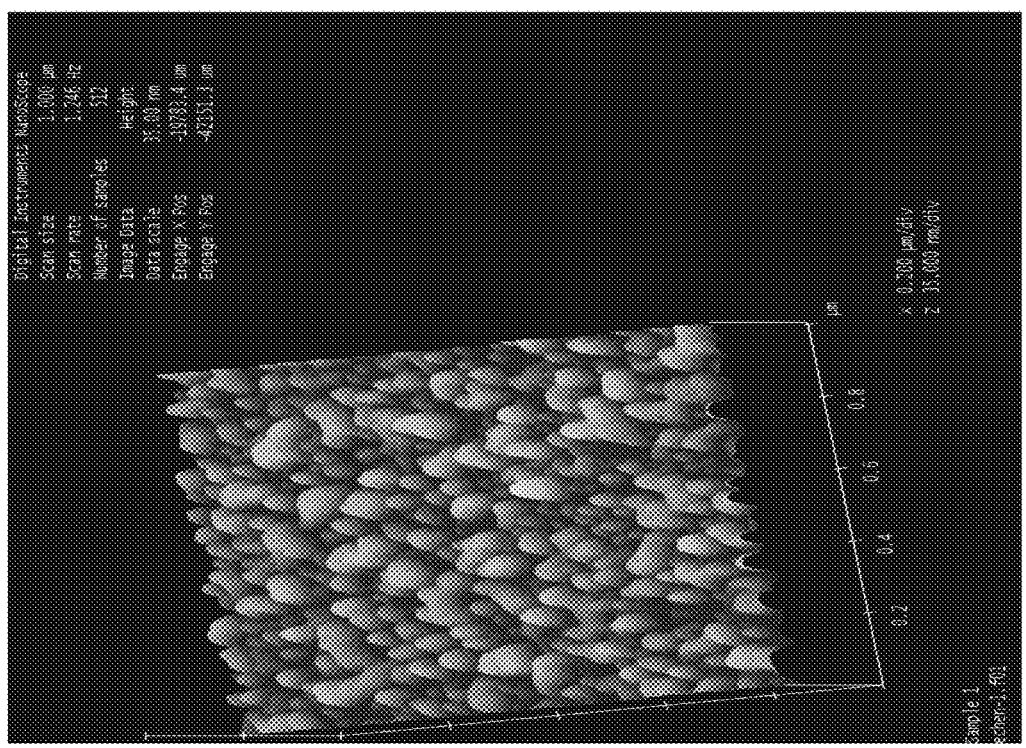

FIG. 42 depicts the 2D AFM image of the SAM organic conductive membrane in nano-island structure in 1.0 μm².

Figure 43:
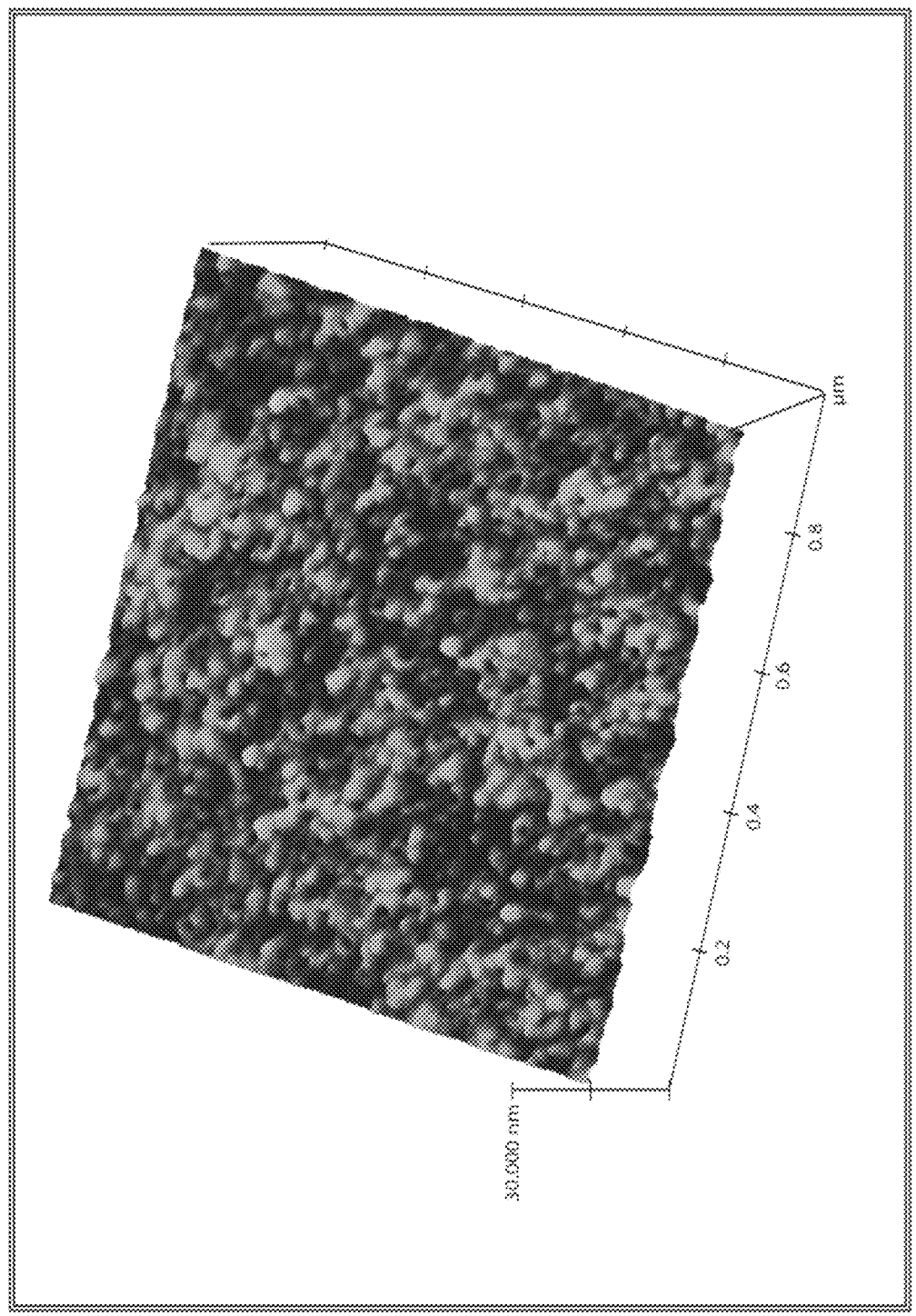

FIG. 43 depicts the bird-view of the 3D AFM image of the SAM organic conductive membrane in uniform nanopore array in 1.0 μm².

Figure 44:
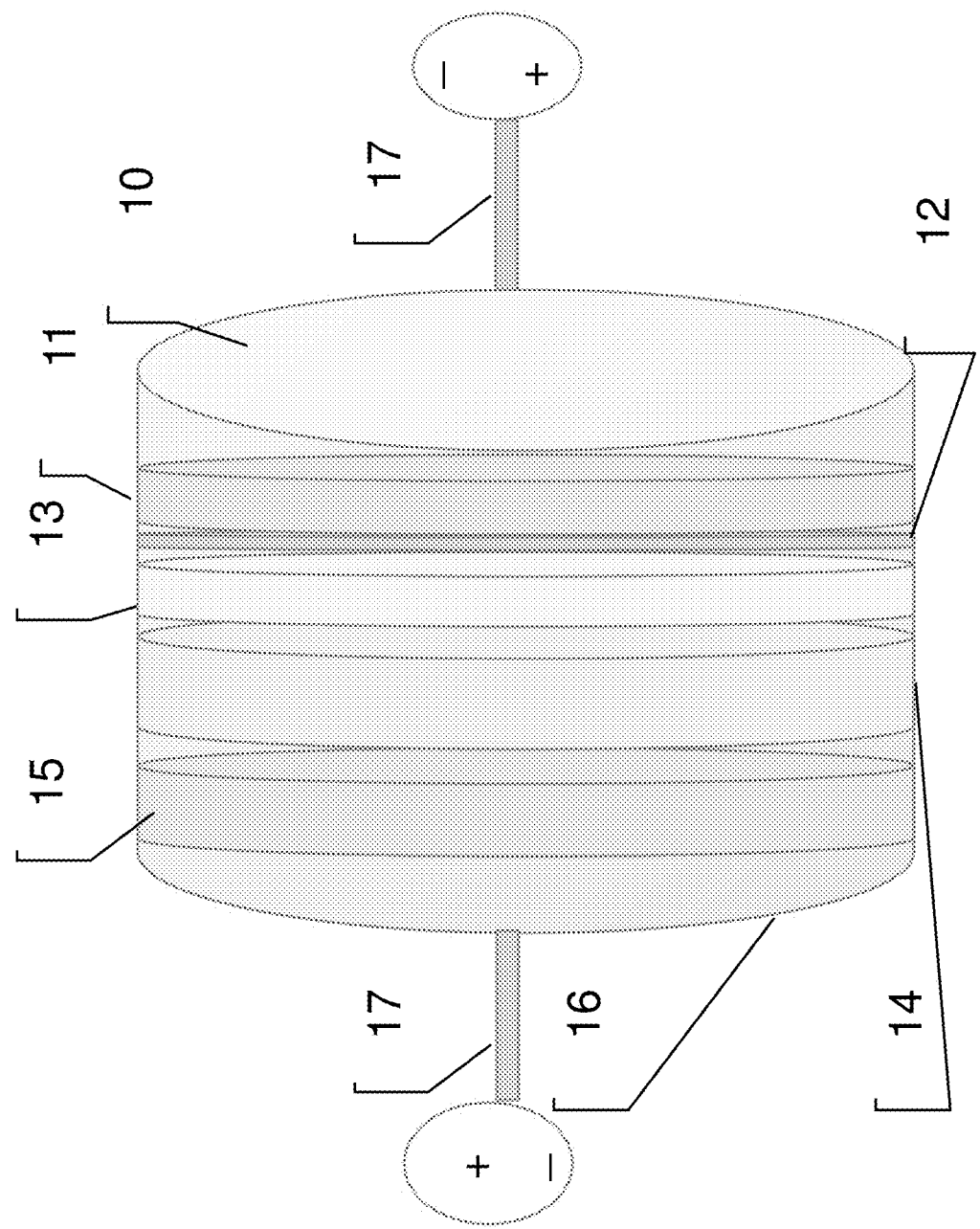

FIG. 44 depicts the schematic components in engineering design of the superconductor/memcapacitor device in a side-view. "10" is the gold electrode with 50 nm thickness adherences on a flexible plastic plate substrate; "11" is the self-assembling membrane (SAM) comprising of conductive cross-linked organic polymer, where the monolayer membrane has uniform nanopore array structure; "12" is the dielectric insulator; "13" is a "Controllable and Adjustable State-Switch Vale", i.e., it is able to switch between a memristive state to a superconducting state, which is the cover layer of o-nitrophenyl acetate in a mixture of imidazolyl derived mono-substitute β-dimethylcyclodextrin (m-β-DMCD, in short, MCD) with $ZnCl_2$ in methanol, "14" is the SAM comprising of superconductive cross-linked organic polymer and transition metal multiple layer membrane having uniform "roof-shingle" like macrostructure and "mitochondria" like nanostructure that comprises curvature lattice pattern forming nanotubules with zinc atoms on the top joints; "15" is the bottom layer of the superconducting SAM under "14", which is a normal conductive organic polymer SAM comprising of uniform nanoisland structure; "16" is the gold electrode with 50 nm thickness adherences on a flexible plastic plate substrate; "17" is the switchable metal connector lead, because of the superconductive/memcapacitive function.

Figure 45A:
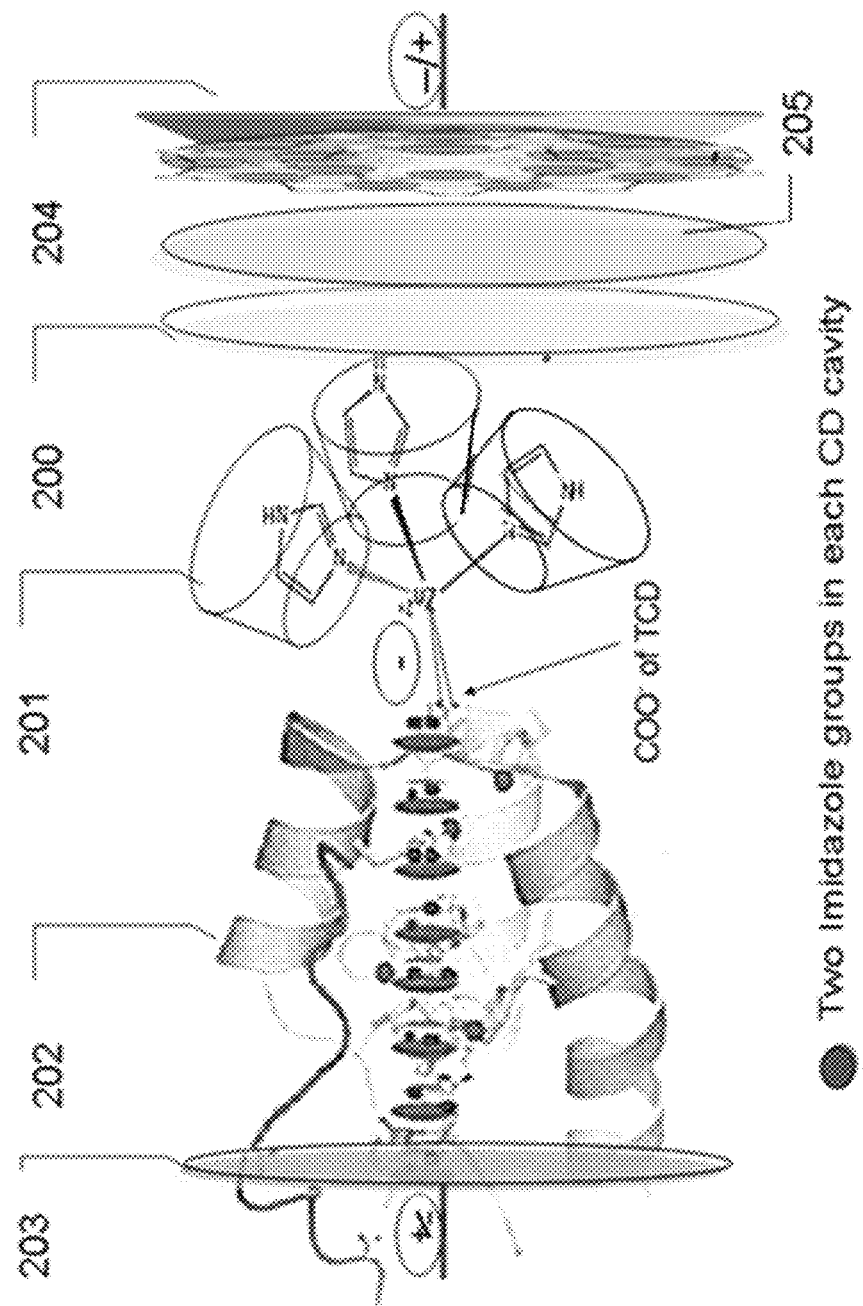

FIG. 45A depicts the art illustration of the proposed direct electron-relay mechanism in the superconductor/memcapacitor device. "200" refers to the MCD . . . o-NPA inclusion complex cover layer with 1 mg/mL MCD and 3 mM o-NPA; "201" refers to the group in "200" interacts with the "201" simplified biomimetic matrix metal proteinase (BMMP) forming the superconducting SAM layer "202" with immobilized cross-linked organic-transitional metal zinc in the membrane of bM-β-DMCD . . . TCD . . . PEG . . . PVP . . . $ZnCl_2$, "202" is the direct-electron-relay superconducting SAM forming relay between 200 . . . 201 . . . 202 in the chain of 3MCD/(His)N $Zn^{++}$ . . . $COO^-$ of TCD . . . (bM-β-DMCD)$_n$/(His)$_2$N")$_n$. The right hand side is the simplified MMP model, and the induced direct bio-communication was shown through the zinc ion coordinating with both of the $COO^-$ of TCD and the receptor groups of two imidazolyl in bm-β-DMCD cavity, i.e., by the coordination geometry, proton and electron transfers and the displacement of water molecules which formed the long electron-relay chain based on a favorable low LG. Notice of the ribbon in "202" represents the TCD . . . PEG forming biomimetic protein's C-terminal and PEG . . . PVP forming Biomimetic protein's N-terminal wrapping around the cross-bar between vertical oriented toroidal CD cavity and horizontal orientated toroidal CD cavity, see in FIG. 2B. "203" refers to the normal 50 nm thickness gold electrode on a flexible plastic plate having a switchable connecting gold lead; "204" refers to the cross-linked organic polymer membrane with nanopore structure of MCD . . . PEG . . . PVP on 50 nm thickness gold electrode with a plastic plate and a gold connect lead; "205" refers to a dielectric insulator in 1M methanol.

Figure 45C:
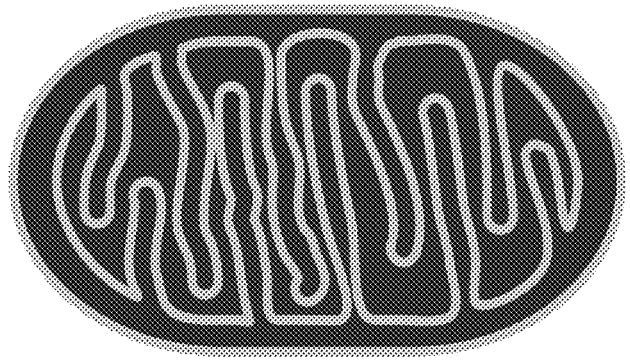
Figure 45B:
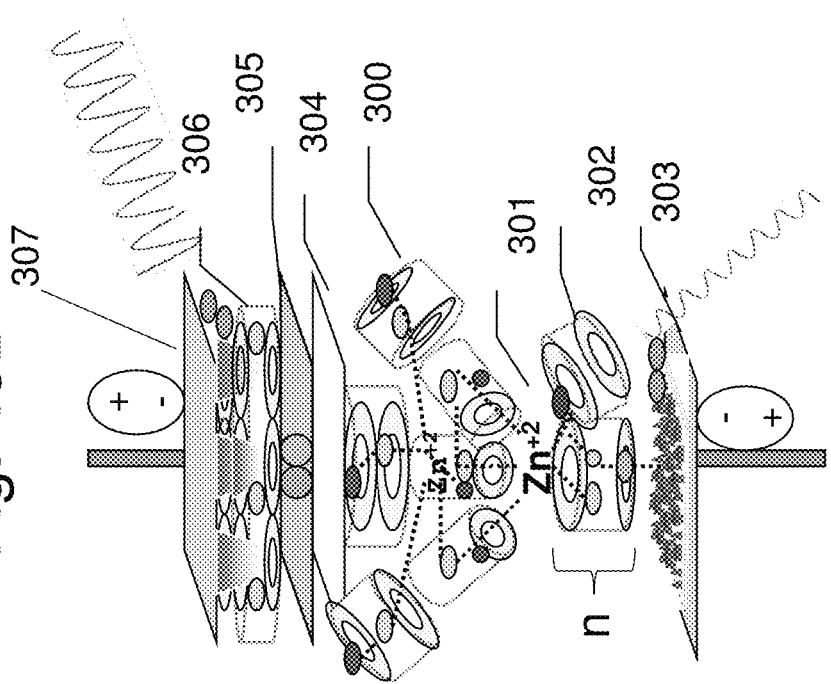

FIG. 45B depicts the configuration layout of the cross-bar characteristics in mamristive/memcapacitive in the invented superconductor/memcapacitor device: FIG. 45B's labels are similar to FIG. 45A, i.e., "300" refers to the zinc-imidazole of MCD coordination chelating in two schemes: (1) the zinc ion chelates with four imidazole groups of MCD and one COO⁻ group of o-NPA; "301" refers to zinc ion chelates with three imidazole groups of MCDs and one COO⁻ group of TCD and one more ligand coordinates with imidazole group in bM-β-DMCD; "302" refers to the repeating processing of n units; "303" refers to the nanoislands structure membrane on 50 nm thickness gold electrode on a plastic substrate with a switchable gold electronic connect lead; the nanoisland membrane comprises of TCD . . . PEG . . . PVP . . . β-CD copolymer, that mimics choline acetyltransferase (CHAT); (2) "304" refers to the MCD . . . o-NPA inclusion complex cover layer as shown in 300. The zinc ion chelates with four imidazole groups in MCDs that included o-NPA in the toroidal cavities and one COO⁻ of the o-NPA; (3) "305" is the dielectric insulator that is one type of the Josephson junction; (4) "306" refers to the nanopore array membrane comprises of MCD . . . PEG . . . PVP on a 50 nm thickness switchable gold electrode; (5) due to the formation of strong direct electron-relay system that the configured device enables harvesting energy and superconducting spontaneously at zero applied electric potential with high open circuit potential. "307" refers the switchable gold electrode.

FIG. 45C depicts the art model of the mitochondria that the invented superconductor/memcapacitor device intended to mimic one of the important energy producing function of the mitochondria and its eternal structure.

Figure 45D:
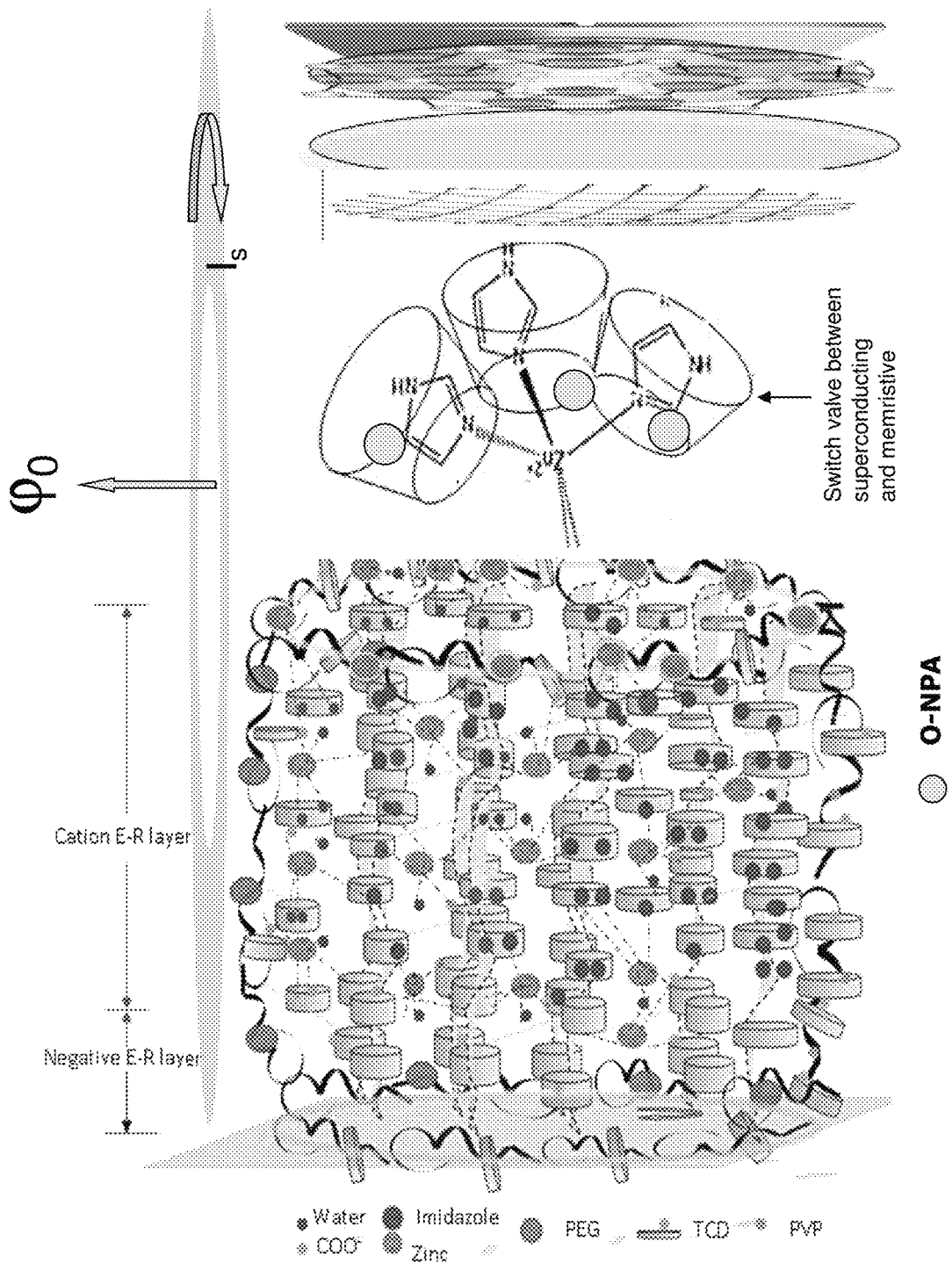

FIG. 45D depicts a functional device model after spiked a final concentration of 3 mM o-NPA in the 1.82 mM $ZnCl_2$ and 1 mg/mL MCD in the 1 M methanol solution. The zinc cations in the media are chelating with the COO⁻ groups of TCD or o-NPA in the cage membrane and the imidizole groups in the mono and bis imidazole modified β-DMCD cavity, and the MCD cavity was included with o-NPA, therefore the zinc-finger like media acted as (1) a controllable and adjustable state-switcher to switch between a mem-element state and a superconducting state; (2) an another layer of cover sheet to partially block the larger pore of the dielectric insulator (blue color) and partially forming electron relay and cation expel with the membrane cage functional groups. The bottom layer membrane on the gold electrode is a negative E-R layer, and the second layer is a cation E-R layer.

Figure 46:
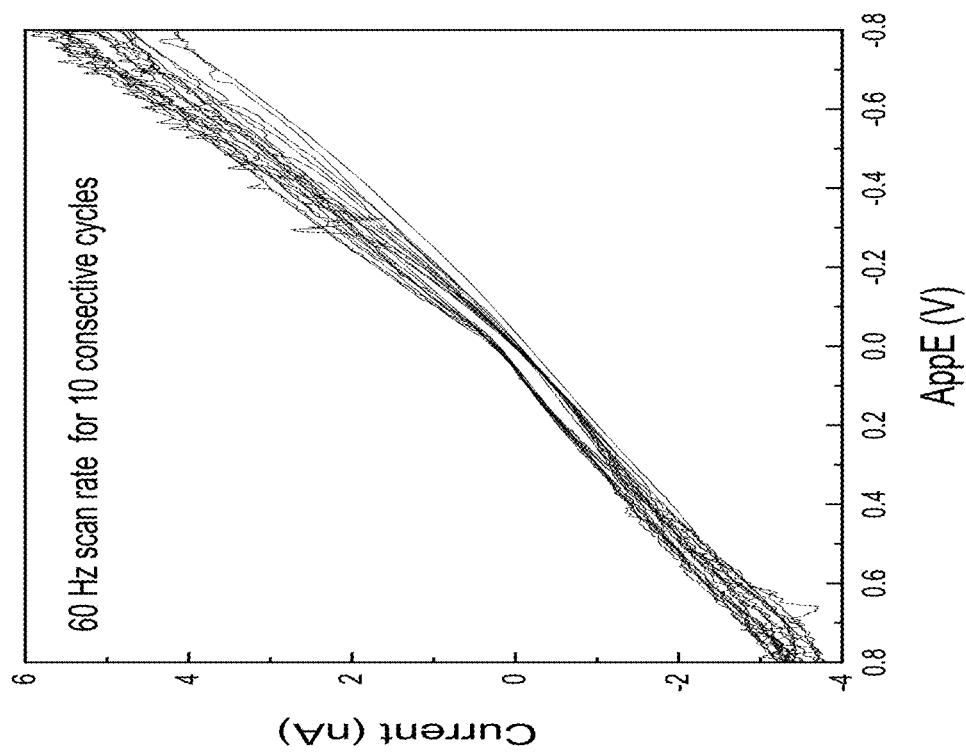

FIG. 46A depicts the memristive i-V curve of the superconductor/memcapacitor device of Au/biomimetic mitochondria-insulator-nanopore/Au at room temperature under normal pressure with scan rate 160 Hz in 1.82 mM $ZnCl_2$ and 1 mg/mL MCD in 1 M MeOH(a); with 1.82 mM $ZnCl_2$ and 1 mg/mL MCD and 3 mM o-NPA in 1 M MeOH(b). FIG. 46B depicts the memristive i-V curve of the Au/biomimetic mitochondria without a dielectric insulator device under same condition with 60 Hz scan rate under 1.82 mM $ZnCl_2$ and 1 mg/mL MCD in 1M MeOH (a); with 1.82 mM $ZnCl_2$ and 1 mg/mL MCD and 3 mM o-NPA in 1M MeOH (b).

Figure 47:
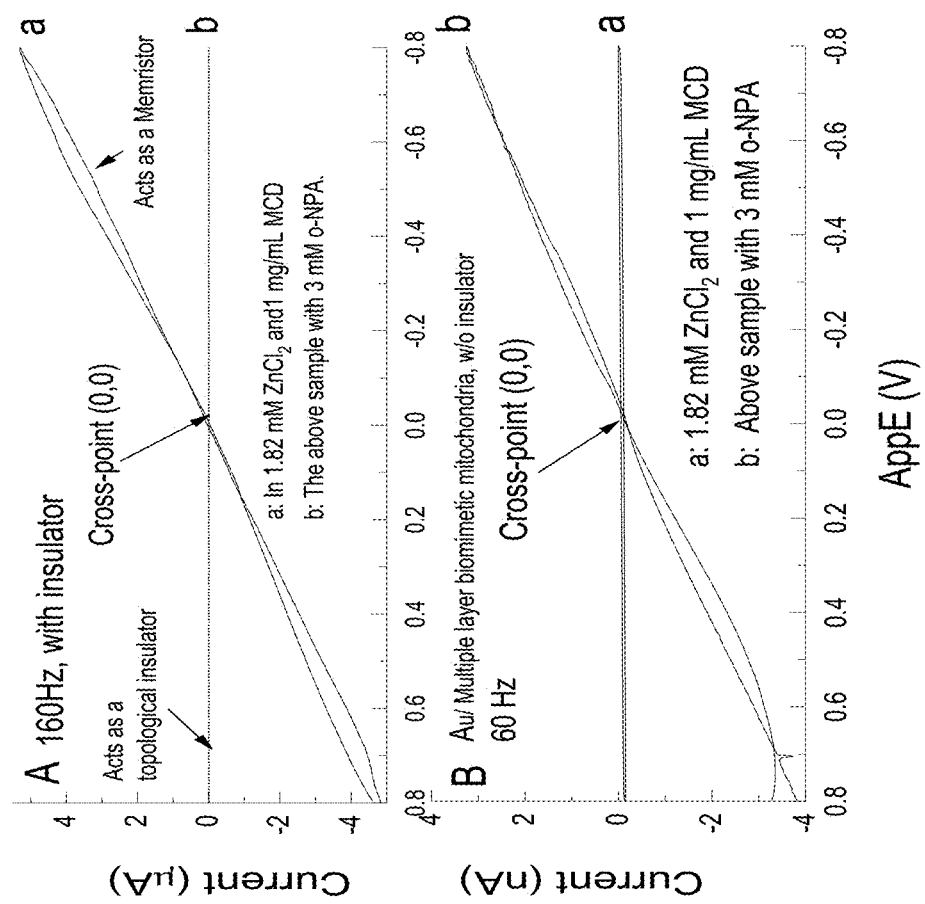

FIG. 47 depicts the memristive i-V curve of the Au/biomimetic mitochondria device, i. e., without the dielectric insulator and without the nanopore semiconductor membrane, a pure gold electrode lead connected with the cathode, the Au/multiple-layer superlative membrane electrode connected with the anode lead, under 60 Hz scan rate under same conditions as same as FIG. 46B (b), but with 10 consecutive cycles.

FIG. 48A depicts the 3D plot of a dynamic relationship between voltage, special capacitance and density of conductivity of the Au/biomimetic mitochondria device (Au/S—I) with 60 Hz scan rate of 10 consecutive scans under 1.82 mM $ZnCl_2$, 3 mM o-NPA and 1 mg/mL MCD in 1M MeOH.

FIG. 48B depicts the 2D contour map of voltage, special capacitance and density of conductivity among AppE covered from 2Δ to −2Δ. 1Δ=0.001V in the first segment scan for 10 consecutive times of the Au/biomimetic mitochondria device (Au/S—I) with 60 Hz scan rate. The curvature Fermi energy plane was labeled as the dark color line.

Figure 49:
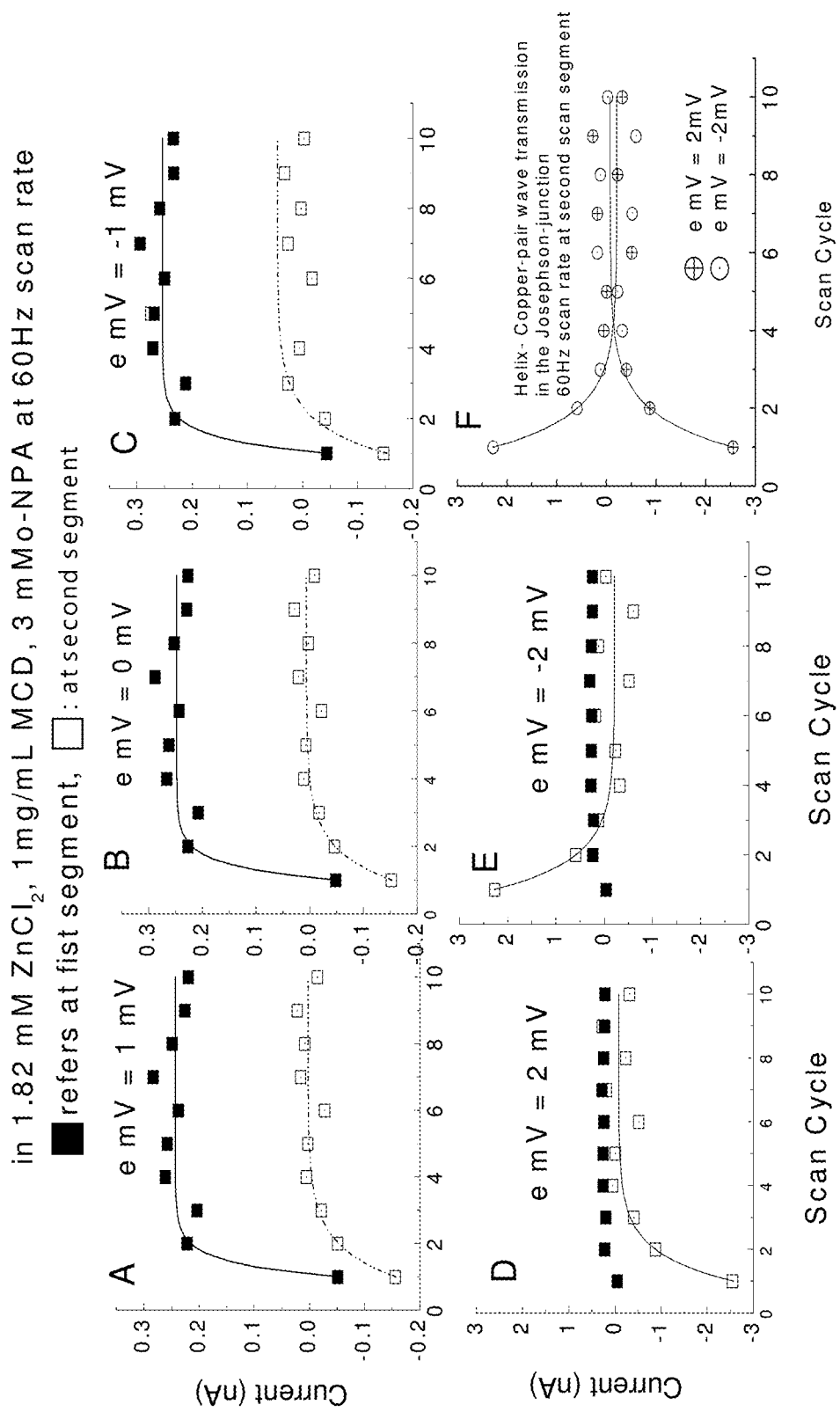

FIG. 49 depicts the trend helix-cooper pair wave transmission from different scan cycles affects on the peak current at different applied potential in the ±2 mV Josephson junction window under the same conditions of the media and scan rate as FIG. 48A. Solid Square refers to the first segment scan (the forward scan) from 1.0 mV to −1.0 mV; open square refers to the second scan (the backward scan) from −1.0 mV to 1.0 mV vs. scan cycles, and the peak current values were shown on the curves was at 1 mV as seen for Panel A; the peak current values were shown on the curves was at zero V as seen for Panel B; the peak current values were shown on the curves was at −1.0 mV as seen for Panel C; at 2 mV as seen for Panel D, at −2.0 mV as seen for Panel E, and Panel F refers to the curves covered the peak current at 2 mV and −2 mV for the backward scan over 10 cycles.

FIG. 50A depicts the 2D contour map of voltage, special capacitance and density of conductivity among ±2Δ, ±1Δ and 1Δ=0.0001V in the full 2 segments (includes forward and backward scans) for 10 consecutive cycles of the Au/biomimetic mitochondria device with 60 Hz scan rate. The curvature Fermi energy plane was labeled as the dark color line.

FIG. 50B depicts the 3D map of FIG. 50A.

Figures 51A, 51B:
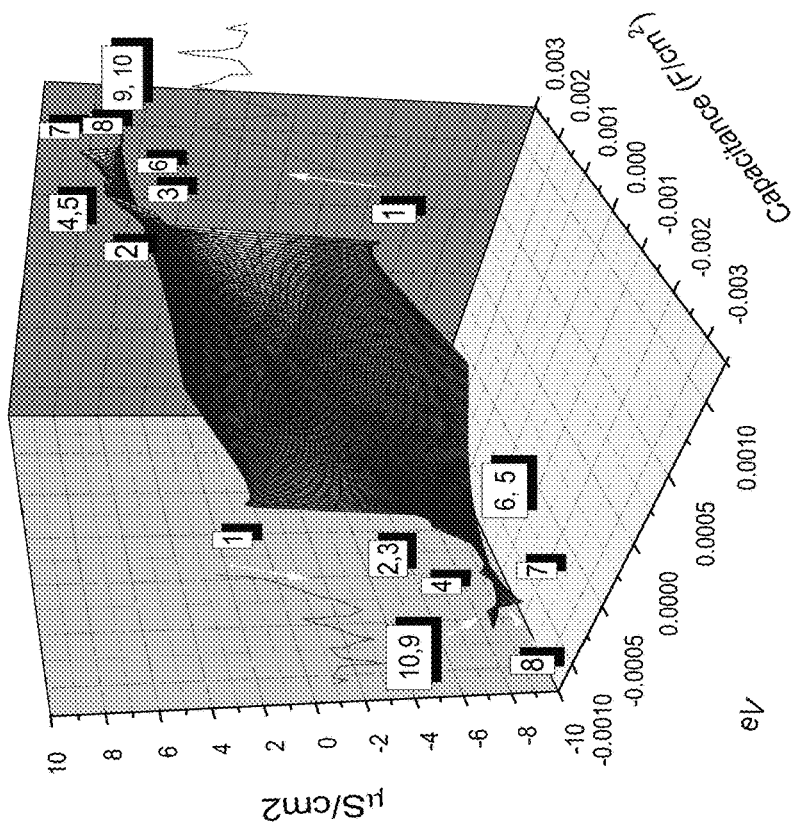
Figure 51C:
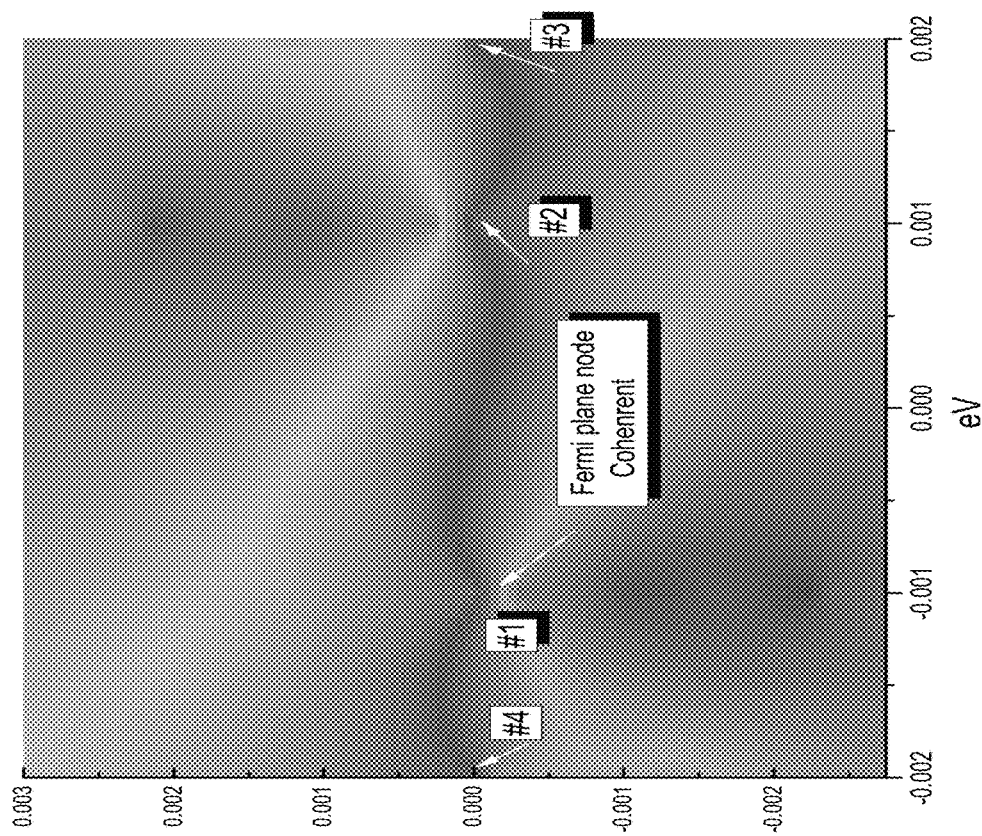

FIG. 51A depicts the cooper pair action in the Josephson Junction in the 3D dynamic map of each of the 10 scan trend regarding the relationship between voltage, special capacitance and density of conductivity at the first scan segment from 1 mV to −1 mV covered from ±1Δ and 0.000V. 1Δ=0.001V of the Au/biomimetic mitochondria device with 60 Hz scan rate. FIG. 51B depicts the 2D map of FIG. 51A. FIG. 51C depicts the image of the helix-cooper pair energy wave transmission superconductivity density related to memcapasitance and voltage change.

Figure 52A:
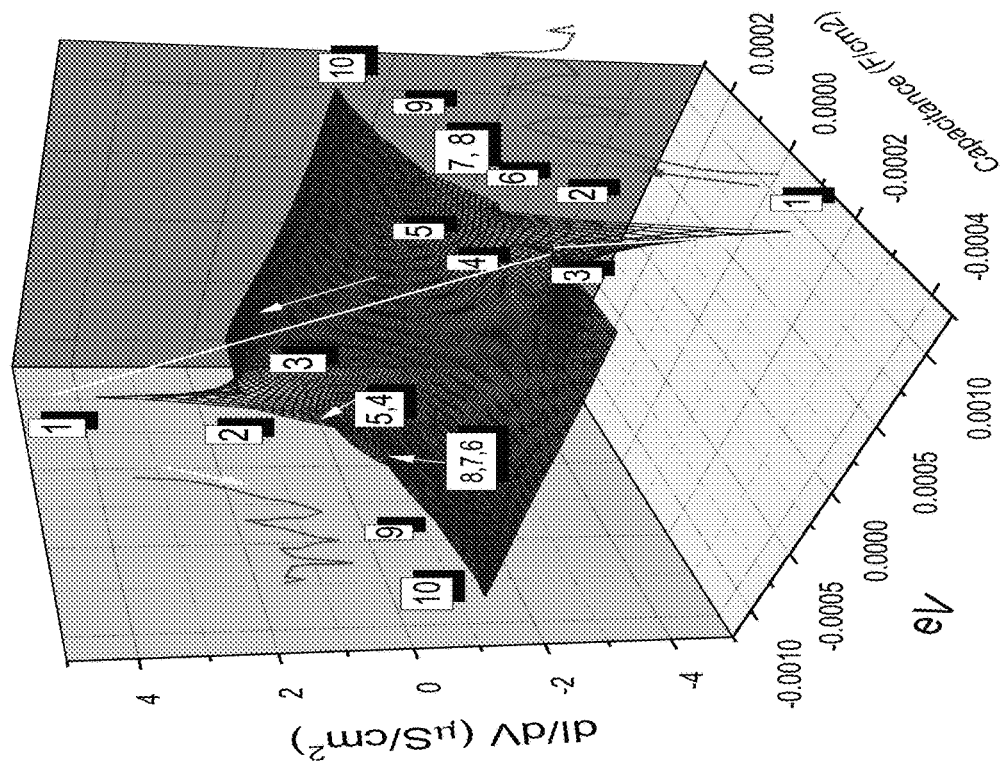
Figure 52B:
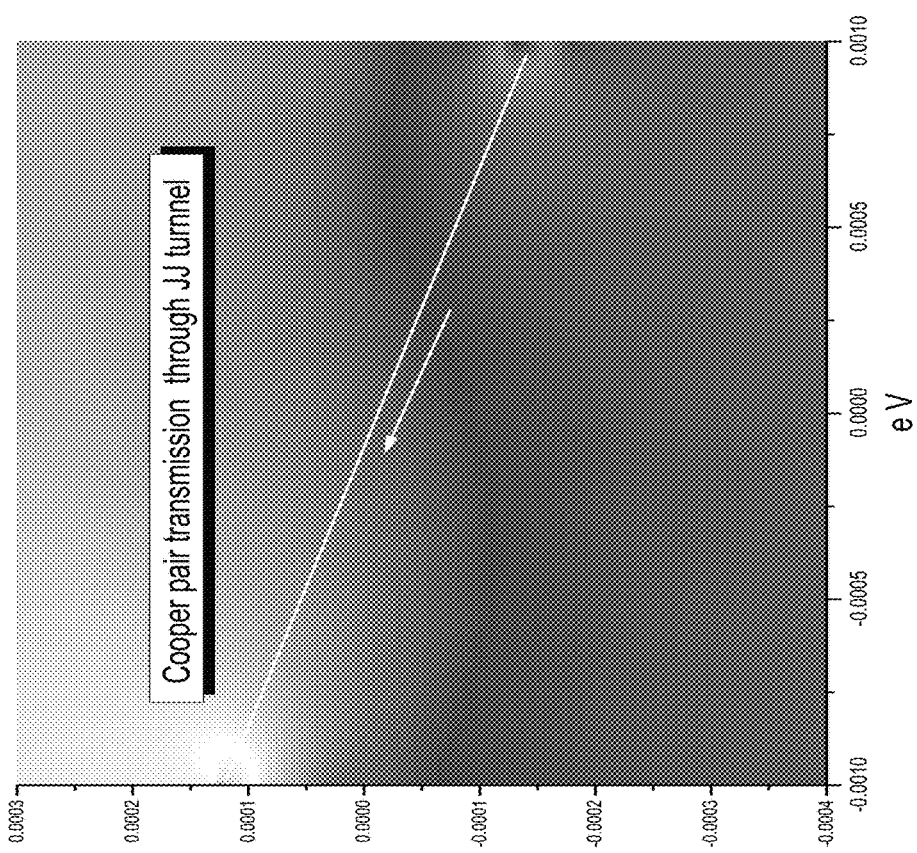
Figure 52C:
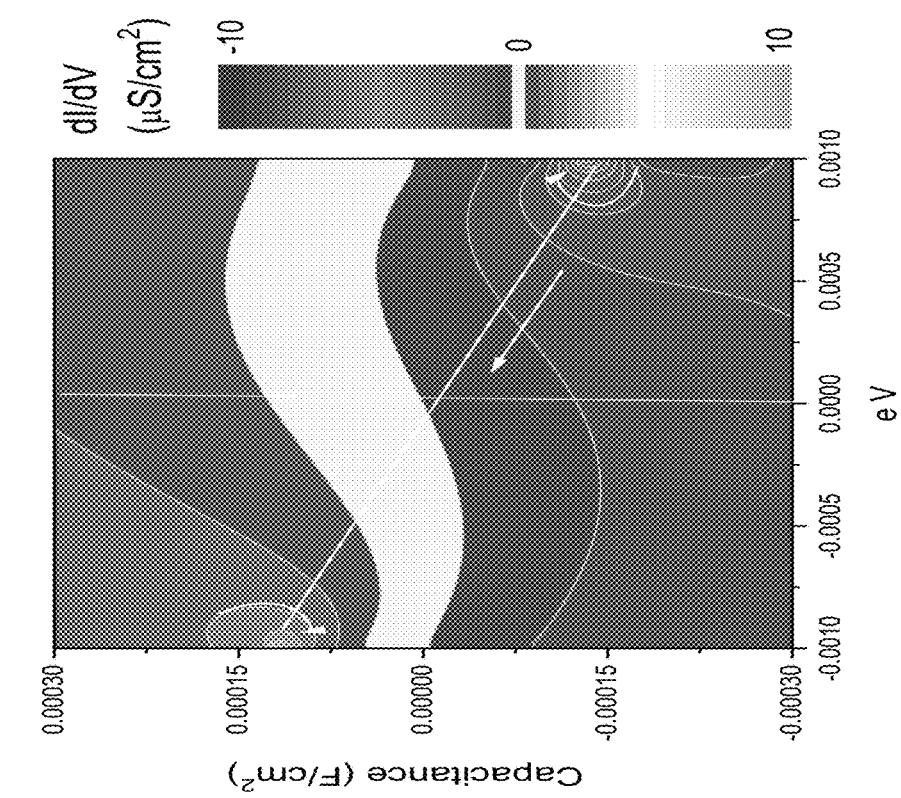

FIG. 52A depicts the cooper pair action in the Josephson Junction in the 3D dynamic map of each of the 10 scan trend regarding the relationship between voltage, special capacitance and density of conductivity at the second scan segment from −1.0 mV to 1.0 mV covered from −1Δ to +1Δ. 1Δ=0.001V of the Au/biomimetic mitochondria device with 60 Hz scan rate. FIG. 52B depicts the 2D map of FIG. 52A. FIG. 52C depicts the image of the helix-cooper pair energy wave transmission superconductivity density related to memcapasitance and voltage change.

Figure 53B:
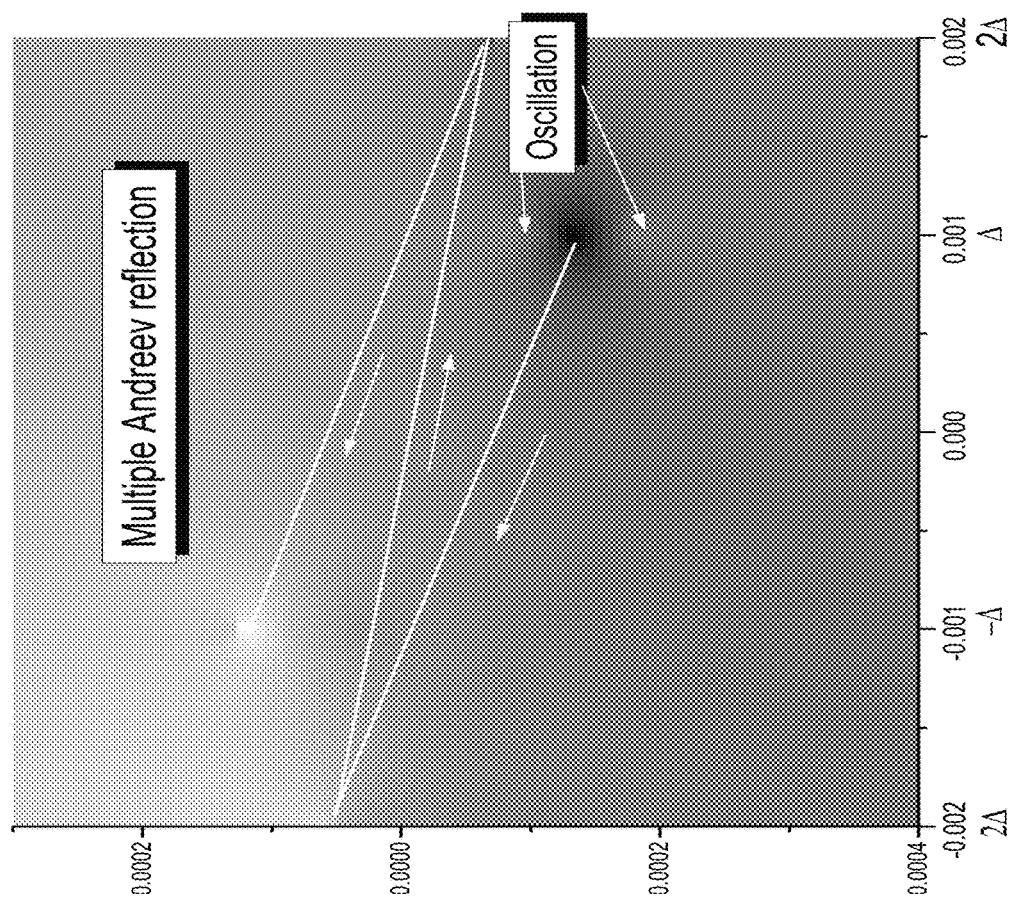
Figure 53A:
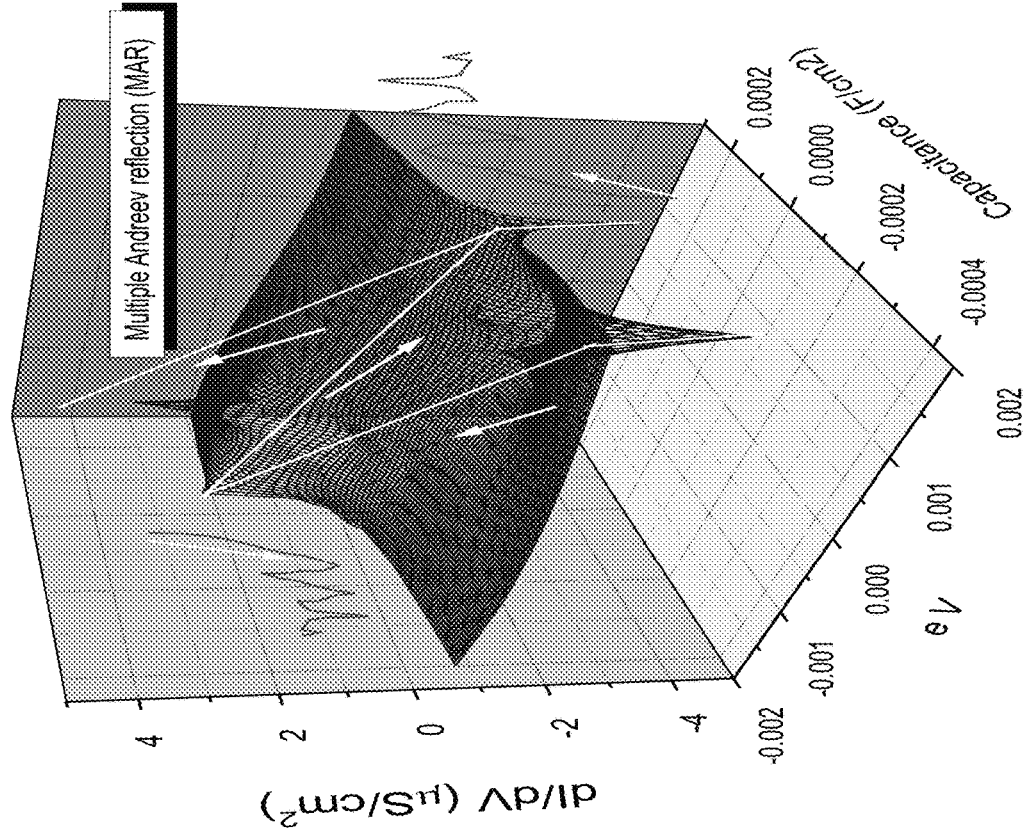
Figure 53C:
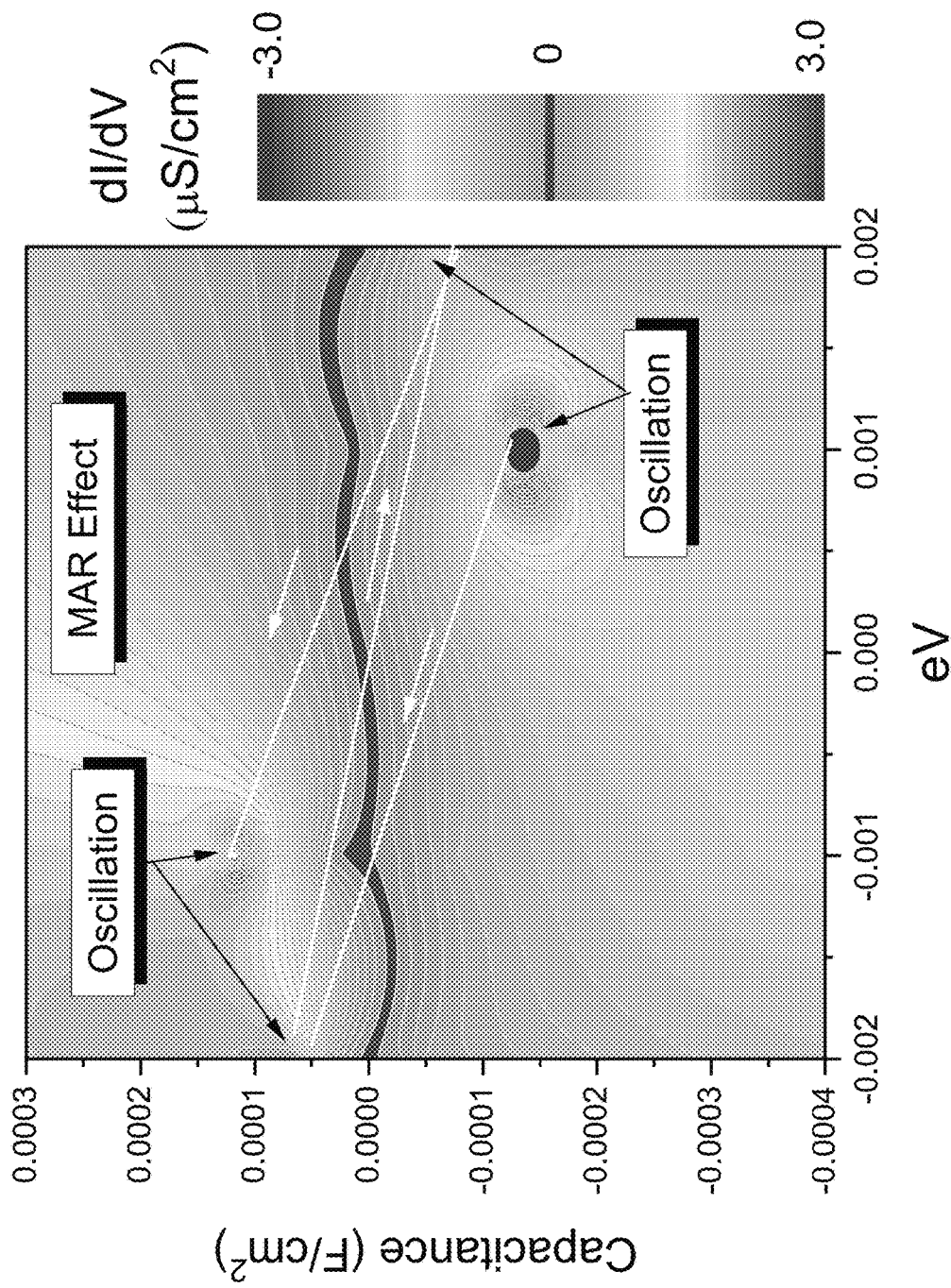

FIG. 53A depicts the cooper pair action in the Josephson Junction with multiple Andreev reflection (MAR) in the 3D dynamic map of each of the 10 scan trend regarding the relationship between voltage, special capacitance and density of conductivity at the second scan segment from −2.0 mV to 2.0 mV covered from −2Δ to +2Δ for 10 consecutive times of the Au/biomimetic mitochondria device (Au/S—I) with 60 Hz scan rate. FIG. 53B depicts the MAR oscillation image energy wave transmission superconductivity density related to memcapasitance and voltage change. FIG. 53C depicts the 2D contour map.

Figure 54:
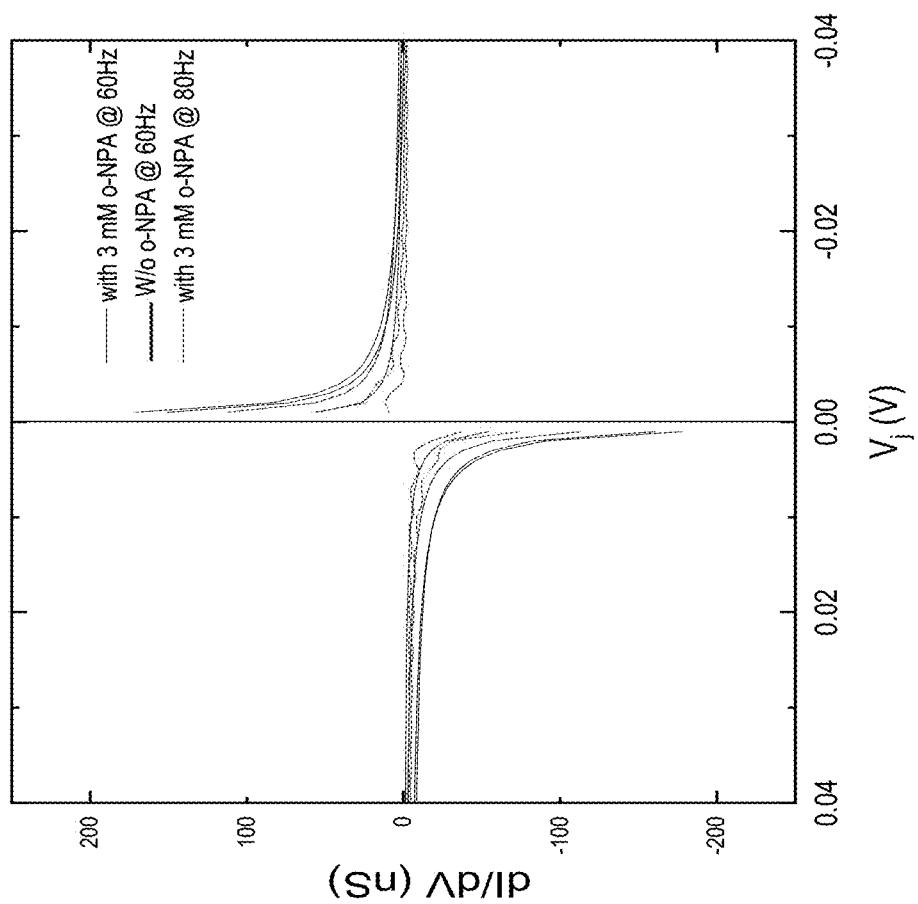

FIG. 54 depicts the plot of $(2e^2/h)$ (dI/dV) vs. eV from −0.04V to 0.04V for study of the superconductivity at zero electric field of the AU/biomimetic mitochondria SAM in 1M MeOH with 1.82 mM $ZnCl_2$, 1.0 mg/mL MCD and 3 mm o-NPA in consecutive 10 cycles scans under 60 Hz scan rate.

Figure 55:
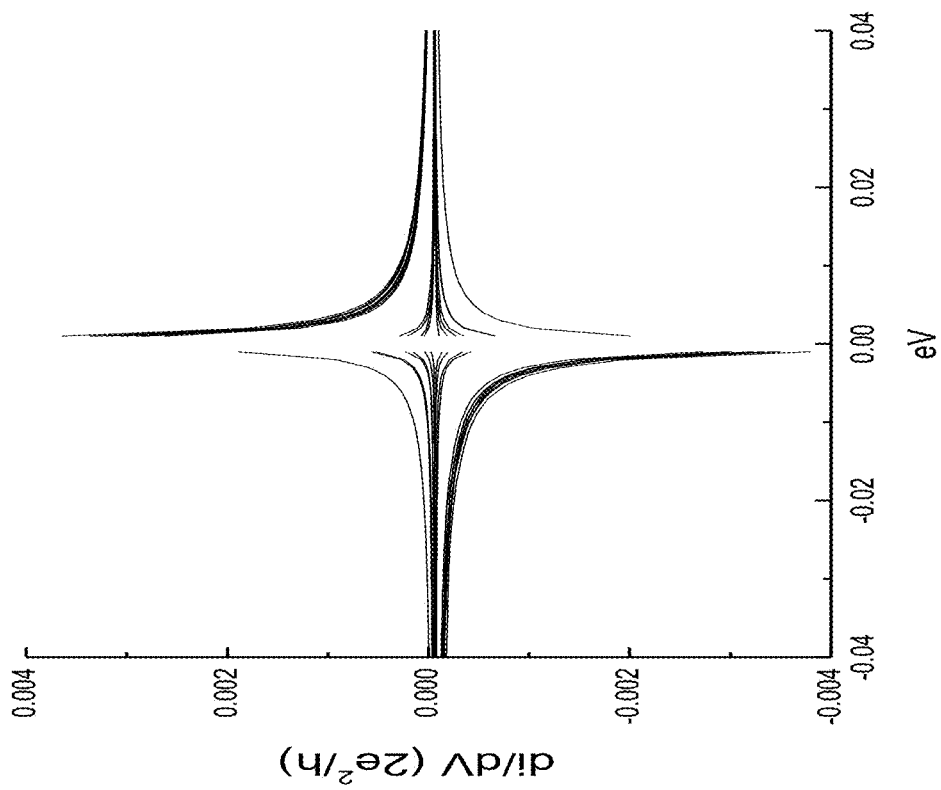

FIG. 55 depicts the plot of dI/dV (in nS) vs. eV from −0.04V to 0.04V for study of the superconductivity at zero electric field of the AU/biomimetic mitochondria SAM in 1M MeOH with 1.82 mM $ZnCl_2$, 1.0 mg/mL MCD comparing conditions with or w/o 3 mM o-NPA.

FIG. 56 depicts the study of JJ effect on initial rate of open circuit potential vs. the first 2 s of discharge energy of Au/biomimetic mitochondria in 1M MeOH with 1.82 mM $ZnCl_2$, 1.0 mg/mL MCD and 3 mM o-NPA using the Open Circuit Potential (OPO) method comparing with the control in 1M methanol only.

Figure 57B:
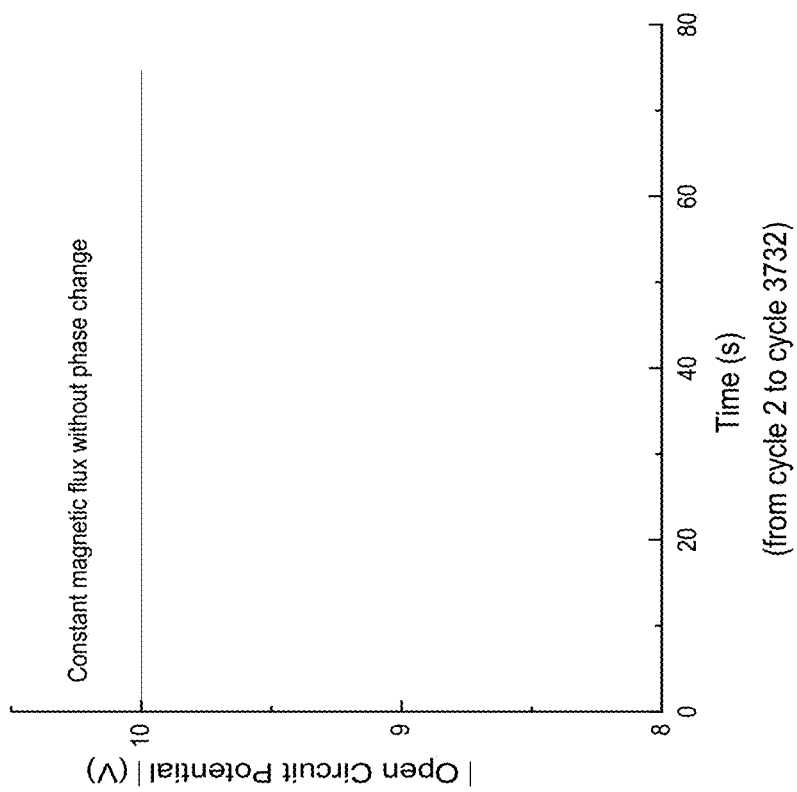
Figure 57A:
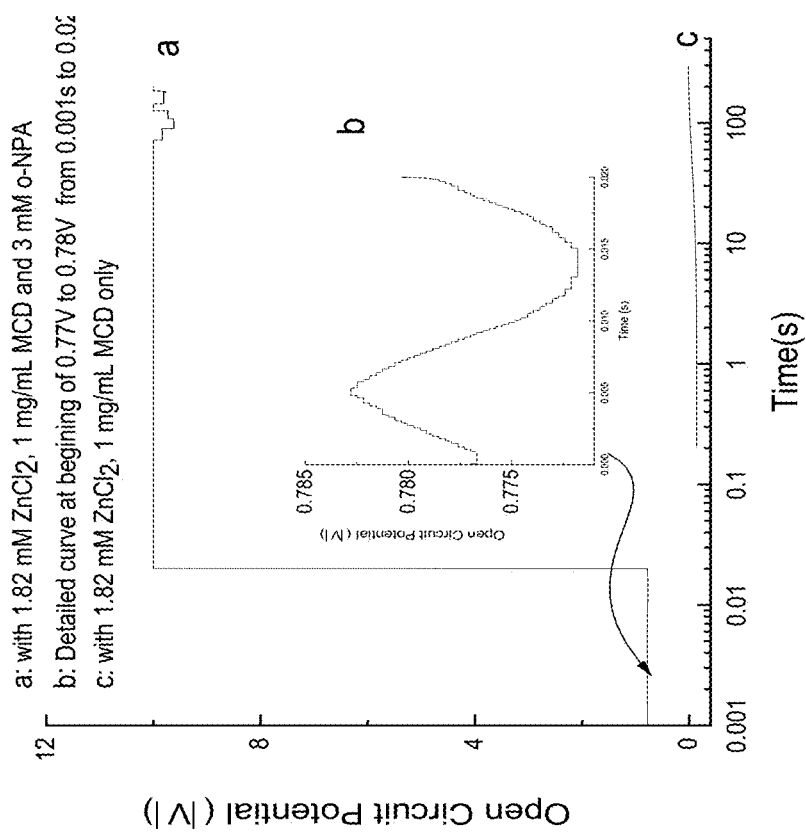
Figure 57C:
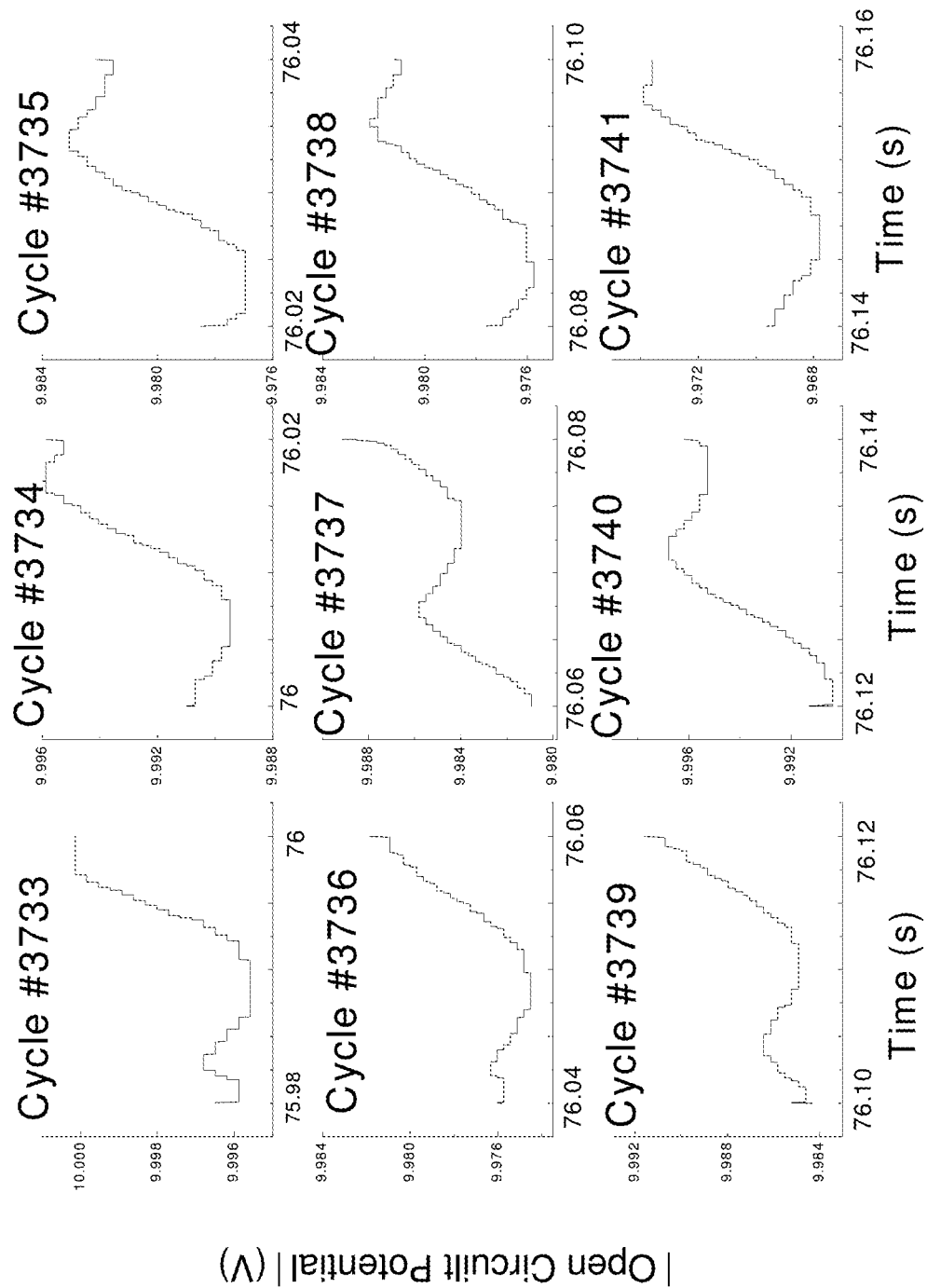

FIG. 57A depicts the Cooper Pair's non-linear amplification of increase potential in the tunnel of Josephson junction of the S-I-S device of Au/Biomimetic mitochondria-I-nanopore/Au under open circuit condition at current=0. With 1.82 mM $ZnCl_2$, 1 mg/mL MCD and 3 mM o-NPA (a); Detailed curve at the beginning of 0.77V to 0.78V from 0.001 s to 0.02 s (b); With 1.82 mM $ZnCl_2$, 1 mg/mL MCD only (c). FIG. 57B depicts an absolute constant voltage 10V without a phase change between cycle #2 to cycle #3732 at current=0, and it lasted of 74.64 s. After that, in FIG. 57C Panel Cycle #3733, it depicts the OPO voltage curve is in an irregular sine wave shape from 9.998V to 10V; Panel Cycle #3734 changed the phase from sine to cosine, intensity was from 9.99V to 9.996V; Panel cycle #3735, the phase also changed and the intensity from 9.978V to 9.98; the similar observations are observed in Panel Cycle #3736, Cycle #3737, #3738, #3739, #3740 and #3741 with phase change and 2 mV intensity change from 9.97 to 9.99.

Figure 58:
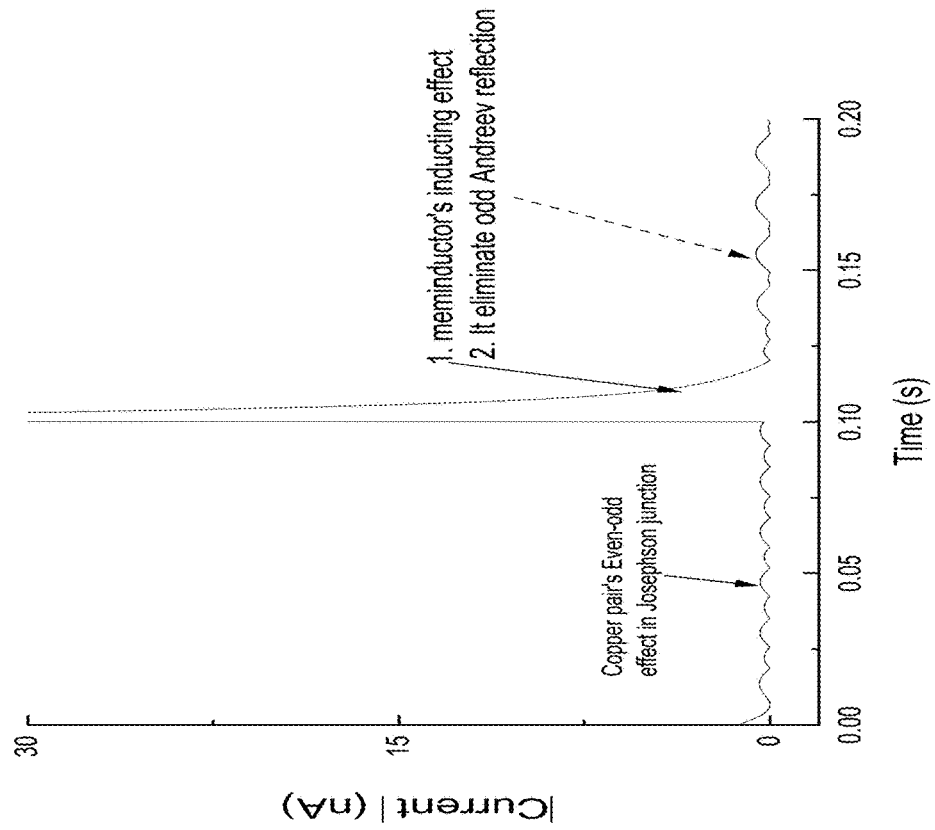

FIG. 58 depicts the Cooper Pair's Even-odd effect in the AC current pattern of the Au/S—I-S/Au device in 1.82 mM $ZnCl_2$, 1 mg/mL MCD and 3 mM o-NPA in 1M MeOH measured current after the device finished 9999 discharge/charge cycles.

Figure 59:
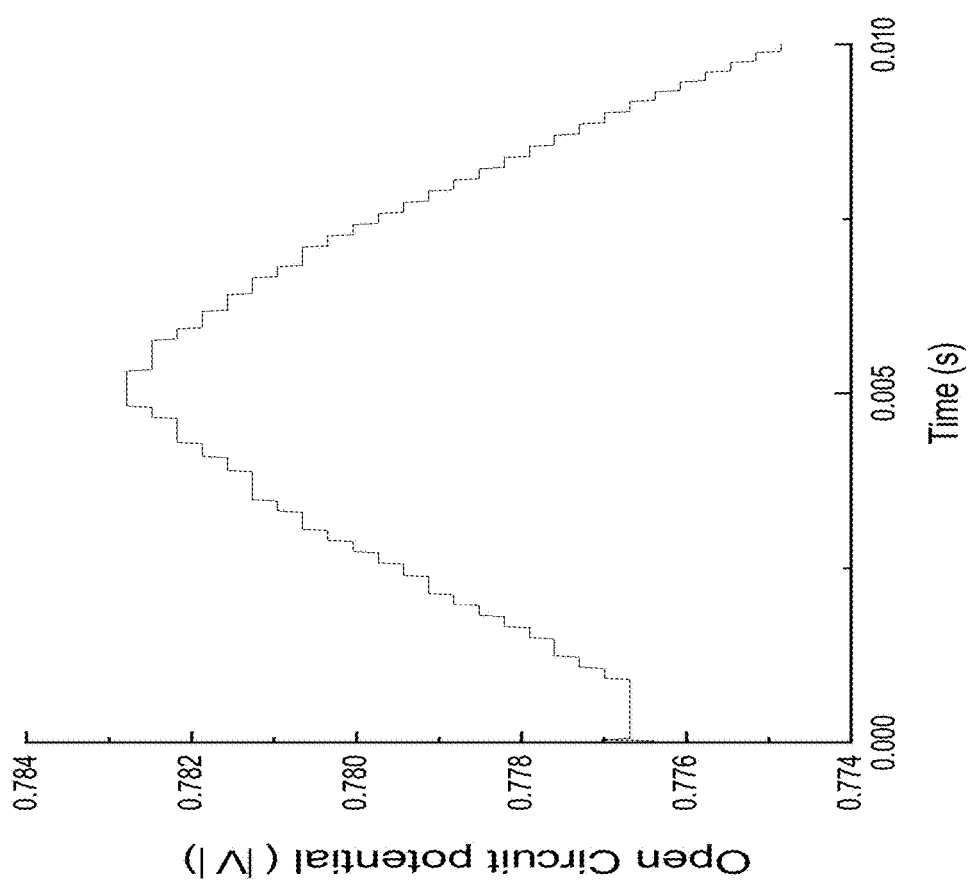

FIG. 59 depicts an enlarged view of the Cooper Pair's Even-odd effect in the AC voltage pattern of the Au/S—I-S/Au device in FIG. 57 (a).

FIG. 60A depicts the scan rate frequency affects on the charge density due to the phase change property of the Au/S—I-S/Au device in 1.82 mM $ZnCl_2$, 1 mg/mL MCD and 3 mM o-NPA in 1M MeOH at the voltage window between 0.12V to −0.12V at scan rate 1000 mV/s, 2500 mV/s (FIG. 60B), and 9000 mV/s (FIG. 60C).

Figure 60E:
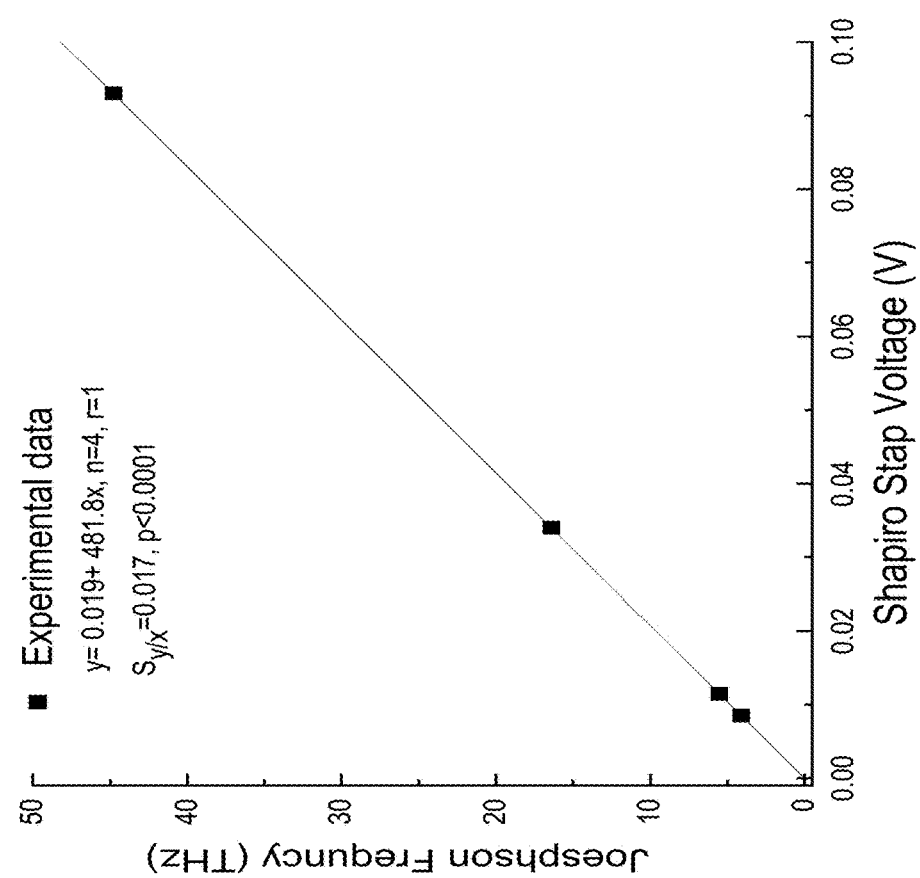
Figure 60D:
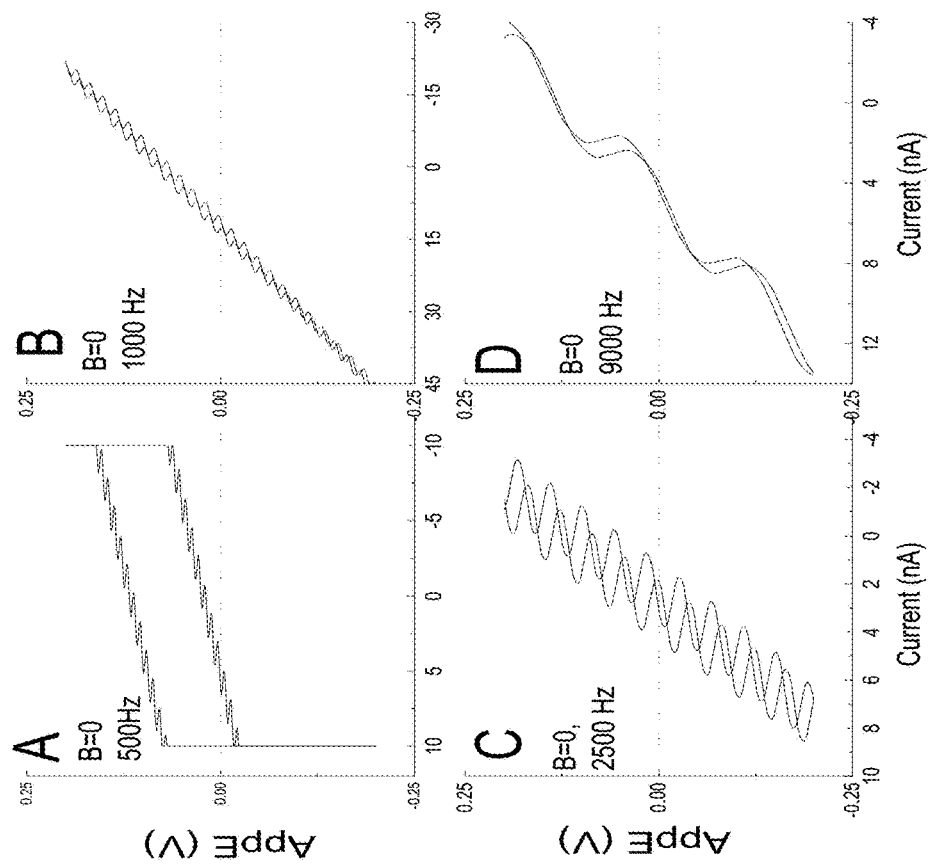
Figure 60G:
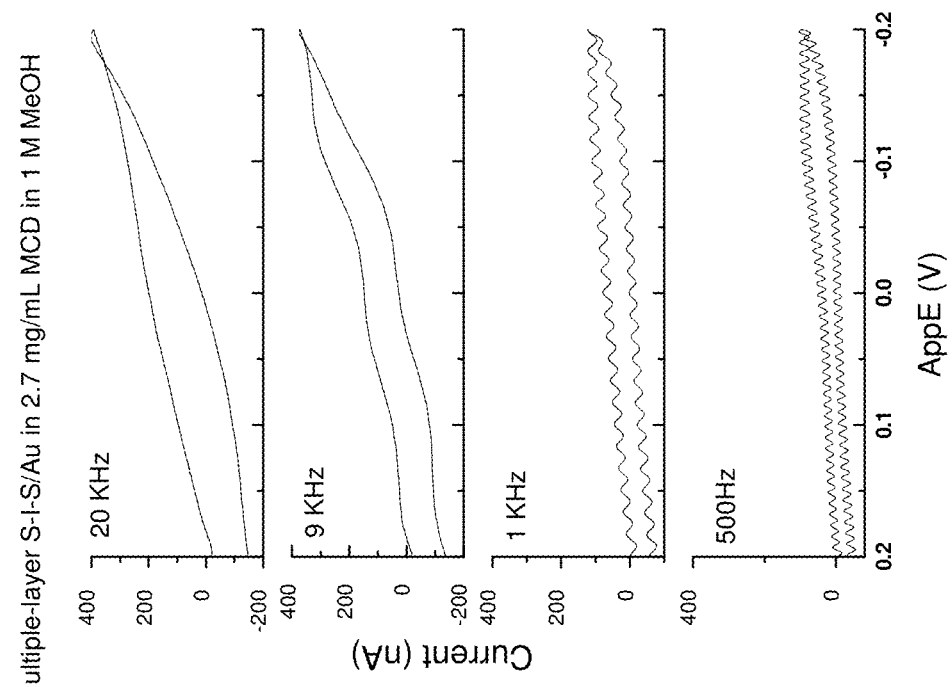
Figure 60F:
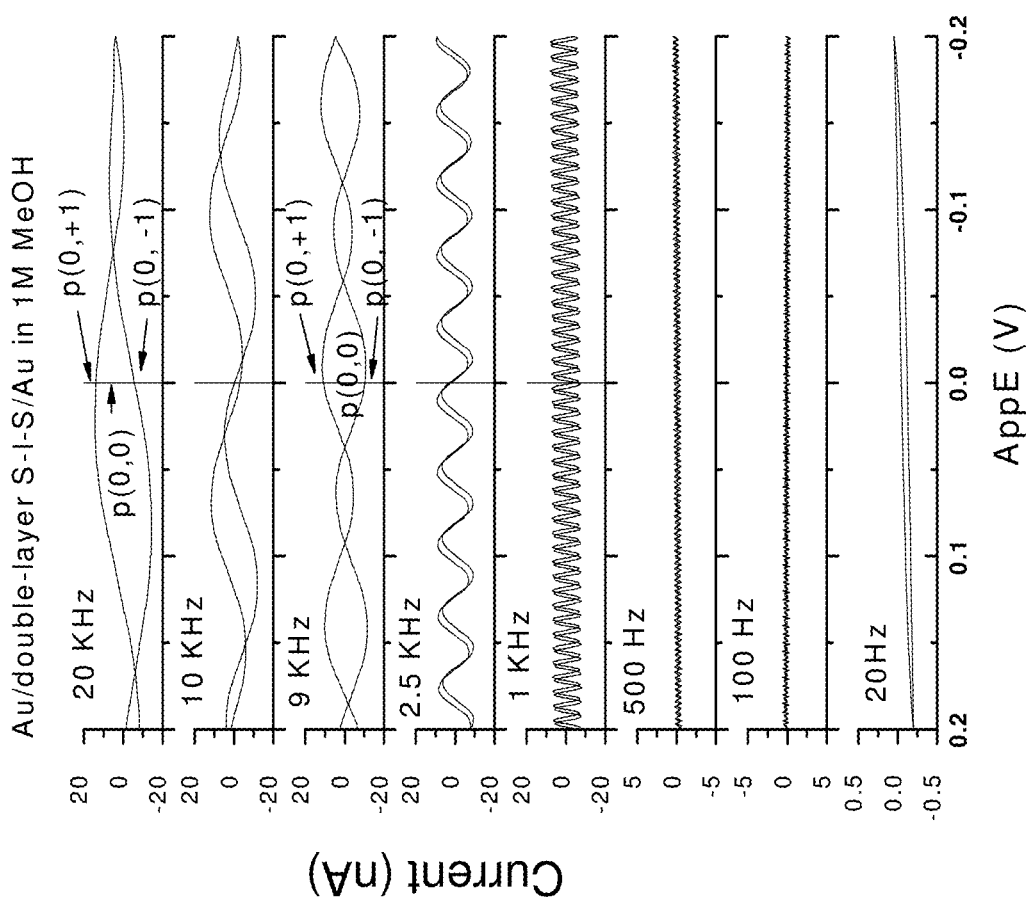
Figure 60I:
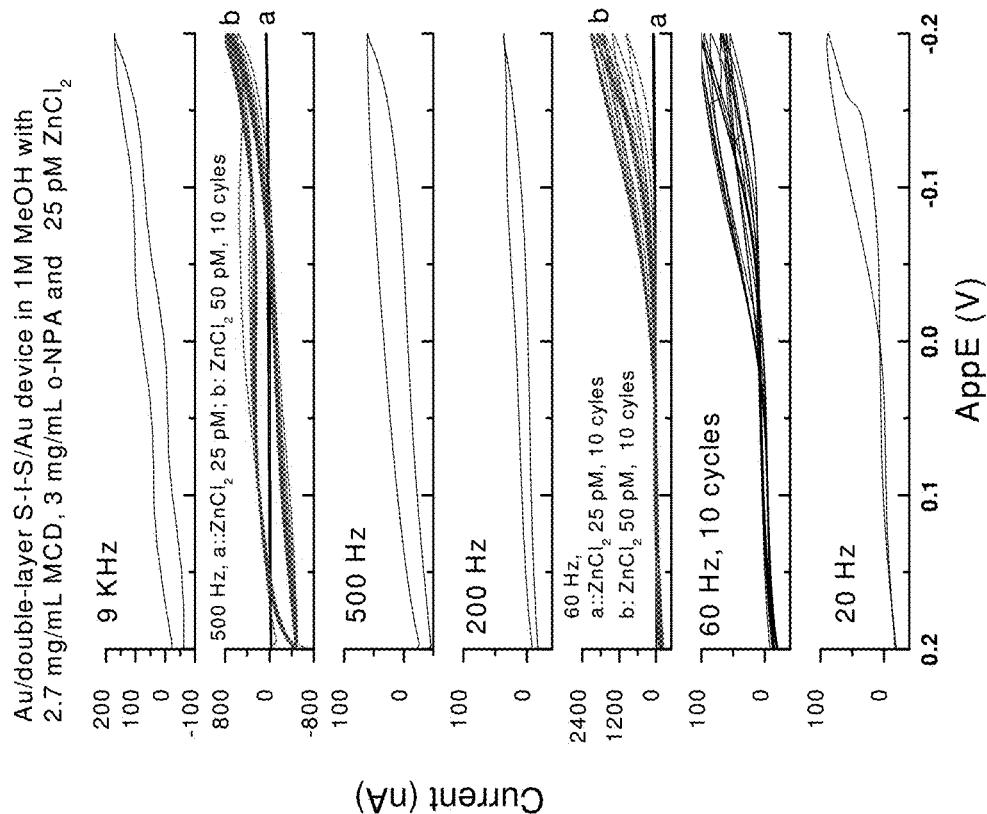
Figure 60H:
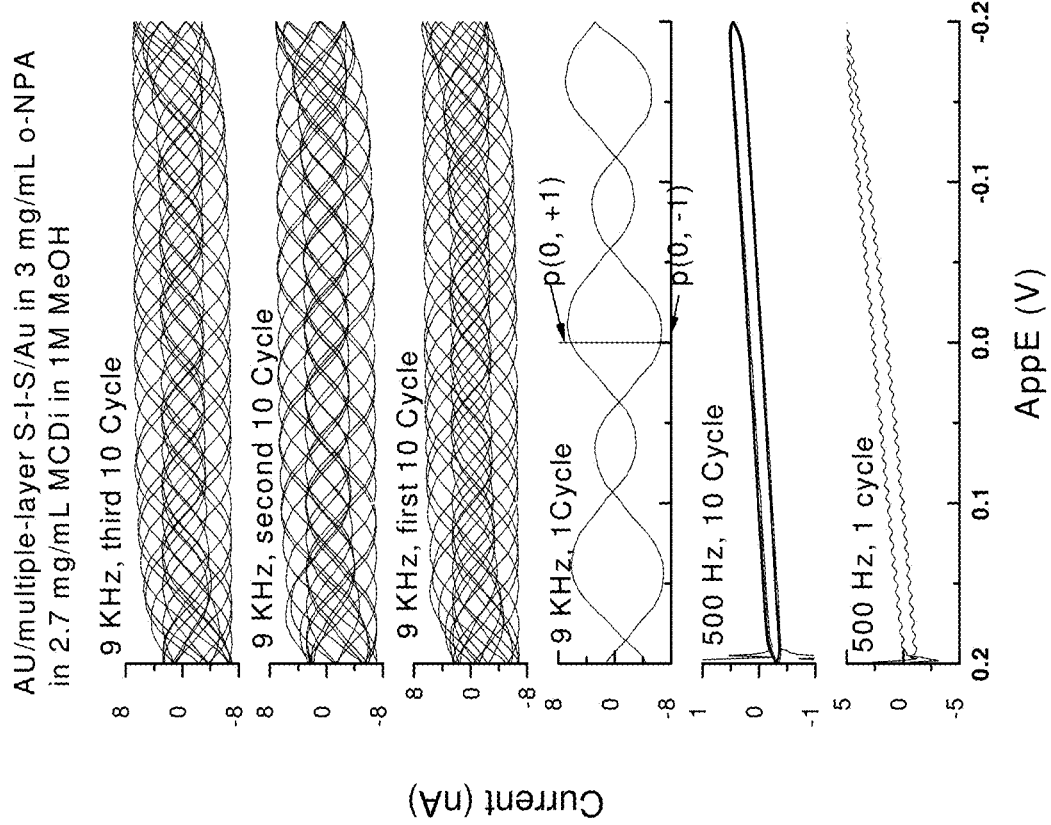
Figure 60K:
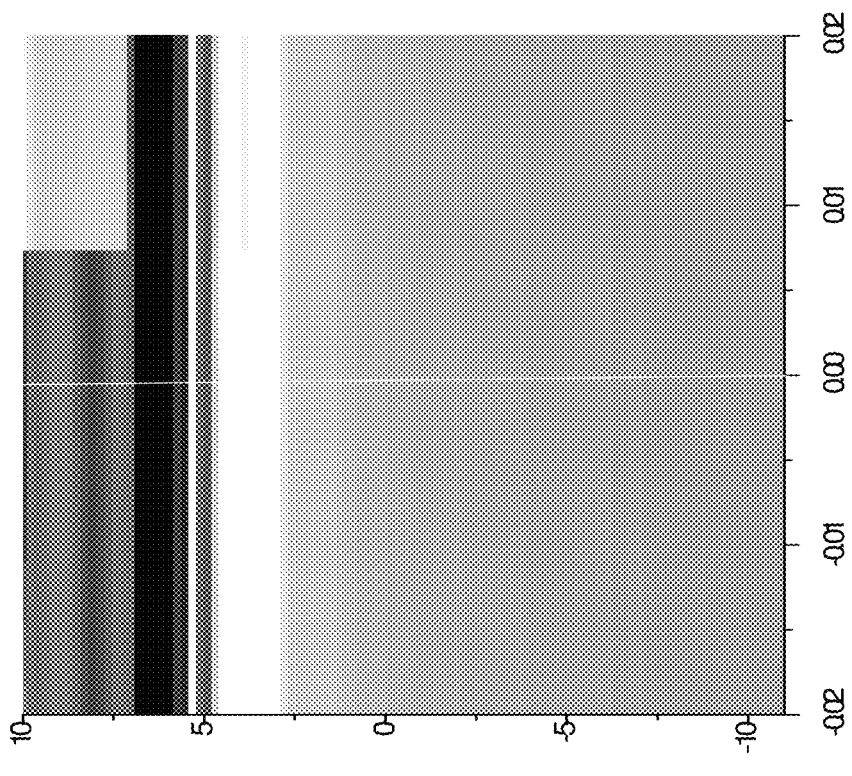
Figure 60J:
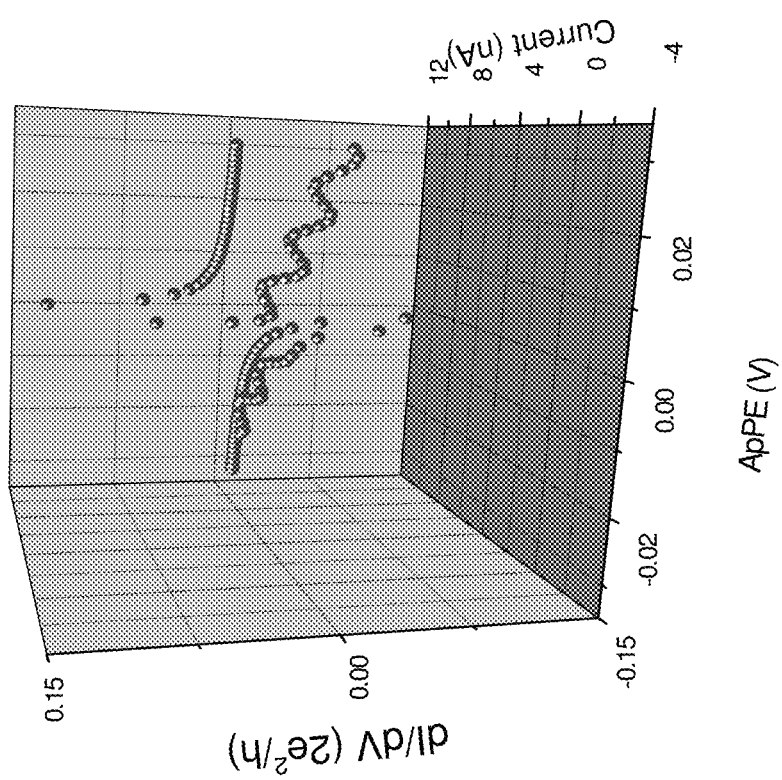

FIG. 60D Panel A depicts Scan rate effects on the current intensity and Shapiro step voltage in the Au/S—I-S/Au device in the media of 1.82 mM $ZnCl_2$, 1 mg/mL mono substituted imidazole-β-dimethyl cyclodextrin (mM-β-DMCD) and 3 mM o-NPA in 1M MeOH at a scan rate 500 Hz, 1000 Hz (Panel B), 2500 Hz (Panel C), and 9000 Hz (Panel D). FIG. 60E depicts the linear relationship between the Josephson frequency and the Shapiro step voltage by using the Least-Square linear regression plot. FIG. 60F depicts the scan rate effects on i-V curves of the Au/S—I-S/Au device in 1 M methanol from 20 Hz to 25 KHz. FIG. 60G depicts 2.7 mg/mL MCD's "Loosing of the Knot" of the superconducting effect through the scan rate change on i-V curves of the same device in 1 M methanol from 500 Hz to 20 KHz. FIG. 60H depicts a 3 mg/mL o-NPA's "Tight of the Knot" ability to recover the superconductivity through the scan rate change from 500 Hz to 9 KHz on i-V curves. At 9 KHz, for three times of 10 consecutive 10 scan cycles are shown. FIG. 60I depicts the zinc-finger's "fine-tune" ability for switch state between mem-element characteristics to superconducting by sensing and adjusting when zinc concentrations from 25 pM to 50 pM in the above media with scan arte from 20 Hz to 9 KHz. FIG. 60J depicts the "State-Switcher" of the "Zinc-finger" complex fine-tune the state to quantum super conductivity in a 3D plot of the quantum conductance vs. applied potential and vs. current in a zinc ion concentration 1.82 mM, MCD 1 mg/mL and 3 mg/mL o-NPA in 1 M MeOH with scan rate 500 Hz that the Cooper pairs penetrate a 133 μM dielectric insulator. FIG. 60K depicts an image of 2D quantum conductance band at zero-bias with y-axis is current vs. bias potential as x-axis, and the highest quantum conductance band and sub bands are shown.

Figure 61B:
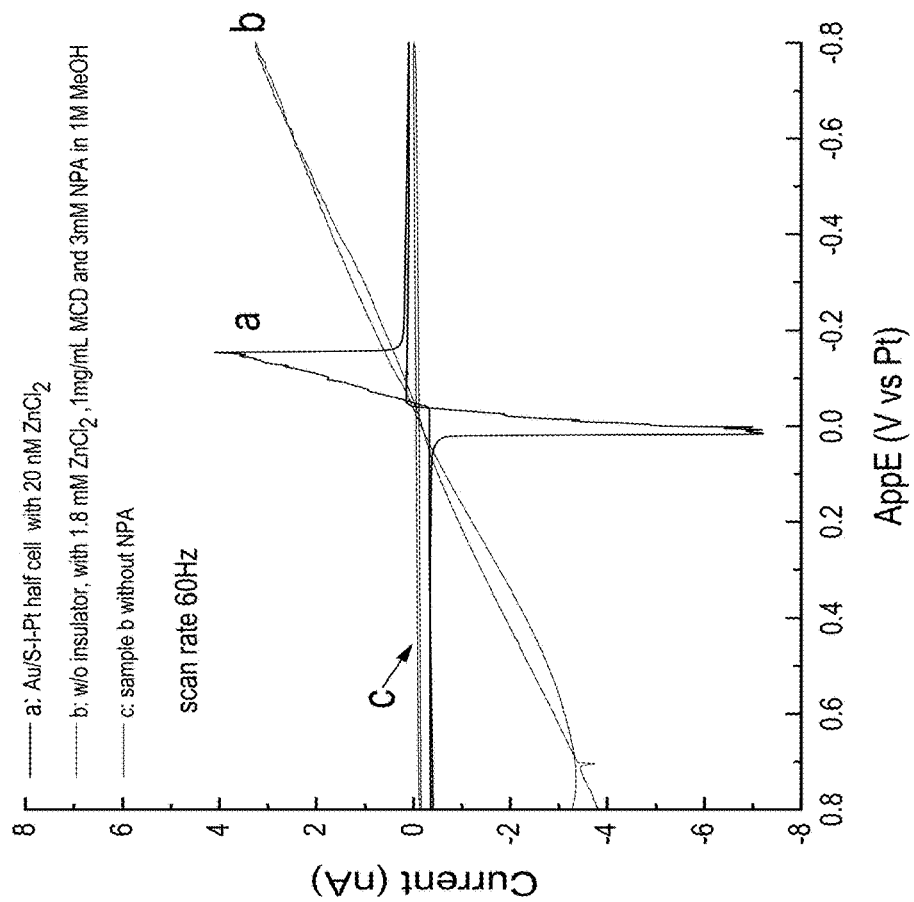
Figure 61A:
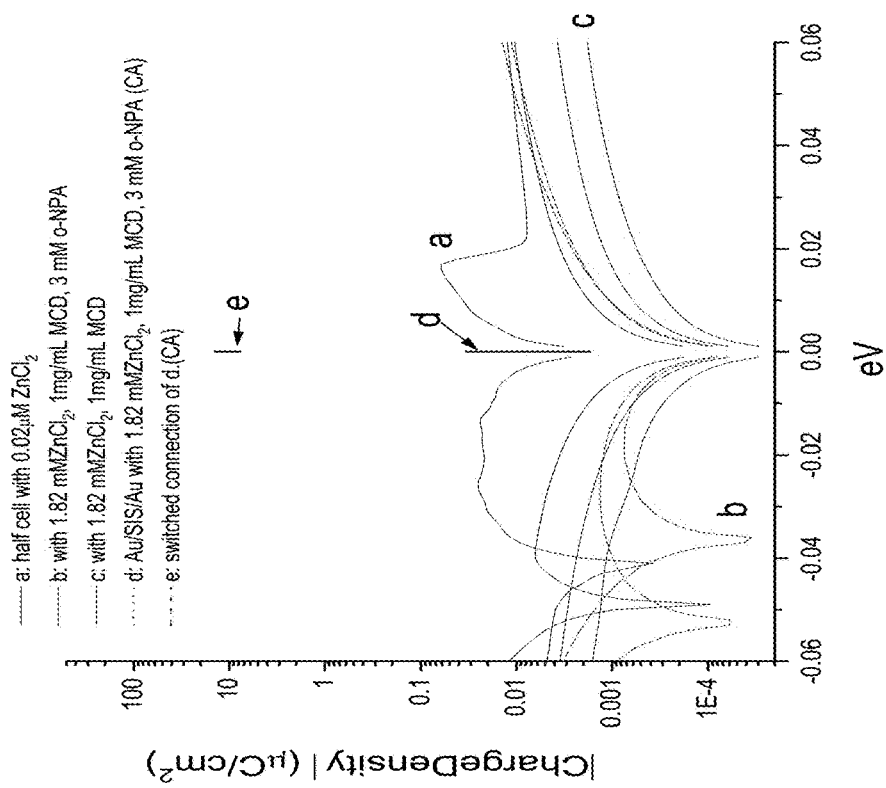

FIG. 61A depicts the superconductivity affects on charge density near the JJ location from −0.06 to 0.06V in a full Au/S—I-S/Au cell compared with a half cell of Au/S—I-Pt in various solutions under scan rate 60 Hz by the CV and the CA method, respectively. A half cell with 0.02 mM $ZnCl_2$ (a); With 1.82 mM $ZnCl_2$, 1 mg/mL MCD, 3 mM o-NPA (b); With 1.82 mM $ZnCl_2$, 1 mg/mL MCD (c); Au/SIS/Au with 1.82 mM$ZnCl_2$, 1 mg/mL MCD, 3 mM o-NPA (CA) (d); Switched connection of d (CA) (e).

FIG. 61B depicts the superconductivity affects on current intensity from 0.8V to −0.8V in (a): Au/S—I-Pt half cell with 20 nM $ZnCl_2$ (b) Without an insulator, with 1.8 mM $ZnCl_2$, 1 mg/mL MCD and 3 mM NPA in 1M MeOH; (c), sample b without NPA.

Figure 61C:
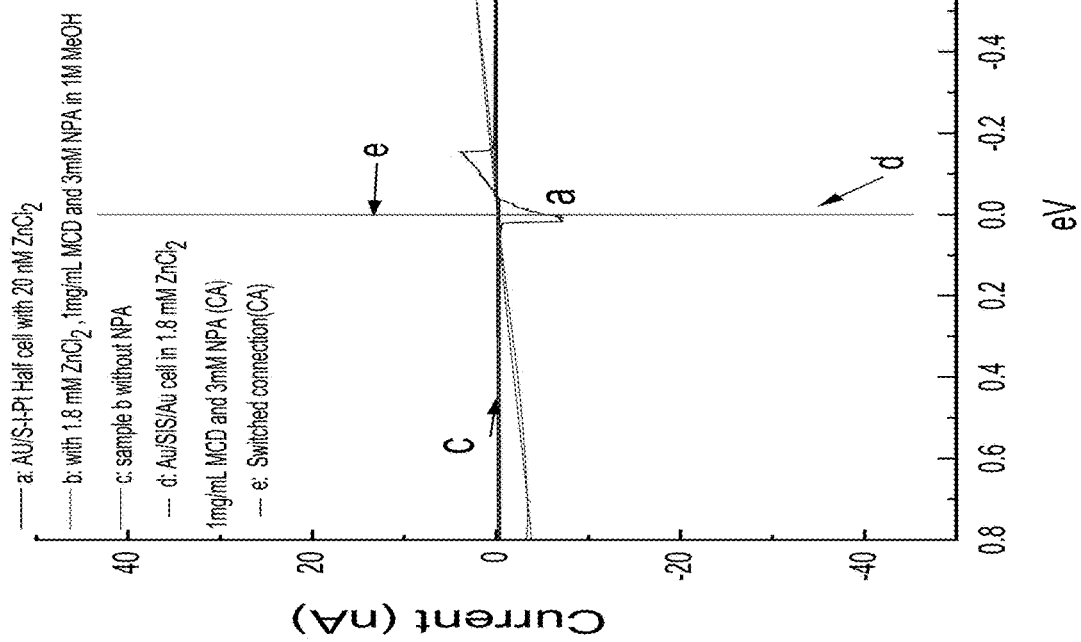

FIG. 61C depicts the superconductivity affects on current intensity in a full cell of Au/S—I-S/AU and a Au/S—I-Pt half cell in various solutions by the CV and the CA method, respectively from 0.8V to −0.8V. In an Au/S—I-Pt half cell with 20 nM $ZnCl_2$ (a); With 1.8 mM ZnCl2, 1 mg/mL MCD and 3 mM NPA in 1M MeOH (b); Sample b without NPA (c); A full superconductor/memcapacitor device Au/SIS/Au in 1.8 mM $ZnCl_2$ and 1.0 mg/mL MCD and 3.0 mM NPA (CA method) (d) and Switched connection (CA method) (e).

Figure 62:
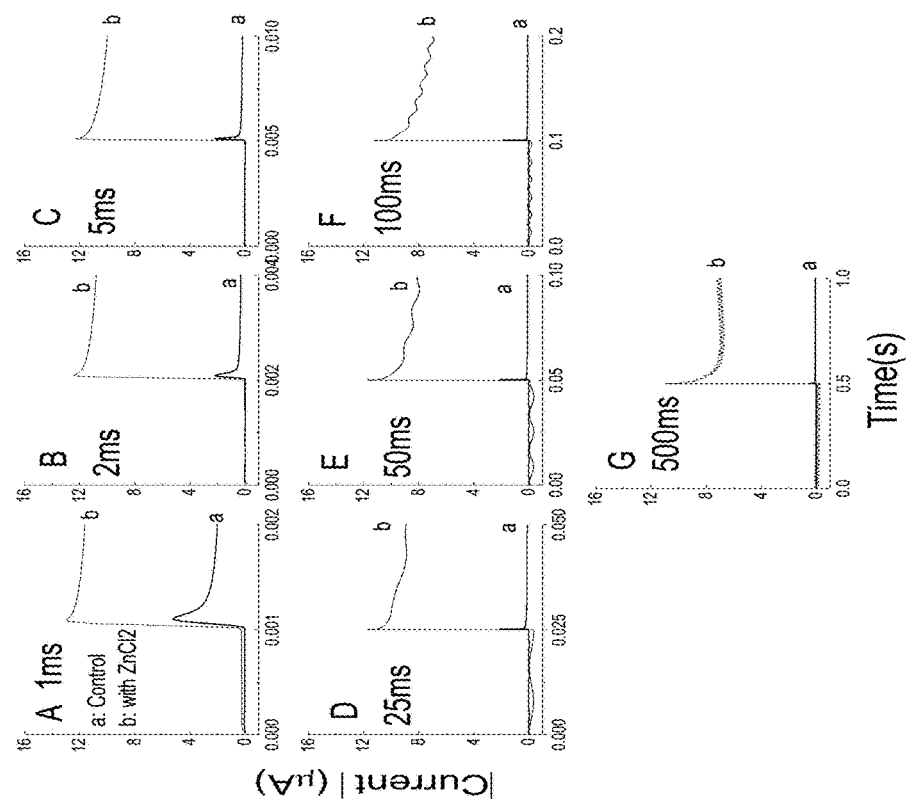

FIG. 62 depict results of seven curves of current vs. time using the CA method at the initial voltage=0, step voltage=10 mV and 600 mV, respectively at seven different time intervals of 1 ms for Panel A, 2 ms for Panel B, 5 ms for Panel C, 25 ms for Panel D, 50 ms for Panel E, 100 ms for Panel F and 500 ms for Panel G in the Au/S—I-S/Au of Au/biomimetic mitochondria-insulator-nanopore/Au superconductor/memcapacitor device in 1.82 mM $ZnCl_2$, 1 mg/mL MCD in 1 M MeOH, respectively for "a" curve, compared the control curve as "b" in each of the 7 panels.

Figure 63:
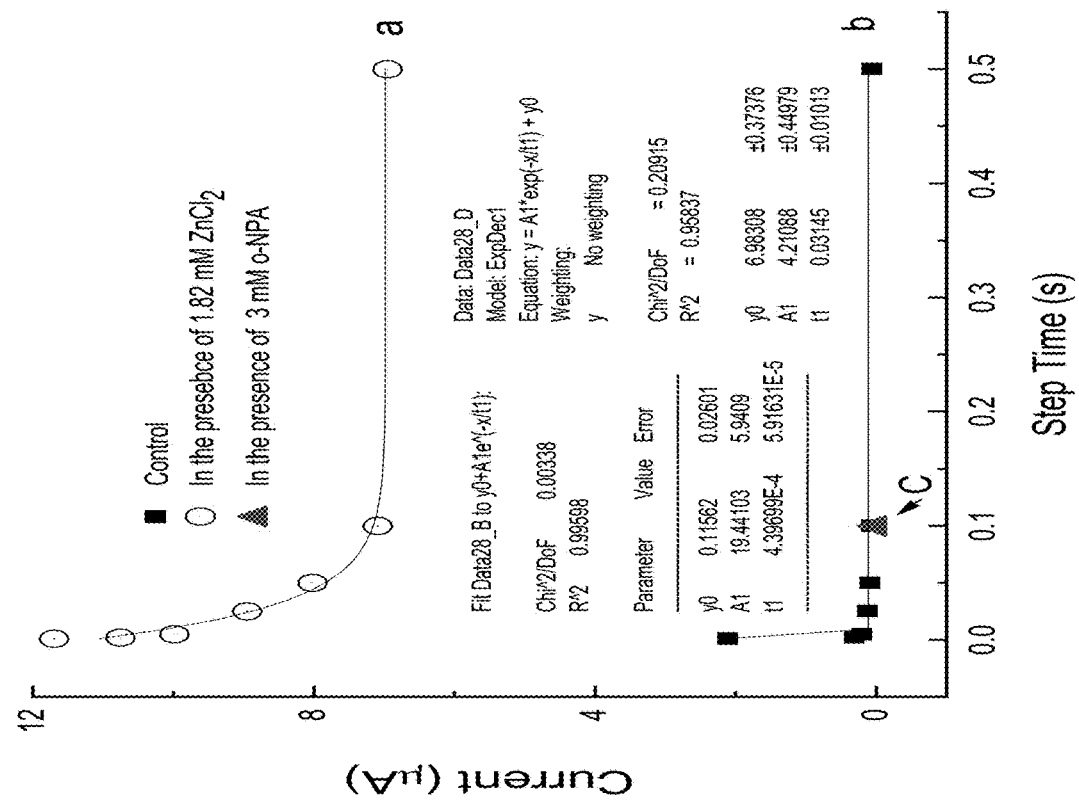

FIG. 63 depicts the o-NPA effects on current intensity through the plot of current vs. time interval in FIG. 62, for without o-NPA: (1) the controls were expressed as the solid black square as the line (b); (2) with 1.82 mM $ZnCl_2$ expressed as open circles as the line (a). The red triangle is for in the above solution in the line "a" with an additional spiked 3 mM o-NPA (final concentration) expressed as the point (C).

Figure 64:
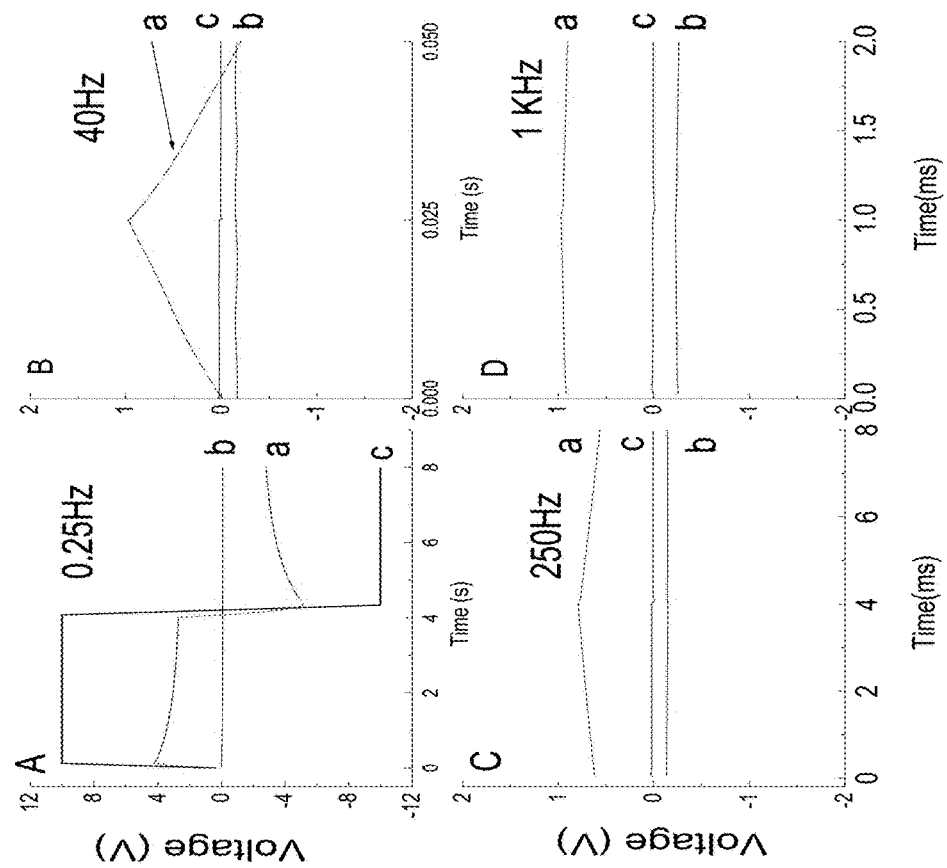

FIG. 64 depicts frequency factor affects on the spontaneous voltage discharge/charge curves between the Au/S—I-S/Au device 1 compared with the Device 2 of Au/Superconductor/mamcapacitor sensor. (a) depicts the plot of voltage curves vs. time in the AU/Superconductor/memcapacitor sensor without an insulator, i.e., the Device 2, and without an Au/nanopore SAM electrode in 1.82 mM $ZnCl_2$ and 1 mg/mL MCD and 3 mM o-NPA; the full superconductor/memcapacitor device as Device 1, AU/S-I-S/AU in 1.82 mM $ZnCl_2$ and 1.0 mg/mL MCD, without o-NPA curve as (b); the Device 1's voltage vs. time curve in 1.82 mM $ZnCl_2$ and 1 mg/mL MCD with 3 mM o-NPA under ±10 nA in 1 M MeOH as (c); Panel A is at 0.25 Hz; 40 Hz as shown in Panel B; 250 Hz as shown in Panel C and 1 KHz as shown in Panel D. Data rate was same 50 kHz for all panels.

Figure 65B:
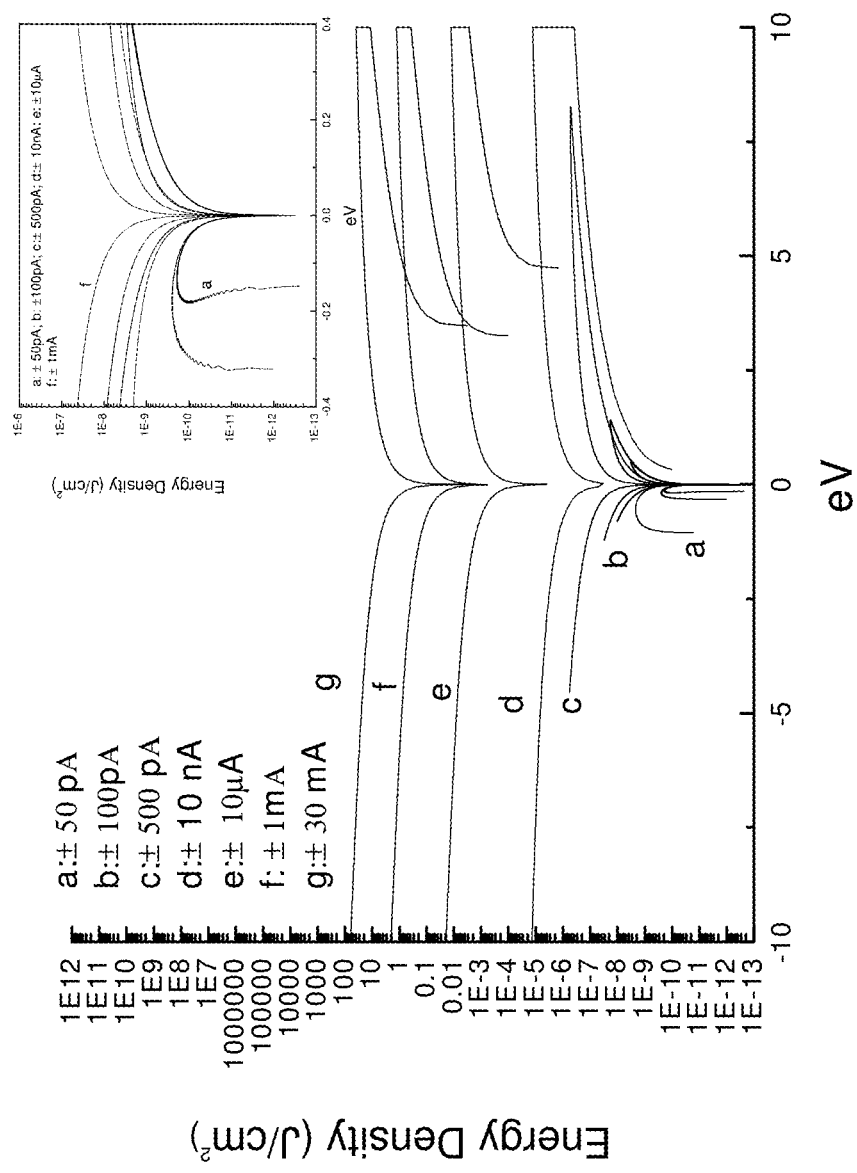

FIG. 65A depicts plots of voltage vs. time at different current levels in 7 levels: ±50 pA, ±100 pA, ±500 pA, ±10 nA, ±10 µA, ±1 mA, ±30 mA in order to study the current factor affects on the voltage intensity in the device of Au/Superconductor biomimetic mitochondria/insulator/nanopore SAM/Au device in 1.82 mM $ZnCl_2$, 1.0 mg/mL MCD and 3.0 mM o-NPA in 1M MeOH at 0.25 Hz. FIG. 65B depicts plots of energy density vs. voltage at different current levels in 7 levels: ±50 pA, ±100 pA, ±500 pA, ±10 nA, ±10 µA, ±1 mA, ±30 mA in order to study the current factor affects on the energy density in the device of Au/Superconductor biomimetic mitochondria/insulator/nanopore SAM/Au device in 1.82 mM $ZnCl_2$, 1.0 mg/mL MCD and 3.0 mM o-NPA in 1M MeOH at 0.25 Hz. The insert was the enlargement of the plots from the lower current level.

Figure 66A:
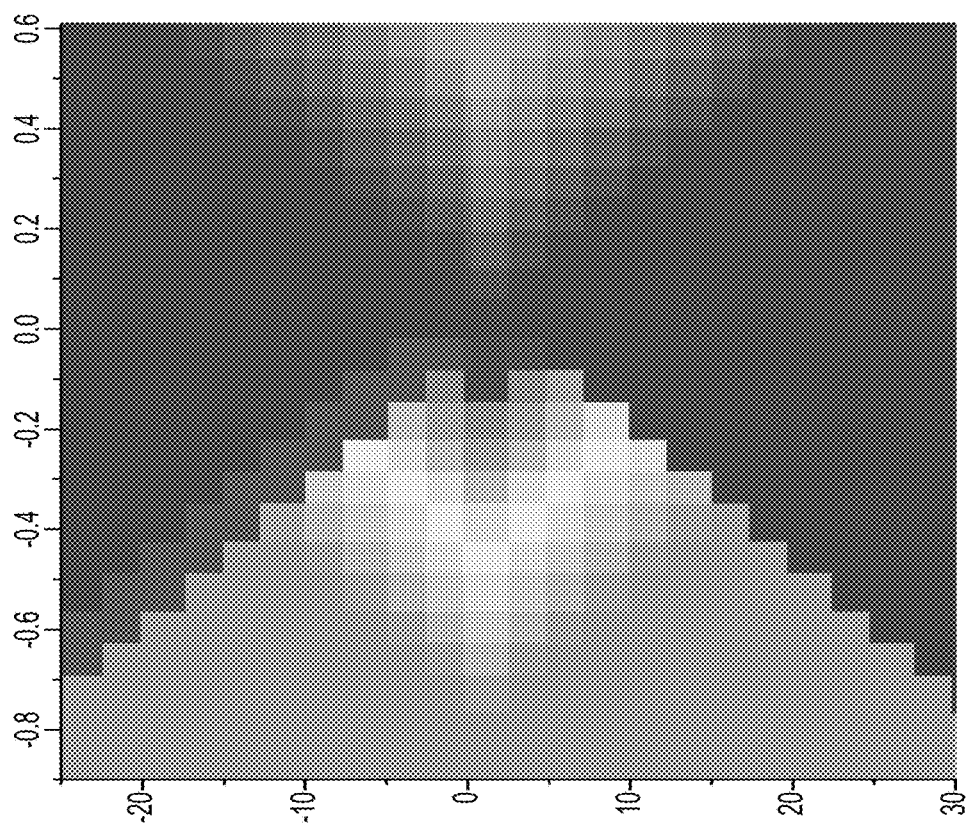
Figure 66B:
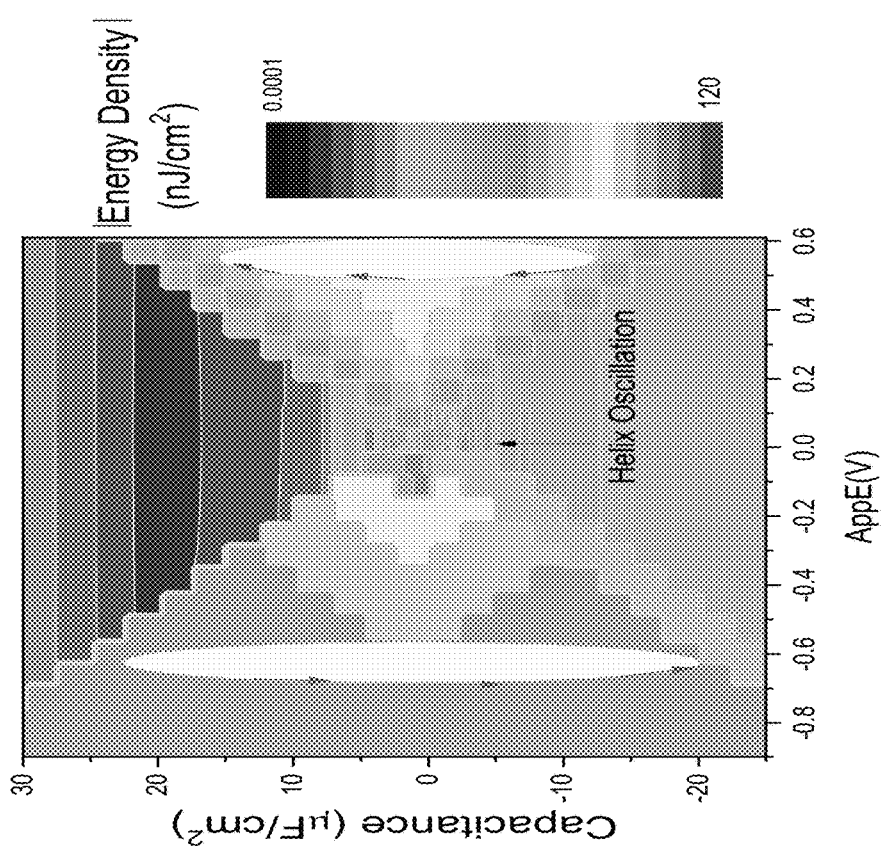

FIG. 66A depicts the Cooper Pair's Helix-oscillation in the JJ tunneling reflection affects on energy density as Z axis (in absolute value), capacitance as Y axis and voltage as X axis in the Au/S—I-S/Au device in 1.82 mM $ZnCl_2$, 1.0 mg/mL MCD and 3 mM o-NPA at ±50 pA current at 0.25 Hz. FIG. 66B depicts the 2D double helix-cone shape optical image of the energy density map related to capacitance and voltage of FIG. 66A. FIG. 66C depicts the 3D map of FIG. 66A.

Figure 67:
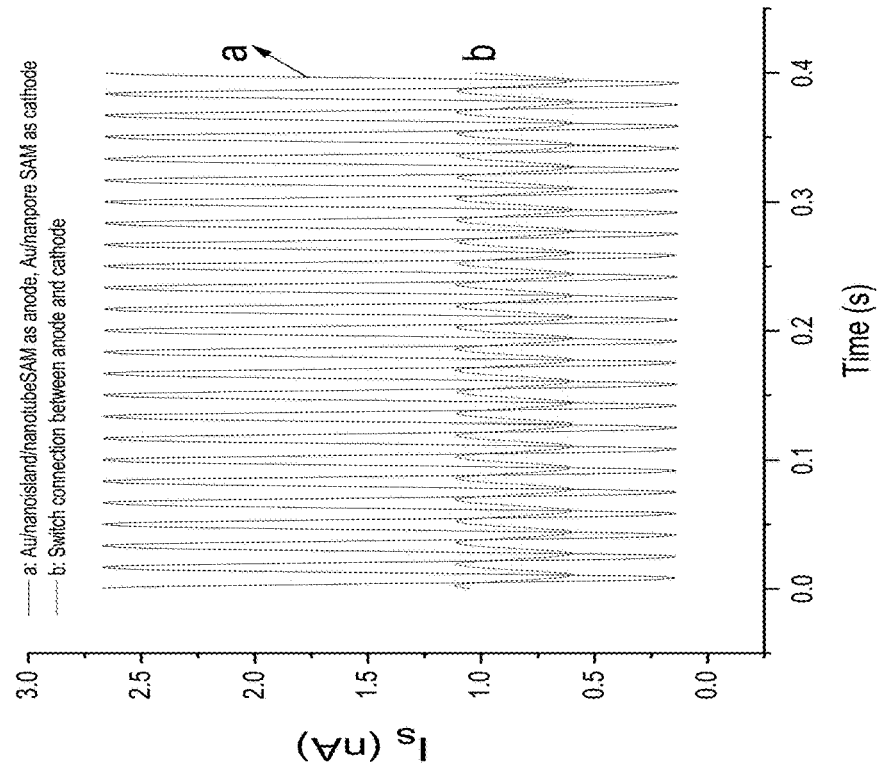

FIG. 67 depicts the plot of AC $I_s$ current vs. time for spontaneous energy harvesting under zero applied potential at each of two steps of 200 ms at the AU/S-I-S/Au device under 1.82 mM $ZnCl_2$, 1.0 mg/mL MCD in 1M MeOH with 3.0 mM o-NPA with connections of Au/Biomimetic mitochondria SAM (nanotube of organic-Zn polymer on top of nanoisland of CHAT)-I as anode, the Au/nanopore SAM as cathode as shown (a); Switched connection as (b).

Figure 68A:
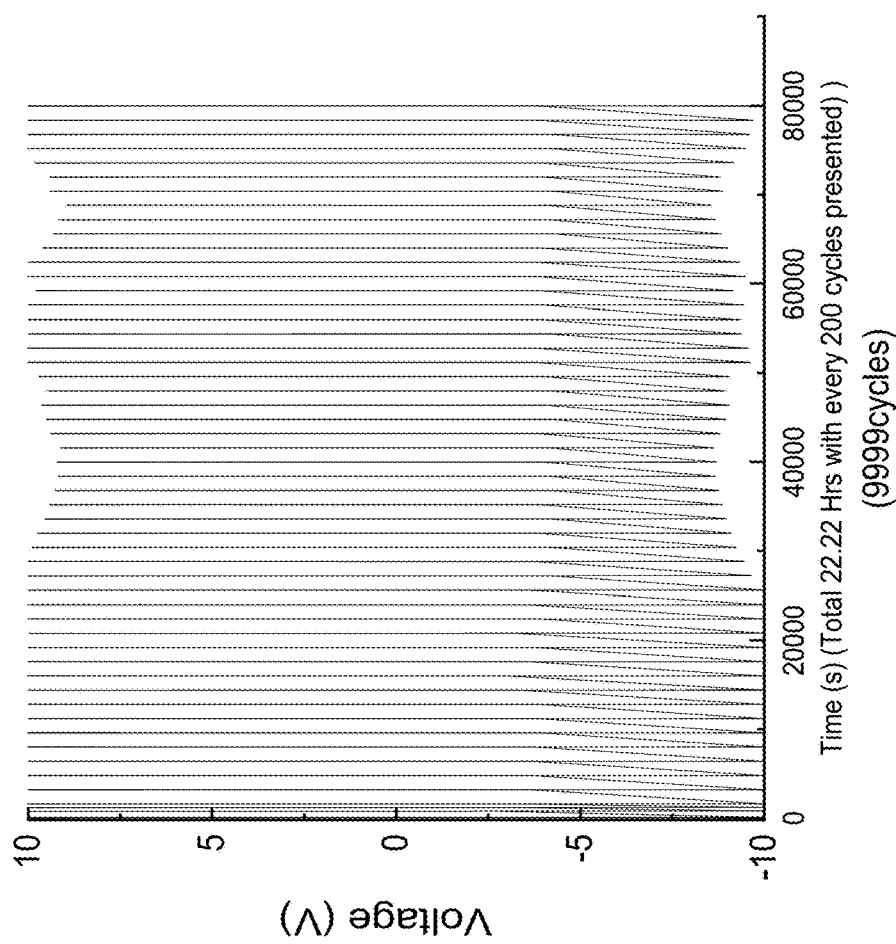
Figure 68B:
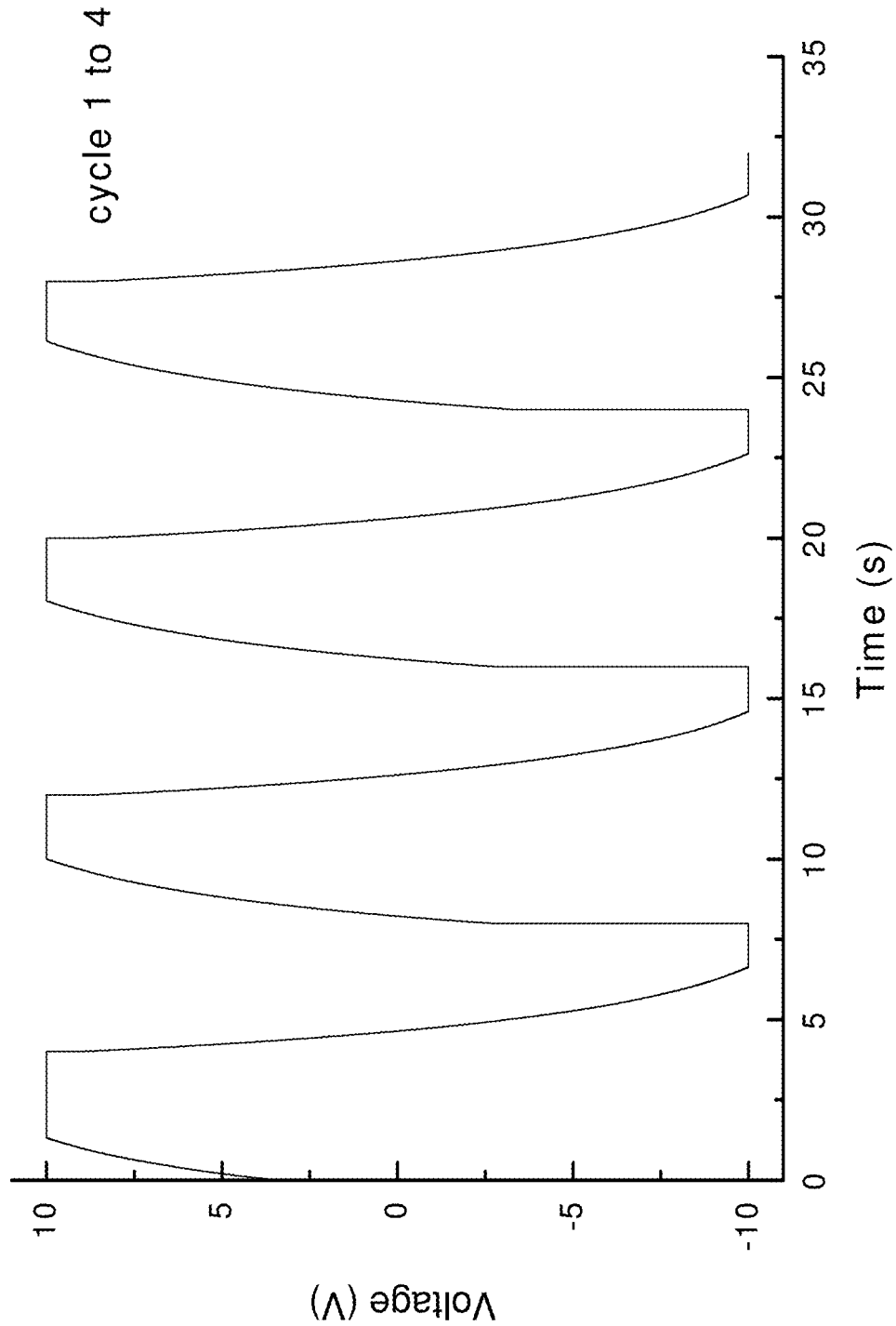

FIG. 68A depicts the Au/S—I-S/Au device's real-world performance for conducting discharge/charge 9999 cycles with total 22.22 hrs at room temperature at normal pressure maintaining ±10V at ±30 mA in 1.82 mM $ZnCl_2$, 1.0 mg/mL MCD in 1M MeOH with 3.0 mM o-NPA. FIG. 68B depicts the first 4 cycles in discharge/charge for voltage vs. time at 0.25 Hz as the conventional testing frequency.

Figure 69B:
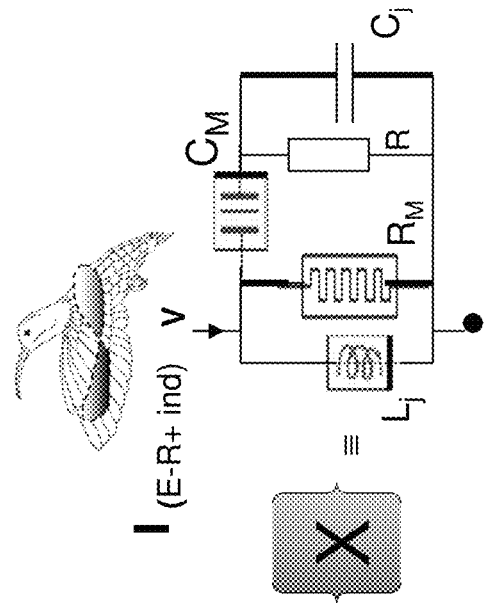
Figure 69A:
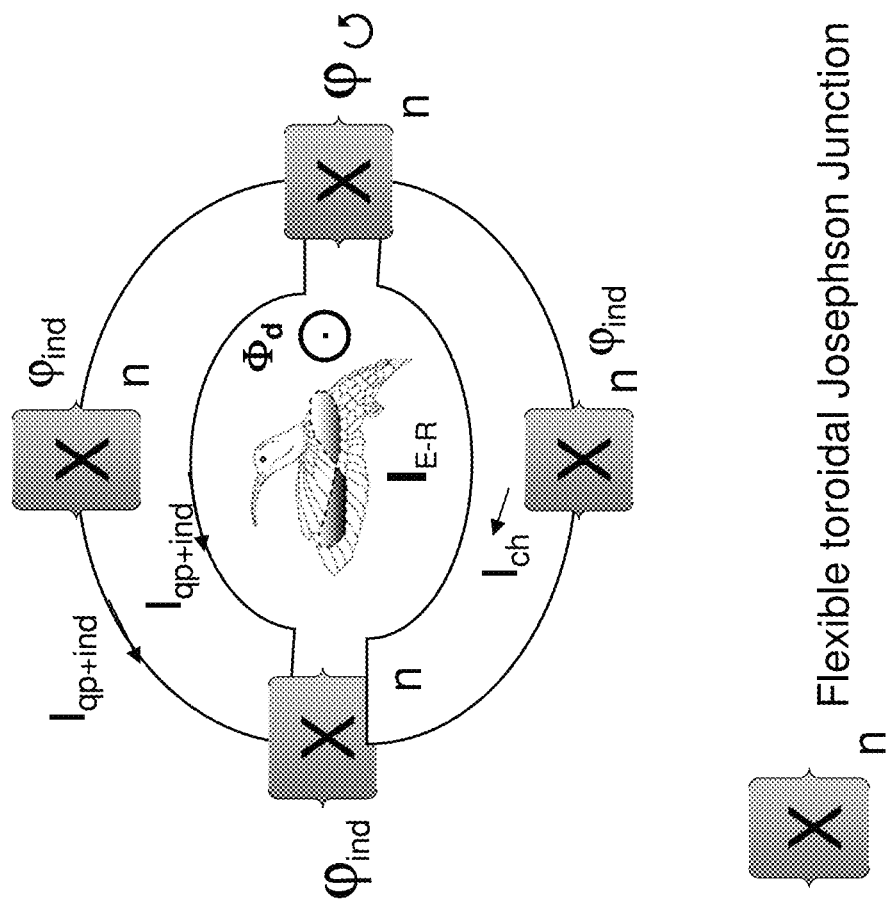

FIG. 69A depicts the circuitry symbol of the Flexible Toroidal Josephson Junction Electronic Quantum Qubit (FTJJEQUBIT) comprising of at least 4 or more junctions and a self-powered switchable reversible electron-relay in the center which is the fundamental function of the biomimetic self-assembled membrane (SAM) that the memselement construction relies on.

FIG. 69B depicts the superconducting FTJJ circuit configuration with the mem-inductor, mem-ristor and Josephson junction connected in parallel, $L_j$ is the inductance of the Josephson junction, $R_M$ is the resistance of the memristor, $C_j$ is the capacitance of the Josephson junction; the memcapacitor is connected in serials having the $C_M$ means memcapacitance. The power supply is based on the intrinsic E-R and its inductive current providing an open circuit potential cross the device.

DETAILED DESCRIPTION OF THE INVENTION

Example 1—Fabrication of the Nanostructured Biomimetic Self-Assembling Membranes (SAM)

The nanostructured biomimetic ACHE SAM with the vertical bridged conformational "Mutated ACHE Gorge" was freshly prepared. Polyethylene glycol diglycidyl ether (PEG), triacetyl-β-cyclodextrin (T-CD), poly(4-vinylpyridine) (PVP) were purchased from Sigma. PVP was purified before use. The mono derivative dimethyl β-cyclodextrin named as (mM-β-DMCD) was generally synthesized according to the published procedures [35]. The appropriate amount of solutions of individual polymer and reagents were prepared [36]. The mixture solution was made up by mM-β-DMCD (2 g/L to 2.5 g/L, T-CD 2-3 mM, PEG 2 g/L-3 g/L and PVP (40 mg/dL-80 mg/dL), the mixture was incubated in 37 C for 2-3 hrs, then added 0.02M o-NPA with the molar ratio to TCD in the range of (500-1000):1 to the mixture for device 1 with a flat membrane with nanopores. The vertical bridge membrane with nanopores for device 2 did not apply o-NPA. The Au electrode has 50 nm thicknesses and 3 mm in diameter. The mixture solution was injected onto the surface of the electrode and was incubated for 48 hrs at incubator [36]. After that, the further clean and incubating procedures were followed by literature 36.

The nanostructured biomimetic "Normal ACHE Gorge" neuronal network SAM with the flat bridged conformation, nanopores and lattices was freshly prepared by adding appropriate amount of o-nitrophenyl acetate (o-NPA) into the above described mixture solution for construction of the vertical bridged ACHE SAM. All other procedures were followed by literature 36.

Example 2—AFM Measurements

Figure 1A:
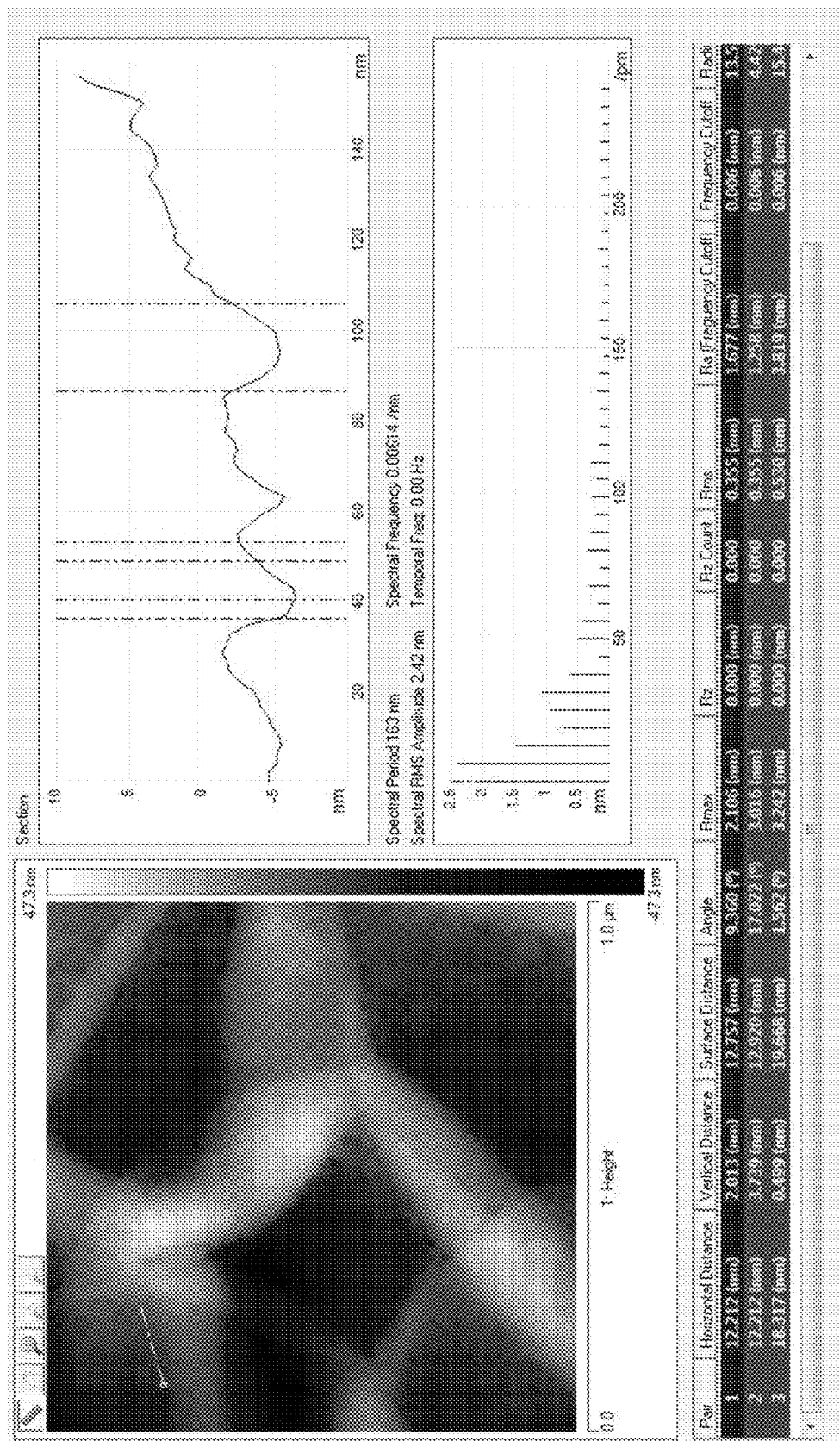
FIG. 1A is a face-to-face view of the three-dimensional atomic force microscopy (AFM) image of the nanostructured "ATP Lid" with a vertical bridge and the cross section analysis results were presented in the table.
Figure 1C:
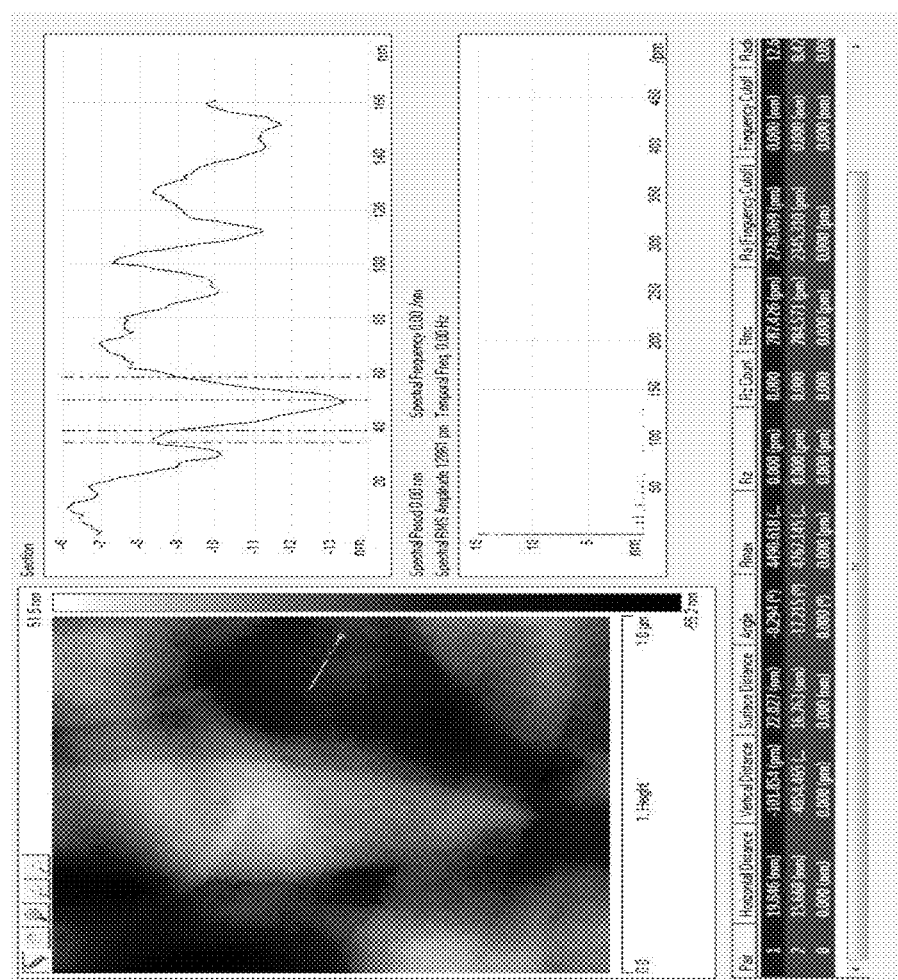
FIG. 1C is a side view of the vertical bridge as shown in the 2D AFM image with the bridge deepness in cross section analysis.
Figure 1B:
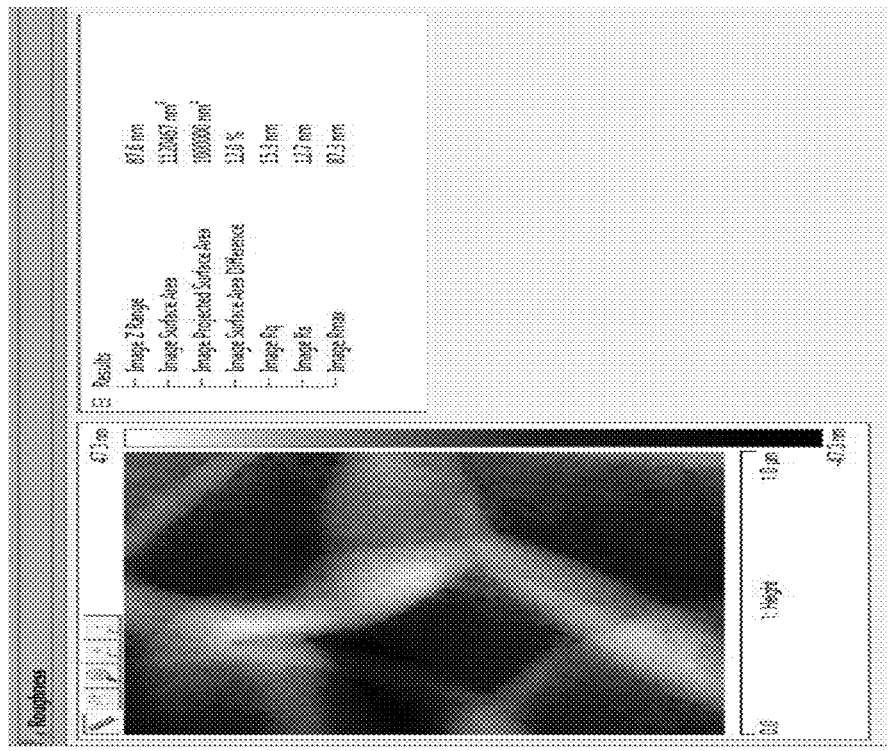
FIG. 1B is a face-to-face view of the vertical bridge with the AFM results in membrane surface roughness measurements in Peak-to-Valley (Z range), and the Root Mean Square (RMS), and Average Roughness ($R_a$) were shown in the results table that are corresponding to this image.
Figure 1E:
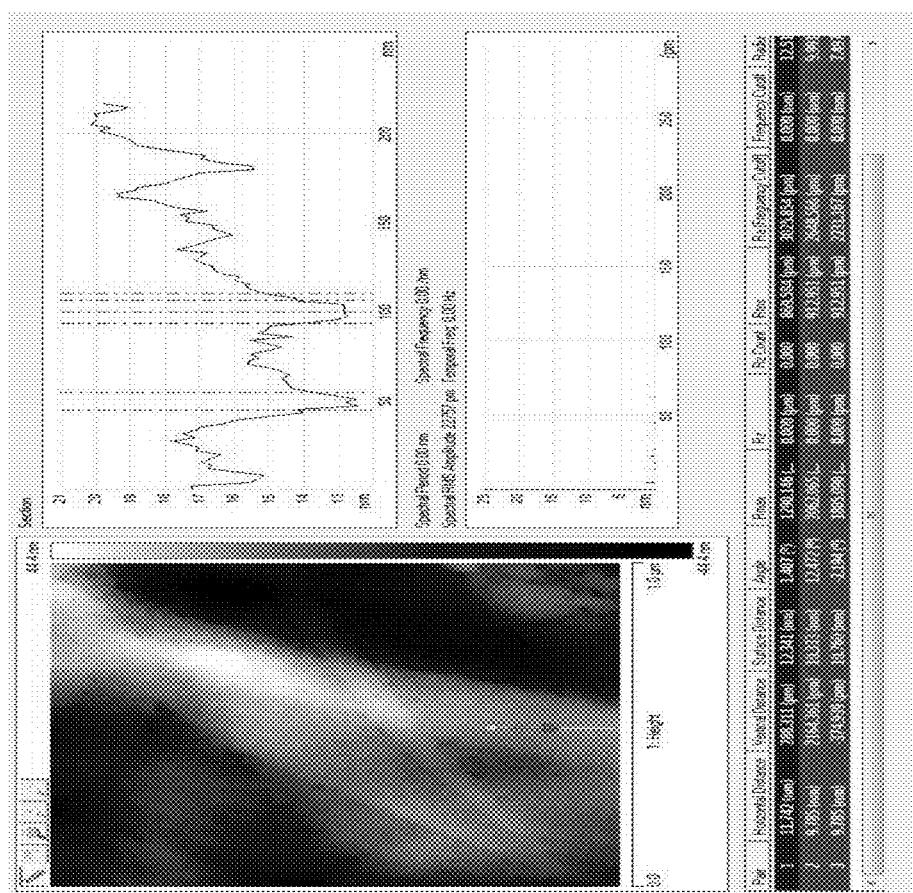
Figure 1D:
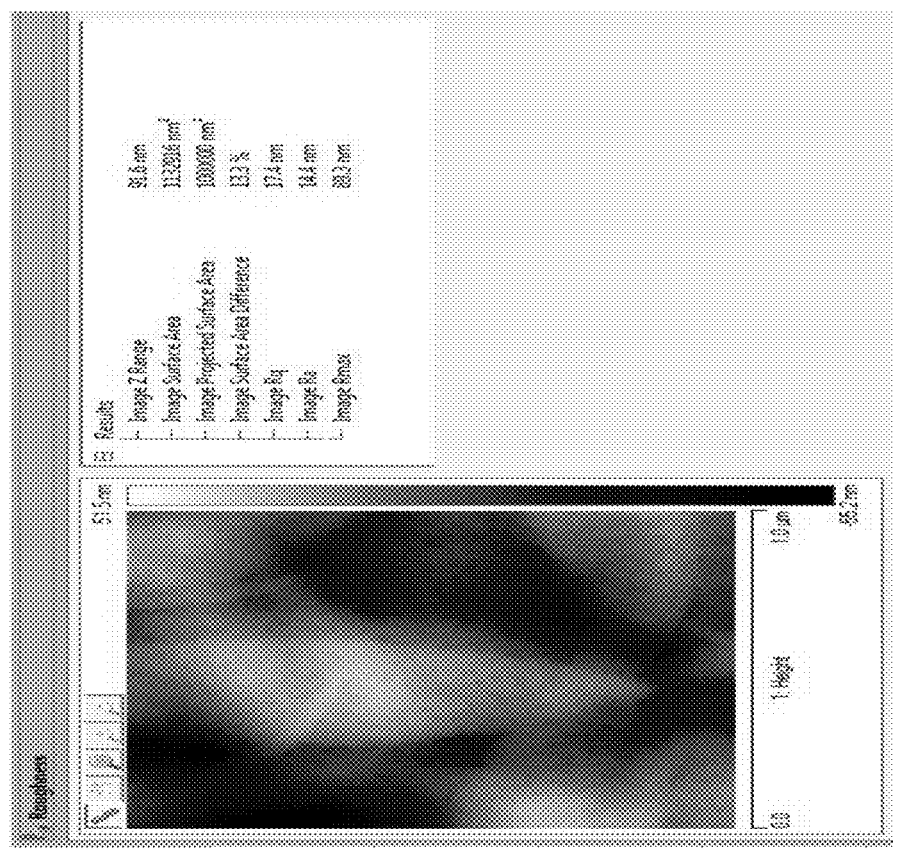
FIG. 1D shows the AFM specification of the surface roughness results based on the side view.

The morphology of the three CD-SAMs were characterized by using an instrument (model Multimode 8 ScanAsyst, Bruker, Pa.). Data collected in PeakForce Tapping Mode. Probes used were ScanAsyst-air probes (Bruker, Pa.). The silicon tips on silicon nitride cantilevers have 2-5 nm radius. The nominal spring constant 0.4 N/m was used. NanoScope Analysis v1.40r2 software was used. FIG. 1A illustrates the vertical conformational AFM image of ACHE bridge structure by cross analysis. The average "breathing pore" vertical height by cross section analysis is 3.74 nm with the pore width of 12.2-18 nm and the RMS (surface morphology) is 3.55 nm. The lattice distributed pores can be seen in the image. The bridge vertical height is 47.3 nm with the length of 940 nm. FIG. 1B illustrates the membrane specifications in roughness is 15.2 nm and the membrane surface thickness is 47.3 nm. FIG. 1C shows the bridge vertically oriented of 51.5 nm, underneath of the bridge is the "breath pore" with pore diameter of 15-20 nm and depth of 0.5 nm and the surface roughness is 0.287 nm. FIG. 1D shows the membrane surface roughness is 17.4 nm. FIG. 1E shows the AFM image of the shining horizontal cross bar associated with the vertical bridge of FIG. 1A. The cross bar channel width is 200-600 nm and height is 44.4 nm, and length is 1100 nm. Underneath of the bridge are "breathing pores" of 0.2 nm in depth and 10-12 nm in diameter with RMS value 0.9 nm. FIG. 1F shows the membrane surface morphology in 17.9 nm. FIG. 1G shows the AFM in a larger window view of 9 µm² and we can see the breathing pores distributed evenly filled inside of each orderly square lattices and the bridges are on top with a vertical fall difference of 50-100 nm.

Figure 2B:
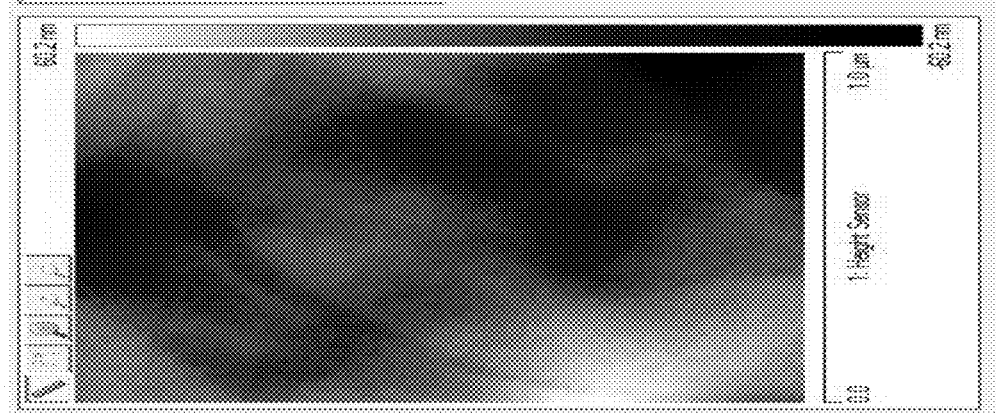
FIG. 2B is the AFM of the "ATP Lid" flat bridge specifications with the roughness values are also shown for this image.
Figure 2A:
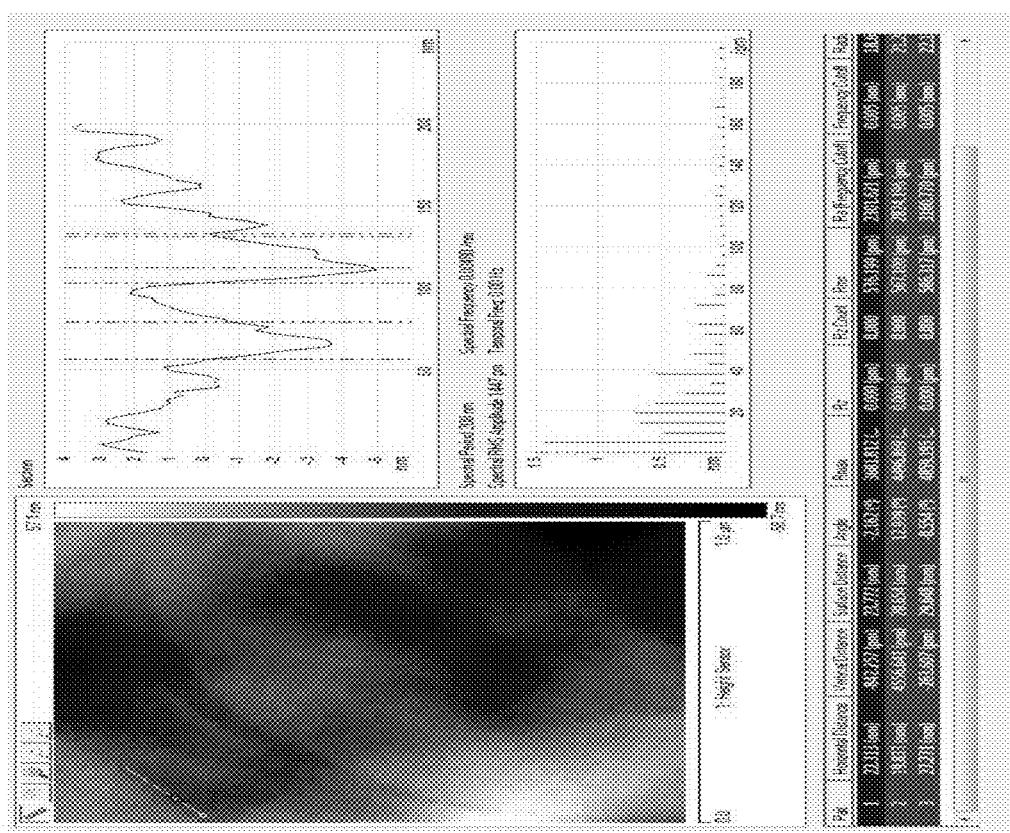
FIG. 2A shows the AFM image of the nanostructured "ATP Lid" with a flat horizontal bridge and the cross section analysis results were shown in the table listed below.
Figure 2D:
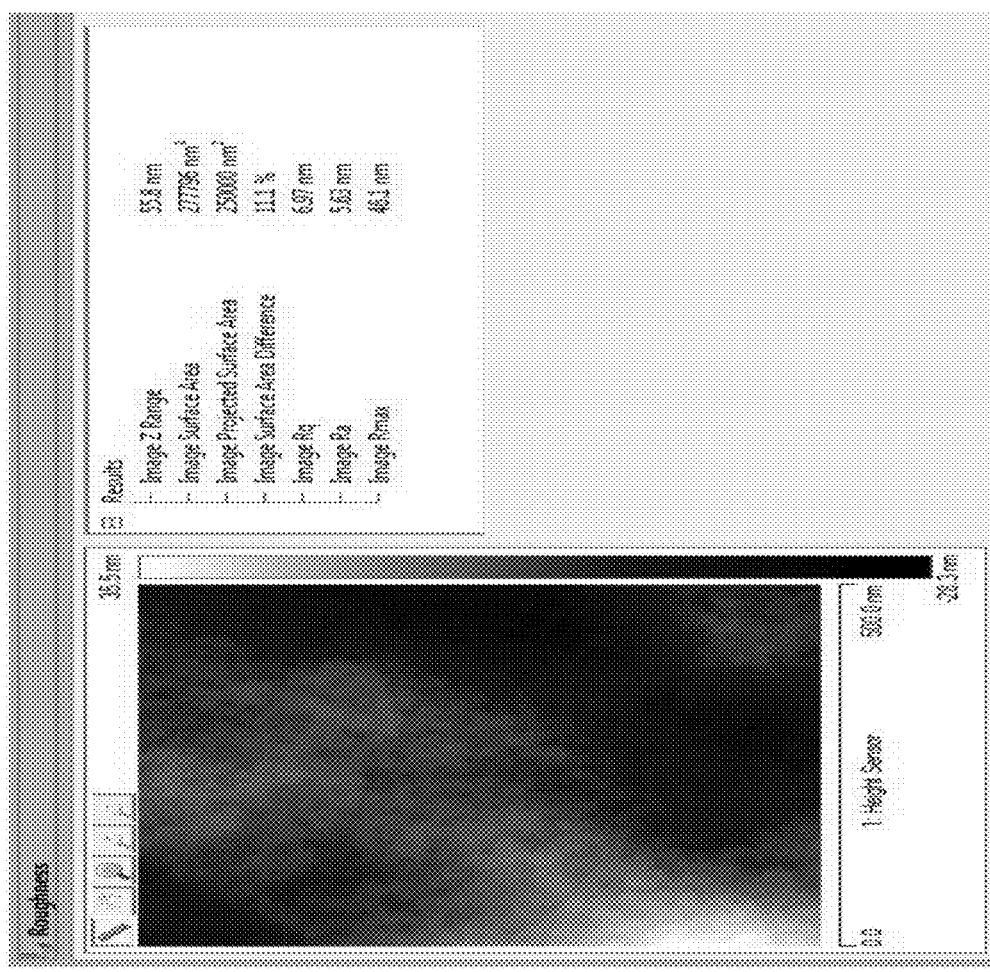
FIG. 2D shows the AFM specification of the surface roughness of the horizontal bridge with the 3D image of the flat "ATP Lid".
Figure 2C:
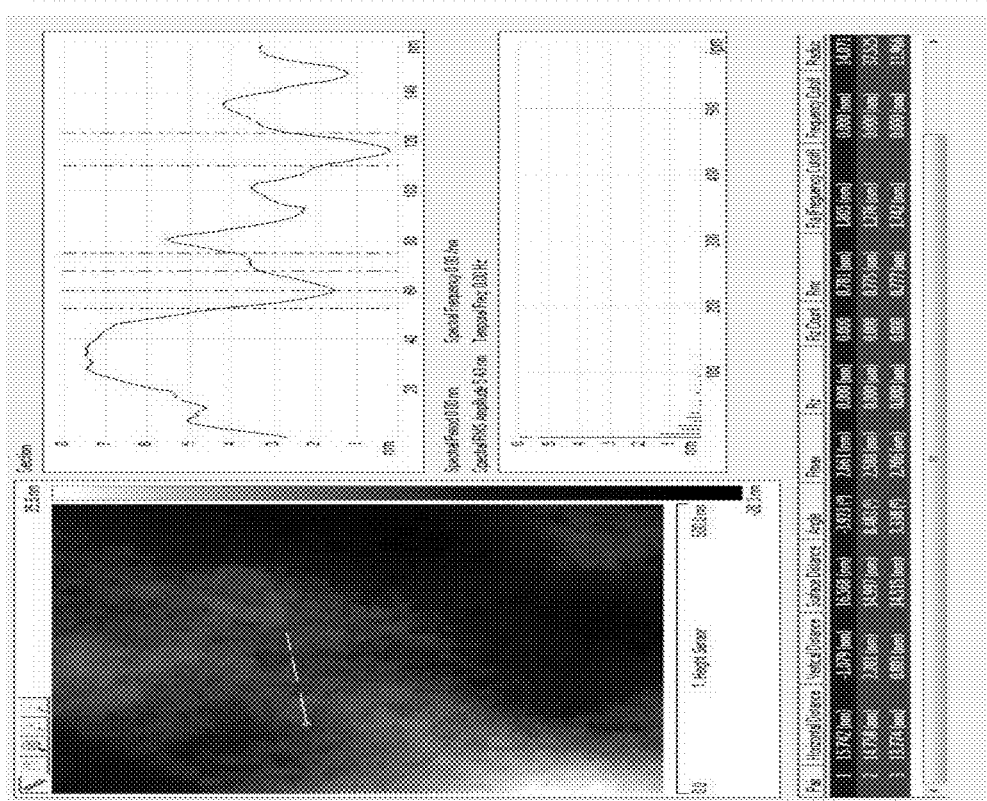
FIG. 2C shows the close look of the bridge surface in cross section analysis.
Figure 2F:
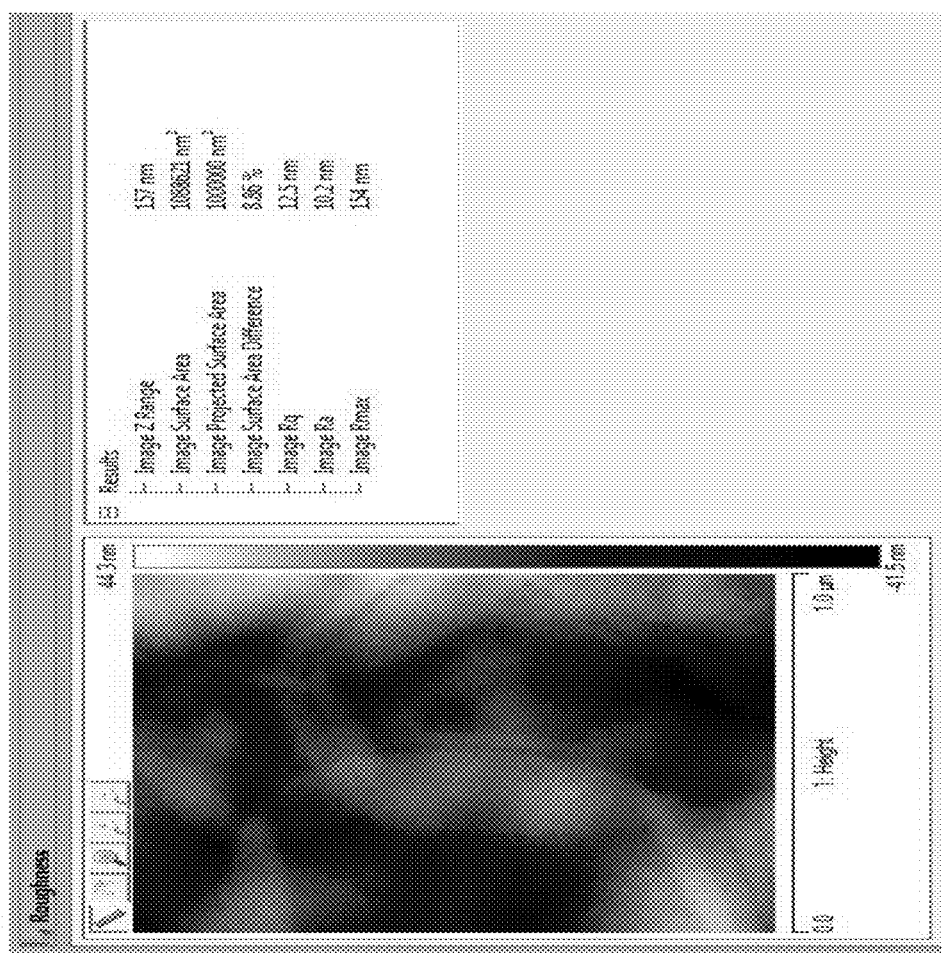
FIG. 2E shows the enlarged AFM of the "Breathing-pore" nearby the bridge for the cross-section analysis and FIG. 2F is the AFM specifications of the "Breathing-pore".
Figure 2E:
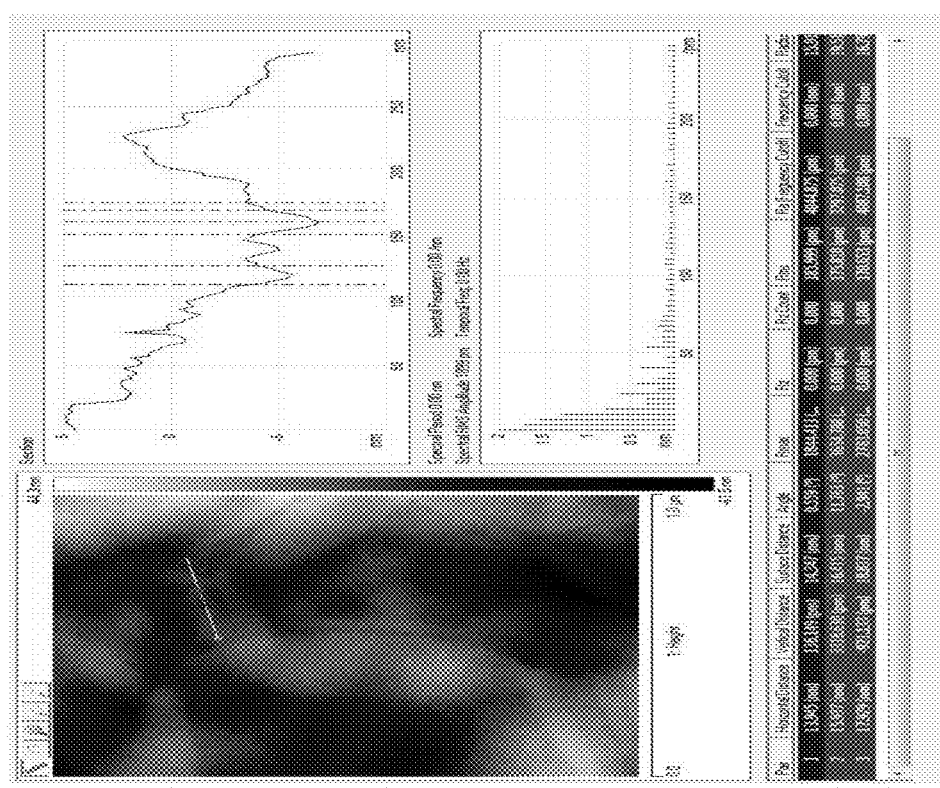

The significant structures difference from figures shown above are the SAM fabricated by added o-NPA in the mixture of mM-β-DMCD, T-CD, PEG and PVP, that formed a flat bridge with nanopores. FIG. 2A shows the flat bridge with width 330 nm and length in 1.4 µm by cross section analysis with RMS 0.6 nm in the image. Nanopores can be seen on each side of the bridge; the pores on the left side of the bridge have a depth 0.3-0.8 nm and diameter 20-30 nm. FIG. 2B shows the membrane morphology specification in thickness 60.2 nm with the roughness 15.1 nm. FIG. 2C shows the pore size having 14-16 nm diameters on the right hand side of the flat bridge with the pore depth 0.1-2.3 nm by the cross-analysis AFM. The RMS value is 0.8 nm in a small scale view window of 500×500 nm. FIG. 2D shows the AFM specification of the surface roughness or the horizontal bridge. The body of the horizontal flat bridge was densely covered with thousands uniformly and orderly orientated donuts shaped "fish scales", density of $10^7$ pores/$cm^2$, with the average donuts size of 22 nm in diameter and the pores in the center are 9-10 nm in diameter shown in FIG. 2D. FIG. 2E shows the AFM image of the "breathing pore" near the flat cross bridge with the pore length among 12-18 nm and the vertical pore depth is 0.1-3.0 nm and the RMS is 0.18 nm by the cross section analysis. FIG. 2F shows the membrane thickness is 44.3 nm and the membrane roughness is 12.5 nm.

Example 3—Mimicking the Active ACHE Gorge and its Linen

Figure 3A:
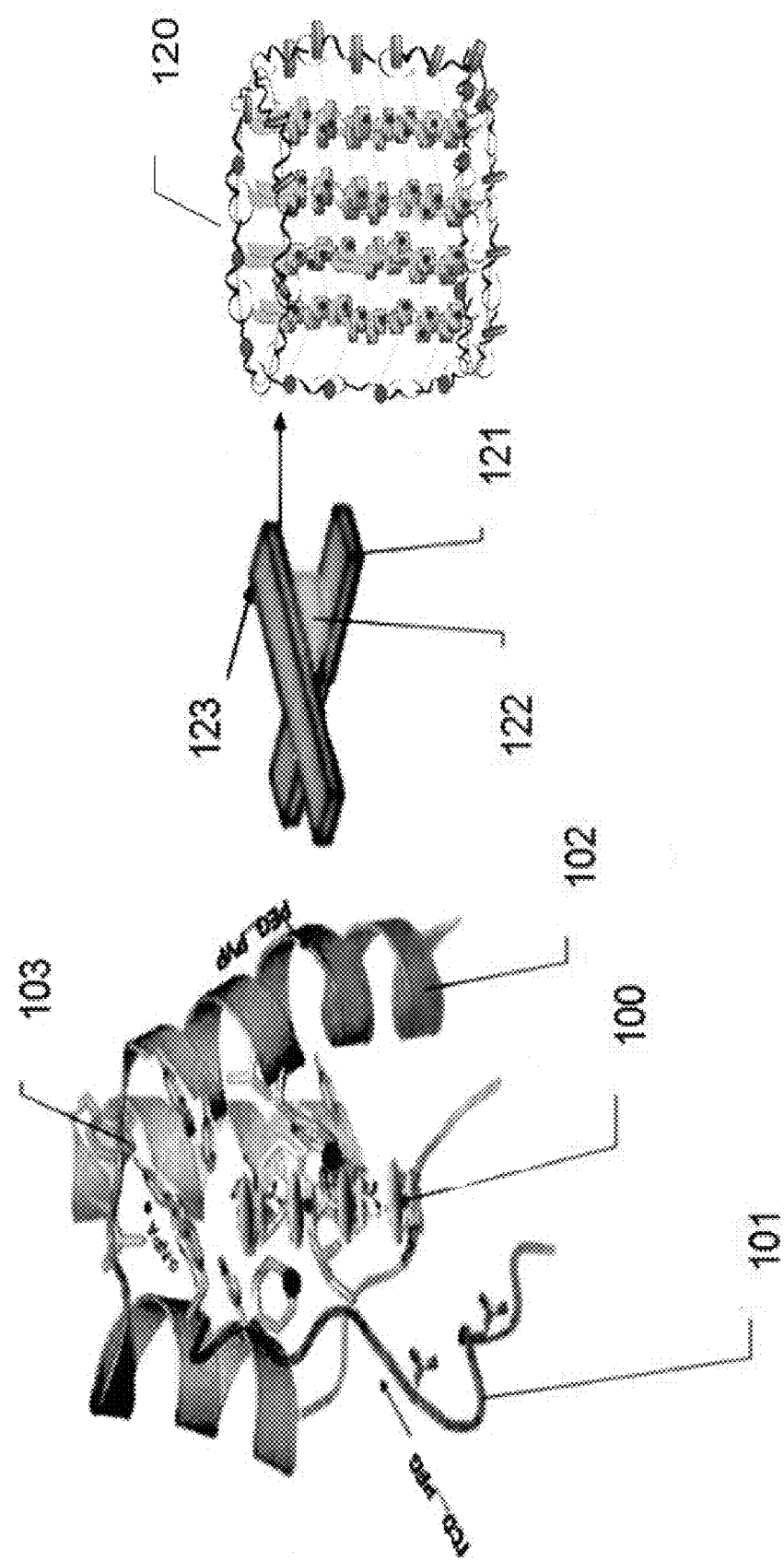
FIG. 3A depicts the art illustration of the SAM molecular polymer architecture for device 1 with an o-NPA linen in the left, "100" refers to the Biomimetic ACHE gorge with M-β-DMCD polymer chain cross-linked with PEP and has one imidazole in the carbon-3 position in each of the CD cavity as shown the red solid dot; "101" refers to the TCD . . . PEG formed polymer chains mimicking the C-terminal; "102" refers to the PVP . . . PEG polymer chains mimicking the N-terminal; "103" refers to the hydrophobic linen of o-NPA. The partial illustration of the cross bar layout from FIG. 4C's "10 to 14" was in the right. "120" refers to the toroidal structure that finally formed as detailed depiction in from "100" to "103". "121" refers to the Au electrode on a plastic substrate; "122" refers to o-NPA linen cross flat bar with TED . . . PEG//TCD . . . PVP polymer wrap; "123" refers to the nano air gap between imidazole CD polymer and the flat bridge.
Figure 3B:
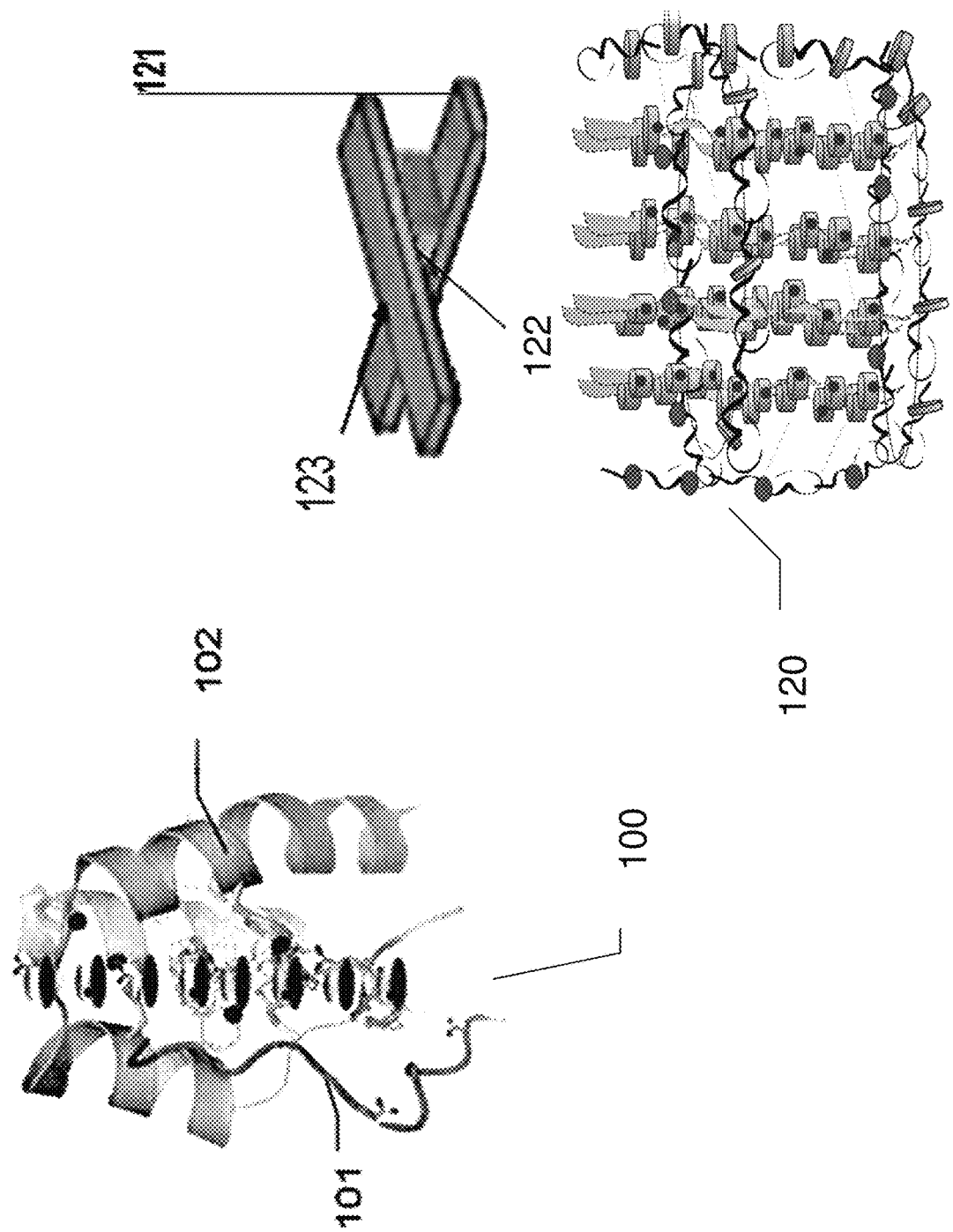
FIG. 3B depicts the art illustration of the SAM molecular polymer architecture of device 2 without an o-NPA linen in the left, and the partial illustration of the cross bar layout from FIG. 4D's "10 to 14" was in the right. "100", "101" and "102" descriptions are same as in FIG. 3A, but device 2 has no "103"—the o-NPA linen. "120" refers to a toroidal comprising of a flat bridges with the TED . . . PEG//TCD . . . PVP polymer wrapping around with the networking by hydrogen bonding; "121" description is same as FIG. 3A. "122" refers to the nano air gaps between the flat bridge and the imidazole CD polymer vertical block; "123" refers to the TED . . . PEG//TCD . . . PVP polymer flat bridge with nanopore.

A "Normal Active Site ACHE Gorge" was defined as a linen-cylinder consists of a bipolar dome with two poles. (1): the positive isopotential pole: esteratic site of five residues containing the catalytic triad (Ser-200, Glu-327, His-440), acyl pocket Phe 288 and Phe-290 [37-40], that was mimicked by polyethylene glycol diglycidyl ether (PEG) (for Ser 200) . . . imidazolyl-dimethyl-β-cyclodextrin (M-CD) (for His 440) . . . triacetyl-β-cyclodextrin (T-CD) (for Glu327). Phe288 and 290 were mimicked by o-NPA. (2) The 14 aromatic residues for gorge lining were mimicked by excess amount of o-NPA (1:500-1000 of T-CD/o-nithophenyl acetate (o-NPA)) and W84 were mimicked by poly(4-vinylpyridine) (PVP); (3) the negative isopotential pole: the Asp-72, Tyr-121, Tyr-70, Tyr-354, and Trp-279 are the residues of the peripheral and were mimicked by TCD . . . PEG polymer and TCD . . . PVP polymers as the anionic site (PAS), F330, Y121 were mimicked by o-NPA, and Trp279 was mimicked by PVP. By knock out all o-NPA out of the network, we define the second device as "Mutated Active Site ACHE Gorge" based on our hypothesis: Lacking of hydrophobic lining in the gorge might be the key issue caused diseases, because the nature of the ACHE gorge might be mem-ristive, mem-capacitive and mem-inductive in nature. FIG. 3A and FIG. 3B depict the Biomimetic ACHE gorge of a "normal brain" and a "mutated brain" gorges, respectively. In FIG. 3A, "100" refers to the biomimetic ACHE gorge with M-β-DMCD polymer chain crosslinked with PEP and has one imidazole in the carbon-3 position in each of the CD cavity as shown the red solid dot; "101" refers to the TCD . . . PEG formed polymer chains mimicking the C-terminal; "102" refers to the PVP . . . PEG polymer chains mimicking the N-terminal; "103" refers to the hydrophobic linen of o-NPA. The partial illustration of the cross bar layout from FIG. 4C's "10 to 14" was in the right. "120" refers to the toroidal structure that finally formed as detailed depiction in from "100" to "103". "121" refers to the Au electrode on a plastic substrate; "122" refers to o-NPA linen cross flat bar with TED . . . PEG//TCD . . . PVP polymer wrap; "123" refers to the nano air gap between imidazole CD polymer and the flat bridge. FIG. 3B depicts the art illustration of the SAM molecular polymer architecture of device 2 without an o-NPA linen in the left, and the partial illustration of the cross bar layout from FIG. 4D's "10 to 14" was in the right. "100", "101" and "102" descriptions are same as in FIG. 3A, but device 2 has no "103"—the o-NPA linen. "120" refers to a toroidal comprising of a flat bridges with the TED . . . PEG//TCD . . . PVP polymer wrapping around with the networking by hydrogen bonding; "121" description is same as FIG. 3A. "122" refers to the nano air gaps between the flat bridge and the imidazole CD polymer vertical block; "123" refers to the TED . . . PEG//TCD . . . PVP polymer flat bridge with nanopore.

Example 4—Engineering the Devices

The "Normal ACHE Gorge" Neuronal Network Device

Figure 4B:
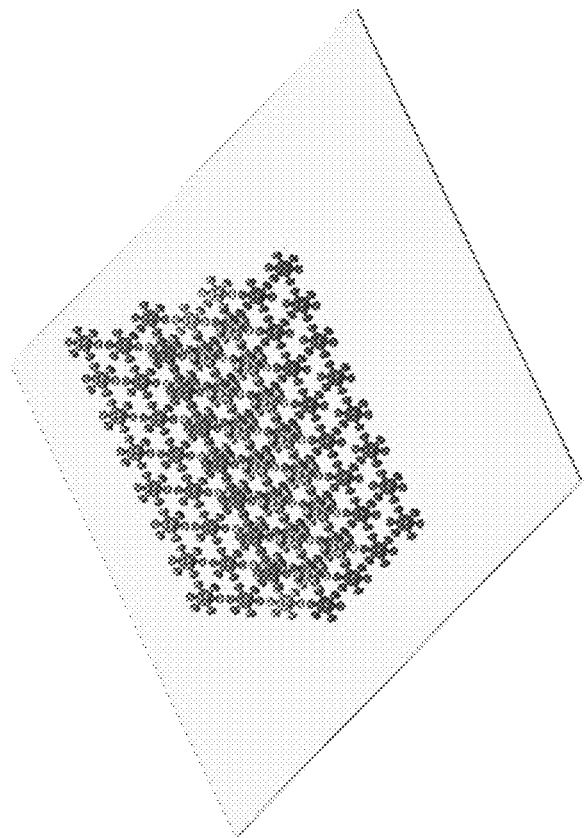
FIG. 4B depicts the art model of the working device 2, the "mutated ACHE gorge neuron" prosthesis. The dark blue, purple and browns represented the connections are partially alignment with each other, that formed a stairway type of molecular architecture that sited on a light green plate of 50 nm thickness gold onto a flexible plastic plate. The linen of the ACHE gorge was missing.
Figure 4A:
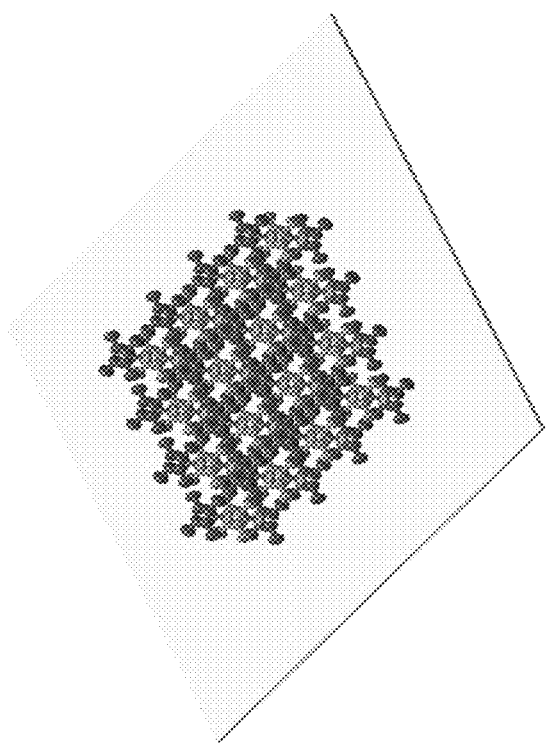
FIG. 4A depicts the art model of the memcapacitor 1 of "normal brain ACHE gorge". The light green color substrate is a 50 nm thickness pure gold plate attached onto a flexible plastic plate. The model consists of green balls and sticks in the top and bottom layer covered with conductive cross-linked polymers; the oranges represent the inner "ACHE Gorge" neuronal axons in narrow cylinders connected through the neuronal terminals and dendrites as truncated donuts in a compact flat metrics.
Figure 4C:
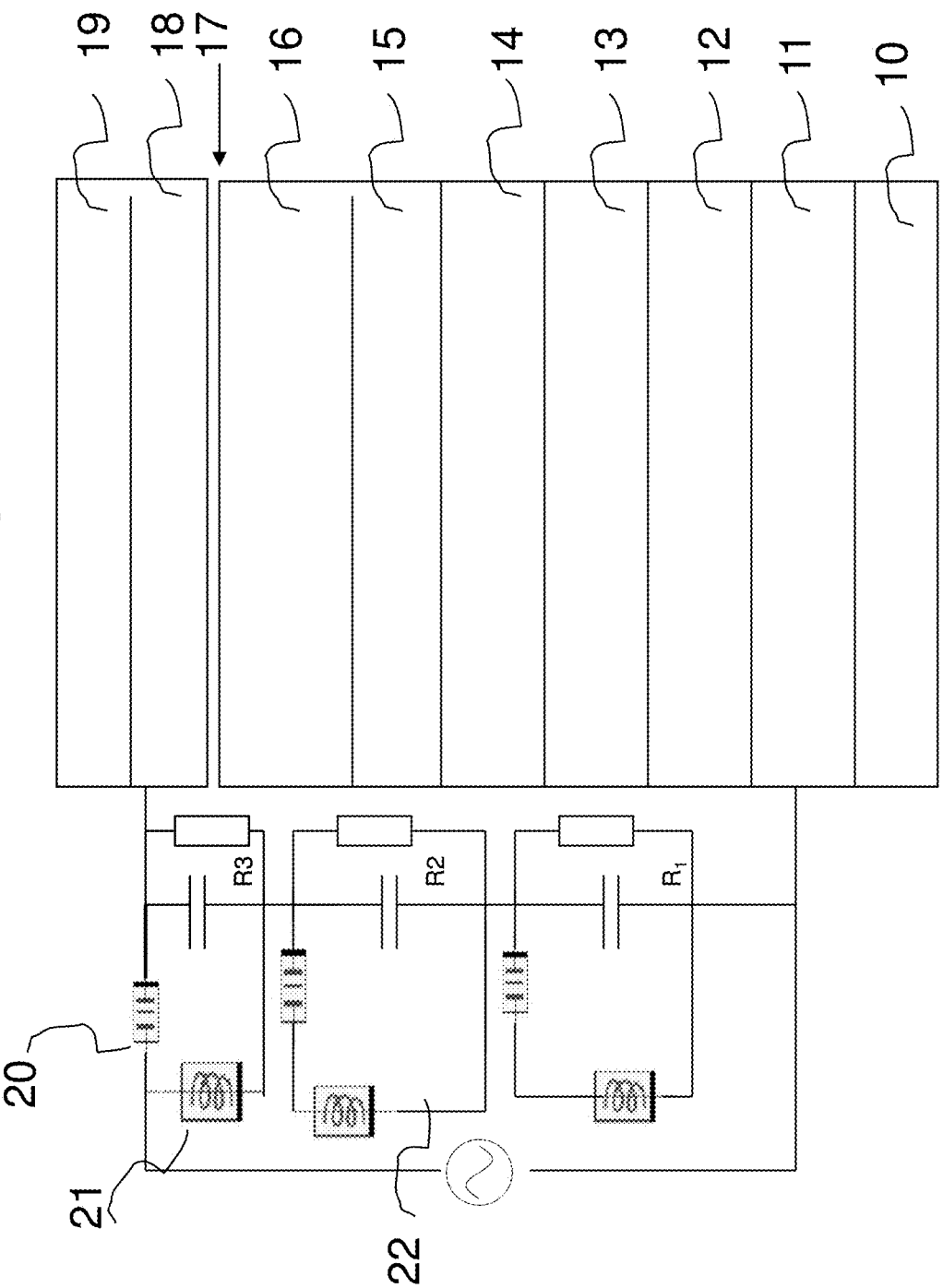
FIG. 4C depicts the schematic components of the device 1 having different layers and each one servers their own functions. "10" is the plastic plate; "11" is the Au, or Pt, or metal electrode; "12" is the imidazolyl derived mono-substitute β-dimethylcyclodextrin (m-β-DMCD, in short, MCD) cross-linked with PEG, PVP and TCD forming a self-assembled conductive organic membrane with positive and negative electron-relay circular current flow inside the cavity with opposite direction separated by nano air gap; "13" is the nano air gap between two chucked CD "donuts-like" cavity; "14" is the o-NPA formed ACHE gorge linen with other residue groups through hydrogen bonding or hydrophobic bounding wrapped around the cross bars with the TCD . . . PEG//TCD . . . PVP polymers; "15" is the nano air gap between the NPA linen and the polymer TCD . . . MCD . . . PEG . . . PVP; "16" is horizontal cross bars of NPA linen with polymer TCD . . . PEG//TCD . . . PVP; "17" is the slot for injection of biological sample; "18" is the 50 nm thickness pure gold electrode without a membrane; "19" is the plastic substrate; "20" is the memcapacitor; "21" is the meminductor; "22" is the schematic circuitry box indicating the mems-transformer function of the device 1's design based on step 10 to 19 that may produce functions equivalent to the electric circuitry box drawn on the left-hand side proposed.

The "Normal ACHE Gorge" Neuronal Network Device was built by arrays of 3D cross bars by self-assembling technology with the above section mentioned membrane in FIG. 3A. The FIG. 3A on the right-hand side is the illustration of the 3D cross bar, the vertical green bar presented here was made by the architecture of a vertical double-layer cylinder with an inner core cylinder consists of a chain of cyclodextrin chunked "donut" shape, hollow in the center, as pendants and the PEG as the necklace chain between the two relay circuits is the nanometer air gap serves as the dielectric substance; the basement bar was made of the gold; The horizontal bar was made by the o-NPA formed hydrogen bounding or hydrophobic interaction with the TCD . . . PEG//TCD . . . PVP wrapped around the flat bridge structure. This is a partial illustration of the cross bar essential block, as shown the coil wrapped in a toroid. The detailed illustrations were shown in FIG. 4A as an art model and in FIG. 4C is for a detail explanation. "10" is the plastic plate; "11" is the Au, or Pt, or metal electrode; "12" is the imidazolyl derived mono-substitute β-dimethylcyclodextrin (m-β-DMCD, in short, MCD) cross-linked with PEG, PVP and TCD forming a self-assembled conductive organic membrane with positive and negative electron-relay circular current flow inside the cavity; "13" is the nano air gap between two chucked CD "donuts-like" cavity; "14" is the o-NPA formed ACHE gorge linen with other residue groups through hydrogen bonding wrapped around the cross bars with the TCD . . . PEG//TCD . . . PVP polymers; "15" is the nano air gap between the NPA linen and the polymer TCD . . . MCD . . . PEG . . . PVP; "16" is horizontal cross bars of NPA linen with polymer TCD . . . PEG//TCD . . . PVP; "17" is the slot for injection of biological sample; "18" is the 50 nm thickness pure gold electrode without a membrane; "19" is the plastic substrate; "20" is the memcapacitor; "21" is the meminductor; "22" is the schematic circuitry box indicating the function of the device 1's design from 10 to 19.

The left-hand side of FIG. 4C depicts the electronic circuit function of the device 1's engineering architecture, that consists of 3 elements of memcapacitors, three memristors and three meminductors connected to be functioning as a "normal ACHE neuronal circuitry" to have an alternative voltage output and changed resistance and capacitance. The air gap between the CD cavity is much smaller than the air gap between the flat NPA mash bridge and the rim of the CD cavity. The variations air gaps at different sections in the flow chart reflect the essence of the flexibility, neuronal plasticity possible.

The "Mutated ACHE Gorge" Neuronal Network Device

The "Mutated ACHE Gorge" neuronal network device was built by arrays of 3D cross bars by self-assembling technology with the above section mentioned membrane in FIG. 3B. The FIG. 3B on the right-hand side is the illustration of the 3D cross bar, the vertical green bar proposed here was made by the architecture of a vertical double-layer cylinder with an inner core cylinder consists of a chain of cyclodextrin chunked "donuts" shape, hollow in the center, as pendants and the PEG as the necklace chain between the two relay circuits is the nanometer air gap serves as the dielectric substance, such as for Device 1 in FIG. 2A-2G, the 3D lattice between the flat bridge and the top rim of the surface of the pores has gaps of 40-56 nm; yet the Device 2 has gaps between 6-121 nm in FIG. 1A-1G. Device 2 can become a hybridized memristor with bridges having 115 nm apart in height, and the Device 2 has uniform distance between the bridge and the top rim of the nanopore. Hence related to Device 1, Device 2 has less characteristics of electric synapse than Sensor 1, especially at the SWS, the circuitry may be damaged due to the missing a key NPA linen that leads to a "born with" electric flow disadvantage due to the air gap was too large; the basement bar was made of the gold; The horizontal bar was made by the TCD . . . PEG//TCD . . . PVP wrap around the horizontal bars made by W84 from PVP through hydrogen bounding, that is too loose to form a well balanced one electronic unit of memrisor-memcapacitor-meminductor. This is a partial illustration of the cross bar essential block, as shown the coil wrapped in a toroid. The detailed illustrations were shown in FIG. 4B as an art model with stair type architecture and in FIG. 4D depicts the schematic components of the device 2 having different layers and each one serves their own functions. "10" is the plastic plate; "11" is the Au, or Pt, or metal electrode; "12" is the imidazolyl derived monosubstitute β-dimethylcyclodextrin (m-β-DMCD, in short, MCD) cross-linked with PEG, PVP and TCD forming self-assembled conductive organic membrane with positive electron-relay circular current flow; "13" is the nano air gap between two chucked CD "donuts-like" cavity; "14" is the cross-bar consists of polymers residue groups having negative electron-relay circular current of MCD . . . PEG . . . PVP wrapping around with ribbon of TCD . . . PEG//TCD . . . PVP; "15" is nano air gap between 14 and 15 cross-bars; "16" is cross bar of MCD . . . TCD . . . PEG . . . PVP cross-linked polymer; "17" is the slot for injection of biological sample; "18" is the 50 nm thickness pure gold electrode without membrane; "19" is the plastic substrate.

Example 5—The Device Circuitry

Figure 5:
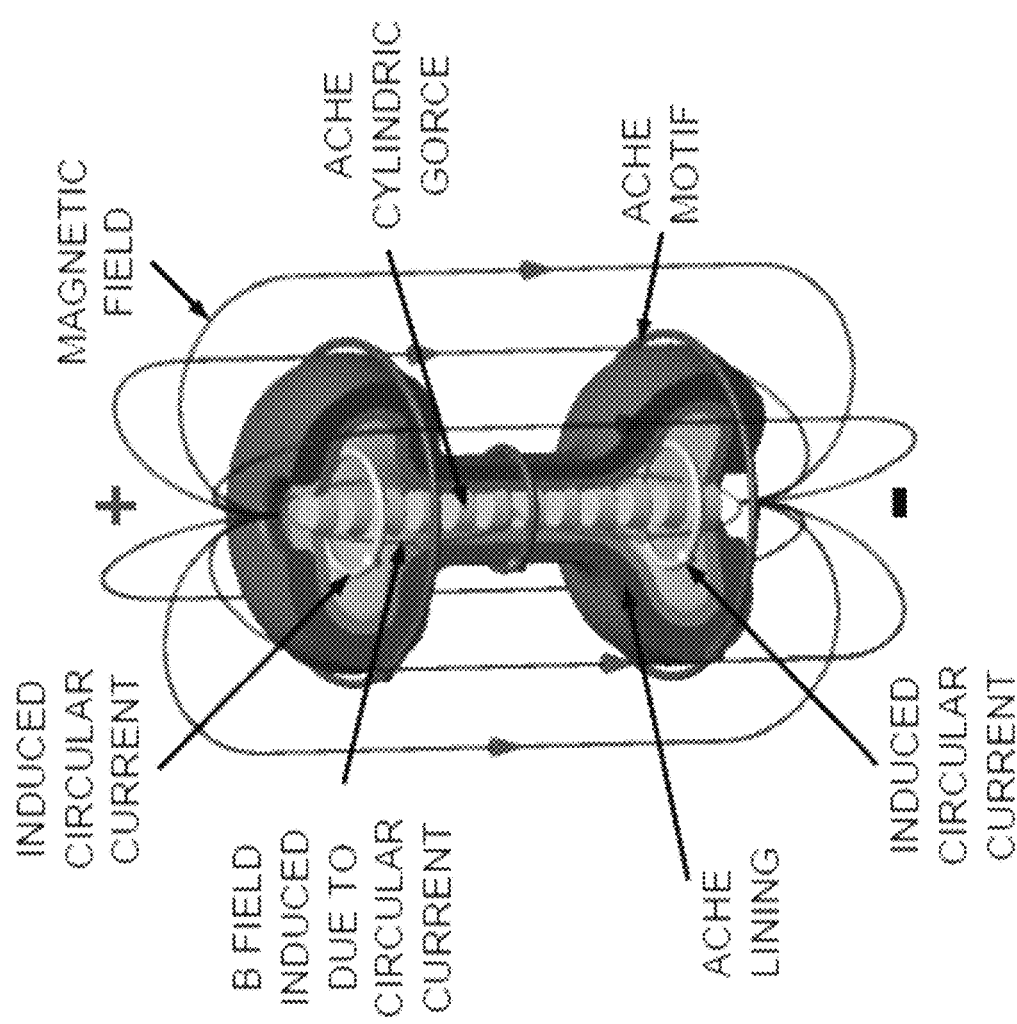
FIG. 5 depicts the model of the electromagnetic field of the mems-transformer and the eddy current for device 1.

The device 1 or device 2 circuitry consists of a memcapacitor, a memristor and a meminductor connected in series as shown in the left-hand side of the circuitry in FIG. 4C. This is a well known Tank Circuit, that the resonate circuit provides voltage amplification and a reversed sign. [http://en.wikipedia.org/wiki/LC_circuit]. The three in one system was proposed and explained in literature [41]. The detail example of the device 1 as a mems-transformer model's electromagnetic fields was depicted in FIG. 5. FIG. 5 depicts the model of the electromagnetic field of the mems-transformer and the eddy current for device 1. The blue line of the magnetic B field outside of the core cylinder is zero, only the induced circular eddy current as yellow color produced a magnetic B field inside of the core cylinder as seen to perpendicular to the blue magnetic line was the purple line. This down-bell double toroidal structure is a key function for human memory and intelligent communication consciously in wave forms; hence the ACHE gorge is the primary neuron groups provide an advanced function for human that was distinguished from other creatures.

Memristors are devices made of nanolayers that have the capability to mimic neuronal synapse with a characteristic of hysteresis loop in the i-V curve [41-46]. A memristor is a semiconductor whose resistance varies as a function of flux and charge. This allows it to "remember" what has passed through the circuit [28, 41-43]. In the equation 1, where I(t) is the current passing through the memristor, and V(t) is the potential across it, and G({x},t) which is the non-leaner conductance with state dependent. {x} is the state variable.

$$I(t)=G(\{x\},V,t)V(t) \tag{1}$$

Figure 7:
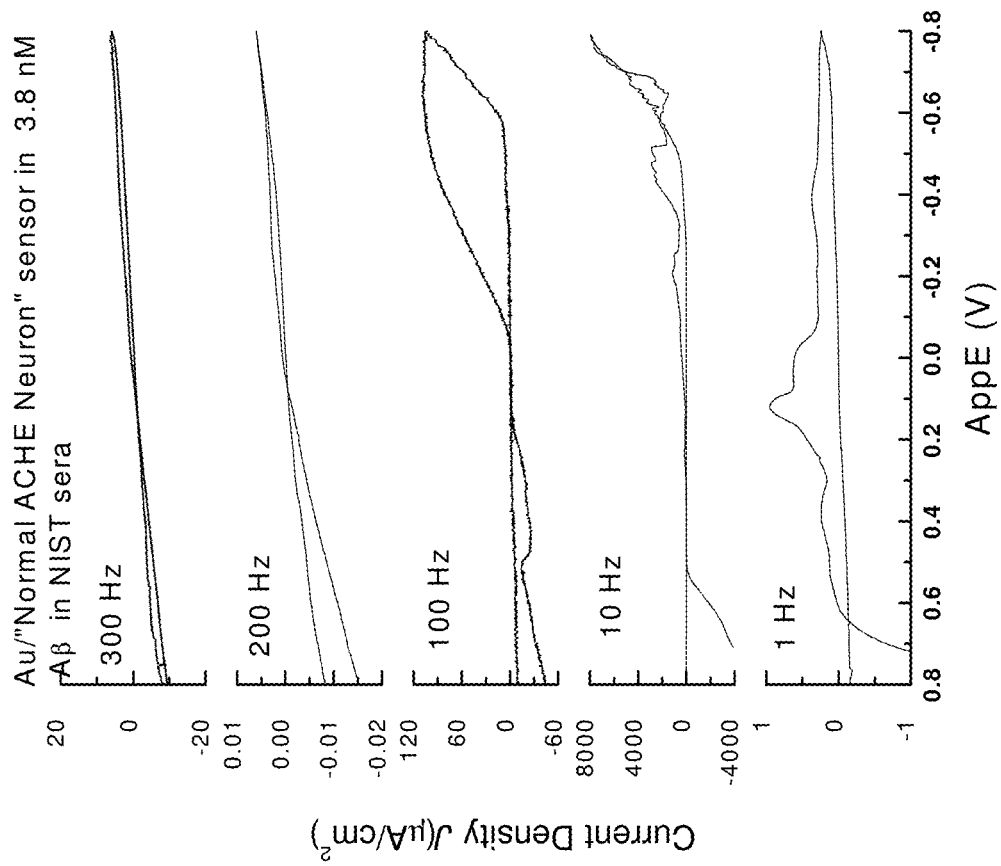
FIG. 7 depicts CV profiles of device 1 in 3.8 nM Aβ in same serum as in FIG. 6.
Figure 6:
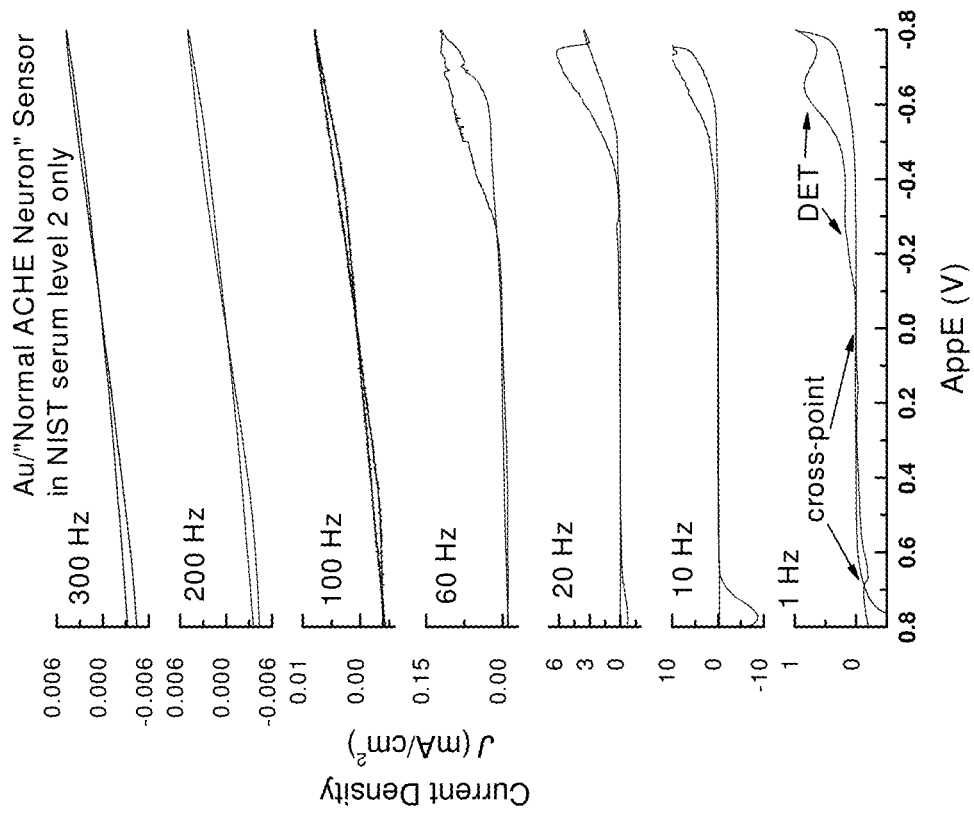
FIG. 6 depicts device 1's CV profiles without spiking Aβ in NIST serum over frequency 1-300 Hz. The DETs peak and the cross-point locations are labeled in arrows.
Figure 8:
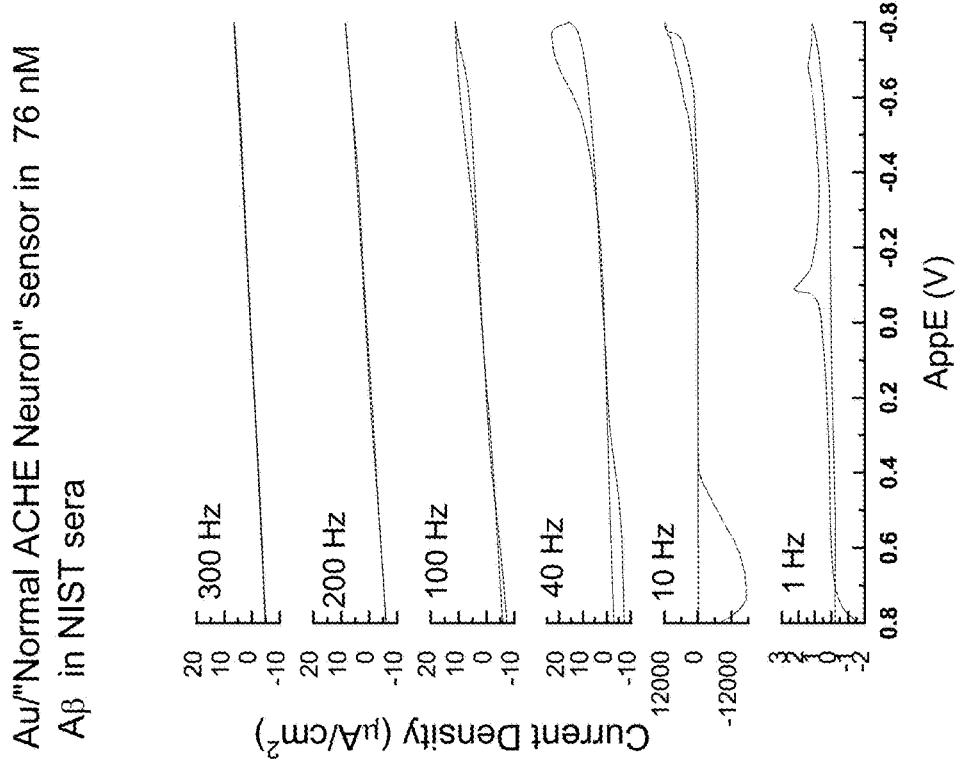
FIG. 8 illustrates CV profiles of device 1 with 76 nM Aβ in same serum as in FIG. 6.

Device 1's hysteresis i-V profiles measured by the cyclic voltammetry (CV) method are presented in FIG. 6 in NIST serum without Aβ. Data Acquisitions were conducted by connecting the memristor chips with an electrochemical station (Epsilon, BASi, IN) with the BASi software package in the computer. The gold chip consists of three gold leads, the center circle gold chip with the Biomimetic membrane is connected to the anode, and the pure gold electrode without a membrane is connected to the cathode electrode, and the gold electrode is connected to the reference electrode at a fixed scan rate under an applied electrochemical potential, the current was recorded due to the change of a direct electron-relay (DET) either in oxidation or reduction direction. DET phenomenon is a key event in sensing and energy storage that led to our several inventions [47-51]. FIG. 6 has scan rate changed from 1-300 Hz over the potential range of −800 mV to 800 mV as shown in FIG. 6 in the NIST reference SRM 965A human serum without Aβ. The characteristics of hysteresis are the loop with a pinch (as called for a cross-point) switched at zero applied potential and zero current as shown in FIG. 6-8. The intensity of the DET peak was reduced by a hundred times, and the cross-point locations were moved nonlinearly toward to negative field as frequency increased in the presence of 3.8 nM and 76 nM Aβ as shown in FIGS. 7 and 8, respectively compared to without Aβ. Various concentrations of Aβ reduced the DET peak intensity by 94-99% in SWS frequency more than any other frequencies. Device 1 showed significant bipolar nonlinear hysteresis through the CV curves at low frequency, and linear hysteresis at high frequency.

Figure 9:
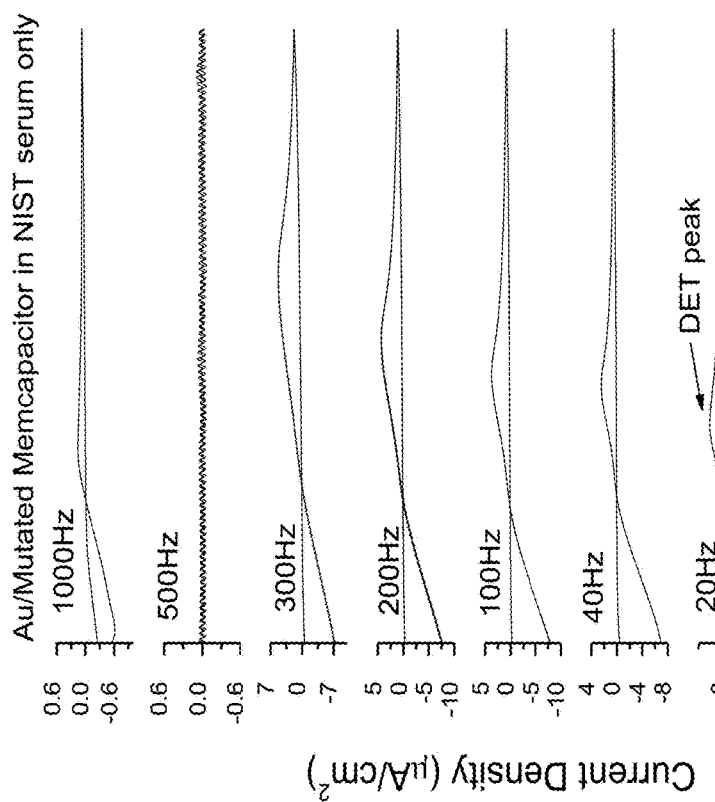
FIG. 9 depicts CV profiles of device 2 without spiking Aβ over scan frequencies 1 to 1 kHz in NIST human serum.
Figure 10:
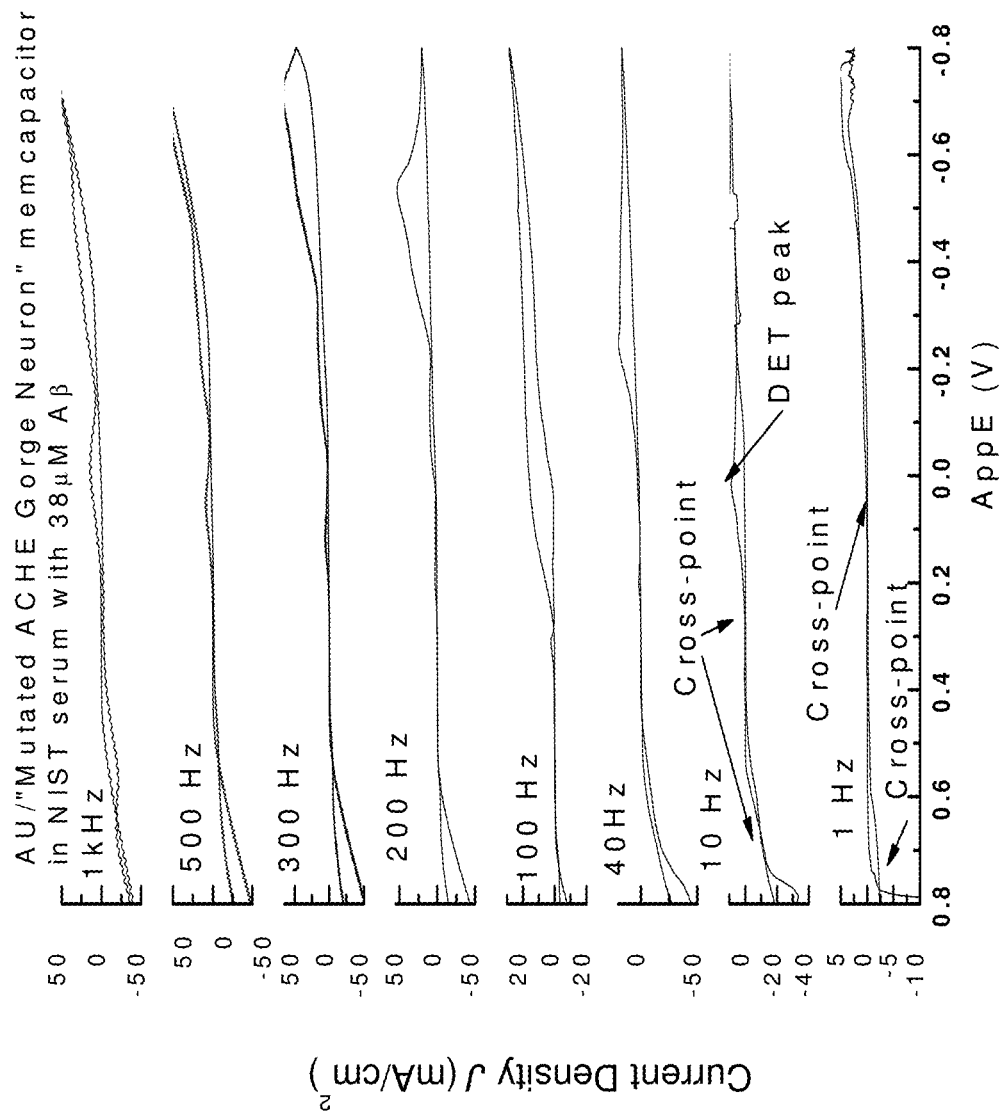
FIG. 10 depicts CV profiles with 38 μM Aβ of device 2 over scan frequencies 1 Hz to 1 kHz in NIST human serum.

Device 2's memristor characteristics was shown in FIGS. 9 and 10 in NIST human serum without AB and with 38 μM Aβ, respectively over the scan frequencies 1-10 KHz. Device 2 was unable to sense at nM level. Under the influence of Aβ, it exponentially increased the DET reduction peak intensity, and the peak moved toward negative potential drastically as frequency increased thus indicating a significant circular current exists driven by the toroid forces due to the broken ACHE gorge linen [52]; multiple cross-points occurred over the whole frequency range. Again, the CV curves approved the device 2 has a bipolar double toroidal domes cylinder structure with an unusual electromagnetic disturbance inside of the gorge.

Example—7 Characteristics of Mems-Capacitors

The Synapse Energy Profiles Impacted by the Presence of Aβ

A total charge of a memcapacitor is a function of a state dependent of capacitance and the potential across it, where q(t) is the total charge on the capacitor, and V (t) is the potential across it. A capacitance C({x}, t) which is state dependent [28].

$$q(t)=C(\{x\},V,t)V(t) \tag{1}$$

The synapse energy profiles data Acquisitions were conducted by connecting the memcapacitor chips, the gold lead with nano-biomimetic membrane was connected to the anode, the bare gold lead was connected to the cathode, so was the reference connected to the pure gold lead, then the cable was connected with an electrochemical station (Epsilon, BASi, IN) with the BASi software package in the computer. The double step chronopotentiometry (DSCPO) method was used to measure the voltage change upon applied an alternative small current under ±10 nA with data rate 0.001 s at 0.25 Hz and 2×10$^{-5}$ s data rate over the frequency range of 40 Hz-1 kHz were chosen under the room temperature. The time for action potential and resting potential (discharge vs. charge steps) have to be settled in a desired time frame. The real time data was acquainted under this program. In this invention, the Origin 9.0 software was used for data analysis and plotting figures.

Figure 11B:
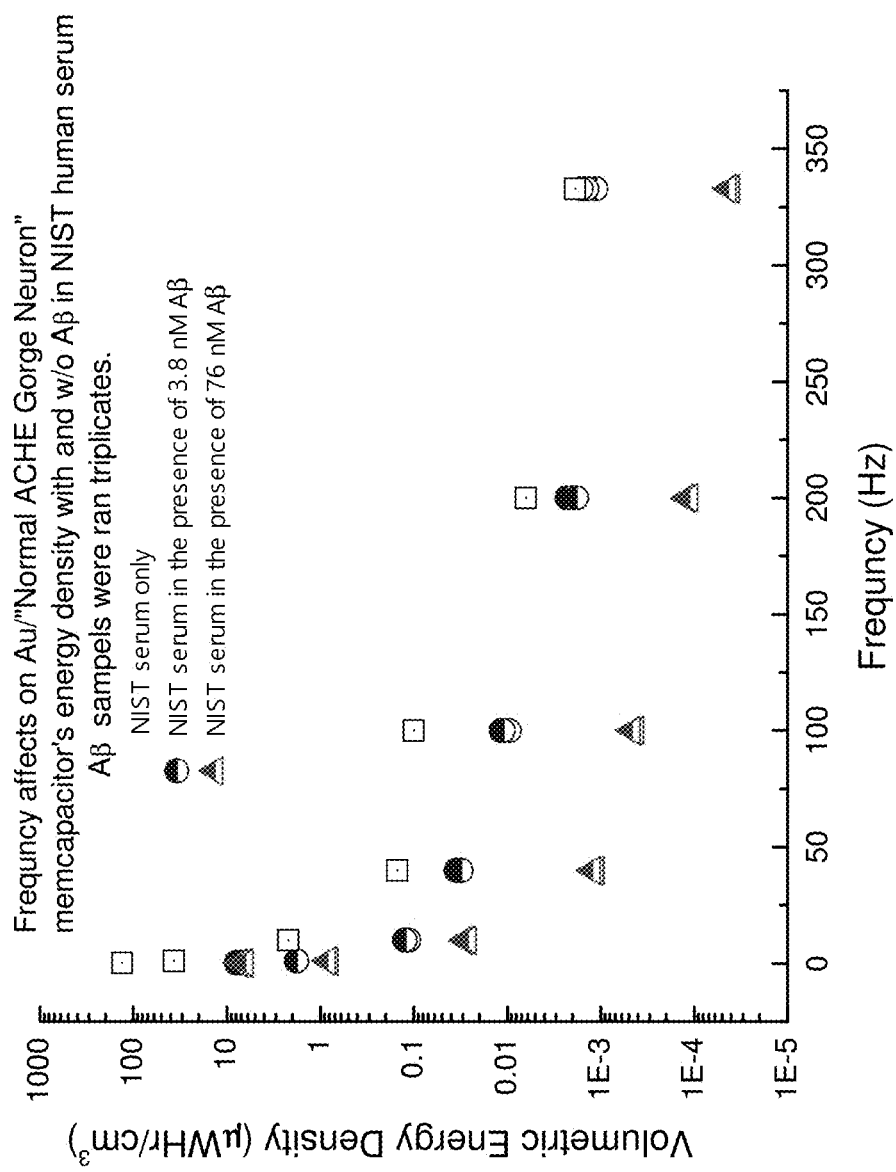
FIG. 11B depicts the profiles of various concentrations of Aβ impacting on the device 1's performance in volumetric energy density vs. change of frequencies from 0.25 Hz to 333 Hz compared without spiking Aβ in NIST standard human serum at ±10 nA at room temperature with each sample run triplicates.

Device 1: Aβ concentrations of 3.8 nM and 76 nM had exponentially significantly reduced signal intensity at lower frequencies over 0.25-1 (SWS) Hz compared at higher frequencies from 10-1000 Hz in device 1, as shown in the DSCPO original data in FIG. 11A$_1$, FIG. 11A$_2$ and FIG. 11A$_3$ for spiked Aβ=0, 3.8 nM and 76 nM, respectively. FIG. 11B depicted the volumetric energy density plot vs. frequencies 0.25 Hz to 333 Hz for comparison of with or without Aβ. The key characteristic of a memcapacitor is the nonlinearity impact of charge on frequencies; we have demonstrated using CV and DSCPO method that at lower frequency has higher impact of charge to the peak intensity (either current, or voltage) than at higher frequencies nonlinearly. Overall, Device 1 is very sensitive to the presence of Aβ than device 2.

Figure 13:
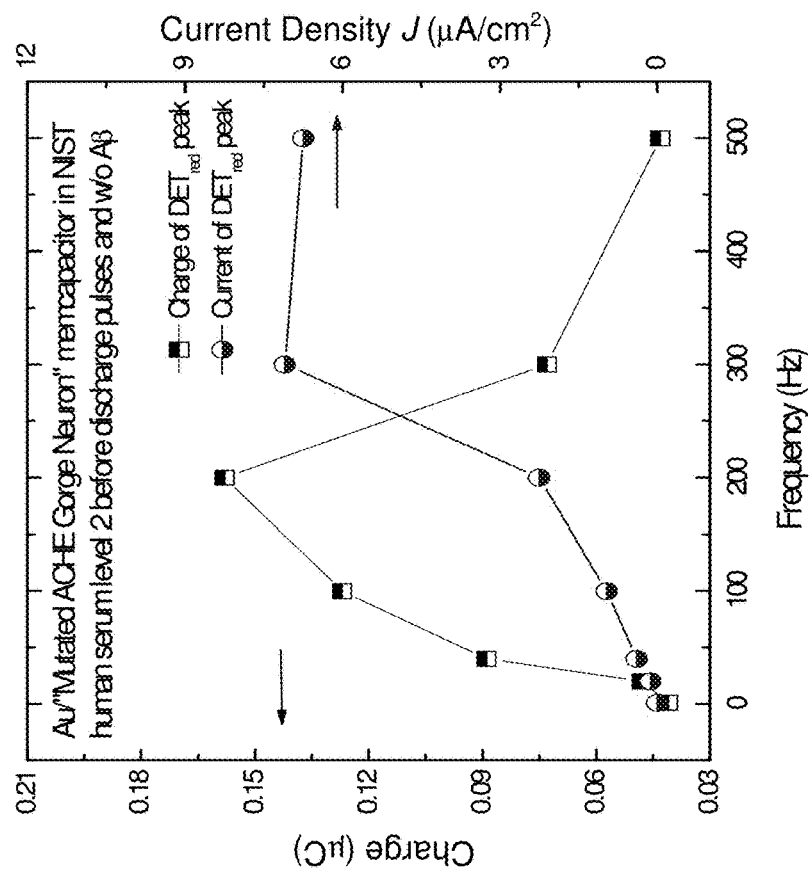
FIG. 13 depicts the memcapacitor characteristics of non-linearity of charge vs. frequencies and the current density vs. frequencies before discharge pulses and without spiking Aβ, respectively for device 2 in NIST serum with certified blood glucose level 2.

Device 2: It has very small energy discharge magnitude compared with device 1 using the voltage sensing method, regardless of whether device 2 is with or without Aβ over 0.25, 40 to 250 Hz, as shown in FIG. 12A, FIG. 12B and FIG. 12C, respectively. Device 1 has a several magnitude higher intensity at SWS than device 2. Device 2 is in short of the characteristics as a memcapacitor in respect to the capacitance nonlinearity impacts on the voltage as frequency increase using the DSCPO method as seen in FIG. 12A, FIG. 12B and FIG. 12C. However, FIG. 13 demonstrated the perfect memcapacitor behavior of charge of the DET peak at an applied voltage vs. frequency for device 2 over 1-500 Hz, which is nonlinear when frequency increased to >200 Hz, the charge values were dropped abruptly based on the data obtained from FIGS. 9 and 10 using the CV method.

Figure 14:
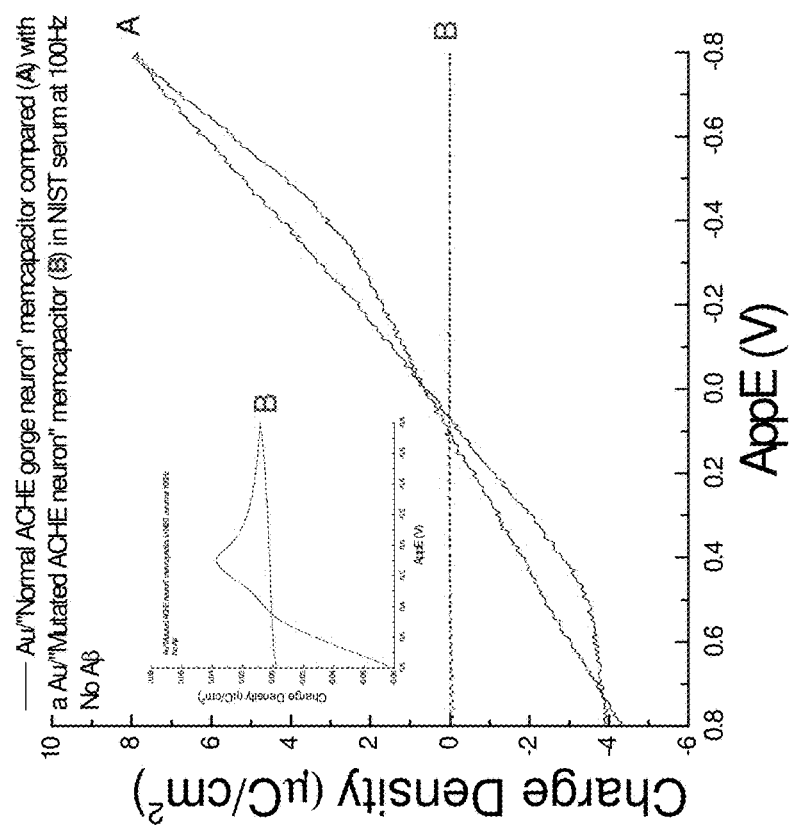
FIG. 14 depicts the memristor's characteristics of charge density vs. potential with hysteresis pinch at different potentials compared with device 1 (blue curve) and 2 (red) at 100 Hz using the CV method in NIST serum without Aβ.

Another example of the specific characters is the charge vs. voltage at 100 Hz using a CV method for Device 1 compared with Device 2 in pure NIST serum without AB in FIG. 14. Device 1 demonstrated a typical memcapacitor's behavior that the charge density is a function of the product between voltage and capacitance, and also dependents on the state of the capacitance, because the capacitance is various in positive and negative. Device 1's switch is at zero potential, but Device 2's pinch point moved far away from it. At −0.7V, Device 1 has the highest negative capacitance of 10 μF/cm$^2$ compared with Device 2 with a positive capacitance of 2.7×10$^{-3}$ μF/cm$^2$, it means Device 1 has a great potential to be spontaneously discharge an electron than accept an electron. In contrast, Device 2 has a hard time to fire a synapse. Even at +0.1V, Device 2 has its highest capacitance of +0.37 μF/cm$^2$ compared Device 1 still has a negative capacitance of −0.37 μF/cm$^2$.

Example—8 the Nanostructure Mems-Transformer

Characteristics of Mems-Inductor

The memory of the inductance can depend on both the magnetization history as well as on the geometrical changes of the inductor [28].

$$\Phi(t)=L(\{x\},I(t)) \quad (1)$$

where Φ(t) is the flux-linkage (integral of the voltage), I(t) the current, and the inductance L depends also on some state variables with their own equations of motion[28].

Figure 16:
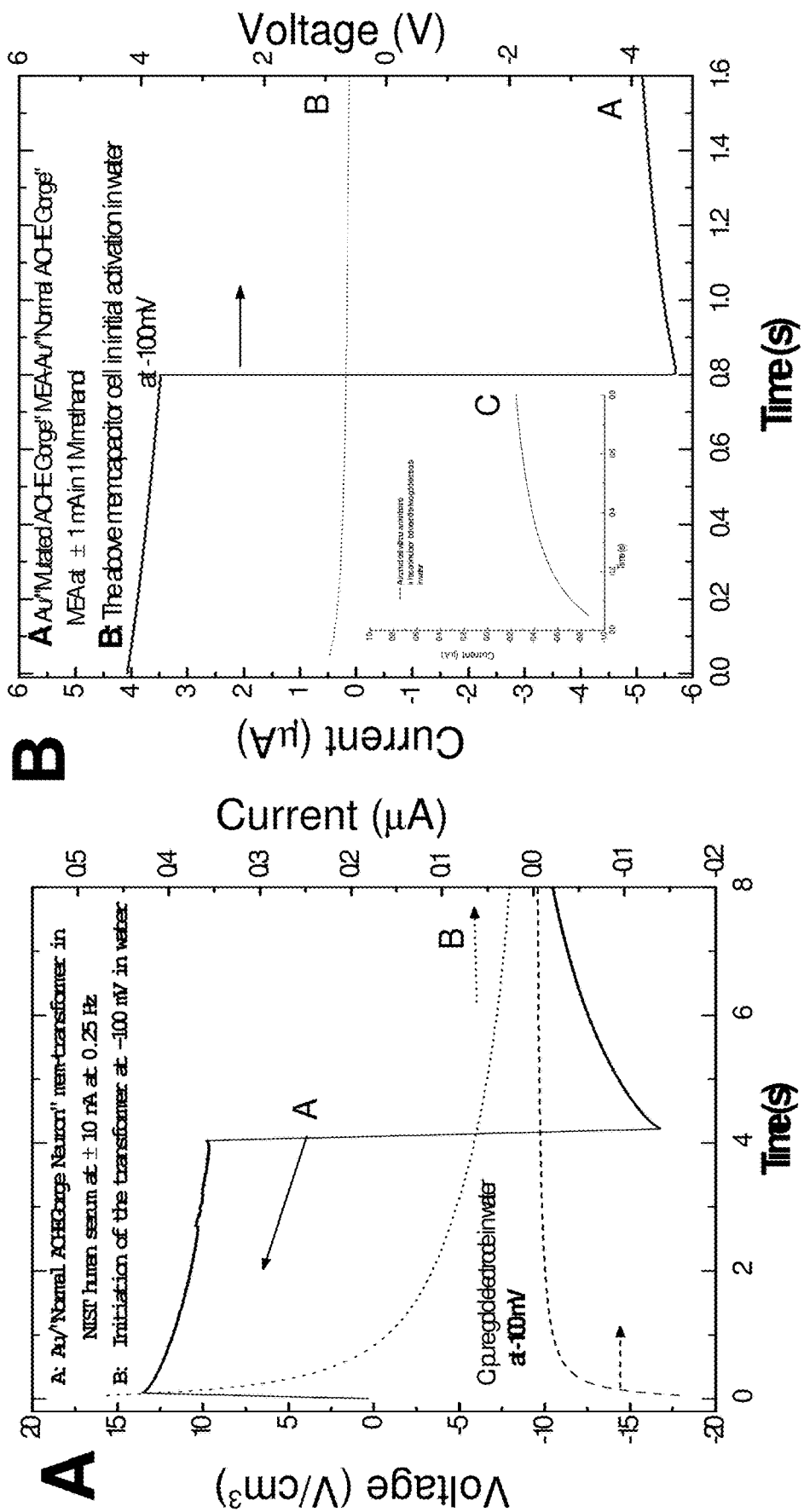
FIG. 16 panel A depicts the toroidal transformer's out put voltage amplification effect using a simple Au/"Normal ACHE Gorge neuron" mems-transformer with flat bridge/nanopore AFM configuration in NIST human serum without spiking Aβ at ±10 nA at 0.25 Hz (a); Against the control of the same device in aqueous solution for the initiation of the device at −100 mV (b); Against the control of the pure gold electrode in aqueous solution at −100 mV.
Figure 16:
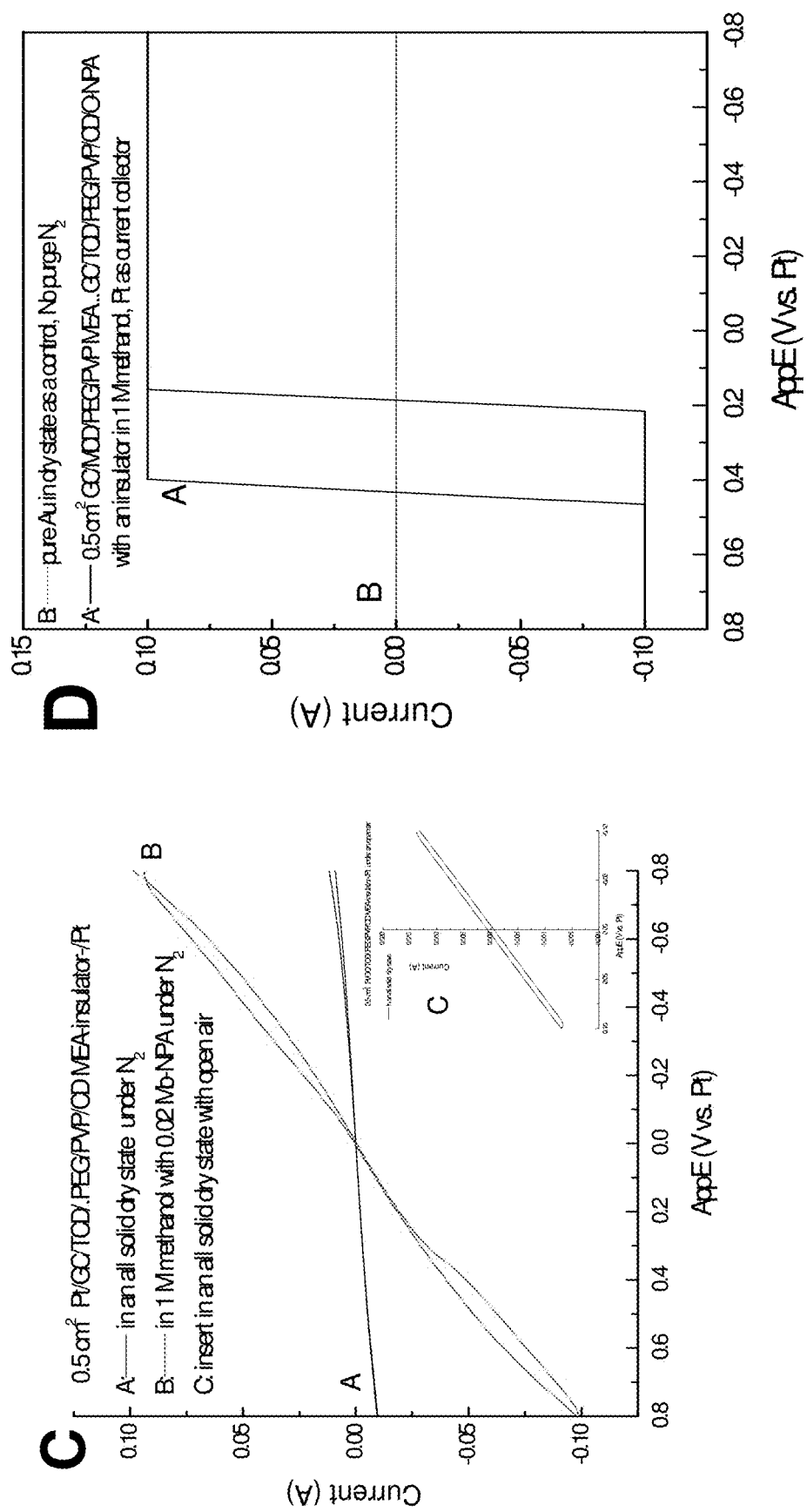

The discharge potential curve at 0.25 Hz (4 s) is about 14.7V/cm$^3$ according to FIG. 11A$_1$ and it reversed the sign to a resting potential of −15V/cm$^3$, that was amplified by 150-fold at each end compared with the initial applied potential for active of the device, it was −0.1V as shown the initial activation curve b in FIG. 16 panel B. This event has confirmed that the device has the equivalent function of the resonate tank circuit, that is a voltage amplifier.

Figure 15:
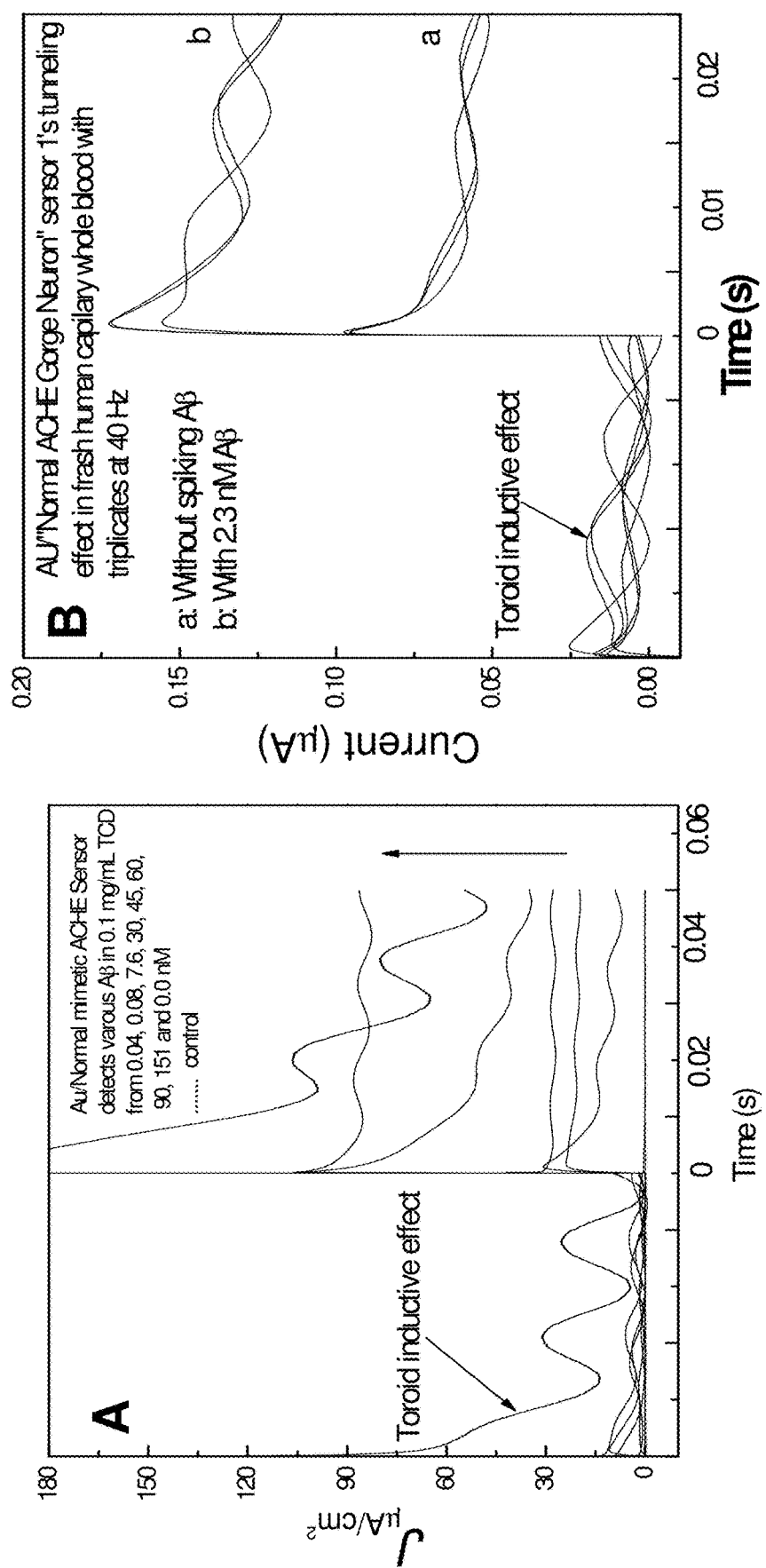
FIG. 15 panel A depicts the toroidal transformer's longitudinal tunneling effect and the DC/AC convertor effect due to the electromagnetic inductivity on device 1 with a flat ACHE gorge bridge/nanopore configuration using a CA method with a DC voltage $E_0$=0 mV, $E_1$=−50 mV, $E_2$=−200 mV with 50 ms at each of two steps with 80 KHz data rate at various concentration levels of Aβ from 0.04, 0.08, 7.6, 30, 45, 60, 90, 151 nM in aqueous solution with 0.1 mg/mL TCD stabilizer against the control of 0.1 mg/mL TCD in aqueous solution.

It also is an alternative current amplifier under a DC potential of −0.2V in fresh human capillary whole blood specimens with triplicates using a chronoamperometric (CA) method was shown in FIG. 15. The AC out put current curves indicate a longitudinal cylinder tunneling effect exist that was caused by the bipolar double toroidal nano-channeling ACHE gorge formation of the membrane against an initial activation/equilibrium at −0.1V DC potential with an s-s current 1.3 nA, which the biomimetic ACHE cylinder has amplified the current by 46-fold without adding any circuitry, that offers a significant advantage of reducing the system size and avoiding lose energy compared to the pure electronic circuitry assembling method. Because the present invention is solely based on the unity of bipolar memristor/memcapaciot/meminductor membrane formed the innovative transformer in double toroid vertex architecture shown in FIG. 5B, hence there was no heat produced because of the field dominating rather than thermal dominating, based on the teaching from the literature [53].

An electromagnetic transformer is an electrical device that transforms voltage levels between two circuits. A transformer operation is based on the principle of electric induction. When a changing magnetic flux links to a circuit and a voltage is induced or electromotive force (emf) is induced in the circuit. The induced voltage is proportional to the number of turns linked to the changing flux [65-66]. The present invention utilized the principles of induction through a self-assembled cross-linked membrane as shown the models in FIGS. 3A and 3B along with the AFM images from FIG. 1A to FIG. 1G, and from FIG. 2A to FIG. 2F that facilitates a center core-form of solenoid that consists of a chain of "donut"-shaped cyclodextrin cavities described in example 3 [00064], and the green color polymer chains shown in FIGS. 3A and 3B facilitate the out layer toroid covering the center solenoid, and stabled by the horizontal hydrogen bonding and hydrophobic bounding. When a potential is applied to the system, there is an inductive effect happened in the center core, so promoted an amplification of the outlet voltage as shown in FIG. 16 panel A curve 3 A increased the volumetric voltage density by 130-fold compared with the initial applied potential of −100 mV. By fitting a linear regression model of the normalized volumetric voltage density divided by the mean data, we obtained the equation to solve the initial rate within the first 10 ms is y=0.2+148x, r=0.998, Sy/x=0.03, p<0.0001; while the control for the initial rate of increased current after normalization of the current divided by the mean current produced an equation of y=−2+7.7x, r=0.99, Sy/x=0.09, p<0.09 within the first 150 ms in curve C. The result indicates the mems-transformer has about 20-fold faster initial rate to raise the voltage than do to the current that is an evidence of the eternal toroid mem-inductivity gain.

FIG. 16 panel B depicts the curve A has 54-fold increased the voltage intensity as well as the raising speed compared with the control curve C, that has a very slow rate of current increase, the phenomena explained a net inductance gain through the inner core toroid; The toroid fall time of the voltage is slower than that of the control curve C compared with curve A when switched, and the curve C in current drop, indicates an inductance gain. The inductance gain phenomena also show in FIG. 15 panel A and B, the sine waved base line curves were dropping slowly than that of the control as Aβ concentration increases, that indicates an inductance gain. In FIG. 15 panel B the curve "a" has a signal AC current intensity increased by 14-fold using human capillary whole blood specimen without spiking Aβ compared with the control shown in FIG. 15 panel A. Wherein, the transformer is also a DC to AC converter converting DC current to an AC wave shown in FIG. 15 in aqueous and in human whole blood media.

Example 9—Evidence of the Nanometer Air Gap Existence in the Mems-Transformer

FIG. 16 panel C depicts a 0.5 cm$^2$ GC membrane electrode assembling (MEA) comprising of a self-assembled membrane of TCD/PEG/PVP/β-cyclodextrin (CD) co-polymer with an insulator and a Pt current collector at each end in solid dry state under nitrogen as curve "A", compared with the same solid dry device in an open air situation as the insert curve "C", Curve "C" has the typical behavior as a meminductor (includes the origin in the hysteresis loop) with an order of magnitude higher current raise slope in a perfect diagonal related to origin than that of curve "A" and it also has a 1.5-fold higher current intensity than curve A. That indicates air gap is a crucial element in the toroidal type transformer to make functions more effectively and flexible. The curve "B" has shown the typical hysteresis loop at the cross-pint of origin with a current intensity of 10-fold higher than that of curve "A", and 7-fold higher than curve "C" in 1 M methanol in the presence of 0.02 M o-NPA under nitrogen, that indicates o-NPA is the most important element in the toroid to make the function properly to lining the ACHE gorge cylindered cavity. The rates to switch current directions over the scanned potential range from the lowest potential to the highest potential for the three curves in decrease order are: Curve C>Curve B>Curve A with the values of 2.7 mA/s>2.5 mA/s>0.14 mA/s under the same scan rate of 20 mV/s. In another words, the values of 135 mA/V>125 mA/V>6.8 mA/V scanned voltage to switch the current is curve C the most efficient one as a transformer having the nanometer air gap in the toroid. Curve B also confirmed the FIG. 16 panel D depicts an energy cell consists of a 0.5 cm$^2$ GC/MCD/PEG/PVP MEA and a 0.5 cm$^2$ GC/TCD/PEG/PVP/CD/O-NPA MEA separated with an insulator connected with Pt wires at each end in 1 M methanol without nitrogen as curve "A" compared with the control of a pure gold in solid stage without an insulator in dryness as curve "B". Curve A has very normal transformer characteristics as cited in literature [65]. Herein, the devices made either with GC or gold with membranes described in FIG. 16 panels A, B C and D work well either air-free or with air; However for a toroid with a membrane of MCD/PEG/PVP/TCD without a laminate agent o-NPA, it needs nano air gap to avoid destruction.

Example 9—the "Sensory Biomarkers"

From the CV profiles, we constructed a Hippocampal-neocortical (HPC-NECOR) biomimetic neural sensory prosthesis as a control. The "Sensory Biomarkers" components were defined: locations of Direct Electron Transfer (DET) peaks in mV, the Hysteresis switch point location in mV. In lieu of all human sensory organs produced smile, vision, touch, taste and sound, are all transformed from an outside stimuli to chemical and electric synapses and it went to the CNS for processing information and give a feedback to the organs. Above section has demonstrated the invention is a closely mimicking the ACHE gorge's radio wave producing bipolar double toroid vertex, hence it is necessary to define such a sensory using the key characteristics of the mem-elements, the pinch field location and the DET peak location in the field. The circular current forma by the DET peak at the bipolar poles were the important electrochemical biomarkers. We are especially interested in the orientations of the biomarkers at SWS, because dysfunction spatiotemporal orientations are associated with diseases.

Example 10—Making of Energy-Sensory Images

Using the CV method to build a data matrix for a sensory prosthesis: the locations of the values of the DET peaks in mV were set up in Y-axis, the Hysteresis switch point location values were in mV set up in X-axis and Frequency associated with the biomarkers were entered in Hz (Z-axis). The real-time data obtained from the voltage sensing DSCPO method was converted to volumetric energy density, $E=C_s \cdot (\Delta V)^2/(2 \times 3600)$, $C_s$: specific volumetric capacitance $C_s=[-i \cdot \Delta t/\Delta V]/L$, $C_s$ is in F/cm$^3$ [54-55], the $\Delta t$ is time change in second, $\Delta V$ is voltage change in V, i is current in Amps, and L is volume in cm$^3$. The energy density data were infused into the sensory matrix sheet before Aβ and compared with that of after Aβ was spiked, and each matrix sheet has a fixed Aβ concentration. The frequencies are covered from the lowest to highest. The lowest frequency reflects a darker color and the high frequency is in a bright color. Following is the flow chart for building the 3D synapse map and the optical images of the energy-sensory interaction. It is a tool for identify early asymptomatic diseases by find the pHFOs in an electric synapse level.

Example 11—Assessing CR Dysfunction, Memory Status and Predicting of "Epilepsy" and "AD"

Evaluation of the CR dysfunction, memory status and predicting of "epilepsy" and "AD" is in two-fold: First is the energy-sensory mapping through the HFO or the pHFO. Forming HFO indicates good memory because of promoting right circuitry flow and network circuitry conformation, and forming pHFO indicates loss of memory because of the mischief circuitry flow direction and conformation, especially through the CR abnormality in the SWS; second is to calculate the sensitivity of the energy density per second using the linear regression model at a fixed Aβ concentration against that without Aβ. Prediction of "epilepsy" or "AD" was accessed by identifying the presence of the pHFO center through the energy-sensory map.

Recently, our ACH sensors have demonstrated the capability for detection of Aβ [56]. Reports show the ACHE has been overly expressed in cancer and AD, and pharmaceutical companies developed drugs to inhibit the ACHE expressions in order to increase the level of ACH [57-58]. Therefore, the purpose of the research is to test the hypothesis that ACH may restore the broken hippocampus-neocortical neuronal circuitry by using a biomimetic ACHE gorge memcapacitor/memristor device in vitro during SWS. Our next goal is to verify the relationship between a normal HFO in hippocampus-neocortical neuronal circuitry and the pHFO after the ACH added into the Aβ-spiked human serum communicates with our neuronal network device. The scope of this section is to focus on the ACH applications on the memristor/memcapacitor/meminductor device before and after presence of Aβ and to verify the hypothesis that applying ACH at SWS will be able to repair Aβ's damage on the Biomimetic neuron prosthesis, and implies the direction to go for the potential patients who suffer the neuronal damages.

The Energy-Sensory Image output comprises five steps: (1) identify the "Sensory Biomarker" (2) at the biomarker potential locations enter discharge pulse energy data into the DET peak potential location in the "y" data column, and enter data at its spatial location of the cross-point in the "x" column, then enter scan frequency data in the "z" column; (3) convert the xyz columns to a random correlative gridding matrix; (4) highlight the matrix and convert the matrix (5) plot the 3D energy-sensory interactive dynamic synapse map; contour map and the optical image, respectively.

Example 11A—Circadian Rhythm Profiles

Figure 17:
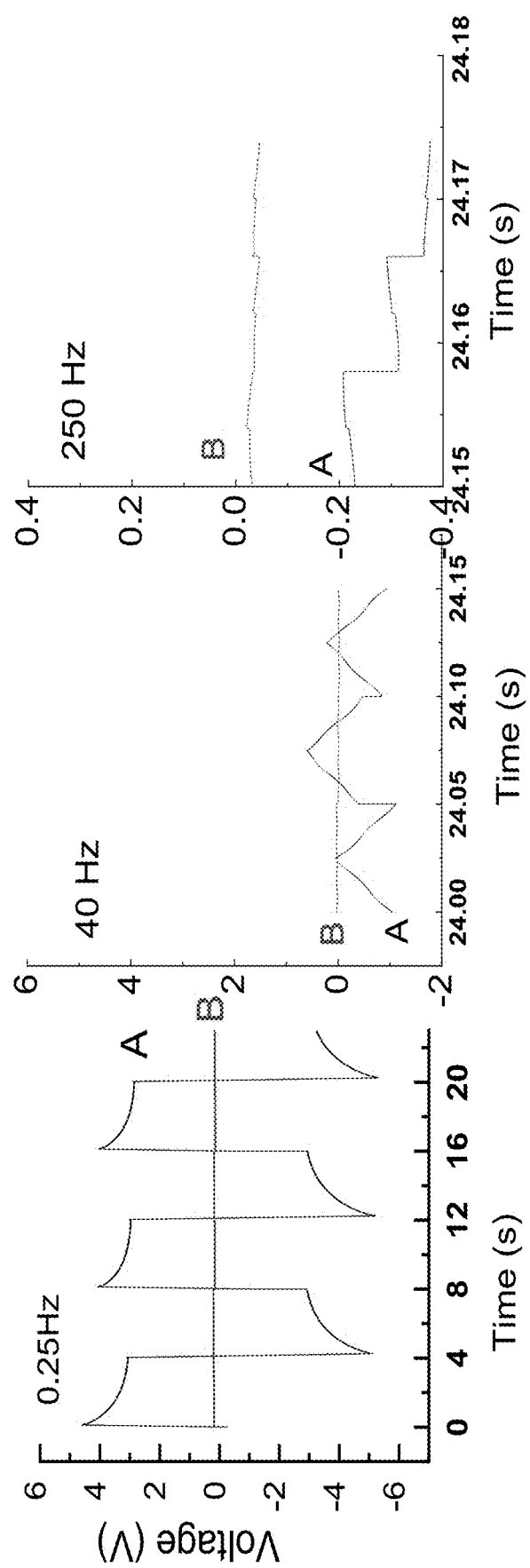
FIG. 17 illustrates the CR profiles at ±10 nA in 0.25, 40 and 250 Hz using the DSCPO method, respectively, from device 1 (blue) compared with device 2 (red) in NIST serum without Aβ. Curves are averaged for three runs.

The CR profiles are presented in FIG. 17. Without spiking Aβ, Device 1's original signal intensity at SWS is a hundred times stronger than the "mutated ACHE" neural device 2's signal over three replications. That indicates device 2, with a broken internal ACHE lining HPC-NECOR neuron network, has a pool memory during SWS and a dysfunctional CR. The damaged ACHE cylinder gorge device has very low net voltage discharge magnitude in SWS compared at other frequencies indicating the CR dysfunction regardless with or without Aβ over 0.25, 40 to 250 Hz shown in FIG. 17. Our former work revealed that a "normal ACHE gorge" memcapacitor device has several magnitude higher voltage intensities at SWS than this device [59] and that indicates there is a lack of memory consolidation. FIG. 17 shows the device 2 is not sensitive to energy change in the presence of Aβ. Aβ drags the energy toward a more negative field. In the middle panel of FIG. 17, the phase lag and change frequency occurred from 40 Hz to 160 Hz indicating the neural network synapse is abnormal.

Example 12—Assessing the ACH's Repairing Function

Figure 19:
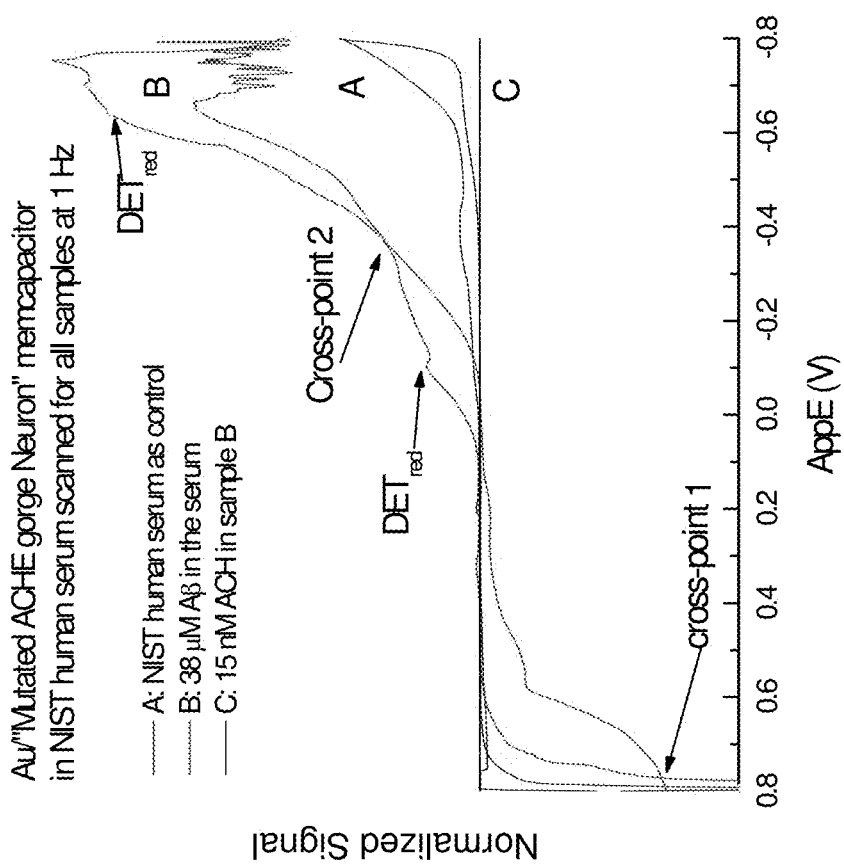
FIG. 19 depicts the CV profiles under the same conditions as in FIG. 18 for device 2.
Figure 18:
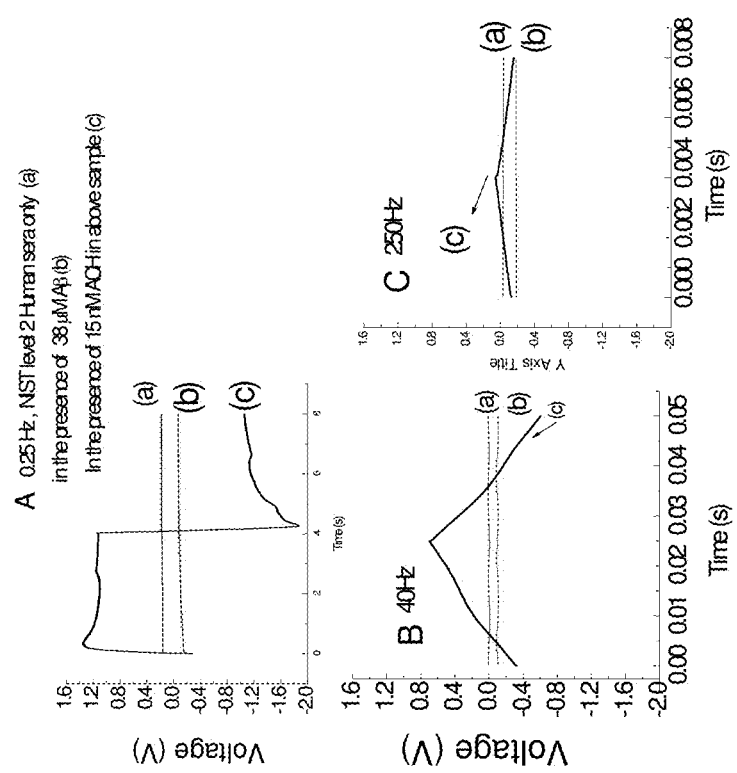
FIG. 18 depicts ACH repairs dysfunction CR at SWS using device 2. The blue line refers to serum only without Aβ and no ACH as "a"; the red line refers to in the presence of 38 μM Aβ as "b" and the black line refers to after a 15 nM ACH presence in the above Aβ serum as "c" at ±10 nA in 0.25 Hz (A), 40 Hz(B) and 250 Hz (C), respectively.

Evaluations of ACH's repairing of neuronal network circuitry damage is in two-fold: first is to analyze the energy-sensory map and see the pHFO situation before and after ACH applied; second is to calculate the sensitivity of the energy density per second change using the linear regression model at a 38 μM Aβ concentration against that without Aβ over 0.25-250 Hz using DSCPO method. ACH repairs dysfunctional CR at SWS was demonstrated in FIG. 18 using Device 2, regardless of whether conditions are with or without Aβ with the DSCPO method. With ACH, the device 2 discharges highest voltage at SWS compared to that at 40 and 250 Hz. All curves were averaged for three replicates. Electric synapse strength enhanced by orders of magnitude, it means the memory of the damaged neuronal prosthesis was restored, and it also implies to the potential patient that uses the 15 nM ACH at SWS is a right path to repair memory damage. However, it is only a suggestion, because the appropriate dosage has not established yet. The inversed trend was reflected in FIG. 19 from the CV profiles as expected, however, after applied the ACH, the Aβ signal was eliminated.

Figure 21:
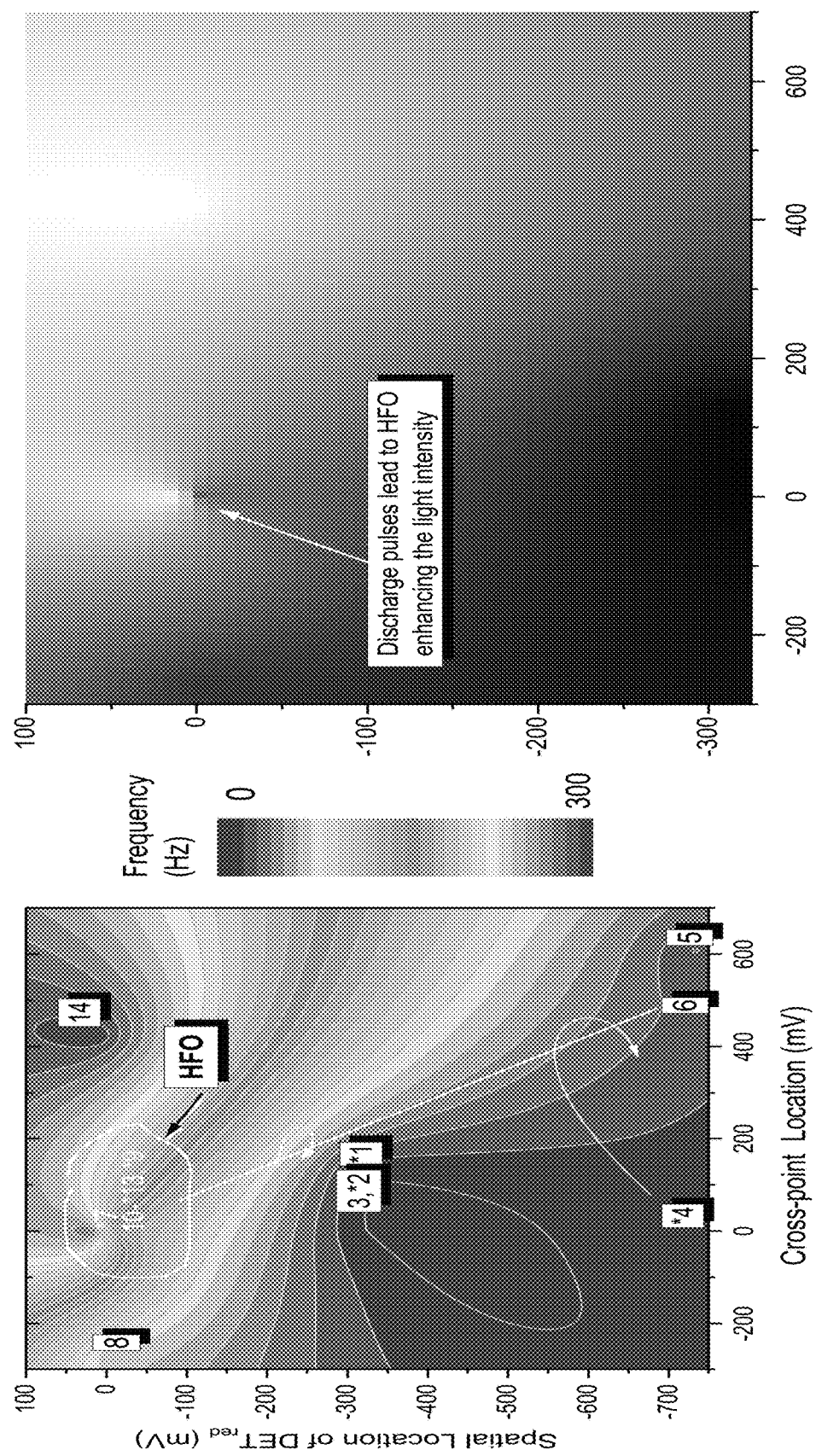
In FIG. 21 the Panel A depicts the synapse circuitry dynamic 3D Energy-Sensory map of Device 1 interacted with NIST serum after discharges synapse pulses and infused the pulse energies into the matrix and labeled as * were shown, and without Aβ. The reentrant point was labeled. The panel B depicts the contour map at the same definitions of axis. The HFO was labeled. The panel C depicts the optical image of the Energy-Sensory map. The HFO was labeled in the optical image.
Figure 22:
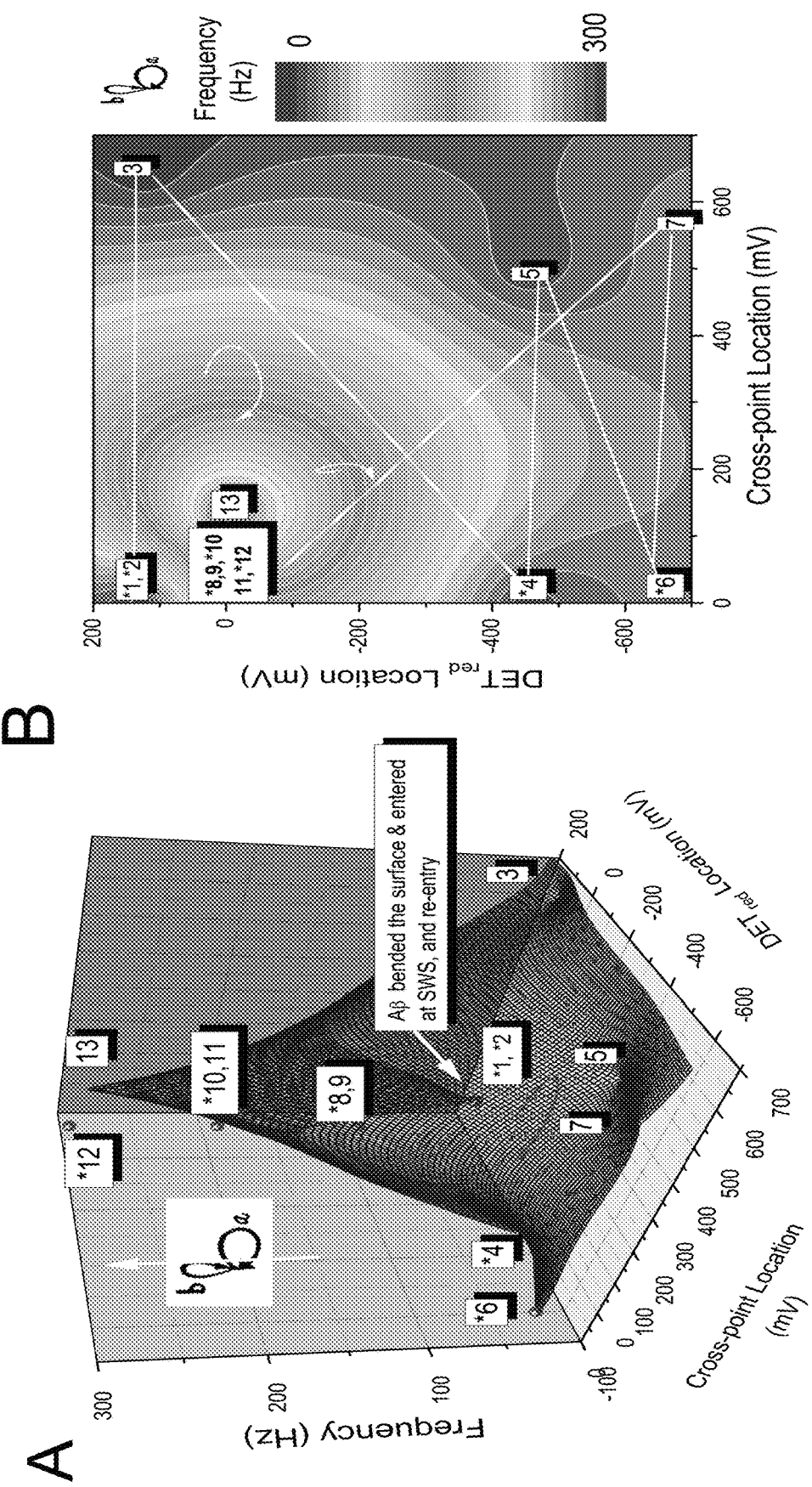
In FIG. 22 the panel A depicts the synapse circuitry dynamic 3D Energy-Sensory map of Device 1 interacted with NIST serum after discharges synapse pulses and infused the pulse energies into the matrix and labeled as * were shown, and with 3.8 nM Aβ. The bad reentrant center was labeled. The panel B depicts the contour map at the same definitions of axis. The panel C depicts the optical image of the Energy-Sensory map. Aβ depositions were labeled.
Figure 23:
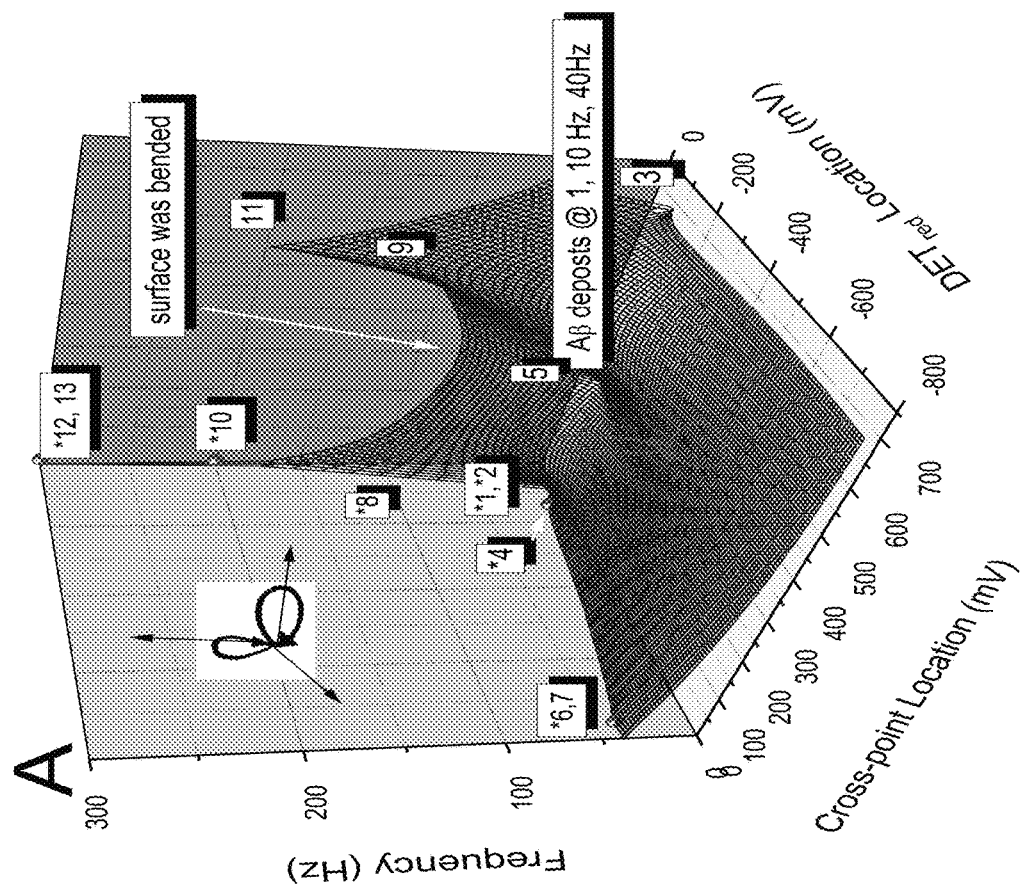
In FIG. 23 the panel A depicts the synapse circuitry dynamic 3D Energy-Sensory map in Panel A of Device 1 interacted with NIST serum after discharges synapse pulses and infused the pulse energies into the matrix and labeled as * were shown, and with 76 nM Aβ. The bad reentrant point was identified with the induction point identified with arrow. The panel B depicts the contour map. The panel C depicts the optical image of the Energy-Sensory map with Aβ depositions were labeled.
Figure 22:
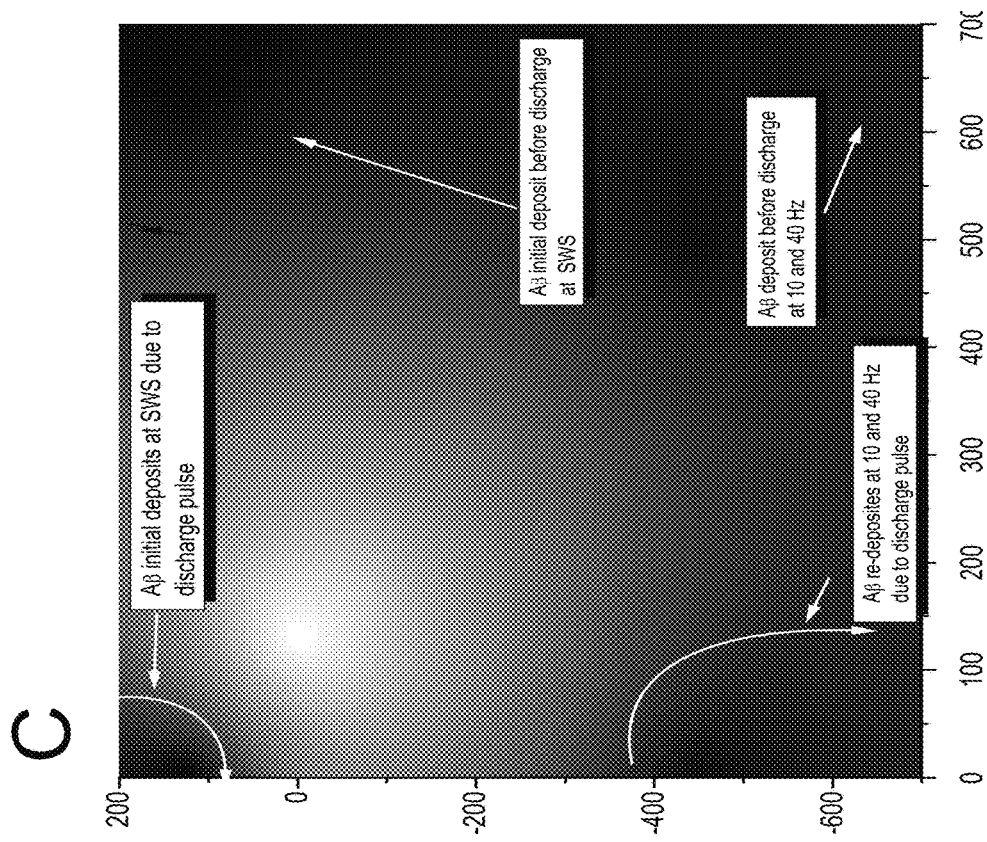
Figure 23:
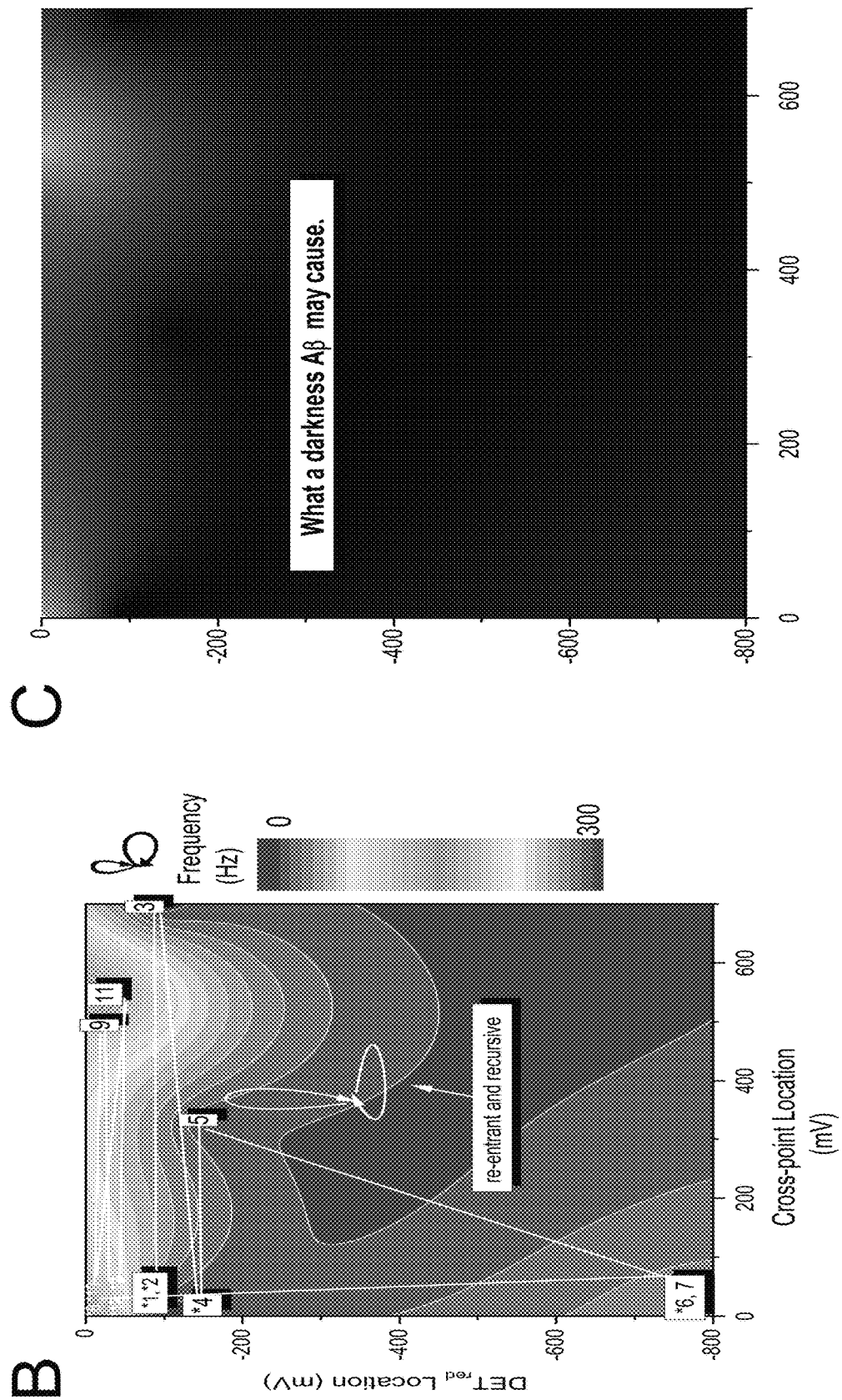

Example 13—Using Energy-Sensory Technology to Predict and Monitor the Early Signs of Neuronal Diseases The goals of using Energy-Sensory image map technology are to predict and monitor early signs of neuronal related diseases, here we use AD, epilepsy and dysfunction CR as examples. Device 1's energy-sensory images without Aβ are presented in FIGS. 20 and 21. For the initial "neural network prosthesis" before discharging a pulse, the circuitry synapse networking flow is an "8" shape on a flat 45° surface without forming HFO in FIG. 20 panel A. The contour map is in panel B and the optical image in panel C has strong light intensity indicating the healthiness of the left or right-side of semi sphere in neocortex-hyppocampus in contact with the human serum. After the neural network discharged pulses, the HFO was formed and labeled in FIG. 21 with locations at the "Sensory Origin" (SO) (cross-point 0.0 mV, DET 0.0 mV) over 60-140 Hz. The bright star-like image in FIG. 21 panel C optical image was reflected at the exact spatiotemporal location in FIG. 21 panel A and B and indicates the HFO is a good reentrant center; not only does it have the same circuitry flow direction, it also enhances the brain energy and memory. It was initiated by a yellow circle located at the bottom floor overlapping the SO, shown in FIG. 21 panel A, from neocortical to hippocampus through entorhinal cortex (EC)-subiculum-CA1-CA3-DG flowing on a 45° flat surface. It has an agreement with the observation made from FIG. 17 that the normal neuron device 1 has a better CR function than device 2 in voltage discharge intensity at SWS using the DSCPO method. In contrast, Aβ in the biomimetic neural network environment, acted not only as a biomaterial, but also as an agent to kill the good HFO by altering the network circuitry confirmation from a flat orientation to a vertical stereo structure; changing the circuitry direction by close to DET's 0 mV; and re depositing Aβ in multiple areas at neocortex through mutated-reentrant with bended surfaces as worsened in the order of FIG. 21<FIG. 22<FIG. 23 with a heavy damage in SWS discharge pulses. Hence device I demonstrated its function to monitor the early CR dysfunction by using the energy-sensory image technology. As the concentration increases from 3.8 to 76 nM Aβ, the light intensity in the images were greatly darkened from 60% at 3.8 nM to 96% at 76 nM. It indicates a brain volume loss by the correspondence percentage of light intensity diminish. To a "normal ACHE gorge neuron network" device 1, at 76 nM level, the brain faces "life-threatening" danger and yet without any symptom of epilepsy, because of lack of the pHFO induction center. However, the "death" was caused by the neuron shrinkage from both of the neocortex and the hippocampus neurons loss evidenced by our images in FIG. 23. The event has matched with the clinical fMRI evidences [60-61]. Schuff's group reported a multiple-center clinical study for AD, it discovered the hippocampus volume loss is proportional to the severity of AD progress [60]. Vijayakumar's study revealed AD patients' hippocampus volumes reduced by 25% compared with the control group and led to a same conclusion as drawn from Schuff [61]. Detailed explanations of the neuronal loss for AD see reference 62.

Figure 25:
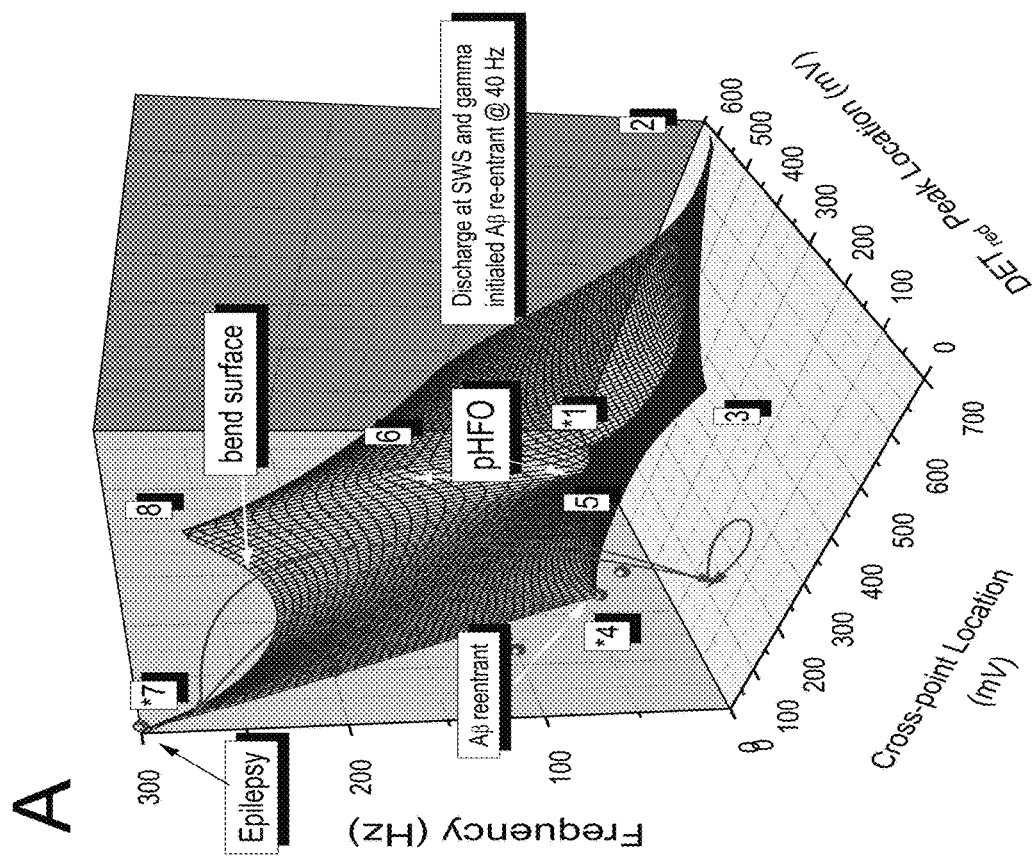
FIG. 25 in the Panel A depicts the synapse circuitry dynamic 3D Energy-Sensory map of Device 2 interacted with NIST serum after discharges synapse pulses and infused the pulse energies into the matrix and labeled as * were shown, and without Aβ as "Epilepsy stage 1" and "asumptomatic". The pHFO were labeled. The e epilepsy point was labeled. The Panel B depicts the contour map with the pHFO were labeled. The Panel C depicts the optical image of the Energy-Sensory map. The pHFO was labeled in the optical image.
Figure 24:
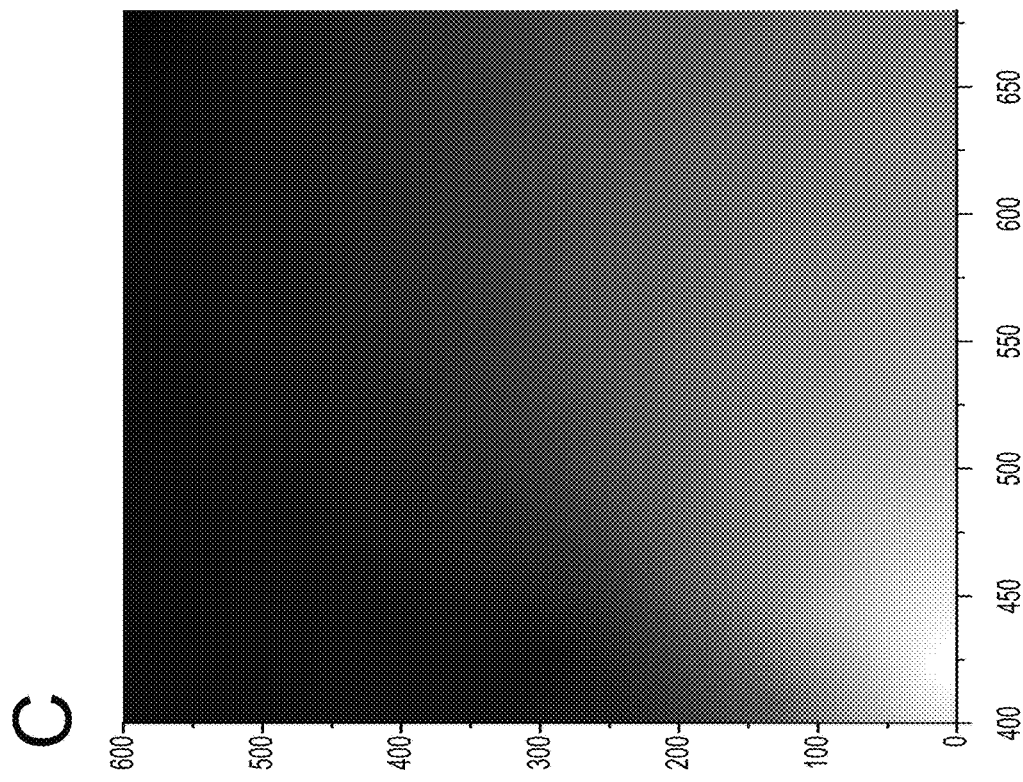
FIG. 24 in Panel A it depicts the synapse circuitry dynamic 3D Energy-Sensory map of Device 2 interacted with NIST serum before discharges a synapse pulse, and without Aβ as "Epilepsy stage 0". The Panel B depicts the contour map and the Panel C depicts the optical image of the Energy-Sensory map.

"Mutated Neural Network" Device 2. Four stages of AD or epilepsy are presented in 6 groups of figures from FIGS. 24 to 29. Each group consists of three panels of figures as similar as above section. The epilepsies are a spectrum of brain disorders impacted by or presented in a wide range of diseases, such as diabetes, cancer, traumatic brain injury, brain tube deficiency, Alzheimer's, asthma, heart failure, Parkinson's and depression. The degrees of severity vary. There is an urgent unmet need to predict epilepsy in order to develop devices that are able to reliably predict and monitor seizures and help avoid life-threading episode. Our "mutated ACHE gorge" neural device is able to provide first-hand information regarding the prognosis of epilepsy in different stages when the neural toxin Aβ in high concentration interacts with the damaged prosthesis in an electric field. The sensory brain prosthesis was built by the biomarker CV data with only one cross-point and one $DET_{red}$ peak locations at each of the frequencies from 1 to 300 Hz without Aβ; there was no brain synapse pulse discharged. Three categories of maps are presented in 3D Energy—Sensory map before energy infusion without Aβ, as shown in FIG. 24 panel A, there was no pHFO to be observed. Panel B in FIG. 24 is the contour map, the panel C shows the original "damaged neuron" device 2's light image, and the light intensity was a 1-2% of the "normal ACHE neuron" device 1 at the same situation compared in FIG. 20 in the panel C. FIG. 24 presents the AD or Epilepsy in "Stage Zero". The epilepsy or AD "stage 1" sensory prosthesis was built by the biomarkers CV data with only one cross-point and one $DET_{red}$ peak locations at each of the frequencies from 1 to 300 Hz without Aβ; the brain pulse discharges energy values at 0.25, 40 and 250 Hz were infused in the matrix without Aβ was defined as "Stage One" for epilepsy and AD. It was presented in FIG. 25. The pHFO center can be seen in all three panel figures after discharged pulses and without Aβ. The network circuitry surface has more curvature than FIG. 24 panel A, and the direction of the circuitry flows against that of the original network current flow and was initiated by the energy infusion at SWS, as shown in the panel B with the pHFO shown as a dark mark image; the potential epilepsy center created can be seen at the (0, 0) mV sensory origin (SO) in the optical image in the panel C in FIG. 25. It paved a road for reentrant of pHFO and Aβ, and this nonsymptomatic stage was defined as "Stage One" for epilepsy or AD.

Figures 26, 27:
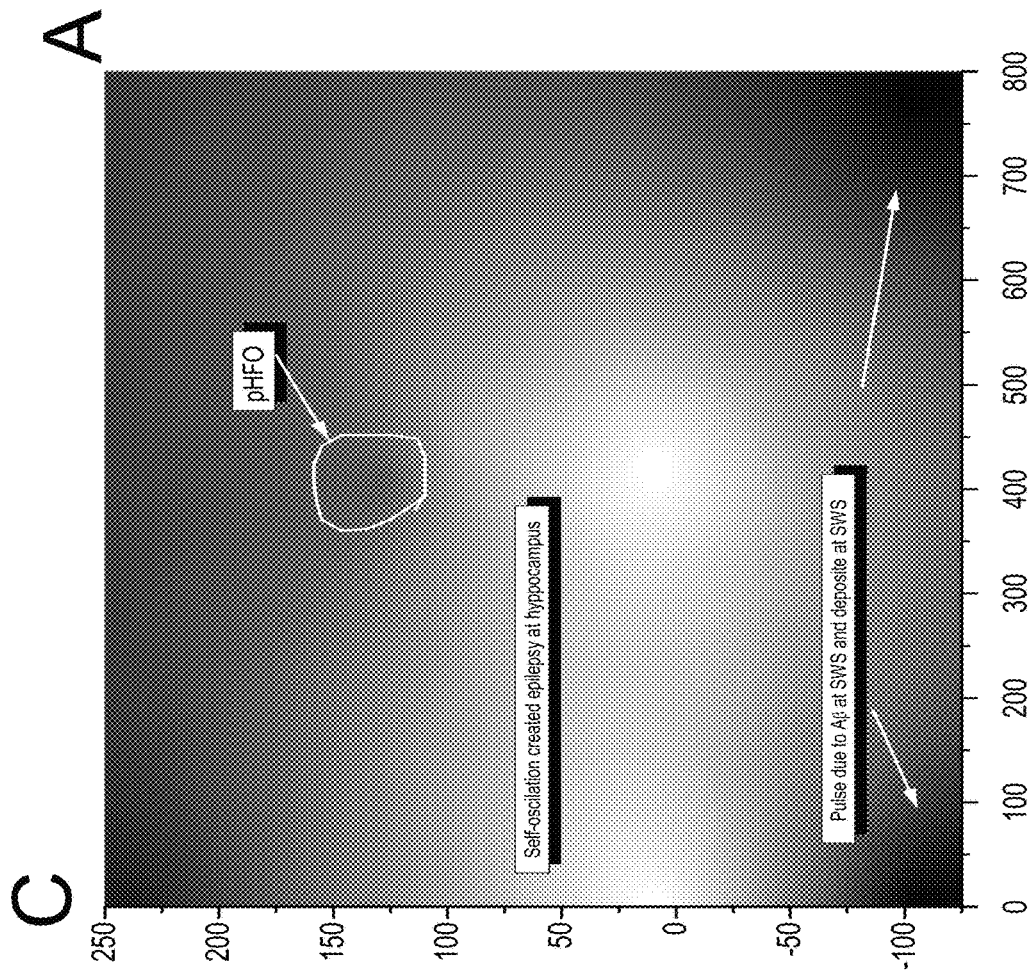
FIG. 26 in the Panel A depicts the synapse circuitry dynamic 3D Energy-Sensory map of Device 2 interacted with NIST serum after discharges synapse pulses and infused the pulse energy with 38 μM Aβ at SWS Hz into the matrix as **, other discharge pulses infused in the matrix in higher frequencies without Aβ, and labeled as * were shown. The pHFO were labeled, as "Epilepsy stage 2" and is "asymptomatic". The epilepsy site was labeled. The Aβ reentrant sport was identified. The Panel B depicts the contour map with the pHFO were labeled as the "weak sport" of draining energy. The epilepsy site was labeled. The Aβ depositions were labeled as arrows. The Panel C depicts the optical image of the Energy-Sensory map. The pHFO was labeled in the optical image.
FIG. 27 in the Panel A depicts the synapse circuitry dynamic 3D Energy-Sensory map of Device 2 interacted with NIST serum after discharges a synapse pulse at 0.25 Hz, and infused the pulse energy under the condition of with 38 μM Aβ into the matrix as a * and the neural network prosthesis built under the same concentration of Aβ from 1 to 10 Hz with 2 DET peaks and 2 cross-point locations at each frequency; DET and cross-point CV data from 40 Hz to 300 Hz have no Aβ, so same as to the discharge pulses infused in the matrix, without Aβ. The 2 pHFO inducing centers were labeled. This is "Epilepsy stage 3" and is "symptomatic". The Aβ reentrant center was labeled. The epilepsy site was labeled. The Panel B depicts the contour map with the pHFO were labeled as the "weak sport" of draining energy. The epilepsy site was labeled. The Aβ depositions were shown as the dark blue colors. The Panel C depicts the optical image of the Energy-Sensory map. The pHFO was labeled in the optical image. The epilepsy center was labeled. Aβ depositions were labeled.

The second stage was under the conditions: the prosthesis made by the sensory biomarker CV data from 40-300 Hz was without Aβ, but the biomarker's CV data at 1 Hz was with Aβ, so it was same for the discharge energy pulses, at 0.25 Hz with Aβ, and pulses discharged at 40 Hz and 250 Hz without Aβ. It indicates Aβ only invades the neocortex, not entered the deep brain. It was found there is an epilepsy center at the DET peak location of 0 mV and the cross-point 0 mV, and it clearly self-synchronized with the brain network at the sensory location of the cross-point at 420 mV and the DET location at 0 mV at 250 Hz with a small amount of Aβ deposited, as shown in FIG. 26 for the symptomatic AD or epilepsy with short-term memory loss, and led to dysfunctional sensory. The circuitry flow surface was more bended and the direction was anti origin compared in FIG. 24 panel A, and FIG. 26 panel A has an identified reentrant spot, and the energy sinking hole was the pHFO spot and was labeled in the panel B of FIG. 26. The CA1 sector has been identified as an extremely vulnerable spot to traumatic insult; however the explicit mechanism is unknown according to literature [63]. Using the invented device 2, the vulnerable spot was shown and shorn a light with the flow circuitry and conformation information to the researchers. One epilepsy center was labeled in the contour map as well as in the panel C, the light image map.

The third stage was under the conditions: the discharge pulse energies infused in the matrix were under the similar conditions as in stage 2, but the sensory "prosthesis" matrix made from the CV data of sensory biomarkers used 2 cross-points and 2 $DET_{red}$ peaks at 1 and 10 Hz, respectively according to the CV curves in FIG. 10. This means Aβ is able to influence the formation of sensory biomarkers, hence the stage 3 AD or epilepsy has increased pHFO centers with larger Aβ depositions, therefore the prosthesis's original light intensity was greatly reduced. Numbers of pHFO as a "mutated reentrant center" were increased, and areas of Aβ depositions increased which led to a deep darkened brain image with the light intensity reduced by more than 90%, it means the volume of the hippocampus brain was reduced by 90% as shown in FIG. 27 panel A, B and C. This stage is the Aβ in deposition in neocortex, while the epilepsy is not in domination. Aβ formed new sensory biomarkers are important to notice that played a crucial role to be in control of the AD.

Figure 29:
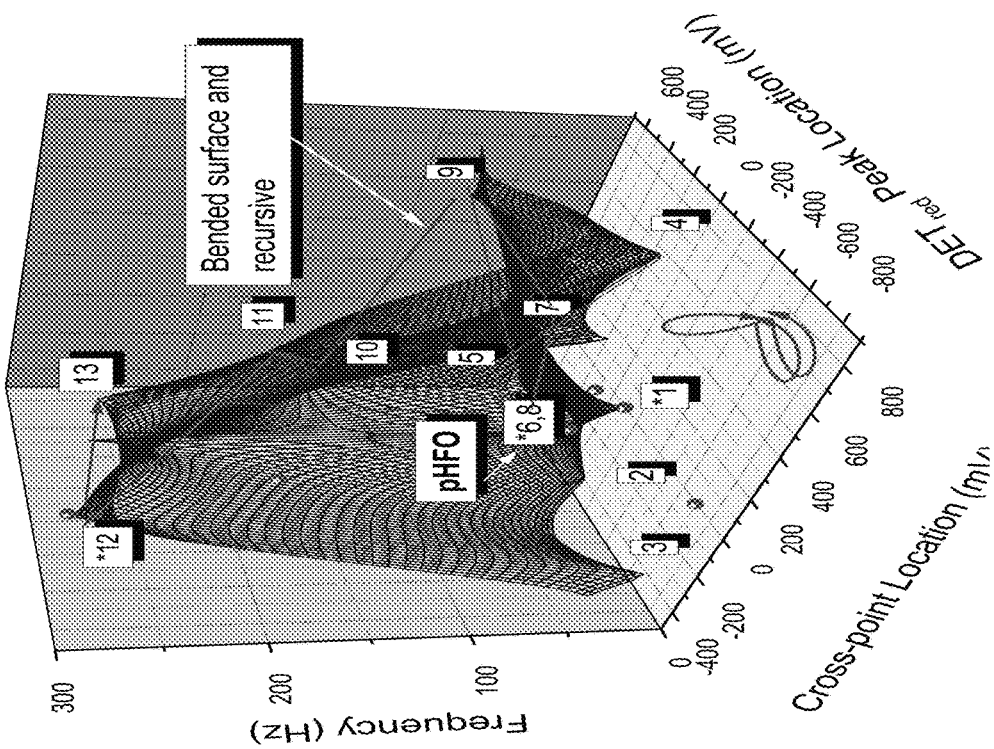
FIG. 29 in the Panel A depicts the synapse circuitry dynamic 3D Energy-Sensory map of Device 2 interacted with NIST serum under the condition of with 38 μM Aβ after discharges a synapse pulse at 0.25, 40 and 250 Hz, respectively, and infused the pulse energies into the matrix as a * and the neural network prosthesis built under the same concentration of Aβ over 1 to 300 Hz with multiple DET peaks and multiple cross-point locations at this range. This is "Epilepsy stage 4B" and is life "threatening symptomatic". The Aβ multiple reentrant centers were labeled. The Panel B depicts the contour map with the pHFO was labeled as the "weak sport" of draining energy. The epilepsy sites were labeled. The Aβ depositions were shown as the dark blue colors. The Panel C depicts the black-white optical image of the Energy-Sensory map with the pHFO were labeled in the optical image. The 5 epilepsy centers were labeled. AB depositions were labeled. The Panel D depicts the colorful optical image of the Energy-Sensory about the spatiotemporal trajectory using neither a tracer nor a dye.
Figure 28:
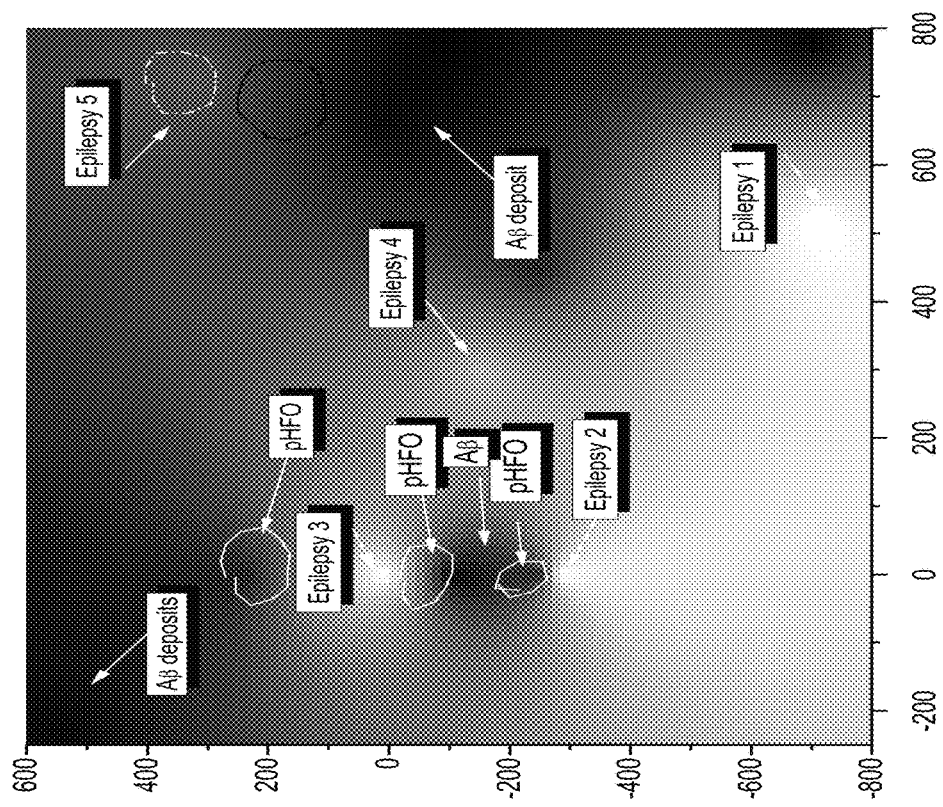
FIG. 28 in the Panel A depicts the synapse circuitry dynamic 3D Energy-Sensory map of Device 2 interacted with NIST serum after discharges a synapse pulse at 0.25 Hz, and infused the pulse energy under the condition of with 38 μM Aβ at 0.25, 40 and 300 Hz into the matrix as a * and the neural network prosthesis built under the same concentration of Aβ over 1 to 300 Hz with multiple DET peaks and multiple cross-point locations at this range. This is "Epilepsy stage 4A" and is life "threatening symptomatic". The Aβ multiple reentrant centers were labeled. The Panel B depicts the contour map with the pHFO were labeled as the "weak sport" of draining energy. The epilepsy sites were labeled. The Aβ depositions were shown as the dark blue colors. The Panel C depicts the optical image of the Energy-Sensory map with the pHFO were labeled in the optical image. The epilepsy centers were labeled. Aβ depositions were labeled.

The "Epilepsy IV" is a "life threatening stage" in stage 4A and 4B parallel situations. The sensory "prosthesis" made from the CV data of sensory biomarkers used multiple $DET_{red}$ and multiple cross-points over 1-300 Hz with 38 μM Aβ. The manner of discharge pulses are same as stage 3, that discharge energy pulses at 0.25 Hz with 38 μM Aβ, and pulses discharged at 40 Hz and 300 Hz without Aβ. The Aβ's accumulation in cortex is no longer a predominate factor, rather than to transform the epilepsy as a dominate factor at hippocampus with an evidence of forming 4 epilepsy centers and 4 pHFO centers as shown in FIG. 28 panel B and C. The 3 pHFOs were in alignment at cross-point 0 mV and one of the pHFO was alignment at DET 0 mV forming a channel led to epilepsy synchronized over 40-300 Hz in the hippocampus. An "eye of tornado" in the center of the channel as a dark sport as seen due to the overheated epilepsy-causing the edema of hippocampus, which is in agreement with the clinical acute epilepsy stage reported with hyppocampus edema and hyper-intense initially, then late atrophies [64] as shown in the panel B of FIG. 28. The FIG. 28A shows the circuitry surface conformation as a standing beast and the synapse current flow direction consisted of three clock wise flow circles and one counter clock flow circle, and the flow circles in neocortex is perpendicular to that of the hippocampus that a "tornado" forming force was in place bearing destruction capability, as a fire vertex that is spontaneous and difficult to put off. We had identified this force as a toroid destruction force caused by the missing of the ACHE gorge linen through our experiment study [24]. The end stage AD patients who suffer symptoms of epilepsy, in volunteering mussel contraction have matched the stage 4A. Stage 4B is same for the prosthesis building as for 4A, that all biomarkers' CV data obtained with Aβ over 1-300 Hz; but the energy infused entered the matrix by pulse discharge through the entire range of frequencies are with Aβ. FIG. 29 panel A shows the synapse circuitry with two anti clockwise circles of 1 to 4, and 4 to 7 forming surfaces almost paralleled to the neocortex, however at the reentrant point at number 7 at 40 Hz as the reentrant point that connected to a flow surface from number #7 to #13 which is perpendicular to the early formed circles. The synapse flows from 40 Hz at #7 to #13 at 300 Hz is in a manner of helix has given to the epilepsy a new level of fire vertex with the epilepsy center #1, #2 and #3 in 300 Hz in the hippocampus with severe edema and the two more epilepsy centers are mobile in 100-200 Hz. It is an agreement with the clinical observations that the epilepsy hurts the hippocampus more severe than to hurt the neocortex [64] as shown in the panels B and C in FIG. 29. FIG. 29 panel D depicts the colorful optical image of the progressing of the AD or epilepsy using neither a tracer nor a dye.

Figure 30:
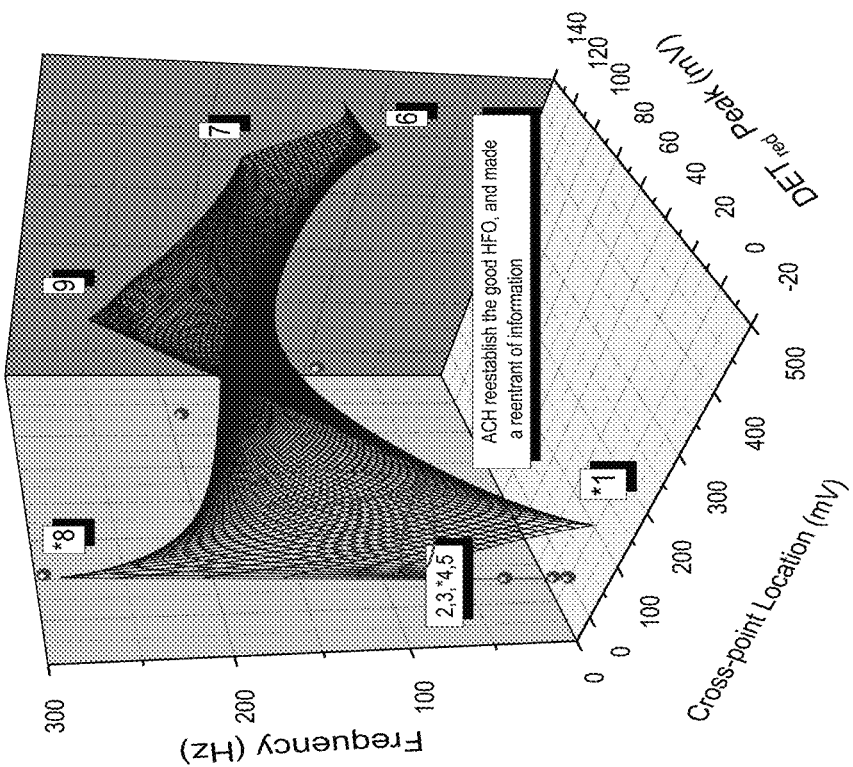
FIG. 30 Panel A depicts the synapse circuitry dynamic 3D Energy-Sensory map of Device 2 interacted with NIST serum after discharges synapse pulses and infused the pulse energy under the condition with 38 μM Aβ and 15 nM ACH at 0.25, 40 Hz and 250 Hz, respectively into the matrix as *, shown as "Early recovery" to repair a level 2.5 "epilepsy" or AD. The brain network prosthesis was made from the CV data with the same concentration of Aβ and ACH over 1-40 Hz, except the 2 mM o-NPA also presence in the solutions in 10 and 40 Hz, respectively. The CV data obtained to build the brain prosthesis from 100-300 Hz there was no reagent was present, only pure NIST serum with the assumption of Aβ will not be able to penetrate from nerocortex into the hippocampus area at an early stage of AD or epilepsy. The positive memory reentrant was labeled. There were no multiple DET and multiple cross-points in the matrix. The Panel B depicts the contour map with the HFO labeled. The Panel C depicts the optical image of the Energy-Sensory map. The HFO was labeled in the optical image.
Figure 29:
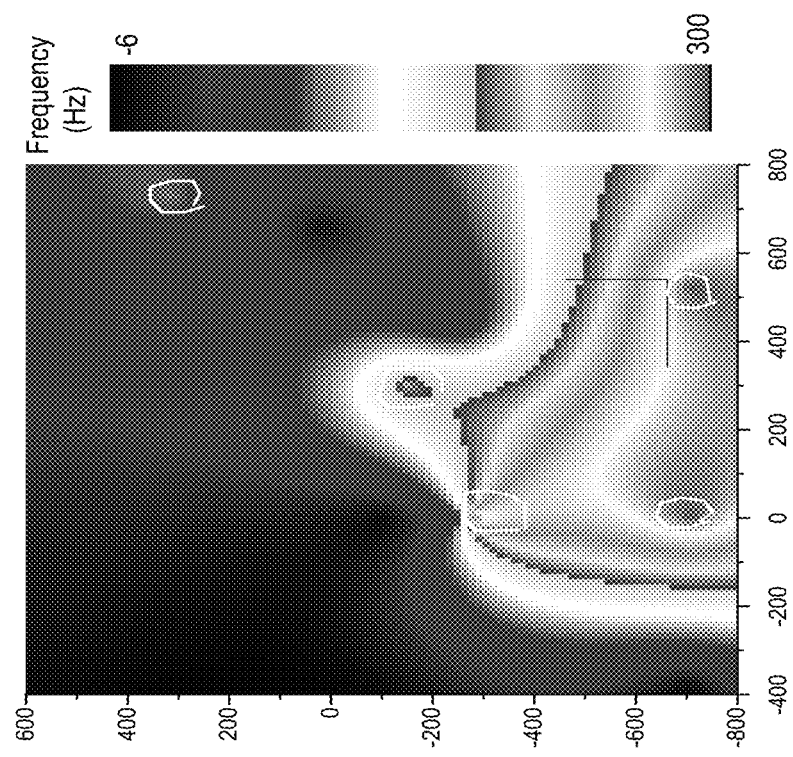
Figure 30:
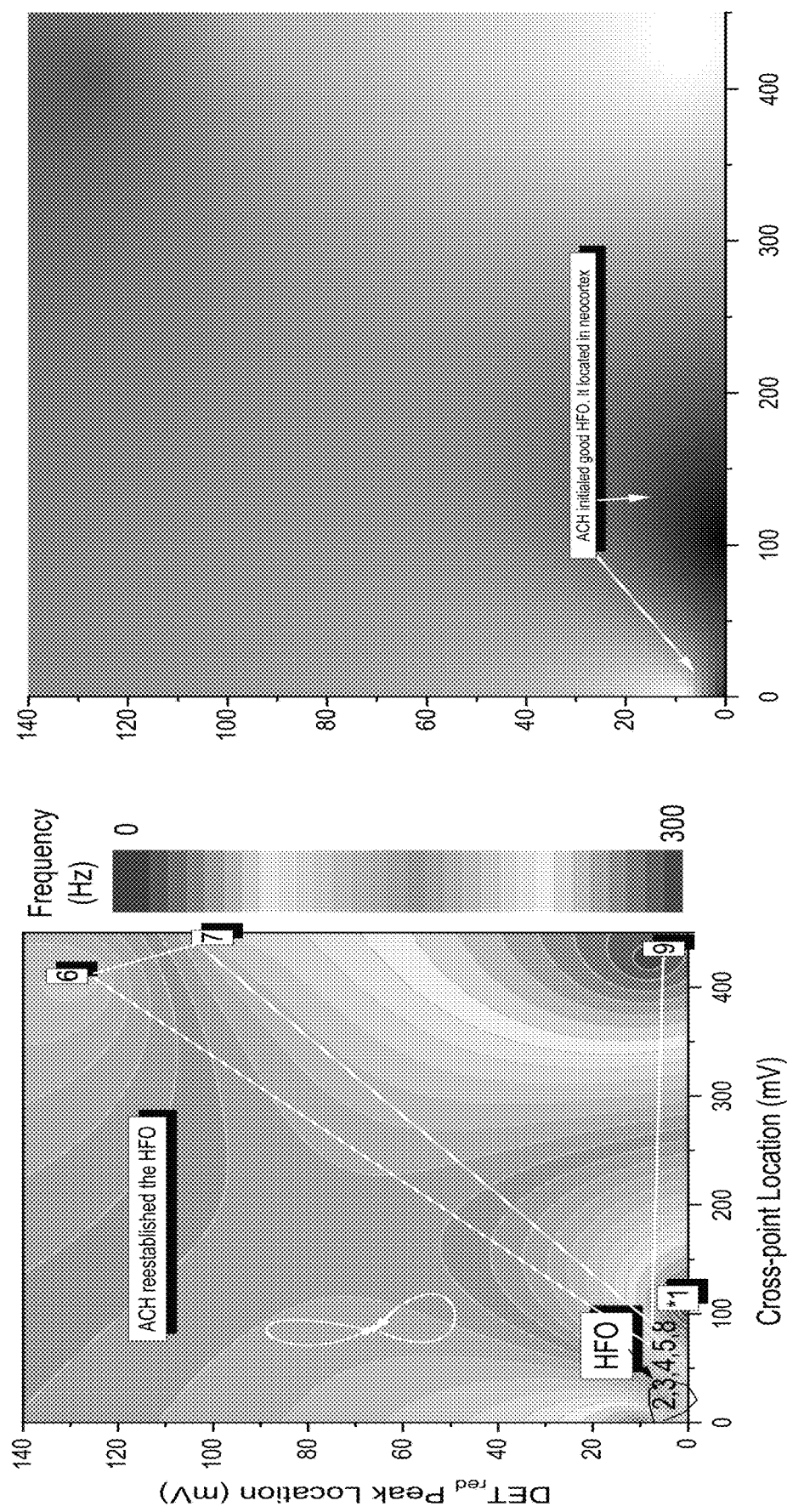
Figure 32:
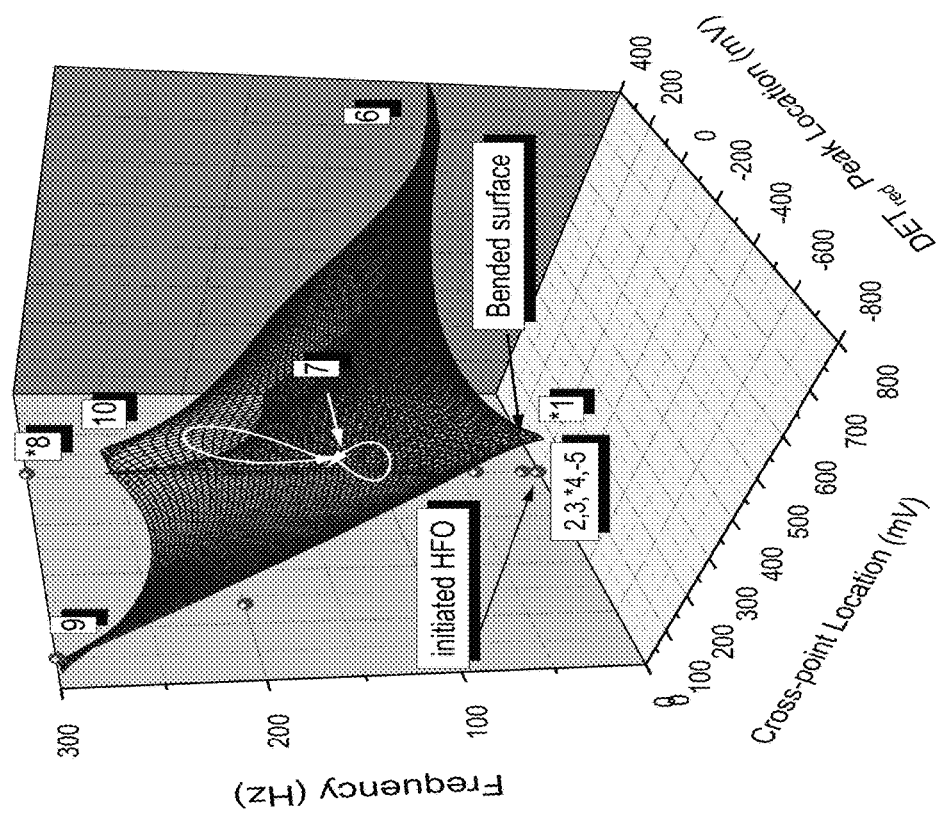
FIG. 32 the Panel A depicts the synapse circuitry dynamic 3D Energy-Sensory map of Device 2 interacted with NIST serum after discharges synapse pulses and infused the pulse energy under the condition with 38 μM Aβ and 15 nM ACH at 0.25, 40 Hz and 250 Hz, respectively into the matrix as *, shown as "Early recovery" on "Epilepsy stage 4B" or AD. The experimental conditions and explanations are same as above section. The Panel B depicts the contour map with the HFO labeled. Epilepsy centers were also labeled. Panel C depicts the optical image of the Energy-Sensory map. The HFO was labeled in the optical image. The epilepsy centers were labeled.
Figure 31:
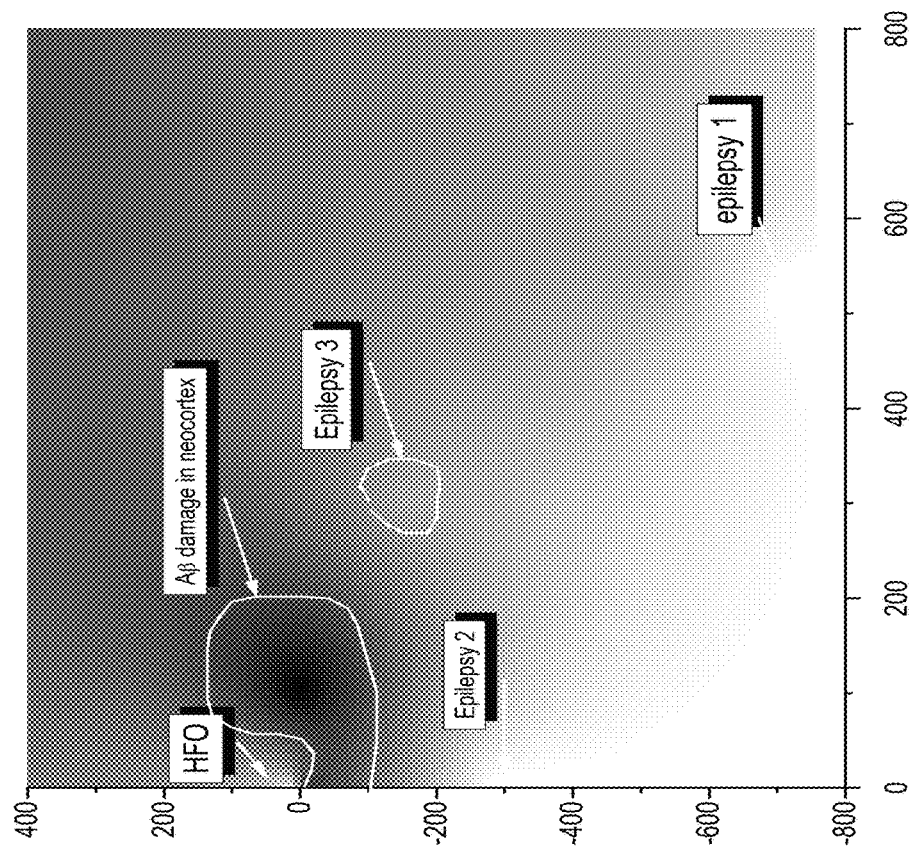
FIG. 31 the Panel A depicts the synapse circuitry dynamic 3D Energy-Sensory map of Device 2 interacted with NIST serum after discharges synapse pulses and infused the pulse energy under the condition with 38 μM Aβ and 15 nM ACH at 0.25, 40 Hz and 250 Hz, respectively into the matrix as *, shown as "Early recovery" on "Epilepsy stage 4A" or AD. The brain network prosthesis was made from the CV data with the same concentration of Aβ and ACH over 1-40 Hz, except the 2 mM o-NPA also presence in the solutions in 10 and 40 Hz, respectively. The CV data obtained to build the brain prosthesis from 100-300 Hz with 38 μM Aβ. There were multiple DET and multiple cross-points in the matrix. The Panel B depicts the contour map with the HFO labeled. Epilepsy centers were also labeled. The Panel C depicts the optical image of the Energy-Sensory map. The HFO was labeled in the optical image. The epilepsy centers were labeled.

Example 14—Applications in Assessing Repairing of "Damaged Neuron" in "Hippocampus" by the Energy-Sensory Images The early treatment of 15 nM ACH at "Epilepsy or AD Stage 2" in NIST serum with spiked Aβ had received great results. The sensory prosthesis was modified under the conditions: at 1 Hz with 38 µM Aβ in human serum with 15 nM ACH, the biomarker CV data obtained at 10 and 40 Hz had 2 mM o-NPA treated the above mentioned serum containing ACH and A13; 100-300 Hz was serum only; the energy infused entered the data matrix from the discharge energy pulses: at 0.25 Hz and 40 Hz with ACH and Aβ; at 250 Hz was pure serum. FIG. 30 panel A showed the synapse flow circuitry was again in a flat "8-shape" and ACH presence at SWS had initiated a formation of HFO located at the origin (0, 0) mV and removed the pHFO spot as shown in the panel B of the contour plot, so the sensory prosthesis's light was restored and enlightened as shown in the panel C of the light image. The key of the recovery is established the hydrophobic linen at the reentrant gamma frequency (40 Hz had been identified is the weak spot in hippocampus) and ACH imitated right direction and conformation of synapse flow at SWS. However, at a late stage of 4A or 4B, even treated with the same procedures, the completely restoration is not possible as seen in FIG. 31 panel A, B and C for stage 4A and FIG. 32 panel A, B and C for stage 4B, respectively. Even the HFO was created by the treatment procedures, and the brain sensory prosthesis light intensity become great, but the numbers of the epilepsy centers did not completely erased, it still remains several. It is called "non curable". At an early stage treatment, it is much better.

Example 15—Quantitation of Re-Entrant

Figure 33:
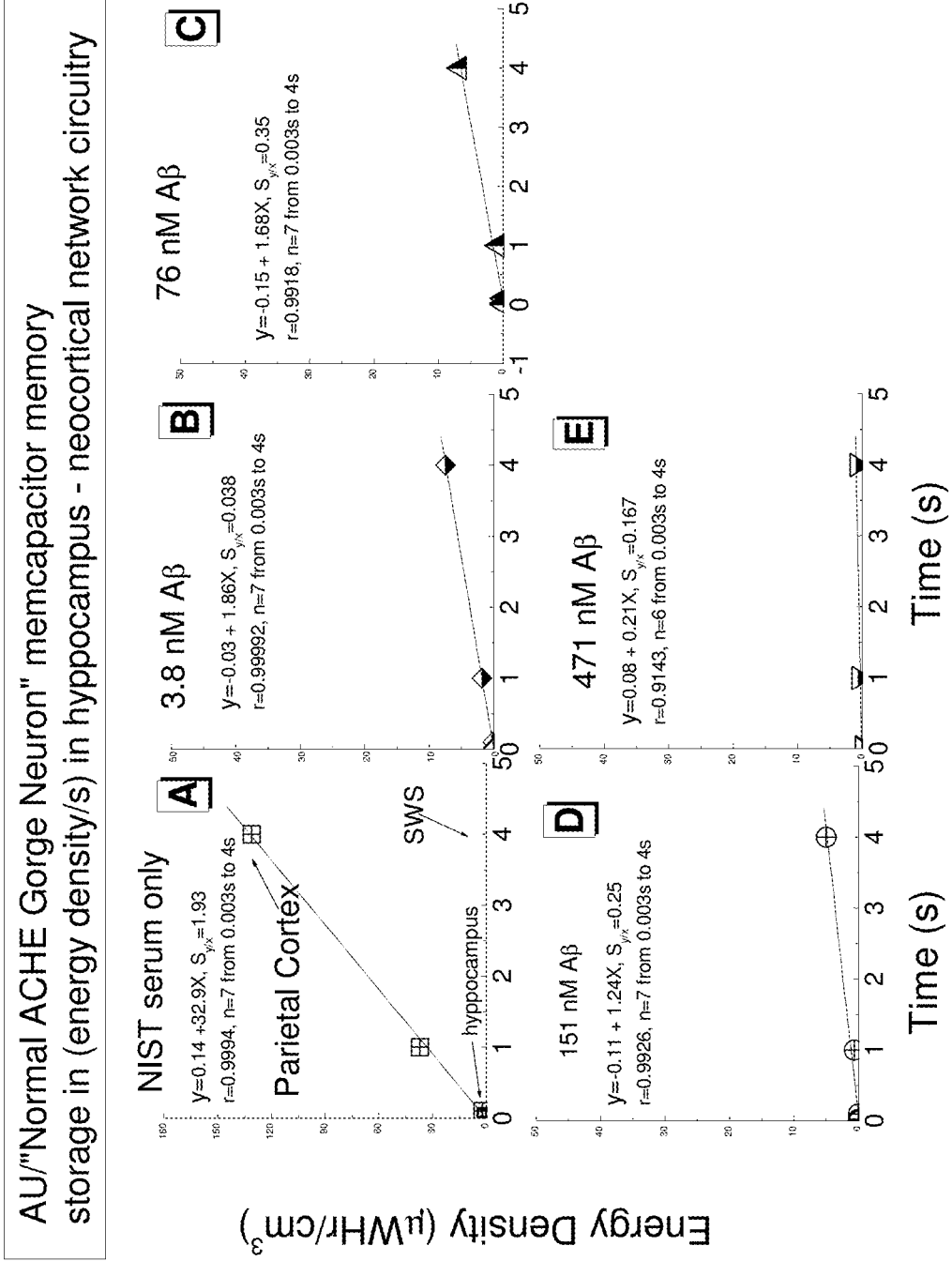
FIG. 33 depicts the linear least-square regressions of energy density vs. time for with and without Aβ, respectively for Device 1 in NIST human serum specimens. The Panel A depicts the conditions of NIST serum only without spiking Aβ covered the time from 0.004 to 4 s. The Panel B under the conditions with 3.8 nM Aβ, the Panel C with 76 nM Aβ, the Panel D with 151 nM Aβ and the Panel E with 471 nM Aβ.

We had qualified the memory reentry and recursive using the energy-sensory image technology in above sections through HFOs. This section is to establish the quantitation of the reentrant events. Without Aβ, device 1 has the appropriate reentrant time frame to store-retrieve information for 18, 20, 26.6, 160-fold higher reentry energy sensitivity compared at 3.8, 76, 151 and 471 nM Aβ, respectively, and the desire for a low energy per bit consumption in pJ/bit/µm$^3$ was in a reversed order as shown in Table 1. The results were calculated by a linear regression model. Support data are shown in FIG. 33. All results are less than 0.01 pJ/bit/µm$^3$, that is the goal of 2020 [5] for chips in the slope column, except without Aβ, which is 0.1186 pJ/bit/µm$^3$, and that is a magnitude advance over current reported performance [5].

TABLE 1

Information storage and retrieve sensitivity fitting by the linear least-squire equation between energy density vs. time (s) using device 1.

| Aβ nM | Slope Reentry Sensitivity (pJ/bit/µm$^3$)/s | r | Top range Reentry pJ/bit/µm$^3$ | Bottom range Reentry pJ/bit/µm$^3$ |
|---|---|---|---|---|
| 0 | 0.11862 | 0.9994 | 0.4716 | 6.84E-6 |
| 3.8 | 0.0067 | 0.9999 | 0.02675 | 1.188E-4 |
| 76 | 0.00605 | 0.9918 | 0.02434 | 4.32E-6 |
| 151 | 0.00446 | 0.9926 | 0.01789 | 3.6E-6 |
| 471 | 7.56E-4 | 0.9143 | 0.00302 | 6.12E-7 |

Early non-symptomatic epilepsy was identified and predicted by device 2 due to pHFO and large areas of Aβ re-depositions. Our data shown early CR dysfunction is not due to the entrance of Aβ for device 2, but the damaged ACHE gorge linen itself along with a synapse pulse discharge at SWS, which initiated a pHFO sport synchronized with the brain motif. Aβ played a heavy damage when pHFO occurred. We have identified the weak spot in the hippocampus that positively linked to epilepsy. Device 1 is more sensitive about AB damage in an early stage because of its HFO with higher reentrant energy sensitivity of 0.12 pj/bit/s/µm$^3$ without Aβ compared with 13 aj/bit/s/µm$^3$/nM over 3.8-471 nM range over 0.003-4 s. Device 1 reliably detected early CR dysfunction.

For Device 2, the results of linear regression of the volumetric energy density vs. time after 15 nM ACH applied in the 38 µM Aβ produced an equation of y=−0.075+9.89x, r=1.0 $S_{y/x}$=0.055, over 0.25-250 Hz, p<0.001, over the energy range from 39.5 µWHr/cm$^3$ at 0.25 Hz to 3.76×10$^3$ µWHr/cm$^3$ at 250 Hz. The memory at neocortex-hippocampus reached 30% of the strength of a healthy brain for the long-term memory [59].

TABLE 2

Information storage and retrieve sensitivity fitting by the linear least-squire equation between energy density vs. time (s) using device 2.

| ACH nM | Aβ µM | Slope Reentry Sensitivity (pJbit/µm$^3$)/s | r | Top range Reentry pJ/bit/µm$^3$ | Bottom range Reentry pJ/bit/µm$^3$ |
|---|---|---|---|---|---|
| 0 | 0 | 0.0002 | 0.88 | 0.00079 | 4.0 × 10$^{-7}$ |
| 0 | 38 | 0.000058 | 0.78 | 0.00088 | 5.3.0 × 10$^{-7}$ |
| 15 | 38 | 0.0356 | 1.00 | 0.1422 | 1.35 × 10$^{-5}$ |

REFERENCES

1. Indiveri G, Linares-Barranco B, Legenstein R et al., Integration of nanoscale memristor synapses in neuromorphic computing architectures, arxiv:1302:7007V1, 2013.
2. Chua, L O. Memristor The Missing Circuit Element IEEE Transactions on Circuit Theory, CT-18 (5): 507-519, 1971.
3. Chua, L O. Resistance switching memories are memristors, *Applied Physics A* 102 (4): 765-783, 2011.
4. *Artificial synapses could lead to advanced computer memory and machines that mimic biological brains, HRL Laboratories*, Mar. 23, 2012.
5. Chips 2020, the frontier of nanoelectronics, Editor B. Hoefflinger, Springer, 2012.
6. Advances in neuromorphic memristor science and applications, Editor Kozma R, Pino R E, Pazienza G E Springer Series in cognitive and neural systems, 2012.
7. Chen E T, Thornton J T, Ngatchou C, Duh S H, Nanostructured Memristor Sensor Mimics Acetylcholinesterase (ACHE) Active Sites In The Gorge For fM Detection Of Acetylcholine, NSTi-Nanotech, 2, 200-203, 2014.
8. www.iom.edu/sleep report
9. Slats D, Claassen J A H R, Verbeekb M M, Overeem S, Reciprocal interactions between sleep, circadian rhythms and Alzheimer's disease: Focus on the role of hypocretin and melatonin, Ageing Research Reviews 12, 188-200, 2013.
10. Yan J J el al., Protection against β-amyloid peptide toxicity in vivo with long-term administration of folic acid, British J of Pharmacology, 133, 89-96, 2001.
11. Toledo J B, Shaw L M, Trojanewski, Plasma amyloid beta measurements, a desired but elusive Alzheimer's disease biomarker, Alzheimer's Research and Therapy 5(8), doi:10.1186/alzrt162, 2013.
12. Dobrawolka J A et al. Diurnal patterns of soluble Aβ precursor proteins metabolites in the human central nervous system, Plos One, 9(3), e89998, 2014.
13. Morley J E and Favi S A, The role of amyloid-beta in the regulation of memory, Biochemical Pharmacology, 88(4), 479-485, 2014.

14. Roh J H, Huang Y, Bero A W et al., Disruption of sleep-wake cycle and Diurnalfluctuation of β-amyloid in mice with Alzheimer's disease pathology, Science Translational Medicine 4, 150ra-122, 2012.

15. Duh S H, Thornton J T, Kissinger P T and Chen E T, A Nanobiomimetic Neuronal Memcapacitor Serves as a Voltage Sensor and an Amperometry Sensor for Reagentless Direct Detection of Sub pM Soluble Amyloid-beta, NSTi-NanoTech, in press, 2015.

16. Chen E T, Thornton J and Mulchi Jr C. Mapping Circular Current for a Single Brain Cancer Cell's Spatial-Temporal Orientations Based on a Memristor/Memcapacitor, Sensors & Transducers, 183(12), 72-83, 2014.

17. Steffen G and Born J P, Low acetylcholine during slow-wave sleep is critical for declarative memory consolidation, PNAS, 101(7), 2140-2144, 2004.

18. Power A E, Slow-wave sleep, acetylcholine, and memory consolidation, PNAS, 101(7), 1795-1796C, 2004.

19. Edelman G M and Gally J A, Reentry: A key mechanism for integration of brain function, Frontiers in Integrative Neuroscience, 2013. doi: 10.3389/fnint.2013.00063

20. Raffone A, Srinivasan N and Leeuwen C V, Perceptual awareness and its neural basis: bridging experimental and theoretical paradigms, Phil. Trans. R. Soc. B 369: 20130203. http://dx.doi.org/10.1098/rstb.2013.0203

21. Kauffman L H, Self-reference and recursive forms, J Social Biology Structure, 10, 53-72, 1987.

22. Chen E T, Thorten J, Ngatchou C, Duh S-H, Kissinger P T, Nanostructured biomimetic pyruvate dehydrogenase complex (PDC) sensors selectively detect single brain cancer cell having the ability to mimic the "ATP Lid", NSTi-NanoTech 2, 107-110, 2013.

23. Chen E T and Thornton J, Nanostructured Acetylcholinesterase (ACHE) Memristor/Memcapacitor Mimicks Brachyhypopomus Electric Fish's Signal-Cloaking Behavior, NSTi-Cleantech, 3, 63-66, 2014.

24. Cabaret T et al., Electro-grafted organic memristors: Properties and prospects for artificial neural networks based on STDP, Nanotechnology (IEEE-NANO), IEEE 14th International Conference, p 599-504, 2014. 10.1109/NANO.2014.6968169

25. Martínez-Montes E, Valdês-Sosa P A, Miwakeichi F, et al., Concurrent EEG/fMRI analysis by multiway Partial Least Squares, Neuron Image, 22, 1023-1034, 2004.

26. Alvarado-Martinez R, Salgado-Puga K and Pena-Ortega F, Amyloid-beta inhibits olfactory bulb activity and the ability to smell, Plos One, 8(9),e5745, 2013.

27. Pena-Ortega F and Bemal-Pedraza R, Amyloid-beta slows down sensory-induced hyppocampal oscillation, International J of Peptides, 2012, 2012. http://dx.doi.org/10.1155/2012/236289

28. Ventra M D and Pershin Y V, On the physical properties of memristive and memcapacitive and meminductive systems, J of Physics D, arXiv:1302.7063v2, 2013.

29. Jasper's Basic Mechanisms of the Epilepsies, fourth edition by Noebels J L, Voli M, Oxford Press Publisher, NY, 2012.

30. Marshall L, Binder S, Transcranial oscillatory stimulation to research on neural networks, an emphasizes on hippocampus-neocortical rhythms, Frontiers in Human Neuroscience, 7(614), 1-6, 2013.

31. The hippocampus book, edited by Anderson P, Morris R, Amaral D, Bliss T and O'keefe J, Oxford University Press, 2007.

32. El-Kady M F, Strong V, Dubin S, Kaner R B, Laser Scribing of High-Performance and Flexible Graphene-Based Electrochemical Capacitors, supplement materials, Science 335, 1326, 2012.

33. Miller J R and Outlaw R A and Holloway B C, Graphene double-layer capacitor with ac line-filtering performance, Science, 329, 1637, 2010.

34. Pyka M and Cheng S, Pattern Association and Consolidation Emerges from Connectivity Properties between Cortex and Hippocampus, 9(1), e86016, 2014.

35. Chen E T and Pardue H L, Analytical applications of catalytic properties of modified cyclodextrins, Anal Chem, 65 (19), 2563-2567, 1993.

36. Chen E T, Thornton J T, Ngatchou C, Duh S H and Kissinger P T, Nanostructured Biomimetic Pyruvate Dehydrogenase Complex (PDC) Sensors Selectively Detect Single Brain Cancer Cell Having The Ability To Mimic The "ATP Lid", NSTi-NanoTech (2), 107-110, 2013.

37. Sussman J L, Hard M, Frolow F, Oefner C, Goldman A, Toker L, Silman I, Atomic structure of acetylcholinesterase from Torpedo californica: a prototypic acetylcholine-binding protein. Science 253, 872-879, 1991;

38. Gilson M K, Straatsma T P. McCammon J A, Ripoll D R, Faernan C H, Silman I, Sussman J L, Open "back door" in a molecular dynamics simulation of acetylcholinesterase, Science 263, 1276-1278, 1994.

39. Silman I, Sussmana J L, Acetylcholinesterase: How is structure related to function? Chem Biol Interact. 175, 3-10, 2008.

40. Mira A, Yamashita S, Katakura Y, and Shimizu K. In vitro neuroprotective activities of compounds from Angelica shikokiana makino, Molecules 20, 4813-4832, 2015.

41. Biolek D, Di Ventra M, Pershin Y V, Reliable SPICE Simulations of Memristors, Memcapacitors and Meminductors, Radioengineering 22 (4), 945-968, 2013.

42. Martinez-Rincon J and Pershin Y V, Electron Devices, IEEE Transactions 58 (6), 1809-1812, 2011.

43. Martinez-Rincon J, Ventra M D, Pershin Y V, Solid-State Memcapacitive System with Negative and Diverging Capacitance Physical Review B, 81(19), 195430-1-195430-7, 2010.

44. Pickett M D, Medeiros-Ribeiro G and Williams R S, A Nature Materials, DOI: 10.1038/NMAT3510, 2012.

45. Kozma R, Pino R E, Pazienza G E, Advances in neuomorphic memristor science and applications, Springer publisher, 2012.

46. Ventra M D, Pershin Y V, Nanotechnology 24, 255201, 2013.

47. Chen E T, Nanopore Array Structured Devices for Biosensing and Energy Storage, U.S. Pat. No. 8,641,876, Feb. 4, 2014.

48. Chen E T, Nanopore Structured Electrochemical Biosensor, U.S. Pat. No. 8,083,926, Dec. 27, 2011.

49. Chen E T, Apparatus and Methods for Making High Performance Fuel Cell, U.S. Pat. No. 8,632,925 issued by USPTO, Jan. 21, 2014.

50. Chen E T, Nanostructured Biomimetic Device with Contour Map of Multiple Variable Correlation Method to Visually Display the Cancer Progresses, US 20,140,178, 925, Jun. 26, 2014.

51. Chen E T, Nanobiomimetic Supercapacitors with High Rate High Energy Storage, US 20,140,104,751, Apr. 17, 2014.

52. Chen E T and Thornton J, Nanostructured Acetylcholinesterase (ACHE) Memristor/Memcapacitor Mimicks 53. Yang J J, Strukov D B, and Stewart D R, Memristive devices for computing, Nature Nanotechnology, 8, 13-24, 2013.
54. El-Kady M F, Strong V, Dubin S, Kaner R B, Science 335, 1326, 2012.
55. Miller J R and Outlaw R A and Holloway B C, Graphene double-layer capacitor with ac line-filtering performance, Science, 329, 1637, 2010.
56. Duh S H, Thornton J T, Kissinger P T and Chen E T, NSTi-NanoTech, in press, 2015.
57 Zanini D et al., Biomedicine and Pharmacotherapy 66(4), 249-255, 2012.
58. Gauresh S, Chinmay K, Prashant S, Rupesh S, Kirti L, Sadhana S, Journal of Pharmacy and Bioallied Sciences, 7 (1), 32-36, 2015.
59. Chen E T, Thornton J T and Mulchi J C. Nano-biomimetic Memcapacitor Memory Devices Identify Circadian Rhythm Dysfunction and Predict Early Signs of "Epilepsy" Using Reentrant Energy-Sensory Images, NSTi-NanoTech, in press, 2015.
60. Schuff N, Woerner N et al., MRI of hyppocampal volume loss in early Alzheimer's disease in relation to ApoE genotype and biomarkers, Brain 132, 1067-1077, 2009.
61. Vijayakumar A, and Vijayakumar A, Comparison of Hippocampal Volume in Dementia Subtypes, Internationally Scholarly Research Notices (ISRN) Radiology, 174525/2013. http://dx.doi.org/10.54021/2013/174524
62. Brain circuitry and signaling in psychiatry: Basic science and clinical implications, edited by Kaplan G B and Hammer R P, Amer Psychiatric Pub; 1st edition, 2002.
63. Davolio C C, Greenamy J T, Selective vulnerability of the CA1 region of hippocampus of indirect excitotoxic effects of malonic acid, Neuroscience Letter 192,29-332, 1995.
64. Bronen R A, The status of status: seizures are bad for your brain's health. The American Journal of Neuroradiology 21, 1782, 2000.
65. Delvecchio R M, Feghali B P P T, Shah D M, Ahuja R, Transformer design principles with applications to core-form power transformers, second edition, CRC Press, 2010.
66. McCarthy S et al., Electromagnetic system with no mutual inductance and an inductive gain, U.S. Pat. No. 8,427,805.

Followings are the Specifications in CIP Application

DETAILED DESCRIPTION OF THE INVENTION

Example 1—Fabrication of the Nanobiomimetic Organometallic Superconductor/Mem-Element Qubit Devices with Superlattice Structures The SAM membrane of the device was freshly prepared with two steps: first, by the self-assembling method with compositions of triacetyl-β-cyclodextrin (TCD), polyethylene glycol diglycidyl ether (PEG), poly(4-vinylpyridine) (PVP) and β-cyclodextrin copolymer (β-CD) as a mixture with appropriate proportions and forming nanoisland layer 1 that mimics choline acetyltransferase (CHAT) on a 50 nm gold chip at 35□C for 48 hrs. Second, after a washing and drying process, we deposit the second polymer mixture of bis-substituted dimethyl-□-cyclodextrin (bM-β-DMCD)/ TCD/PEG/PVP and embed it with zinc chloride on the top of the first layer. The compositions and volume ratios of the compositions in the nano-island membrane were disclosed in U.S. Pat. No. 8,632,925 Jan. 21, 2014, and U.S. Pat. No. 9,793,503, Oct. 17, 2017). The second polymer mixture has a volume ratio 40-60%:10-20%:8-10%:8-10%:7-15% for bM-β-DMCD/TCD/PEG/PVP/$ZnCl_2$, respectively. The concentration of bM-β-DMCD is in the range of 5-10 mg/mL in HEPES. The first four components were incubated for 2 hours, and then apply the zinc chloride solution into the mixture. For the first 2 hours, the temperature was kept at 80° C. After that, the temperature was reduced to 37° C. for 96 hours. Other washing and dry procedures we used were based on the literature [48]. Procedures of synthesis and characterization of mM-β-DMCD and bM-β-DMCD were based on the published literature [49].

Example 2—Evaluation of the Friedel-Oscillation in the Superlattice Membrane

The morphology of the AU/SAM was characterized using an Atomic Force Microscope (AFM) (model Dimension Edge AFM, Bruker, Mass.). Data was collected in Tapping-Mode using silicon probes with a 5-10 nm tip radius and ~300 kHz resonance frequency (Probe mode TESPA-V2, Bruker, Mass.). Evaluations of the Friedel-oscillation on the qubit device membrane were conducted based on the AFM images. Friedel-oscillation is a phenomenon of long-range indirect interactions between electrons on the surface [50]. FIG. 34A depicts the photo image of the whole SAM superconductive multiple-layer membrane structure on the screen during setting the probe before taken an AFM image. FIG. 34B depicts a photo image of a curvature cross-bar structure of a roof shingle matrix that is closely mimicking the compact fine membrane structure of the device. FIG. 34C depicts a photo image of matrix sand waves that are mimicking the membrane structure with zinc atoms on top of the device in a macroscopic view. The bird view of the AFM image of the multiple-layer membrane of the device as depicted in FIG. 35 with the section analysis curvature single-wall nanotube with zinc atoms; the highest z is 299.7 nm on 24.2 $\mu m^2$ with surface roughness 77.5 nm related to z-direction of 435 nm, the zinc atoms play a role as an "insulator" or "bridge" in an orderly manner connecting curvature nanotubes in the superlattice in FIG. 35 and FIG. 36. FIG. 36 depicts the close bird-view of the 2D AFM image of the detail conformation orientation of the zinc atoms chelating with groups of cross-linked organic polymers in layers curvature nanotubules forming super-lattices. FIG. 37 depicts the 3D bird-view of the membrane AFM image. FIG. 38A depicts the bird-view of the 2D AFM image of the single wall nanotubule in 1.21 μm2. FIG. 38B depicts the 3D AFM image in the side-view of the single wall nanotubule in 1.0 μm2. FIG. 39 depicts the bird-view of the 2D AFM image of the detailed structure of the single wall nanotubule in 250×250 $nm^2$. FIG. 40 depicts the bird-view of the 2D AFM image of the wave structure of the membrane under the canal as seen in FIG. 41 under the dark long strip canal. FIG. 41 depicts the bird-view of the 2D AFM image of the superconductive SAM membrane of the zinc-organic polymer near the strip canal in 30×30 μm2 comprising of 30-50 qubits uniformly laid and connected on the surface shown as the JJ circuitry connected by flexible zinc atom clusters. The canal was about the size of 24.8 μm×7.6 μm×1.2 μm (LWH). The canal comprised of sine wave membranes as shown in FIG. 40 that covering the canal walls and the canal cavity was filled with air media, therefore the canal became another type of flexible Josephson junction separating the superconductive qubits arrays located on banks of the canal. In average, the 0.031 cm$^2$ electrode comprises about 150,000 qubits in the surface not including the vertical deep 3D qubits if any. It was clearly demonstrated the toroidal JJ array qubits in an orderly matrix with zinc atoms playing a role as the barriers between nano curvature conductive polymer tubes. FIG. 42 depicts the first layer of the 2D AFM image of the SAM organic conductive membrane that mimicked CHAT function in the nano-island structure in 1.0 μm2. FIG. 43 depicts the bird-view of the 3D AFM image of the SAM organic conductive membrane in uniform 20 nm diameter nanopore arrays in 1.0 μm2 that mimicked glucose oxidase's function. The Friedel-oscillation was observed as the zinc atoms oscillate in the connections between 2 or more curvature single-wall nanotubes shown in FIG. 35 and FIG. 36.

Example 3—Engineering Design of an Organo-Metallic Superconductor/MEM-Element Devices The engineering design of the multiple function superconductive/MEM-element device is based on a unique multiple-JJ barrier approach: namely the primary insulator barrier and the secondary barriers: zinc atoms or air in the curvature multiple-layer superlattice. The engineering design of an organo-metallic topological superconductor/MEM-element device was depicted in a side-view as shown in FIG. 44. MEM-element means the memristive, memcapacitive and meminductive circuit elements. In this embodiment, it may mean to use one or two or three of the aspects of the elements as "MEM-element". FIG. 44 depicts the two reversible terminal schematic components from the side-view of the figure in the engineering design of the superconductor/MEM-element device. "10" refers to the gold electrode with 50 nm thickness adherences on a flexible plastic plate substrate; "11" refers to the self-assembling membrane (SAM) comprising of conductive cross-linked organic polymer, where the monolayer membrane has uniform 20 nm in diameter nanopore array structure; "12" refers to a dielectric insulator as the primary JJ barrier; "13" is the cover layer of o-nitrophenyl acetate in a mixture of imidazolyl derived mono-substitute β-dimethylcyclodextrin (mM-β-DMCD, in short, MCD) with $ZnCl_2$ in methanol; "14" is the SAM comprising of superconductive cross-linked organic-transition metal multiple-layer membranes having uniform "roof-shingle" like macrostructure and "mitochondria" like nanostructure that comprises curvature lattice pattern forming nanotubules with zinc atoms on the top joints. Zinc ions act as another Josephson junction barrier as the secondary JJ barrier; "15" is the bottom layer of the superconducting SAM under "14", which is a normal conductive organic polymer SAM comprising of uniform nanoisland structure; "16" is the gold electrode with 50 nm thickness adherences on a flexible plastic plate substrate; "17" is the switchable metal connector lead, to conduct the superconductive/mem-element self-energy sufficient operation in energy harvesting and non-volatile information memory read/writing function and logic function on the same chip, that comprises at least 150k JJ array qubits.

Example 4—Formation of a Controllable and Adjustable State-Switch Valve

A controllable and adjustable state-switch valve (CASSV) invented embodiment described here is a system comprising of multiple elements working together to be capable to switch a device from a mem-state (memristive or mem capacitive) state to a superconducting state as shown in models of FIG. 45A and FIG. 45D. FIG. 45A depicts the art of the "Valve" model in an "On" position for memristive characteristics, i.e., meminductive was depressed, but memcapacitance was increased; it illustrates the proposed direct electron-relay mechanism in the superconductor/mem-element device. "200" refers to the MCD . . . o-NPA inclusion complex cover layer with 1 mg/mL MCD and 3 mM o-NPA; "201" refers to the group in "200" interacts with the "201" simplified biomimetic matrix metal proteinase (BMMP) forming the superconducting SAM layer "202" with immobilized cross-linked organic-transitional metal zinc in the membrane of bM-β-DMCD . . . TCD . . . PEG . . . PVP . . . $ZnCl_2$; "202" is the direct-electron-relay superconducting SAM forming relay between 200 . . . 201 . . . 202 in the chain of 3MCD/(His)N . . . Zn++ . . . COO$^-$ of TCD . . . (bM-β-DMCD)n/((His)2N . . . )n. The right-hand side is the simplified MMP model, and the induced direct bio-communication was shown through the zinc ion coordinating with both of the COO$^-$ of TCD and the receptor groups of two imidazolyl in bm-β-DMCD cavity, i.e., by the coordination geometry, proton and electron transfers and the displacement of water molecules which formed the long electron-relay chain based on a favorable low ΔG. Notice of the ribbon in "202" represents the TCD . . . PEG forming biomimetic protein's C-terminal and PEG . . . PVP forming Biomimetic protein's N-terminal wrapping around the cross-bar between vertical oriented toroidal CD cavity and horizontal orientated toroidal CD cavity, see in FIG. 45B. "203" refers to the normal 50 nm thickness gold electrode on a flexible plastic plate having a switchable connecting gold lead; "204" refers to the cross-linked organic polymer membrane with nanopore structure of MCD . . . PEG . . . PVP on 50 nm thickness gold electrode with a plastic plate and a gold connect lead; "205" refers to a dielectric insulator in 1 M methanol.

The art of the "Valve" model is in an "Off" position for memristive characteristics, but meminductive was increased leads to a superconducting state raised as shown in FIG. 45B and FIG. 45D. FIG. 45B's labels are similar to FIG. 45A, i.e., "300" refers to the zinc-imidazole of MCD coordination in chelating in two schemes: (1) in the media, the zinc cation chelates with four imidazole groups in the MCD cavities and chelates with one COO$^-$ group of o-NPA included in the CD cavity; "301" refers to zinc ion chelates with three imidazole groups of MCDs and one COO$^-$ group of TCD and one more ligand coordinates with imidazole group in bM-β-DMCD in the membrane; "302" refers to the repeating processing of n units; "303" refers to the nanoislands structure membrane on 50 nm thickness gold electrode on a plastic substrate with a switchable gold electronic connect lead; the nanoisland membrane comprises of TCD . . . PEG . . . PVP . . . β-CD copolymer, that mimics choline acetyltransferase (CHAT); (2) "304" refers to the MCD . . . o-NPA inclusion complex cover layer as shown in 300. The zinc ion chelates with four imidazole groups in MCDs that included o-NPA in the toroidal cavities that depressed the memristive, but increased the meminductive, the fifth ligand was chelated with the COO$^-$ of the o-NPA molecule. By changing the o-NPA concentration, the degree of inductivity can be controlled. (3) "305" is the dielectric insulator that is the Josephson junction; (4) "306" refers to the nanopore array membrane comprises of MCD . . . PEG . . . PVP on a 50 nm thickness switchable gold electrode; (5) due to the formation of an "adjustable valve" configuration, so a balanced direct electron transfer system can be enabled for either in harvesting energy and in superconducting spontaneously. "307" refers to the switchable gold electrode.

FIG. 45C depicts the art model of the mitochondria that the invented superconductor/MEM-element device intended to mimic one of the important energy-producing functions of the mitochondria and its eternal structure. FIG. 45D depicts a functional device model after spiked a final concentration of 3 mM o-NPA in the 1.82 mM $ZnCl_2$ and 1 mg/mL MCD in the 1 M methanol solution. The zinc cations in the media are chelating with the $COO^-$ groups of TCD or o-NPA in the cage membrane and the imidizole groups in the mono and bis imidazole modified β-DMCD cavity, and the MCD cavity was included with o-NPA, therefore the zinc-finger like media acted as (1) a controllable and adjustable state-switcher to switch between a mem-element state and a superconducting state; (2) an another layer of cover sheet to partially block the larger pore of the dielectric insulator (blue color) and partially forming electron relay and cation expel with the membrane cage functional groups. The bottom layer membrane on the gold electrode is a negative E-R layer, and the second layer is a cation E-R layer.

Example 5—Evaluation of the Josephson Toroidal Array Qubits' Reentrantable Memory The Mem-elements circuit, such as the memristor's characteristic i-V curves and the diverging frequency were studied using the CV method at the fixed scan rate in room temperature. Memristors are devices made of nanolayers that have the capability to mimic neuronal synapse with a characteristic of a hysteresis loop in the i-V curve [24-26]. A memristor is a semiconductor whose resistance varies as a function of flux and charge. This allows it to "remember" what has passed through the circuit [24-26]. $G(\{x\},t)$ which is state-dependent $$I(t)=G(\{x\},V,t)V(t) \qquad (1)$$

FIG. 46A depicts the memristive i-V curve of the superconductor/MEM-element device of Au/biomimetic mitochondria-insulator-nanopore Biomimetic glucose oxidase/Au at room temperature under normal pressure with scan rate 160 Hz in 1.82 mM $ZnCl_2$ and 1 mg/mL MCD in 1 M MeOH (a); with 1.82 mM $ZnCl_2$ and 1 mg/mL MCD and 3 mM o-NPA in 1 M MeOH (b). FIG. 46B depicts the memristive i-V curve of the Au/biomimetic mitochondria device, without an insulator and without the nanopore membrane under the same condition with 60 Hz scan rate under 1.82 mM $ZnCl_2$ and 1 mg/mL MCD in 1M MeOH (a); with 1.82 mM $ZnCl_2$ and 1 mg/mL MCD and 3 mM o-NPA in 1M MeOH (b). The figures demonstrated scan frequencies impact on the phase change difference between topological behavior and the hysteresis behavior between "0" and "1" switch, while the topological state as "0" and the hysteresis state is "1" under same experimental conditions, and both states are at zero potential. The intensity of the current at 160 Hz under 1.82 mM $ZnCl_2$ and 1 mg/mL MCD in 1 M MeOH are more than three orders of magnitudes higher than that of at 60 Hz scan rate. This indicates the device's multiple utilities: at a lower frequency, the switch is suitable for nA operation without energy dissipation; while at higher frequency its phase switches, avoiding consuming energy. In the presence of o-NPA, at 60 Hz, the $DET_{red}$ current can amplify by 4-fold compared without o-NPA. FIG. 47 depicts the memristive i-V curve of the Au/biomimetic mitochondria device, i. e., without the dielectric insulator and without the nanopore semiconductor membrane, a pure gold electrode lead connected with the cathode, the Au/multiple-layer superlative mitochondria-like membrane electrode connected with the anode lead, with 60 Hz scan rate under same conditions as FIG. 46B (b), but with 10 consecutive cycles' scans.

Example 6—Mapping the Cooper-Pair Wave Transmission Dynamics and the Qubit Relaxation Time Memory DRAM is the most energy-consuming component in a current computing system, because it has extremely high transistor counts, hence the static energy demands are high even in the idle time. The evaluation of the Cooper-pair Wave Transmission Dynamics was conducted through a 3D mapping method with i-V data obtained from the entire memory chip of $3.14 \times 10^6$ μm2 connected with the cathode, and another lead connected with the anode, it is reversible for connection using 10 consecutive cycles with 60 Hz scan rate. The conductance density data as Z, the eV range of ±2 mV as X, and the capacitance data as Y were used to building the maps. The chip has an average 150k qubits. FIG. 48A depicts the 3D plot of a dynamic relationship between voltage, special capacitance and density of conductivity of the toroidal Josephson vortex array memory device with a 60 Hz scan rate of 10 consecutive scans under 1.82 mM $ZnCl_2$, 3 mM o-NPA and 1 mg/mL MCD in 1M MeOH. FIG. 48B depicts the 2D contour map of voltage, special capacitance and density of conductance among AppE covered from 2Δ to −2Δ. 1Δ=0.001V in the first segment scan for 10 consecutive times of the device with 60 Hz scan rate. The curvature Fermi energy plane was labeled as the dark color line. We see the energy gap is quantized in FIG. 48B among the 10 cycle's scans at the first segment that is symmetry with the Fermi energy plan nodes level at ±1 mV and zero capacitance and zero conductance density as "0". The quantum energy gap at ±1 mV has non-zero conductance and non-zero capacitance as "1". There are two circular contours in blue and red color indicates the device is capable to read/write and self-supporting of energy supply due to the negative capacitance, i.e., some spontaneous force presences in the system for storage of energy. The figures demonstrated zinc atoms can be categorized as flexible Josephson junction barrier in an Au/multiple layer superlattice membrane chips in the presence of o-NPA in MCD and 1M methanol solution, produced hysteresis signal strength.

FIG. 49 depicts the trend helix-cooper pair wave transmission from different scan cycles affects on the peak current at the different applied potential in the ±2 mV Josephson junction window under the same conditions of the media and scan rate as FIG. 48A. Solid Square refers to the first segment scan (the forward scan) from 1.0 mV to −1.0 mV; open square refers to the second scan (the backward scan) from −1.0 mV to 1.0 mV vs. scan cycles, and the peak current values were shown on the curves was at 1 mV as seen for Panel A; the peak current values were shown on the curves was at zero V as seen for Panel B; the peak current values were shown on the curves was at −1.0 mV as seen for Panel C; at 2 mV as seen for Panel D, at −2.0 mV as seen for Panel E, and Panel F refers to the curves covered the peak current at 2 mV and −2 mV for the backward scan over 10 cycles. Because the san rate is 60 mV/s, hence from 1 to 10 cycles have a time maximum up to 533.33 s, the results of the first-order exponential rate constant of the DET peak current vs. 10 scan cycles at the first segment within the quantum energy gap ±2 mV at 0, 1, −1, 2, and −2 mV is 0.044, 0.044, 0.0429, 0.0444 and 0.0433/s respectively with the mean value 0.0439/s with an error $\pm 5.6 \times 10^4$/s; the second segment (backward scan) scan has the results of 0.0197, 0.020, 0.0205, 0.0214 and 0.0214/s, respectively, having the mean value with the error is 0.0207±7.1×10$^{-4}$/s. The qubit relaxation time in terms of the first-order rate constant of current vs. time among 10 cycles that is stable in the forward scan segment, same as for the backward scan segment. Using this technology, the qubit relaxation time is two or three orders of magnitude longer than current JJ qubits reported time [18].

Example 7—Mapping of Topological Qubits' Josephson Conductance and Josephson Capacitance Relationship with the Quantum Energy Gap Qubit-based voltage-controlled memcapacitor has the equation of [25]:

$$Q = C_{geom}V - (eC_g/C_\Sigma)\langle\sigma_z\rangle \equiv C_M(X,V)V \quad (2)$$

where $C_{geom} = C_g C_J/C_\Sigma$, $C_g$ is the gate capacitance from the gate capacitor, $C_J$ is the Josephson junction capacitance, $C_\Sigma$ is the total capacitance between the two capacitors; $\langle\sigma_z\rangle$ is the Cooper-pair box term. $C_M$ is the capacitance of the memcapacitor, X stands for the time evolution parameters of the charge in the Cooper-pair box through the $\langle\sigma_z\rangle$ term. V can be both, time-dependent voltage V(t) and constant voltage $V_{dc}$ components. Q is the charge on the external plate of the gate capacitor if considering the system is in the electrostatic situation.

Qubit-based current-induced solitonic meminductor has the equation of [32]:

$$I_s(t) = (I_c/L)|\int_0^L dx \cos \varphi(x,t) \quad (3)$$

where L is the inductance, $I_c$ is the JJ critical current at zero-potential and zero Kelvin temperature, φ is the phase difference.

According to A. M. Zagoskin's theoretical prediction from a toroidal qubit model having either "close" or "open" design that will be naturally protected from 1/f noise at low frequency [14]. "Open" means the toroidal electrode has holes and does not need a π-junction. The ambient noise is protected. We have invented such a toroidal qubit device with characteristics similar to the "Open" model design, except we have flexible multiple—Josephson junctions using zinc atoms, or air, or dielectric insulators as barriers, and the superlattice as the "Open" holes of the membrane on the electrode. Evaluation of the device's topological qubits' Josephson conductance and Josephson capacitance relationship with the quantum energy gap was conducted by continue study the relationship used in Example 6 with the same device, but study how the different scan segment manner impacts on the capacitance and the conductance among the 10 scan cycles. FIG. 50A depicts the 2D contour map of voltage, special capacitance and density of conductivity over the range ±2Δ, ±1Δ and 0V in the full 2 segments (includes the forward and backward scans). The curvature Fermi energy plane was labeled as the dark color line. It was observed that there are many small peaks with negative capacitance vertically appeared at zero potential fields associated with negative conductance; above zero capacitance at zero potential, there are many small overlapped vertical lines shown positive capacitance and positive conductance at zero potential compared with FIG. 48B indicates the two-directional toroidal vortex JJ current positively induced conductance and capacitance at zero potential, as well as induced negative conductance and negative capacitance at zero potential. We can draw a conclusion: the toroidal qubit device operates by self-sufficient energy with a reversible renewable capacitance and conductance at zero potential due to the long-range electro-relay system, herein no needs for an external magnetic field. FIG. 50B depicts the 3D map of FIG. 50A.

FIG. 51A depicts the cooper pair action in the Josephson junction in the 3D dynamic map of each of the 10 scan trend regarding the relationship between the quantum energy gap, special capacitance and density of conductivity at the first scan segment from 1 mV to −1 mV covered from ±1Δ and 0.000V. The typical quantum topological behavior was shown by the clockwise and counter-clockwise current flow with the wave-like pattern within the toroidal JJ barrier. The label of "1" to "10" indicates the scan cycle number with the trajectory special-temporal orientation in conductance density, Δ and special capacitance density relationship and time (t) because the "1" cycle means 53.33 s. The flat surface with a 45° angle indicates the healthy function of the memory device, i.e., hummingbird-like "8"/45° fly pattern, which is the normal neuronal circuitry pattern [45], and herein this invention provides an opportunity as a "quantum neuronal bits" for computing. FIG. 51B depicts the 2D map of FIG. 51A. It demonstrates the quantum computing between "0" and "1" in conductance at zero eV switches at the same zero volts with no energy dissipation. FIG. 51C depicts the image of the helix-cooper pair energy wave transmission superconductivity density related to capacitance within the ±2Δ gap. The Fermi zero conductance plane with nodes at zero capacitance was seen as labeled.

Example 8—Copper Pair's Andreev Reflection

The 3D dynamic map presented in FIG. 52A depicts the cooper pair action in the Josephson Junction barrier at each of the 10 scan trend regarding the relationship between energy gap, special capacitance and density of conductivity at the second scan segment from (backward scan) −1.0 mV to 1.0 mV covered from −1Δ to +1Δ. Similar observations were received compared with FIG. 51A, except the first cycle scan, have the lowest absolute conductance in the forward scan, but for FIG. 52A the first cycle has the highest absolute conductance. All circuit patterns are along the edges of the topological plane. However there are differences, 1) the flat plane of the conductance does not have a perfect 45° angle, 2) the overall conductance is ⅕ of the forward scan and has a capacitance is 10% of the forward scan. 3) the highest conductance in the backward scan is 50% of the forward scan. 4) there are two sharp peaks at the first scan cycle in the backward scan, yet the forward scan does not have the peaks. It may explain the conductance reduced is due to the Andreev reflection [10] as the arrow indicated in FIG. 52A. FIG. 52B depicts the contour map of FIG. 52A with the counter clock and clockwise cooper pair's circular current pattern and the Andreev reflection crossing the Fermi ground energy plane. FIG. 52C depicts the image of the helix-cooper pair energy wave transmission superconductivity density related to capacitance and the quantum energy gap. The cooper pair's presence is seen at the edges of the JJ boundary. This is the first time observing the cooper pair images in the JJ boundary setting.

Multiple Andreev Reflections (MAR) were observed shown in FIG. 53A, it depicts the cooper pair action in the Josephson Junction in the 3D dynamic map of each of the 10 scan trend regarding the relationship between quantum energy gap, special capacitance and density of conductivity at the second scan segment from −2.0 mV to 2.0 mV covered from −2Δ to +2Δ. Arrows show multiple MAR events. FIG.

53B depicts the MAR oscillations image energy wave transmission superconductivity density related to capacitance and quantum energy gap. FIG. 53C depicts the 2D contour map with multiple oscillations and multiple arrows of reflections from the cooper pair. It shows the deep blue circle with ripples in the negative conductance located in the 1Δ barrier associated with negative capacitance, which is stronger than it's counterpart in positive conductance, indicates the MAR was initiated from the negative conductance. We also see the oscillations at different locations as the arrows labeled Example 9—Quantum Conductance FIG. 54 depicts the plot of ($2e^2/h$) dI/dV vs. potential from −0.04V to 0.04V for the study of the superconductivity at the zero-bias field of the AU/biomimetic mitochondria device in 1M MeOH with 1.82 mM $ZnCl_2$, 1.0 mg/mL MCD and 3 mm o-NPA in consecutive 10 cycles scans under 60 Hz scan rate. FIG. 55 depicts the plot of dI/dV vs. potential from −0.04V to 0.04V for the study of the superconductivity using the same device as FIG. 54 with 10 cycle's scans. The molecules o-NPA increased the conductance within the JJ barrier under the same 60 Hz frequency. At 80 Hz, the strength of super conductance was reduced.

Example 10—the Josephson Junction Effect

The hallmarks of the JJ characteristics are (1) at a DC voltage=0, a supercurrent $$I_s = I_c \sin(\Delta\varphi) \quad (4)$$

$I_c$ is critical current, $\Delta\varphi$ is the phase difference between the waves of two superconductors, appears at the DC Josephson junction; (2) at a finite DC voltage, the phase of the supercurrent is change vs. time that caused oscillating at the AC Josephson Junction, which is proportional to $2\,eV_{DC}$, i.e., $$\partial\varphi/\partial t = (2e/h)V_{DC} \quad (5)[7\text{-}8].$$

Open circuit potential with the Au/multiple-layer biomimetic mitochondria device: FIG. 56 depicts the study of JJ effect on the initial rate of open circuit potential (OPO) vs. the first 2 s of discharge energy of the Au/biomimetic mitochondria device using the OPO method comparing with the control. The result from curve "a" has a spontaneous discharge voltage linearly increase at a rate of 1.5 mV/s, which is 2-fold higher compared with the control. This is evidence that the intrinsic electro-relay system within the toroidal cavities is activated under a zero-bias field, which is the driving force for self-powering the qubits Open circuit potential with the Au/(multiple-layer biomimetic mitochondria)"S-I-S" device: the first "S" means superconductor of the Au/multiple-layer biomimetic mitochondria; the "I" means the dielectric insulator; the second "S" means superconductive nanopore biomimetic glucose oxidase membrane/Au. FIG. 57A depicts the Cooper Pair's non-linear amplification of increase potential in the tunnel of Josephson junction under open circuit condition at current=0. Curve "b" at the first 20 ms exhibits the sine wave function with an open circuit potential of 0.79V, the net wave intensity was 11 mV and it lasted for 20 ms, after that it jumped to 10V then stable at 10 V near 100 s as shown in the curve "a". This is the first time we "hear" the second sound from the second wave from the cooper pair. Josephson predicted in a current book that we shall hear the second sound from the second wave of the cooper pair [51]. The first wave is the sine wave "b" and the second wave is the 10V wave. Our experiment showed the moment when a cooper pair coherences tunneling within and cross the barrier and then suddenly degenerates the wave coherence having high open circuit potential occurred when the circuit is in open state. That means the intrinsic wave able to penetrate the micrometer thickness insulator. Due to the instrument limit of the voltage is 10V, therefore we only see 10V, we believe it could be much higher than 10V. The time elapses after the first sine wave to the second high voltage wave is extremely short, and is immeasurable from our instrument. This is evidence of electromagnetic flux presence in the toroidal array cavities induced due to the intrinsic superconducting current at the zero-bias field and confirmed the cooper pair existence. FIG. 57B depicts an absolute constant voltage outcome of 10V without a phase change between cycle #2 to cycle #3732 at current=0, and it lasted of 74.64 s. After that, in FIG. 57C Panel Cycle #3733, it depicts the OPO voltage curve is in an irregular sine wave shape from 9.998V to 10V; Panel Cycle #3734 changed the phase from sine to cosine, intensity was from 9.99V to 9.996V; Panel cycle #3735, the phase also changed and the intensity from 9.978V to 9.98; the similar observations are observed in Panel Cycle #3736, Cycle #3737, #3738, #3739, #3740 and #3741 with phase change and a 2 mV intensity change from 9.97 to 9.99 at current=0. This is the evidence of two-wave Cooper pair observations by the OPO method. We observed the Cooper pair's second wave also reported in the literature in different systems and media by the OPO method [31]. The current invention of observing a two-wave Cooper pair was early filed as a provisional submission in 2017, which is a year earlier than the reported literature. This invention has a time 74.63 s elapse separating the first wave and the second wave under nature happening manner because we never know when and how the second wave will occur, and it is a random occurring situation including the constant discharge voltage and timing. The second Cooper pair event was not known to us at 2017, and regarding the curve observations, none was under our control and it was beyond our knowledge at that time. We had no way to predict when and how the first and the second wave appearances.

Example 11—Cooper Pair's Even-Odd Effect in the Toroidal Array Josephson Junction Cooper pair's even-odd effect was studied through a two-step chronoamperometric method (CA). FIG. 58 depicts the Cooper Pair's Even-odd effect in the AC current pattern of the invented Au/S—I-S/Au device in 1.82 mM $ZnCl_2$, 1 mg/mL MCD and 3 mM o-NPA in 1M MeOH measured current was after the device finished 9999 discharge/charge cycles. The step 1 applied potential is 10 mV, the second potential is 600 mV and the time period is 100 ms per step. There are even-odd effects shown in the first step due to the cooper pair tunneling in the JJ barrier. At the second step, the device's inductance effect was seen as the arrow is shown, and the waves are not in Even-odd fashion, due to the device eliminated the odd Andreev reflection. FIG. 59 depicts an enlarged view of the Cooper Pair's Even-odd effect in the AC voltage pattern of the Au/S—I-S/Au device using an OPO method from FIG. 57 (a) at current=0.

Example 12—the Shapiro Step Affects on the Toroidal JJ Vortex Array with AC Current Having Phase Change The Shapiro Step is a phenomenon that the cooper pair tunnels in the JJ tunnel with steps that look like a saw tooth.

FIG. 60A depicts the scan frequency effects on the charge density due to the phase change property of the cooper pair in the Au/S—I-S/Au device under 1.82 mM $ZnCl_2$, 1 mg/mL MCD and 3 mM o-NPA in 1M MeOH condition at the voltage window between 0.12V to –0.12V at scan rate 1000 mV/s, 2500 mV/s (FIG. 60B), and 9000 mV/s (FIG. 60C), respectively. The scan frequency has a non-linear effects on the Shapiro Step, At 9000 mV/s, the steps diapered, at lower frequency of 1000 mV/s, from 0.12 to 0 V, the AC charge density increased and the steps are in hysteresis; from 0 to –0.12V, the AC current charge density non linearly decreased. At 2500 mV/s, the steps are not evenly distributed having the similar trend of non-linear decrease of the charge density. All the observations are accompanied by the phase change of the AC current as the event obeyed the Josephson first law.

FIG. 60D Panel A depicts Scan rate affects on the current intensity and Shapiro step voltage in the Au/S—I-S/Au device in the media of 1.82 mM $ZnCl_2$, 1 mg/mL mono substituted imidazole-β-dimethyl cyclodextrin (mM-β-DMCD) and 3 mM o-NPA in 1M MeOH at a scan rate 500 Hz, 1000 Hz (Panel B), 2500 Hz (Panel C), and 9000 Hz (Panel D). FIG. 60E depicts the linear relationship between the Josephson frequency and the Shapiro step voltage by using the Least-Square linear regression plot. FIG. 60E depicts the linear relationship, which the slope gives the Josephson constant value between $4.808 \times 10^{14}$-$4.825 \times 10^{14}$ $HzV^1$ from lower and upon limits at 95% CI with a percentage CV value 0.003%. For easy comparison with NIST's published $K_J$ standard of $4.83 \times 10^{14}$ $HzV^{-1}$ having a relative standard uncertainty $6.1 \times 10^{-9}$ [52], whereas our data in relative standard uncertainty $3.52 \times 10^{-8}$ covers 150k to 200k JJ array at room temperature, and NIST covers 1500 JJ array at the cryogenic condition with 0.7 mA output current having a microwave power supply equipment set up. The current is 6.4 nA at zero bias at 500 Hz scan rate (Josephson frequency is 19 MHz), which means our device offers significant benefit as far as energy concerns. The $K_J$ value has a 99.90% agreement with the NIST data, the 0.1% difference is due to the temperature difference we were using.

Example 13—the Controllable and Adjustable State-Switch Valve (CASSV)'s Working Examples In Example 4, we disclosed how to make a CASSV system and explained the expected models for switch from an "On" to an "Off" in a desired state between a Mem-state to a superconducting-state. Following examples are given based on the experimental data as shown from FIG. 60F to FIG. 60K. FIG. 60F depicts the scan rate effects on i-V curves of the Au/S—I-S/Au device in 1 M methanol from 20 Hz to 25 KHz. FIG. 60G depicts 2.7 mg/mL MCD's "Loosing of the Knot" of the superconducting effect through the scan rate change on i-V curves of the same device in 1 M methanol from 500 Hz to 20 KHz. FIG. 60H depicts a 3 mg/mL o-NPA's "Tight of the Knot" ability to recover the superconductivity through the scan rate change from 500 Hz to 9 KHz on i-V curves. At 9 KHz, for three times of 10 consecutive 10 scan cycles are shown. FIG. 60I depicts the zinc-finger's "fine-tune" ability for switch state between mem-element characteristics to superconducting by sensing and adjusting when zinc concentrations from 25 pM to 50 pM in the above media with scan arte from 20 Hz to 9 KHz. FIG. 60J depicts the "State-Switcher" of the "Zinc-finger" complex fine-tune the state to quantum super conductivity in a 3D plot of the quantum conductance vs. applied potential and vs. current in a zinc ion concentration 1.82 mM, MCD 1 mg/mL and 3 mg/mL o-NPA in 1 M MeOH with scan rate 500 Hz that the Cooper pairs penetrate a 133 μM dielectric insulator. FIG. 60K depicts an image of 2D quantum conductance band at zero-bias with y-axis is current vs. bias potential as x-axis, and the highest quantum conductance band and sub bands were shown as the light bands.

Example 14—Josephson Charge Density and Supercurrent Intensity at Zero-Bias

Josephson charge density of the supercurrent at zero-bias was studied by the CV method and the CA method, respectively, by comparing Device 1, the model was shown in FIG. 44, with the Au/multiple layers biomimetic mitochondria-dielectric insulator-pt device as a half cell, in different media at 60 Hz and room temperature. For the CA method, the step potential=0, step time 100 ms was used. FIG. 61A depicts the superconductivity effects on charge density in the JJ location and extended the barrier from –0.06 to 0.06V. The charge density from the supercurrent at zero-bias was show as in "d" and "e" for the qubits cell over the charge density range from 1.7 $nC/cm^2$ to 32.7 $nC/cm^2$ against the range from 8.4 $\mu C/cm^2$ to 12.7 $\mu C/cm^2$ when switch connected with the two leads compared with the half cell has charge density is about 3.2 $nC/cm^2$ within ±1Δ gap in $ZnCl_2$ solution alone.

The full qubit cell's supercurrent and the half cell's supercurrent also were compared and presented in FIG. 61B and FIG. 61C in different media by the CV and CA method, respectively. FIG. 61B depicts the half cell in 20 nM $ZnCl_2$ has a negative supercurrent 7.7 nA at zero-bias in curve "a" and the Au/multiple layer mitochondria devices without insulator exhibited a perfect memristive behavior in curve "b" in the mixture solution of $ZnCl_2$, MCD and o-NPA in 1M MeOH compared curve "c" in 1.8 mM $ZnCl_2$ and 1 mg/mL MCD, that is a flat line. FIG. 61C depicts the supercurrent intensity in the full qubit cell is in the range between 45 nA to –48 nA, which is 5.8-6.2 fold higher than the half cell's supercurrent at zero-bias.

Example 15—Step Time Impacts on Zinc Ion Chelating Indicating the Function of a Zinc Sensor Step time impacts on zinc ion chelating with the functional groups in the membrane were studied using the full cell by the CA method at 7 different step times from 1 ms to 500 ms in 1.82 mM $ZnCl_2$, 1 mg/mL MCD in 1M MeOH without o-NPA compared with the controls. FIG. 62 depict results of seven curves as "b" of current vs. time using the CA method at seven different time intervals of 1 ms for Panel A, 2 ms for Panel B, 5 ms for Panel C, 25 ms for Panel D, 50 ms for Panel E, 100 ms for Panel F and 500 ms for Panel G in the Au/S—I-S/Au compared with the control as the lines "a". It was observed that the peak's sine waves becoming more apparent and relaxed as the step time increased and the peak intensity was in a contrasting trend, decreased. At 500 ms, the shortest X value between oscillation peaks was observed compared with step time 100 ms and 50 ms.

FIG. 63 depicts the plot of current vs. step time of the device. There are 2 exponential decay curves shown, and the curve "a" of with zinc ions, and curve "b" is the control. The current decreased exponentially as the step time increased having first-order rate constants of 2274.3 μA/s vs. 31.8 μAA for the controls against zinc chelating complex, which the zinc complex has a half-life ti value 0.0218 s vs. the control of $3.05 \times 10^{-4}$ s, indicates the chelating process was 71.5-fold slower decay than that of the controls and also with the zinc ions, the device has a magnitude higher signal strength than the controls. To be able to sense the zinc concentration change in 25 pM, 50 pM as shown in FIG. 60I using a CV method, and also shown the 1.82 mM higher concentration in FIGS. 62 and 63 using the CA method has laid a foundation for the zinc complex serve as a CASSV component. It was obvious, in the presence of o-NPA at step time 100 ms at the point "C" in FIG. 63, the current intensity decreased by 276.4-fold compared without o-NPA, that indicates utilizing o-NPA successfully enhanced the ability of the insulator barrier, and also indicated o-NPA further complexes with the zinc-MCD complex made the o-NPA-zinc-MCD complex to be more suitable to be a component of the switchable valve of the CASSV.

Example 16—the Qubit Cell's Magnetic Flux Oscillation from the AC Supercurrent

The qubit cell's magnetic flux oscillation from the AC supercurrent was studied by the Double Step Chronopotentiometric method (DSCPO), i.e., a voltage method under ±10 nA. FIG. 64 depicts the frequency factor effects on the spontaneous voltage discharge/charge curves between the Au/S—I-S/Au device 1 compared with the Device 2 of Au/Superconductor/mamcapacitor sensor. (a) depicts the plot of voltage curves vs. time in the AU/Superconductor/memcapacitor sensor without an insulator, i.e., the Device 2, and without an Au/nanopore SAM electrode in 1.82 mM $ZnCl_2$ and 1 mg/mL MCD and 3 mM o-NPA; the full superconductor/memcapacitor device as Device 1, AU/S-I-S/AU in 1.82 mM $ZnCl_2$ and 1.0 mg/mL MCD, without o-NPA curve as (b); the Device 1's voltage vs. time curve in 1.82 mM $ZnCl_2$ and 1 mg/mL MCD with 3 mM o-NPA under ±10 nA in 1 M MeOH as (c); Panel A is at 0.25 Hz; 40 Hz as shown in Panel B; 250 Hz as shown in Panel C and 1 kHz as shown in Panel D. Data rate was same 50 kHz for all panels. The qubit cell has the highest cell spontaneous discharge voltage is 20V at 0.25 Hz in the presence of $ZnCl_2$, MCD and o-NPA than at other frequencies, and it is a good use for engine or for neuronal circuitry at Slow Wave Sleeping (SWS); At 1 kHz, the voltage reduced to 7.5 mV at ±10 nA.

Example 17—a Device has Multiple Functions in Energy Density

FIG. 65A depicts plots of voltage vs. time at different current levels in 7 levels: ±50 pA, ±100 pA, ±500 pA, ±10 nA, ±10 µA, ±1 mA, ±30 mA in order to study the AC current factor affects on the voltage intensity using the full qubit cell device at 0.25 Hz. It is sensitive at 50 pA level. FIG. 65B depicts plots of energy density vs. voltage at different current levels in 7 levels: ±50 pA, ±100 pA, ±500 pA, ±10 nA, ±10 µA, ±1 mA, ±30 mA in order to study the AC current affects on the energy density using the qubit cell device at 0.25 Hz. The insert was the enlargement of the plots from the lower AC current level. It is evident from the curves that the qubit device can be an energy-saving quantum computing chip with energy density $4.65 \times 10^{-20}$ J/superlattice, i.e., this full qubit device contains 200,000 superlattices occupied $3.14 \times 10^{-6}$ µm², hence, the energy density of the whole device only consumes $9.4 \times 10^{15}$ J energy at ±50 pA, which is self-powered without energy dissipation at zero-bias. In another application, this device can be a good candidate for engine drive purpose at ±30 mA with 20V voltage output.

Example 18—Mapping the Multiple Variable Relationships Among Energy Density, Capacitance and Voltage FIG. 66A depicts the Cooper Pair's Helix-oscillation in the JJ tunneling reflection effects on energy density as Z-axis (in absolute value with a log scale), capacitance as Y-axis and voltage as X-axis used the full qubit Au/S—I-S/Au device at ±50 pA at 0.25 Hz. Noticed there is a helix oscillation occurred at zero-bias with clockwise and counter-clockwise cone energy symmetry. FIG. 66B depicts the 2D double helix-cone shape optical image of the energy density map related to capacitance and voltage of FIG. 66A. FIG. 66C depicts the 3D map of FIG. 66A.

Example 19—AC Supercurrent Oscillation at Zero-Bias

FIG. 67 depicts the plot of AC $I_s$ current vs. time for spontaneous energy harvesting under zero-bias at each of two steps of 200 ms using the full qubit device. The oscillation AC curve "a" was connected as the Au/biomimetic mitochondria end to the anode, then the insulator-nanopore/Au end connected with a cathode; Curve "b" was a connection switched. We see the phase change and the intensity change. These curves demonstrated the Josephson first law of AC superconducting current phase changed.

FIG. 68A depicts the Au/S—I-S/Au device's real-world performance for conducting discharge/charge 9999 cycles with a total of 22.22 hrs at room temperature at normal pressure maintaining ±10V at ±30 mA. There is no energy dissipation event observed, it is reasonable to infer that the self-powered device can operate in infinite cycles because there is a mem-reentrant loop that exists in the system. FIG. 68B depicts the first 4 cycles in discharge/charge for voltage vs. time at 0.25 Hz as the conventional testing frequency for the automobile.

Example 20—Flexible Josephson Toroidal Junction

FIG. 69A depicts the circuitry symbol of the Flexible Toroidal Josephson Junction Superlattice Quantum Qubit (FTJJSLQUBIT) comprising of at least 4 or more junctions and a self-powered switchable reversible electron-relay in the center which is the fundamental function of the biomimetic self-assembled membrane (SAM) that the mems-element construction relies on. The junction materials are various in nature, can comprise of the dielectric insulator, and transitional metal atoms, such as zinc atoms or hydrophobic material, such as NPA; or inert material, such as air. The FTJJ is a component of a circuit that has the mems-inductor and memristor connected in parallel that connected with a mem-capacitor in serial position that produced a circuit having multiple-function once the switchable reversible electron-relay current produced an open circuit potential enough to self-powered the chip circuit, herein such as memory storage, operation, and energy storage in the same device without a need of a microwave power supply. The hummingbird's "8" shape fly pattern is a symbolic representation of the intrinsic electron-relay loop within and between the membranes who initiated the cooper pair tunneling and crossed the JJ barriers.

FIG. 69B depicts the superconducting FTJJ circuit configuration with the mem-inductor, memristor and Josephson junction connected in parallel, $L_j$ is the inductance of the Josephson junction, $R_M$ is the resistance of the memristor, $C_j$ is the capacitance of the Josephson junction; the memcapacitor is connected in serials having the $C_M$ means memcapacitance. The power supply is based on the intrinsic switchable E-R current and its inductive current providing an open circuit potential across the device for initiation as a proactive step.

CONCLUSIONS

Self-powered scale-up toroidal array quantum processing memory device with controllable and adjustable state-switch valves (CASSV) of making and applications at room temperature without applied an external electromagnetic power supply for quantum computing in memory, operation, and energy supply in the One-Device-Assembly was invented and was disclosed. The devices comprise of multiple layer organo-metallic cross-linked polymers having various superlattice structures based on a double poles electron—relay in an electron negative and in an electron positive manner in the membranes that initiated and promoted Cooper pairs coherently transmitting waves in changing phases within and cross the Josephson toroidal flexible junction barriers in 133 μm thickness at zero-bias. As an One-Device-Assembly system, one of the key component is a controllable and adjustable state-switch valve system, which provides delicate balance and enable the whole system serves well when a fJ energy consumption was in demand for the quantum computing qubits; or when an energy storage device stores 1.53 MJ/cm$^2$ at ±10V voltage in demand for a routine working automobile vehicle without energy dissipation. The super-position of the quantum computing and the mem-element reversible circuit loops was benefited by the CASSV system having a low-frequency noise protection, herein embodiments are disclosed.

REFERENCES

[1]. University of Cambridge, Room temperature superconductivity: one step closer to the holy grail of physics, Jul. 9, 2008, www.phys.org

[2] A. Tantillo, Room-temp superconductors could be possible, Brookhaven National Laboratory, Sep. 29, 2016, www.phys.org

[3] M. Stone, "Holy Grail" of superconductors could revolutionize electronics, Aug. 18, 2015, www.gizmodo.com

[4]. A. Nicodemo, What if superconductors could work at room temperature? Apr. 4, 2018, news @Northeastern University

[5] O. A. Mulhanov, System and method for cryogenic hybrid technology computing and memory, U.S. Pat. No. 9,520,180, Dec. 13, 2016.

[6] www.NIST.gov/news-events, Hybrid memory device for superconducting, Jan. 23, 2015.

[7]. D. Drung and J. Beyer, Application in superconducting quantum interference device SQUID, Chapter 8, p245-316, Book: Josephson Junctions, History, Devices, and Applications, Pan Stanford Publishing Pte, Ltd, 2017 edited by E. Wolf, G. Arnold, M. Gurvitch and J. Zasadzinski.

[8] J. Clarke and A. I. Braginski, SQUID Handbook volume 1 and 2, Wiley-VCH, ISBN:3527-40229-2.

[9] B. Back, W. H., Rippard, M. R. Pufall, et. al., Spin-transfer torque switch in nanopillar superconducting-magnetic hybrid Josephson Junction, Physical Review Applied 3, 011001, 2015.

[10]. S. Frolov, Quantum Transport, www.sergeyfrolov.wordpress.com/teaching

[11]. K. K. Likharev, Dynamics of Josephson junctions and circuits, Gordon and Breach Publishers, third printing, the Netherlands, 1996.

[12]. S. Kivelson, Superconductivity and quantum mechanics at Micro-Scale, Stanford University.

[13]. E. Grosfeld and A. Stern, Observing *Majorana* bound states of Josephson vortices in topological superconductors, PNAS, 108(29), 11810-11814, 2011.

[14]. A. M. Zagoskin, A. Chipouline, E. Illichev, et al., Toroidal qubits: naturally-decoupled quit artificial atoms, Arxiv:1406.7678v2, 2014.

[15]. C. Neill, P. Roushan, K. Kechedzhi, et. al., A blue print for demonstrating quantum supremacy with superconducting qubits, Arxiv:17009.06678v1, 2017.

[16]. A. Murphy, D. V. Averin, A. Bezryadin, Nanoscale superconducting memory based on kinetic inductance of asymmetric nanowire loops, New Journal of Physics, 19, 063015, 2017.

[17]. D. Rosenberg, D. Kim, R Das et al., 3D integrated superconducting qubits, NPJ Quantum Information, 3(42), doi:10.1038/s41534-017-0044-0, 2017.

[18]. F. Yan, S. Gustaysson, A. Kama et al., The flux qubit revisited to enhance coherence and reproducibility, Nature Communications 7, 12964, Doi:10.1038, 2016.

[19]. P. J. J. O'Malley, Superconducting Qubits: Dephasing and quantum chemistry, dissertation, University of California Santa Barbara, 2016.

[20]. J. Ku, Meissner qubit: architecture, characterization and vortex-probing applications, dissertation, University of Illinois at Urbana-Champaign, 2016,

[21]. T. Ungerer, I. D. Fey, M. Knebel, Report on disruptive technologies for years 2020-2030.

[22]. M. D. Ventra, Y. V. Pershin, On the physical properties of memristive, memcapacitive, and meminductive systems, Nanotechnology 24, 255201, 2013.

[23]. E. T. Chen, J. Thornton, Nanostructured Acetylcholinesterase (ACHE) Memristor/Memcapacitor Mimicks Brachyhypopomus Electric Fish's Signal-Cloaking Behavior, NSTi-Cleantech 3, 63-66, 2014.

[24]. S. Peotta, M. Di Ventra, Superconducting memristors, Arxiv, 1311.2975v3, 2014.

[25]. S. N. Shevchenko, Y. V. Pershin and F. Nori, Qubit-based memcapacitors and meminductors, Arxiv, 1602, 07230v2, 2016.

[26]. J. Salmiehto, F. Deppe, M. D. Ventra M. Sanz, E. Solano, Quantum memristors with superconducting circuits, Sceintific reports, 7:42044, DOI: 10.1038, 2017.

[27]. S-H. Duh, J. Thornton, P. T. Kissinger and E. T. Chen, Nanobiomimetic Memristor/memcapacitors' Function as a Voltage Sensor for Direct and Reagent-free Detection of sub pg Lipopolysaccharide (LPS) in Different Types of Milks for Infants, *Sensors, Diagnostics & Imaging*, TechConnect Briefs, 4, 140-143, 2016.

[28]. S-H. Duh, J. Thornton, P. T. Kissinger and E. T. Chen, Human Milk Shows Immunological Advantages Over Organic Milk Samples For Infants In the Presence of Lipopolysaccharide (LPS) in 3D Energy Maps Using an Organic Nanobiomimetic Memristor/Memcapacitor, Sensors and Transducers Journal, 203(8), 57-68, 2016.

[29]. E. T. Chen, J. Thornton, P. T. Kissinger and S-H. Duh, The Advantages of Human Milk Recognize the Spatiotemporal Locations of Toxins and Intelligently Bypass Them by Forming a Hummingbird-Like Hovering Neural Network Circuitry Based on an Organic biomimeticcholine Acetyltransferase Memristor/Memcapacitor Prosthesis, Sensors and Transducers Journal, 203(8), 69-83, 2016.

[30]. E. T. Chen, Nanostructured organic memristor/memcapacitor of making with building-in low-to-high frequency switch and a method of inducing an electromagnetic field thereto, U.S. Pat. No. 9,793,503 B2, Oct. 17, 2017.

[31]. E. T. Chen, J. Thornton, P. T. Kissinger and S-H. Duh, Nanobiomimetic Structured Superconductive/Memristive Organo-Metal Devices at Room Temperature Serve as Amperometric Sensors for sub fg/mL Collagen-1 Detection, Techconnect Briefs in Biotech, Biomaterials and Biomedical, 107-110, 2018.

[32]. C. Guarcello, P. Solinas, M. Di Ventra, F. Giaxotto, Solitonic Josephson-based meminductive system, Arxiv, 1610.06807v1, 2016.

[33]. D. Rai, O. Hod and A. Nitzan, J. Physical Chemistry Letters, 2, 2118, 2011.

[34]. R. Islas, T. Heine and G. Merino, Accounts of Chemical Research, 45(2), 215, 2012.

[35]. Idea Diode, http:en.wikipedia.org

[36]. E. T. Chen, J. T. Thornton, C. Ngatchou, S-H. Duh, Nanostructured memristor sensor mimics acetylcholinesterase (ACHE) active sites in the gorge for fM detection of acetylcholine, NSTi-Nanotech 2, 200-203, 2014.

[37]. E. Laviron, J. Electroanal Chem., 101, 19-28, 1979.

[38]. E. T. Chen, J. Thornton, C. Ngatchou, S-H. Duh, P. T. Kissinger, NSTi-Nanotech (3), 115-118, 2013.

[39]. E. T. Chen, Chapter title of Nanostructured biomimetic-enzyme sensing and energy storage, First volume, Third Edition, S. E. Lyshevski, Dekker Encyclopedia of Nanoscience and Nanotechnology, CRC, Mar. 20, 2014.

[40]. E. T. Chen, C. Ngatchou, An electron-relay prototype supercapacitor mimics electrophorus electricus's reversible membrane potential for a high rate discharge pulse, Sensors and Transducers J, 15, special, 42-48, 2012.

[41]. E. T. Chen, Nanostructured Biomimetic Sensing And Energy Storage: Organic Memristor/Memcapacitors, Dekker Encyclopedia of Nanoscience and Nanotechnology, Third Edition, DOI:10.1081/E-ENN3-120054061, Jan. 18, 2017. www.crcnetbase.com

[42]. E. T. Chen, Nanostructured organic memristor/memcapacitor of making with an embedded low-to-high frequency switch and a method of inducing an electromagnetic field, U.S. Pat. No. 9,793,503, Oct. 17, 2017.

[43]. Chen E T, Thornton J and Mulchi Jr C, Nanobiomimetic Memcapacitor Memory Devices Identify Circadian Rhythm Dysfunction and Predict Early Signs of "Epilepsy" Using Reentrant Energy-Sensory Images, Advanced Manufacturing, Electronics and Microsystems: TechConnect Briefs, 200-203, 2015.

[44]. Thornton J, Mulchi, Jr. C, Kissinger P T and Chen E T, Acetylcholine Repairs the Amyloid-beta Damage on Brain Circuitry and Memory Loss From a "Mutated Biomimetic Acetylcholinesterase" Neuronal Memcapacitor During Slow-Wave Sleeping, Advanced Manufacturing, Electronics and Microsystems: TechConnect Briefs, 226-229, 2015

[45]. E. T. Chen, J. T. Thornton and Jr. C. Mulchi, Early Forming a Hummingbird-like Hovering Neural Network Circuitry Pattern with Reentrant Spatiotemporal Energy-Sensory Orientation Privileged to Avoid "Epilepsy" Based on a Biomimetic Acetylcholinesterase Memcapacitor Prosthesis, Sensors and Transducers Journal, 191(8), 84-99, 2015.

[46]. J. T. Thornton, Jr. C. Mulchi, P. T. Kissinger, E. T. Chen, In Vitro Restoration of an Amyloid-Beta Altered Network Circuitry in a 'Mutated Biomimetic Acetylcholinesterase' Memristor/Memcapacitor Neural Prosthesis, Sensors and Transducers Journal, 191(8), 100-113, 2015.

[47]. L. A. Toikka, Self-interference of a toroidal Bose-Einstein condensate, New Journal of Physics, 16, 043011, 2014.

[48]. E. T. Chen, J. T. Thornton, S-H. Duh And P. T. Kissinger, Observation of Fermi Arc Surface States Induced by Organic Memristive/Memcapacitive Devices with a Double-Helical Polarized Single-Wall Nanotube Membrane for Direct Chelating with Matrix Matelloproteinase-2, Sensors and Transducers Journal, 214(7), 69-84, 2017.

[49]. E. T. Chen and H. L. Pardue, Analytical applications of catalytic properties of modified cyclodextrins, Anal. Chem, 65(19), 2583-2587, 1993.

[50]. M. Ternes, M. Pivetta, F. Patthey, and W-D Schneider, Creation, electronic properties, disorder, and melting of two-dimensional surface-state-mediated adatom, Progress in Surface Science 85, 1-27, 2010.

[51]. B. D. Josephson, The theoretical discovery of the Josephson effect, Chapter 1, 1-10, Josephson Junctions, History, Devices, and Applications, Pan Stanford Publishing Pte, Ltd, 2017 edited by E. Wolf, G. Arnold, M. Gurvitch and J. Zasadzinski.

[52]. https://Physics.nest.gov/cgi-bin/cuu/value/kjos. The NIST reference on Constants, Units and Uncertainty.

What is claimed is:

1. A scale-up toroidal array quantum processing memory device comprises of
    (a) a first electrode having a first layer of an organic superconductive membrane on top that membrane was made of arrays of nanoislands with cyclodextrin cavities by self-assembly cross-linked copolymers;
    (b) a second layer comprising of an organometallic superlattice membrane that was made of cross-linked triacetyl-β-cyclodextrin (TCD), polyethylene glycol diglycidyl ether (PEG), poly(4-vinylpyridine) (PVP), bis-imidazole derivatized dimethyl-β-cyclodextrin (bM-β-DMCD) and embedded zinc chloride was fabricated by self-assembly horizontally affixed on top of the first layer membrane;
    (c) Polymer PEG . . . TCD and polymer PVP . . . PEG cross-linked to form polymer chains mimicking a protein choline acetyltransferase (CHAT)'s C-terminal and N-terminal, respectively, and vertically oriented on the surface of the first electrode;
    (d) there are Josephson junction barriers comprised of insulators;
    (e) a second electrode comprises of an electron conductive organic polymer with nanopore array structure membrane;
    (f) Between two Membrane Electrode Assembles (MEA)s there are Controllable and Adjustable State-Switch Valves (CASSV).

2. According to claim 1, wherein a direct electron-relay hysteresis i-V current loop formed between the first layer and the second layer membrane on the first electrode, such as a biomimetic choline acetyltransferase (CHAT) in the first layer . . . a biomimetic Matrix Metalloproteinase (MMP-2) in the second layer . . . zinc ions included mono imidazole derivatized mM-β-DMCD methanol media as an inclusion complex . . . an insulator of the Josephson junction . . . a nanopore membrane on the second electrode when applied a mild electric potential between ±3 mV including a zero-bias.

3. According to claim 2, wherein appropriate concentration of 3 mM o-nitrophenyl acetate (o-NPA) included in the inclusion complex in the methanol solution forms an adjustable valve to switch the memristive state to a superconducting state at zero-bias.

4. According to claim 2, wherein a superposition qubit "1" state of the device establishment is to have at least one of the superconductor's membrane with a Friedel-oscillation in the superlattice membrane.

5. According to claim 2, wherein an E-R system has a nano-curvature biomimetic mitochondria structure with multiple single wall curvature nanotubes connecting each other through transition metal atoms forming a toroidal matrix.

6. The use of a device according to claim 2, a finite supercurrent induced by the electron-relay arises as a self-powering force initiated a long-range Josephson junction of toroidal vortices, i.e., providing intrinsic electromagnetic flux within the JJ boundaries at zero-bias; cooper pairs hop through the junctions causing an oscillation due to phase change, herein AC voltage pulses are produced as the qubit's "1"; by the mem-element's reversible loop, when the voltage down to zero with zero current, the qubit's "0" state is granted.

7. According to claim 4, wherein the oscillating superconducting waves are as a function of time and memory.

8. According to claim 7, wherein the oscillating wave of the superconductor has a circular fashion that the quantum conductance is quantized and proportional to $2\ eV_{dc}$.

9. According to claim 2, wherein materials of the insulator are flexible having at least one of the following: a dielectric, zinc ions, air and zinc fingers in the mM-β-DMCD or bM-β-DMCD cavities with o-NPA included.

10. According to claim 5, wherein the curvature nanotubes have an average diameter of 200 nm with a single lattice occupying 21-25 μm$^2$ with zinc atoms on the edge or at the center.

11. According to claim 10, wherein a Josephson constant value between $4.808 \times 10^{14}$-$4.825 \times 10^{14}$ HzV$^{-1}$ from lower and upon limits at 95% CI with a percentage CV value 0.003%.

12. According to claim 10, wherein the device is a qubit device consuming $9.4 \times 10^{-15}$ J at current ±50 pA at zero-bias.

13. According to claim 10, wherein the device is a energy storage device with charge/discharge 9999 cycles at 0.25 Hz at ±30 mA for 22.22 hours without drifting.

14. According to claim 10, wherein the multiple-layer membrane electrode covered with 150,000 uniform superlattices.

15. According to claim 13, wherein the device stores energy 1.53 MJ/cm$^2$ at ±10V voltage.

16. According to claim 10, wherein a Cooper pair wave of the superconductor penetrates 133 μm Josephson toroidal junction of the dielectric insulator.

17. According to claim 16, wherein the Cooper pair waves arrive in two individual forms at a different arriving time with different phase and different signal intensity happened at zero-bias at room temperature.

18. According to claim 16, wherein the device does not apply an external magnetic field.

19. According to claim 2, wherein an imidazole derivative cycledextrin in the methanol media is a valve to turn "Off" the superconductivity of the device.

20. According to claim 19, wherein appropriate concentrations of 1.82 mM zinc ions included in the o-NPA and MCD inclusion complex is a controllable and adjustable valve to be able to fine-tune between superconductivity and memristivity.

\* \* \* \* \*